(12) United States Patent
Sorek et al.

(10) Patent No.: US 9,353,359 B2
(45) Date of Patent: May 31, 2016

(54) BACTERIAL ANTI-PHAGE DEFENSE SYSTEMS

(71) Applicant: Yeda Research and Development Co. Ltd., Rehovot (IL)

(72) Inventors: Rotem Sorek, Rehovot (IL); Hila Sberro, Rehovot (IL); Azita Leavitt, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/140,793

(22) Filed: Dec. 26, 2013

(65) Prior Publication Data

US 2014/0178353 A1     Jun. 26, 2014

Related U.S. Application Data

(60) Provisional application No. 61/745,838, filed on Dec. 26, 2012.

(51) Int. Cl.
| | |
|---|---|
| *C07K 14/00* | (2006.01) |
| *C12N 9/22* | (2006.01) |
| *C12N 9/12* | (2006.01) |
| *C07K 14/81* | (2006.01) |
| *A61K 38/00* | (2006.01) |

(52) U.S. Cl.
CPC .............. *C12N 9/22* (2013.01); *C07K 14/8107* (2013.01); *C12N 9/1241* (2013.01); *A61K 38/00* (2013.01)

(58) Field of Classification Search
CPC ...................................................... C07K 14/00
See application file for complete search history.

(56) References Cited

U.S. PATENT DOCUMENTS

| | | | |
|---|---|---|---|
| 5,994,118 | A | 11/1999 | Moineau et al. |
| 7,169,911 | B2 | 1/2007 | Durmaz et al. |
| 7,550,576 | B2 | 6/2009 | Klaenhammer et al. |
| 7,754,868 | B2 | 7/2010 | Klaenhammer et al. |

OTHER PUBLICATIONS

Copeland et al. 2007; Complete sequence of Pseudomonus mendocina ymp. EMBL: ABP83335.*
Lucas et al. 2008; Complete sequence of Acidithiobacillus ferrooxidans ATCC 53993. EMBL: ACH83539.1.*
Kerfeld et al. 2009; Complete sequence of plasmid of Amonifex degensii KC4. EMBL: ACX53253.1.*
Lee et al. 2006; Sequence analysis of two cryptic plasmids from Bifidobacterium longum pJO10A and construction of a shuttle cloning vector. Applied Environmental Microbiology 72:527-535. EMBL: ACD97784.1. Alignment Only Being Sent.*
Chenoll et al. 2012; Safety assessment of strain Bifidobacterium longum CECT 7347, a probiotic able to reduce the toxicity and inflammatory potential of gliadin-derived peptides, based on phenotypic traits, whole genome sequencing, and murine trials. EMBL: CCK35109.1.*
Pajon et al. 2010; The genome sequence of Bifidobacterium longum F8. EMBL CBK70404.1.*
Schell et al. 2002; The genome sequence of Bifidobacterium longum reflects its adaptation to the human gastrointestinal tract. PNAS 99:14422-14427. EMBL: AAN25255.1. Alignment Only Being Sent.*
Ward et al. 2010; The genome sequence of *Bifidobacterium* sp. Strain 12_1_47BFAA) EMBL: EFV37145.1.*
DeBoy et al. 2008; Insights into plant cell wall degradation from the genome sequence of soil bacterium Cellvibrio japonicas. J. Bacteriology. 190: 5455-5463. EMBL: ACE84112.1. Alighnment Only Being Sent.*
Larimar et al. 2006; Annotation of the draft genome assembly of delta proteobacterium MLMS-1. EMBL: EAT06598.*
Score Search Results; Percent Identity Comparison of SEQ ID No. 3001 with 45 other '793 sequences. 2015.*
Score Search Results; Percent Identity Comparison of SEQ ID No. 2773 with 45 other '793 sequences. 2015.*
Makarova et al. "Defense Islands in Bacterial and Archaeal Genomes and Prediction of Novel Defense Systems", Journal of Bacteriology, 193(21): 6039-6056, Nov. 2011.

* cited by examiner

*Primary Examiner* — Karen Cochrane Carlson

(57) ABSTRACT

An isolated polypeptide is disclosed comprising an amino acid sequence selected from the group consisting of SEQ ID NOs: 2773-5544 and 11089-11094, wherein the polypeptide has antimicrobial activity. Uses thereof for treating microbial infections are also disclosed.

10 Claims, 13 Drawing Sheets
(10 of 13 Drawing Sheet(s) Filed in Color)

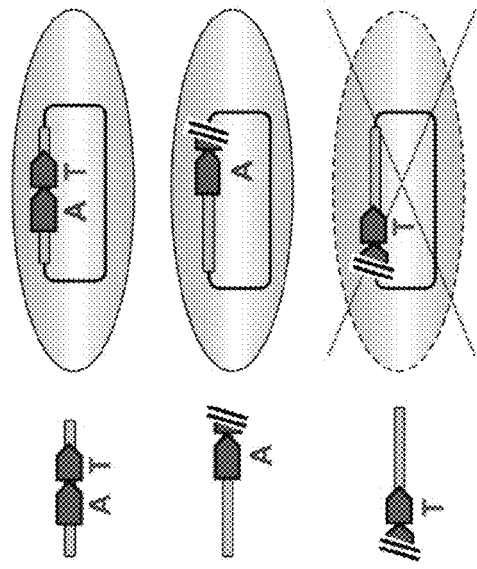
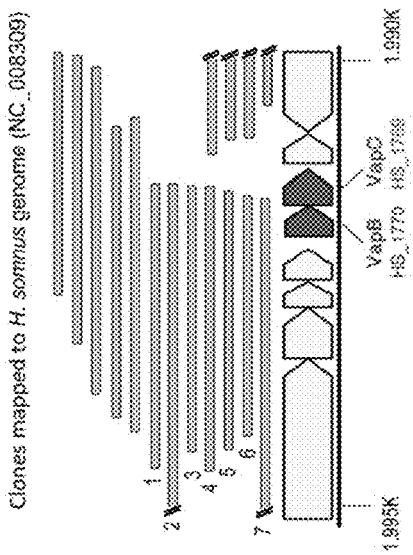

FIG.4B

| Phylum | PsyrAT | PmenAT | RlegAT | SdenAT | SanaAT |
|---|---|---|---|---|---|
| Firmicutes | 3 | 4 |  | 1 |  |
| Chlorobi | 2 |  | 5 |  | 3 |
| Bacteroidetes | 1 | 2 |  |  |  |
| Chlamydiae |  |  | 1 |  |  |
| Planctomycetes |  |  | 1 |  |  |
| Spirochaetes |  | 1 |  |  |  |
| Actinobacteria |  | 40 | 20 | 9 |  |
| Chloroflexi | 3 | 1 |  |  |  |
| Deinococcus-Thermus |  |  |  |  |  |
| Cyanobacteria | 6 | 11 | 3 |  | 1 |
| Deltaproteobacteria | 1 | 4 | 3 | 5 | 2 |
| Epsilonproteobacteria |  |  |  | 2 |  |
| Alphaproteobacteria | 1 | 6 | 16 |  | 1 |
| Betaproteobacteria | 3 | 5 | 8 | 2 | 9 |
| Gammaproteobacteria | 45 | 19 | 7 | 14 | 32 |
| Other Phyla |  | 1 | 5 |  |  |

FIG.4C

| Species | PsyrAT | PmenAT | RlegAT | SdenAT | SanaAT |
|---|---|---|---|---|---|
| Bifidobacterium species |  |  |  | 7 |  |
| Escherichia coli | 35 |  |  |  | 14 |
| Klebsiella pneumoniae |  | 1 |  |  |  |
| Legionella longbeachae |  | 1 |  |  |  |
| Legionella pneumophila |  |  | 2 |  |  |
| Mycobacterium bovis |  | 3 |  |  | 3 |
| Mycobacterium tuberculosis |  | 35 |  |  |  |
| Prevotella timonensis |  | 1 |  |  |  |
| Pseudomonas aeruginosa | 1 |  |  |  |  |
| Shigella dysenteriae | 2 |  |  |  |  |
| Yersinia enterocolitica |  |  |  |  | 1 |

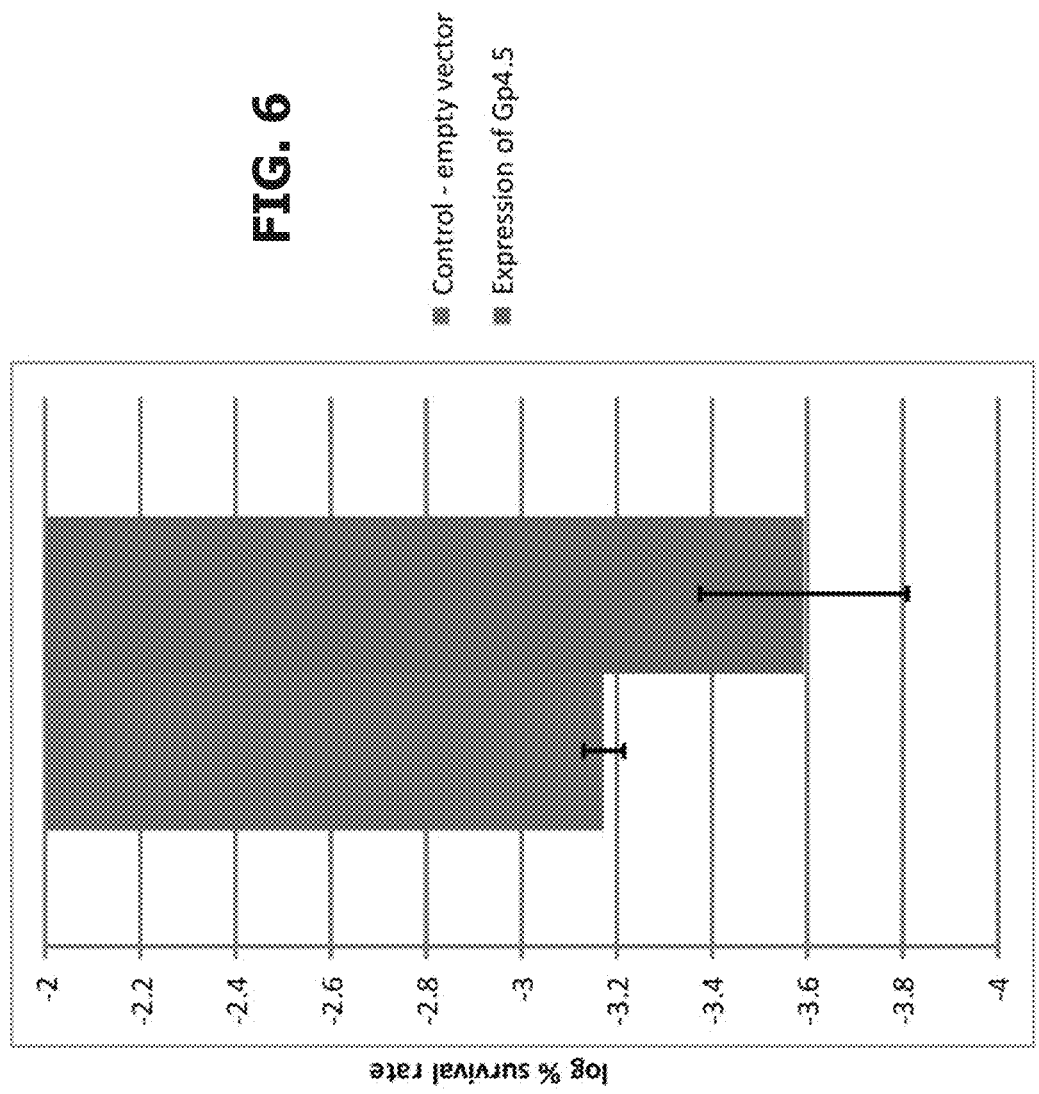

BACTERIAL ANTI-PHAGE DEFENSE SYSTEMS

RELATED APPLICATION

This application claims the benefit of priority under 35 USC §119(e) of U.S. Provisional Patent Application No. 61/745,838 filed Dec. 26, 2012, the contents of which are incorporated herein by reference in their entirety.

GOVERNMENT INTERESTS

Federally Sponsored Research

This invention was made with government support under AI082376 awarded by NIH. The government has certain rights in the invention.

SEQUENCE LISTING STATEMENT

The ASCII file, entitled 57892SequenceListing.txt, created on Nov. 11, 2013, comprising 20,497,456 bytes, submitted concurrently with the filing of this application is incorporated herein by reference.

FIELD AND BACKGROUND OF THE INVENTION

The present invention, in some embodiments thereof, relates to bacterial polypeptides that comprise toxin or antitoxin activity and, more particularly, but not exclusively, to toxin-antitoxin pairs that may be used as bacterial anti-phage defense systems.

A broad array of food products, commodity chemicals, and biotechnology products are manufactured industrially by large-scale bacterial fermentation of various substrates. Because enormous amounts of bacteria are being cultivated each day in large fermentation vats, bacteriophage contamination can rapidly bring fermentations to a halt and cause economic setbacks, and is therefore considered a serious threat in these industries. The dairy fermentation industry has openly acknowledged the problem of phage and has been working with academia and starter culture companies to develop defense strategies and systems to curtail the propagation and evolution of phages for decades.

To survive in the face of perpetual phage attacks, bacteria have developed a variety of anti-phage defense systems (Labrie et al., 2010; Stern and Sorek, 2011). These systems include restriction enzymes that recognize and cleave foreign DNA (King and Murray, 1994), abortive infection (Abi) mechanisms that lead the bacterial cell, upon phage invasion, to commit "suicide", thus protecting the colony against phage spread (Chopin et al., 2005); and the recently identified adaptive defense system called CRISPR/Cas, which uses small RNAs to target invading phage DNA (Deveau et al., 2010; Horvath and Barrangou, 2010; Sorek et al., 2008; van der Oost et al., 2009). Due to the rapid evolution and elaborated biological novelty associated with the bacteria-phage arms race, it is estimated that many additional, yet uncharacterized anti-phage defense systems are encoded by bacteria and archaea to (Makarova et al., 2011; Stern and Sorek, 2011). As part of this continuous arms race, successful phages had also developed numerous counter-resistance mechanisms to overcome bacterial defense (Labrie et al., 2010; Stern and Sorek, 2011).

The growing availability of genomic sequences has elucidated the vast dispersion of toxin-antitoxin (TA) systems in prokaryotic genomes (Shao et al., 2011). These systems (also called TA modules), composed of a toxic gene and a neutralizing gene, were first suggested to function as plasmid 'addiction molecules' (Van Melderen and Saavedra De Bast, 2009; Wozniak and Waldor, 2009), but their prevalent existence on chromosomes (Aizenman et al., 1996; Makarova et al., 2009; Shao et al., 2011) has led to the understanding that this is unlikely their major role. Accumulating evidence suggest that TA modules play pivotal roles in prokaryotic cellular biology including programmed cell death (Hazan et al., 2004), stress response (Christensen et al., 2001), generation of persister cells (Schumacher et al., 2009), biofilm formation (Kim et al., 2009) and phage defense via abortive infection (Fineran et al., 2009; Hazan and Engelberg-Kulka, 2004; Koga et al., 2011; Pecota and Wood, 1996).

The most prevalent kind of TA systems is type II systems, where both toxin and antitoxin are proteins (as opposed to types I and III where the antitoxin is a non-coding RNA (Fineran et al., 2009; Fozo et al.)). The two genes, which reside on the same operon, code for small proteins and inhibition of the toxin is carried out through protein-protein interaction. As a rule, the toxin is a stable protein and the antitoxin is unstable and degrades rapidly by one of the housekeeping bacterial proteases, usually Lon or ClpP (Aizenman et al., 1996; Cherny and Gazit, 2004; Christensen et al., 2004; Christensen et al., 2001; Christensen et al., 2003; Lehnherr and Yarmolinsky, 1995; Roberts et al., 1994; Van Melderen et al., 1996). As a result, continuous production of the antitoxin is required to prevent the toxin's deleterious effects (Van Melderen and Saavedra De Bast, 2009).

A number of reports demonstrate a role for type II TA systems in phage resistance via an Abi mechanism: the extensively studied MazEF system was shown to eliminate P1 phage infection (Hazan and Engelberg-Kulka, 2004), and the recently identified RnlA toxin which is activated following T4 phage infection degrades phage mRNAs (Koga et al., 2011). Type I and Type III TA systems (hok/sok and ToxIN, to respectively) were also shown to provide resistance against phages (Fineran et al., 2009; Pecota and Wood, 1996). However, based on their presence in bacterial 'defense islands', it was hypothesized that TA systems play a much wider role in phage defense (Makarova et al., 2011).

The usage of Abi systems for biotech purposes, especially in protecting dairy industry bacteria from bacteriophages is disclosed in U.S. Pat. Nos. 7,754,868, 7,550,576, 7,169,911 and 5,994,118.

To date, at least 12 families of type II TA systems have been described (Masuda et al., 2012; Shao et al., 2011). Members of these families are widespread in bacterial and archaeal genomes and undergo extensive horizontal gene transfer (Guglielmini et al., 2008; Makarova et al., 2009; Pandey and Gerdes, 2005; Shao et al., 2011). Computational studies based on the 'guilt by association' principle (gene neighbors of known toxins/antitoxins are suspected as antitoxins/toxins themselves) and on other characteristics of TA systems have recently predicted several novel TA families (Leplae et al., 2011; Makarova et al., 2009), which are yet to be validated experimentally.

SUMMARY OF THE INVENTION

According to an aspect of some embodiments of the present invention there is provided an isolated polypeptide comprising an amino acid sequence selected from the group consisting of SEQ ID NOs: 2773-5544 and 11089-11094, wherein the polypeptide has antimicrobial activity.

According to an aspect of some embodiments of the present invention there is provided an isolated polypeptide comprising an amino acid sequence selected from the group consisting of SEQ ID NOs: 8317-11088, wherein the polypeptide protects a microbe from an activity of a toxin.

According to an aspect of some embodiments of the present invention there is provided an isolated polynucleotide comprising a nucleic acid sequence encoding an isolated polypeptide comprising an amino acid sequence selected from the group consisting of SEQ ID NOs: 2773-5544 and 11089-11094, wherein the polypeptide has antimicrobial activity.

According to an aspect of some embodiments of the present invention there is provided an isolated polynucleotide comprising a nucleic acid sequence encoding a polypeptide comprising an amino acid sequence selected from the group consisting of SEQ ID NOs: 8317-11088, wherein the polypeptide protects a microbe from an activity of a toxin.

According to an aspect of some embodiments of the present invention there is provided an anti-microbial composition, comprising a carrier and as an active ingredient an isolated polypeptide comprising an amino acid sequence selected from the group consisting of SEQ ID NOs: 2773-5544 and 11089-11094.

According to an aspect of some embodiments of the present invention there is provided an anti-microbial composition, comprising a carrier and as an active ingredient an isolated polynucleotide comprising a nucleic acid sequence which encodes a polypeptide comprising an amino acid sequence selected from the group consisting of SEQ ID NOs: 2773-5544 and 11089-11094.

According to an aspect of some embodiments of the present invention there is provided method of treating an infection in a subject in need thereof, the method comprising administering to the subject a therapeutically effective amount of the anti-microbial composition described herein, thereby treating the infection.

According to an aspect of some embodiments of the present invention there is provided a solid support coated with an isolated polypeptide comprising an amino acid sequence selected from the group consisting of SEQ ID NOs: 2773-5544.

According to an aspect of some embodiments of the present invention there is provided a method of killing a microbe, the method comprising contacting the microbe with an isolated peptide comprising an amino acid sequence selected from the group consisting of SEQ ID NOs: 2773-5544, thereby killing the microbe.

According to an aspect of some embodiments of the present invention there is provided a method of protecting a microbe from a toxin comprising expressing in the microbe the polypeptide comprising an amino acid sequence selected from the group consisting of SEQ ID NOs: 8317-11088, wherein the polypeptide protects a microbe from an activity of a toxin.

According to an aspect of some embodiments of the present invention there is provided an isolated bacterial population genetically modified to express a toxin and a to cognate antitoxin thereof, the bacterial population being resistant to a lytic activity of a bacteriophage, wherein the toxin comprises an amino acid sequence selected from the group consisting of SEQ ID NOs: 2773-3117, wherein when the toxin comprises an amino acid sequence selected from the group consisting of SEQ ID NO: 2773-2804, the antitoxin comprises an amino acid sequence selected from the group consisting of SEQ ID NO:8317-8348, wherein when the toxin comprises an amino acid sequence selected from the group consisting of SEQ ID NO: 2805-2871, the antitoxin comprises an amino acid sequence selected from the group consisting of SEQ ID NO:8349-8415, wherein when the toxin comprises an amino acid sequence selected from the group consisting of SEQ ID NO: 2872-2935, the antitoxin comprises an amino acid sequence selected from the group consisting of SEQ ID NO:8416-8479, wherein when the toxin comprises an amino acid sequence selected from the group consisting of SEQ ID NO: 2936-3030, the antitoxin comprises an amino acid selected from the group consisting of SEQ ID NO:8480-8574, wherein when the toxin comprises an amino acid sequence selected from the group consisting of SEQ ID NO: 3031-3078, the antitoxin comprises an amino acid sequence selected from the group consisting of SEQ ID NO: 8575-8622, wherein when the toxin comprises an amino acid sequence selected from the group consisting of SEQ ID NO: 3079-3087, the antitoxin comprises an amino acid sequence selected from the group consisting of SEQ ID NO:8623-8631, wherein when the toxin comprises an amino acid sequence selected from the group consisting of SEQ ID NO: 3088-3094, the antitoxin comprises an amino acid sequence selected from the group consisting of SEQ ID NO:8632-8638, wherein when the toxin comprises an amino acid sequence selected from the group consisting of SEQ ID NO: 3095-3109, the antitoxin comprises an amino acid sequence selected from the group consisting of SEQ ID NO:8639-8653, wherein when the toxin comprises an amino acid sequence selected from the group consisting of SEQ ID NO: 3110-3117, the antitoxin comprises an amino acid sequence selected from the group consisting of SEQ ID NO:8654-8661.

According to an aspect of some embodiments of the present invention there is provided a method of protecting a bacterial population from phage attack, the method comprising expressing in the bacterial population a toxin and a cognate antitoxin thereof, wherein the toxin comprises an amino acid sequence selected from the group consisting of SEQ ID NOs: 2773-3117, wherein when the toxin comprises an amino acid sequence selected from the group consisting of SEQ ID NO: 2773-2804, the antitoxin comprises an amino acid sequence selected from the group consisting of SEQ ID NO:8317-8348, wherein when the toxin comprises an amino acid sequence selected from the group consisting of SEQ ID NO: 2805-2871, the antitoxin comprises an amino acid sequence selected from the group consisting of SEQ ID NO:8349-8415, wherein when the toxin comprises an amino acid sequence selected from the group consisting of SEQ ID NO: 2872-2935, the antitoxin comprises an amino acid sequence selected from the group consisting of SEQ ID NO:8416-8479, wherein when the toxin comprises an amino acid sequence selected from the group consisting of SEQ ID NO: 2936-3030, the antitoxin comprises an amino acid selected from the group consisting of SEQ ID NO:8480-8574, wherein when the toxin comprises an amino acid sequence selected from the group consisting of SEQ ID NO: 3031-3078, the antitoxin comprises an amino acid sequence selected from the group consisting of SEQ ID NO: 8575-8622, wherein when the toxin comprises an amino acid sequence selected from the group consisting of SEQ ID NO: 3079-3087, the antitoxin comprises an amino acid sequence selected from the group consisting of SEQ ID NO:8623-8631, wherein when the toxin comprises an amino acid sequence selected from the group consisting of SEQ ID NO: 3088-3094, the antitoxin comprises an amino acid sequence selected from the group consisting of SEQ ID NO:8632-8638, wherein when the toxin comprises an amino acid sequence selected from the group consisting of SEQ ID NO:

3095-3109, the antitoxin comprises an amino acid sequence selected from the group consisting of SEQ ID NO:8639-8653, wherein when the toxin comprises an amino acid sequence selected from the group consisting of SEQ ID NO: 3110-3117, the antitoxin comprises an amino acid sequence selected from the group consisting of SEQ ID NO:8654-8661.

According to an aspect of some embodiments of the present invention there is provided a nucleic acid system comprising:

(i) a first isolated polynucleotide which encodes a toxin, the toxin having an amino acid sequence selected from the group consisting of SEQ ID NOs: 2773-5544; and (ii) a second isolated polynucleotide which encodes a cognate antitoxin to the toxin, the antitoxin having an amino acid sequence selected from the group consisting of SEQ ID NOs: 8317-11088.

According to some embodiments of the invention, the isolated polypeptide comprises an amino acid sequence selected from the group consisting of SEQ ID NOs. 2773-3117 and 11089-11094.

According to some embodiments of the invention, the amino acid sequence consists of the sequences selected from the group as set forth in SEQ ID NOs: 2773-5544.

According to some embodiments of the invention, the isolated polypeptide comprises an amino acid sequence selected from the group consisting of SEQ ID NOs. 8317-8661.

According to some embodiments of the invention, the amino acid sequence consists of the sequences selected from the group as set forth in SEQ ID NOs: 8317-11088.

According to some embodiments of the invention, the isolated peptide comprises at least one naturally occurring amino acid.

According to some embodiments of the invention, the isolated peptide comprises a synthetic amino acid.

According to some embodiments of the invention, the isolated peptide is attached to a cell penetrating agent.

According to some embodiments of the invention, the attached is covalently attached.

According to some embodiments of the invention, the cell penetrating agent is a peptide agent.

According to some embodiments of the invention, the isolated peptide is attached to a sustained-release enhancing agent.

According to some embodiments of the invention, the sustained-release enhancing agent is selected from the group consisting of hyaluronic acid (HA), alginic acid (AA), polyhydroxyethyl methacrylate (Poly-HEMA), polyethylene glycol (PEG), glyme and polyisopropylacrylamide.

According to some embodiments of the invention, the isolated polynucleotide to comprises a nucleic acid sequence selected from the group consisting of SEQ ID NOs: 1-2772.

According to some embodiments of the invention, the isolated polynucleotide comprises a nucleic acid sequence selected from the group consisting of SEQ ID NOs: 5545-8316.

According to some embodiments of the invention, the carrier is a pharmaceutically acceptable carrier.

According to some embodiments of the invention, the antimicrobial composition is formulated for topical application.

According to some embodiments of the invention, the nucleic acid sequence is selected from the group consisting of SEQ ID NOs: 1-2772 and 11095-11100.

According to some embodiments of the invention, the carrier is a pharmaceutically acceptable carrier.

According to some embodiments of the invention, the method further comprises administering to the subject an antibiotic.

According to some embodiments of the invention, the contacting is effected in vivo.

According to some embodiments of the invention, the contacting is effected ex vivo.

According to some embodiments of the invention, the microbe comprises a bacteria.

According to some embodiments of the invention, the isolated polynucleotide is operably linked to a promoter.

According to some embodiments of the invention, the bacterial population is a lactic acid bacterial population.

According to some embodiments of the invention, the bacterial population is of a species selected from the group consisting of *Lactococcus* species, *Streptococcus* species, *Lactobacillus* species, *Leuconostoc* species, *Oenococcus* species, *Pediococcus* species and *Bifidobacterium*.

According to some embodiments of the invention, when the toxin comprises an amino acid sequence selected from the group consisting of SEQ ID NO: 2805-2871, the bacteriophage comprises WT T7 strain.

According to some embodiments of the invention, the first isolated polynucleotide encodes a toxin having an amino acid sequence selected from the group consisting of SEQ ID NOs: 2773-3117; and the second isolated polynucleotide encodes an antitoxin having an amino acid sequence selected from the group consisting of SEQ ID NOs: 8317-8661.

According to some embodiments of the invention, the first isolated polynucleotide and the second isolated polynucleotide are comprised in a non-identical expression vector.

According to some embodiments of the invention, the antimicrobial composition is for treating an infection.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D illustrate that data derived from whole-genome shotgun sequencing exposes toxin-antitoxin pairs. (A) The "Sanger" based process of DNA sequencing involves random genome fragmentation and transformation of DNA fragments into *E. coli*. (B) In a DNA locus spanning a toxin/antitoxin (TA) gene pair, random fragmentation leaving the toxin detached from its cognate antitoxin leads to *E. coli* growth arrest, whereas a fragment containing both genes, or the antitoxin alone, will be propagated and sequenced. (C) A known family of toxin/antitoxin gene pairs, of the VapBC type, was found in 11 of the analyzed genomes. In 7/11 cases the gene pair follows the "TA cloning pattern", significantly higher than the number expected by chance ($p=4\times10^{-3}$). (D) The VapBC locus in *Haemophilus somnus* 129T (accession NC_008309, locus tags HS_1769-HS_1770). Shown are clones (brown) mapped to the reference genome at that locus. Clones covering the antitoxin but not the toxin are numbered. Only five of the 22 clones covering both toxin and antitoxin are shown.

Figure 2:
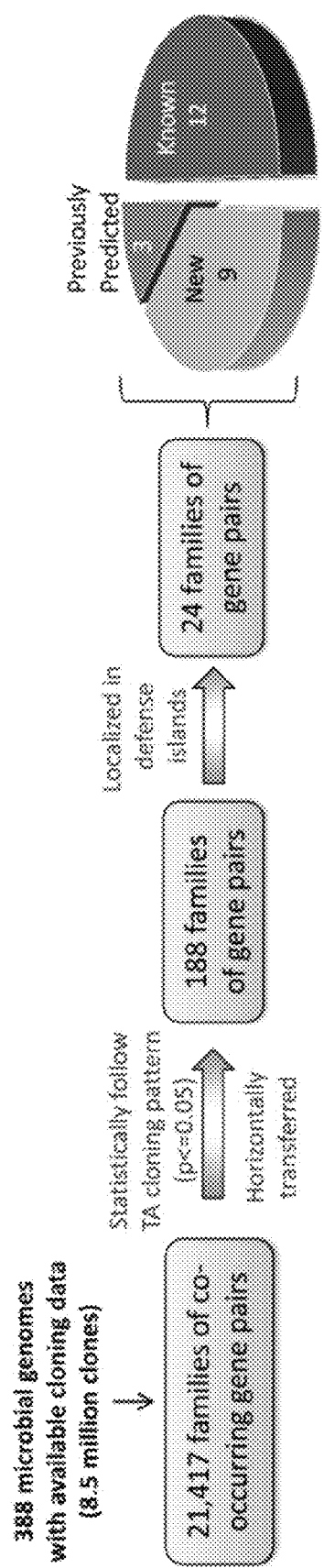

FIG. 2 is a diagram of the workflow for systematic discovery of families of toxin/antitoxin associated with anti-phage defense.

Figure 3A:
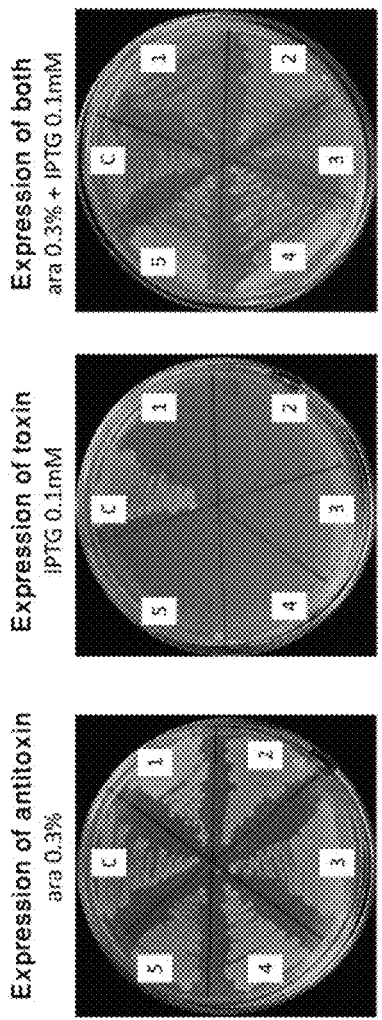
Figure 3B:
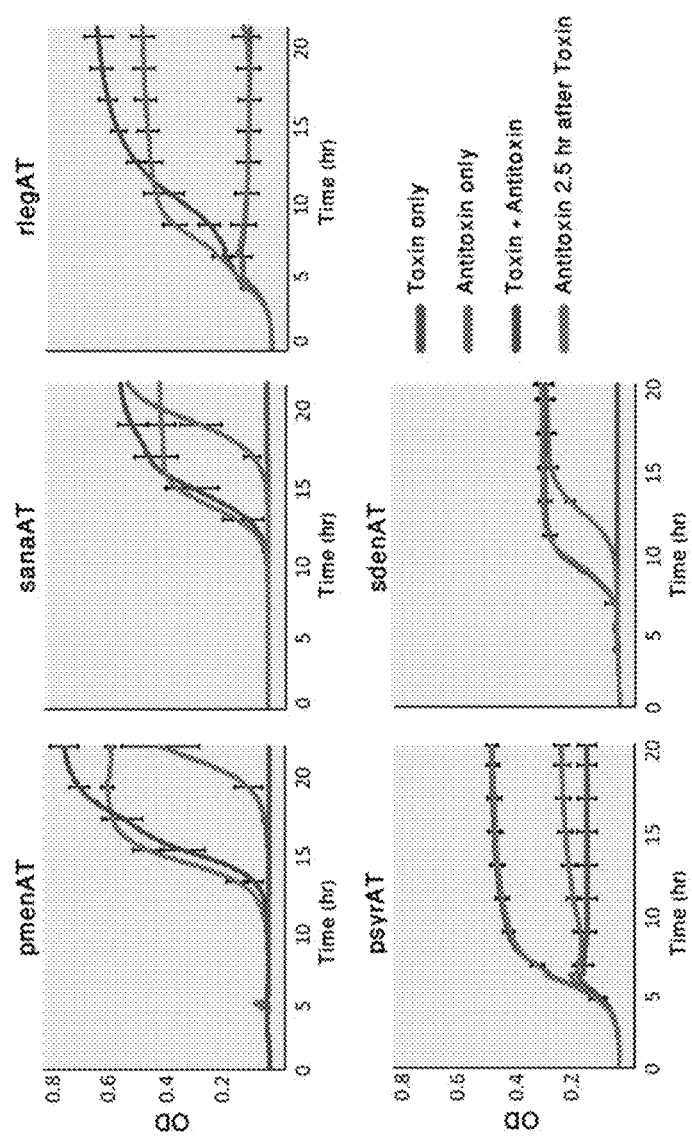
Figure 3C:
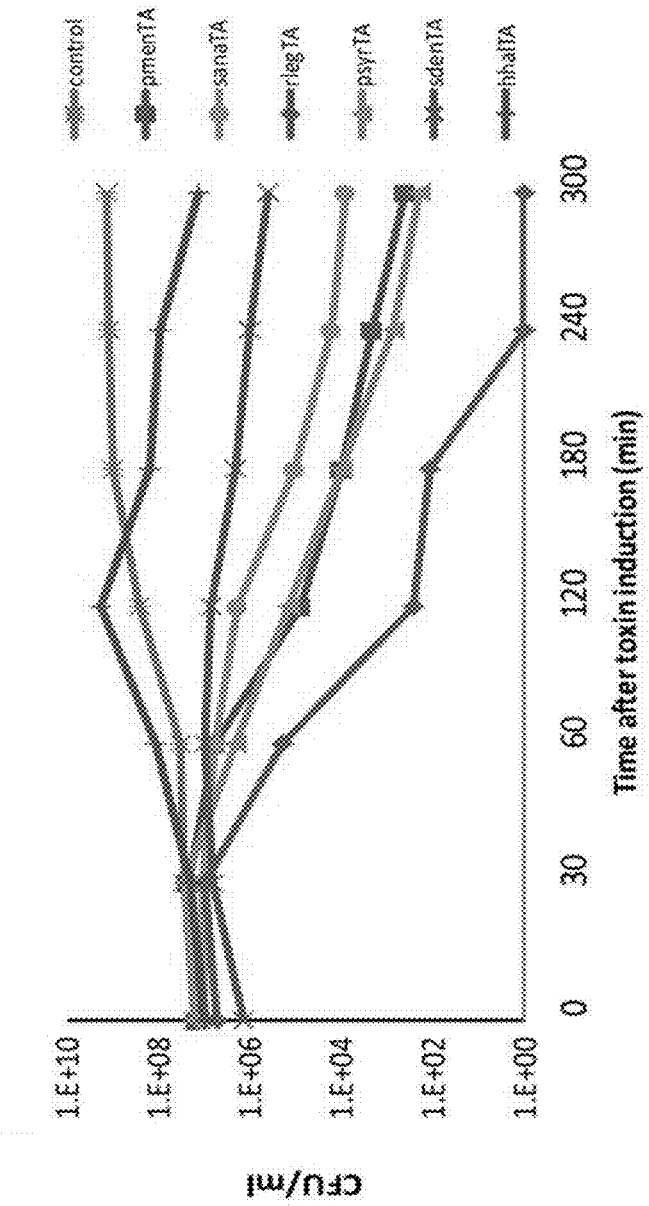

FIGS. 3A-C are graphs and diagrams illustrating properties of novel, experimentally verified TA systems (A) growth of bacteria when only antitoxin is induced (left), only toxin is induced (middle) and both are induced together (right). Toxin and antitoxin were cloned on pRSF (IPTG inducible promoter) and pBAD (arabinose inducible), respectively, in *E. coli* BL21 (DE3) pLysS. C, control bacteria with empty plasmids; 1-pmen system; 2-sana system; 3-psyr system; 4-rleg system; 5-sden system. (B) Kinetics of *E. coli* BL21 (DE3) pLysS growth when toxin and antitoxin are co-expressed simultaneously (purple), alone (red and blue for toxin and antitoxin, respectively) or when antitoxin is induced 2.5 hrs following toxin induction (green). Kinetic measurements were performed on biological triplicates in technical duplicates. (C) Viability assays for cells following exposure to toxin. Transcription of toxin was induced by 100 μM IPTG. At increasing time points following toxin induction (30, 60, 120, 180, 240 and 300 mins) cells were plated on LB-plates containing 0.3% arabinose and no IPTG, to activate antitoxin expression. Colony forming units (CFUs) were determined by colony counting.

Figure 4A:
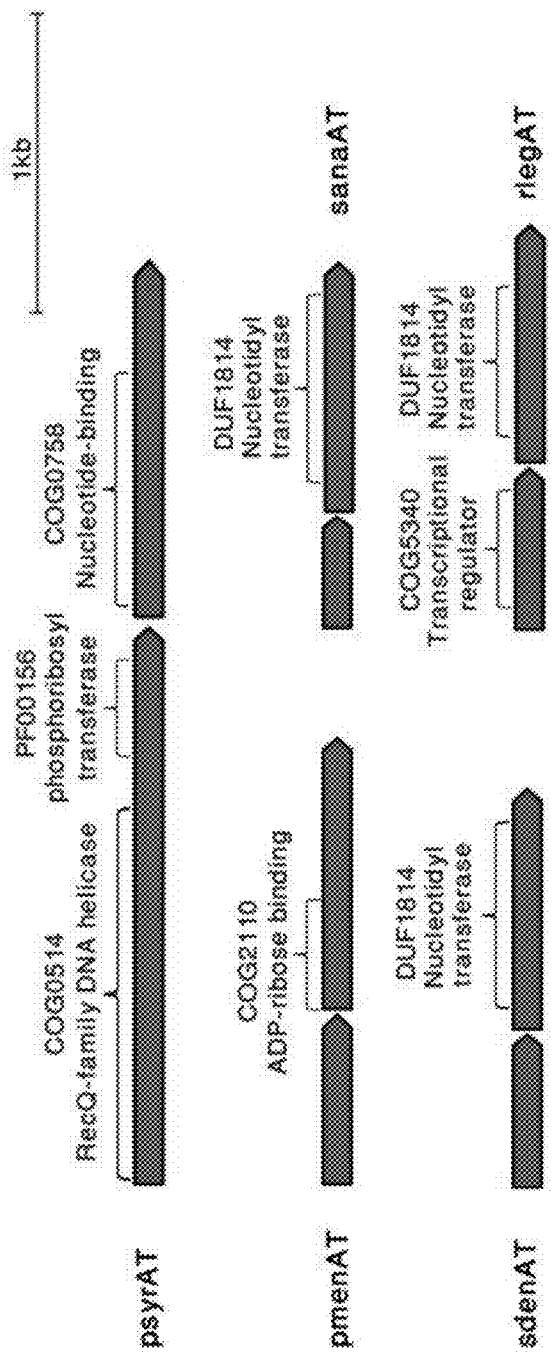

FIG. 4A illustrates operon and domain organization of the validated families Representative pair of each family is shown. For each pair, red and blue genes denote toxin and antitoxin, respectively.

FIGS. 4B-C are tables showing distribution of novel TA system among (B) different bacterial phyla and (C) human associated bacteria. Number of instances of each system within a phylum/bacterial species is indicated, with darker colors indicating higher number of instances.

FIGS. 5A-F illustrate that T7 Gp 4.5 antagonizes abortive infection by interacting with Lon. (A) Illustration of the plaque forming unit (PFU) assays on *E. coli* harboring toxin/antitoxin systems. Efficiency of plating (EOP) was calculated by dividing the number of PFUs obtained for a bacterial lawn expressing the toxin+antitoxin by the number of PFUs obtained on a lawn expressing the antitoxin alone. Bars in panels B, C and E represent average±SD of three independent EOP experiments. (B) EOP experiments with *E. coli* harboring the sanaAT system when infected by WT T7 (left) or by T7Δ4.3Δ4.5Δ4.7 (right). (C) EOP experiments with WT *E. coli* (left) and *E. coli* expressing Gp4.5 (right), when infected by T7Δ4.3Δ4.5Δ4.7. (D) EOP experiments with WT *E. coli* (left) and *E. coli* lacking lon (right), when infected by T7Δ4.3Δ4.5Δ4.7. (E) Co-immunoprecipitation of Lon and 4.5. The *E. coli* Lon protease was Flag-tagged at the N-terminus and expressed within *E. coli* BL21 (DE3) with or without co-expression of gene 4.5. Samples were analyzed by 15% SDS-PAGE. Three left lanes, total soluble proteins; three lanes on the right, following immunoprecipitation with anti-Flag antibody. Co-immunoprecipitation of Lon and 4.5 was validated by mass spectrometry analysis. Numbers on the left denote protein marker sizes in kDa. (F) Western blot analysis on reciprocal co-IP with flag-tagged Gp4.5 and his-tagged Lon Immunoprecipitation was done with anti-Flag antibody.

FIG. 6 is a bar graph demonstrating that expression of gene 4.5 within *E. coli* results in reduced number of persister bacteria. Bacteria were exposed to ampicillin for 5 hours and % formation of persister bacteria was measured. Experiments were performed in triplicates and error bars represent standard error.

Figure 7:
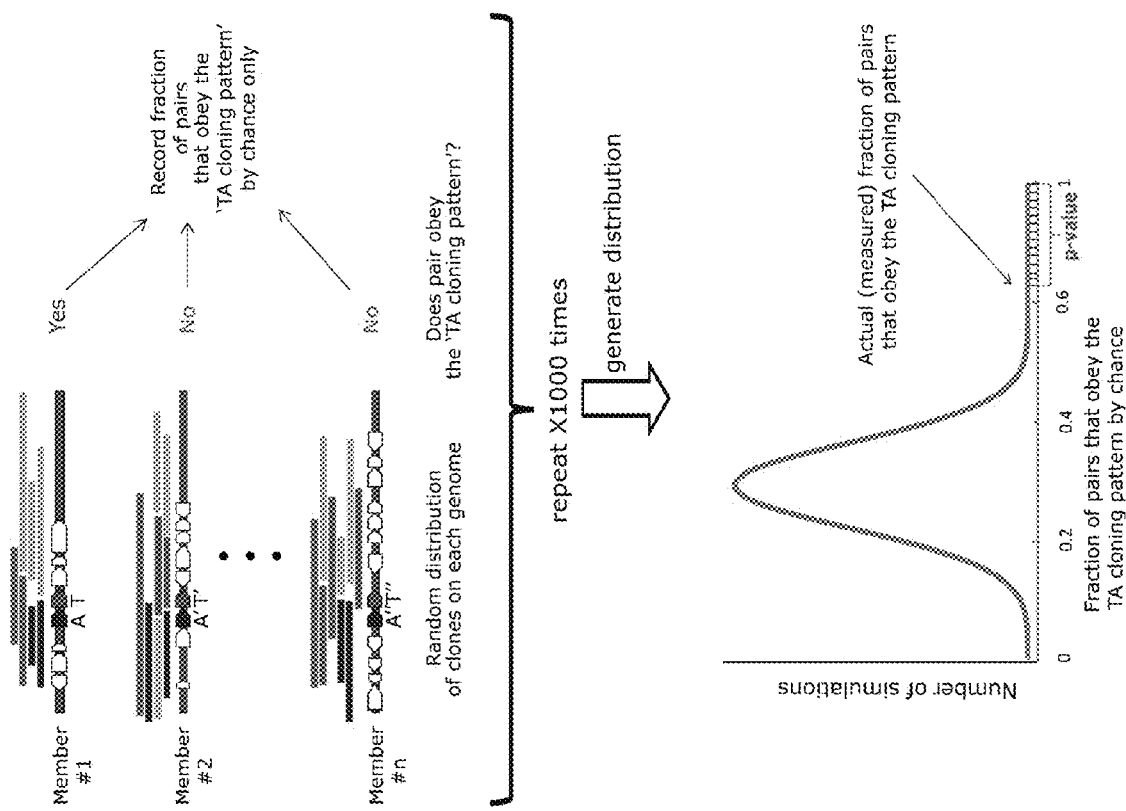

FIG. 7 illustrates the statistical assessment of a family of gene pairs as possibly encoding a toxin-antitoxin module. In each genome where a member of the to family exist, the sequencing clones are re-distributed randomly (maintaining the number of clones and their sizes, but shuffling their positions on the genome). The "TA cloning pattern" for each member is then evaluated based on the randomly distributed clones, and the fraction of members obeying the "TA cloning pattern" by chance is recorded (in the illustration: red, clones that span only the toxin; blue, clones that span only the antitoxin; green, clones that span both genes). This procedure is repeated 1000 times, generating a distribution of fractions. The p-value for a family is determined by comparing the actual fraction of pairs that obey the "TA cloning pattern" to the distribution of fractions obtained using the random clone shuffling.

Figure 8:
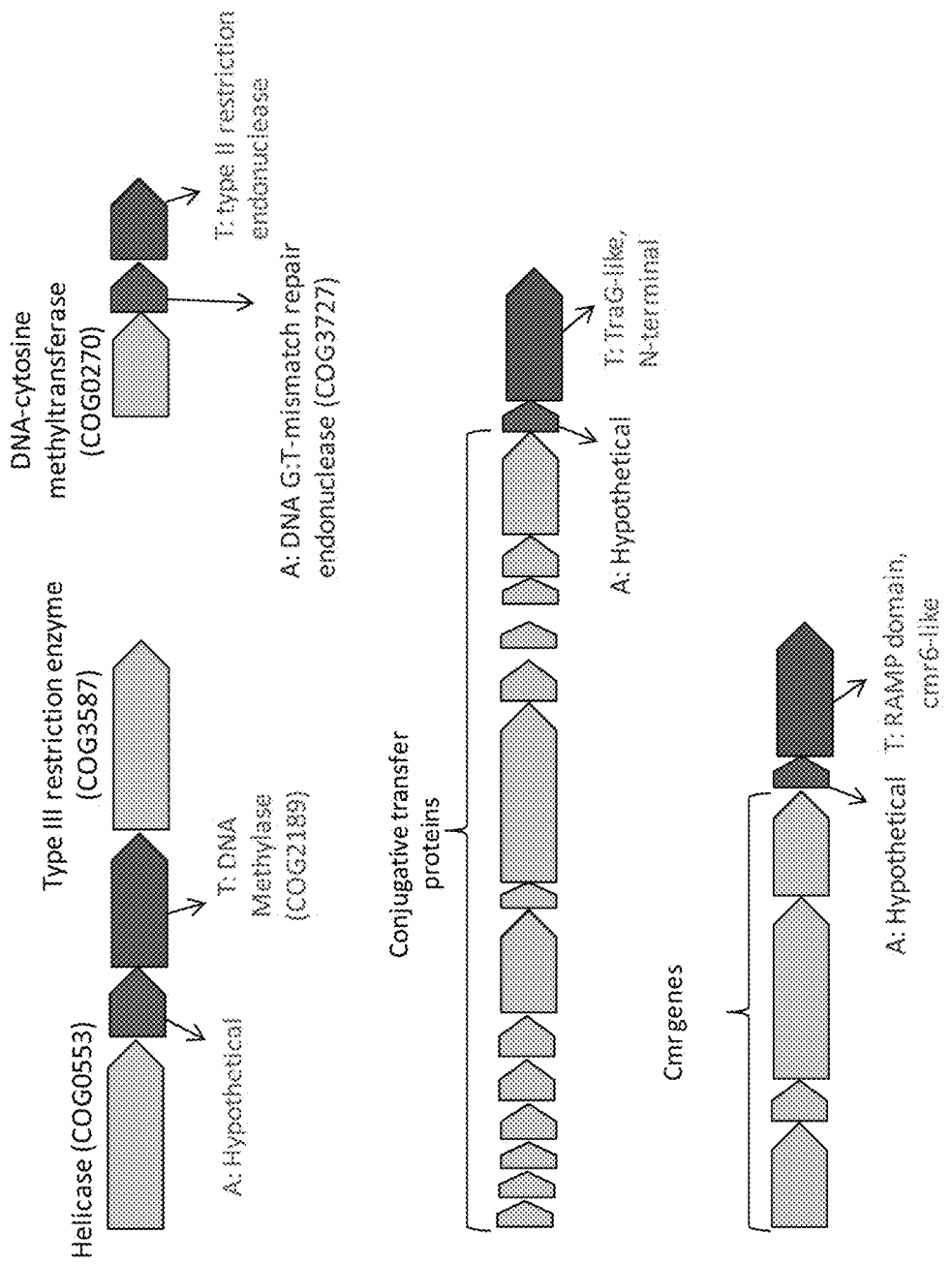

FIG. 8 is a diagram illustrating that predicted new TA systems associate with complex genomic environments. Shown are the schematic environments of 4 systems that are associated with other genes and hence suspected as participating in multi-gene defense systems. Blue and red genes denote putative antitoxin and toxin, respectively; gray genes denote genes associated with the TA system.

Figure 9A:
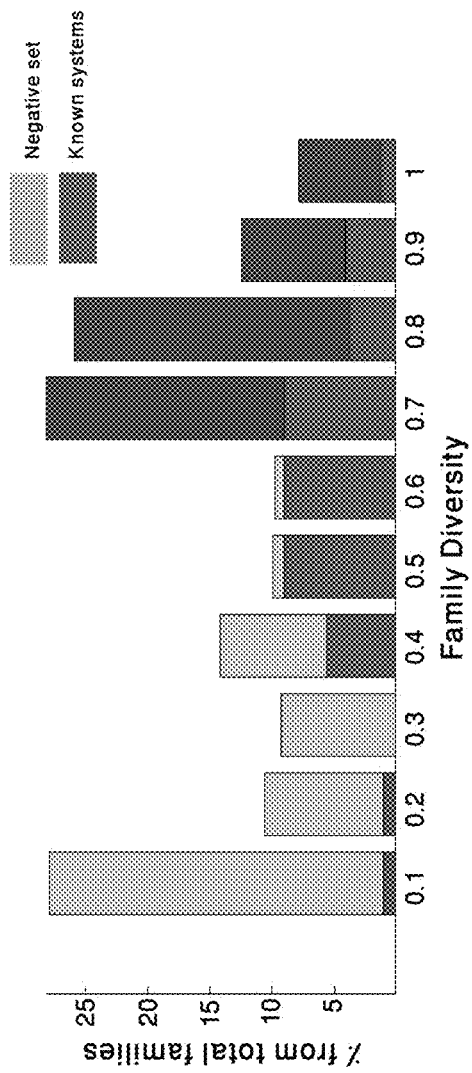
Figure 9B:
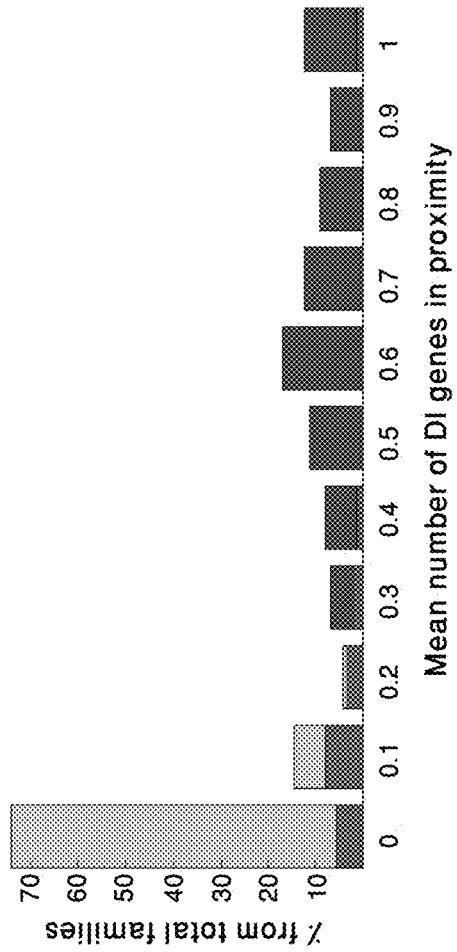

FIGS. 9A-B are bar graphs illustrating properties of known TA families. The 21,417 analyzed families of gene pairs were divided into two sets: a positive set which contains all families in which at least one pair is a known TA system ('Known systems') and a negative which contains the remaining families ('Negative set'). (A) The family diversity measurement for known TA systems (black) as compared to the negative set (light gray) (B) Mean number of defense island (DI) genes localized+/−5 genes away from known TA families (black) as compared to families in the negative set (light gray).

DESCRIPTION OF SPECIFIC EMBODIMENTS
OF THE INVENTION

The present invention, in some embodiments thereof, relates to bacterial polypeptides that comprise toxin and/or antitoxin activity and, more particularly, but not exclusively, to toxin-antitoxin pairs that may be used as bacterial antiphage defense systems.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The toxin-antitoxin (TA) complex of bacteria includes a pair of polypeptides that is encoded by bacterial plasmids or chromosomes. It is postulated that in bacteria these polypeptides function to induce programmed cell death or growth inhibition in response to starvation, phage infection or other adverse conditions. The antitoxins neutralize the cognate toxins by forming tight complexes therewith or by other means. The antitoxins are unstable due to degradation by cellular proteases (e.g., Lon or Clp), whereas toxins are stable polypeptides. Toxin-antitoxin pair examples include the pemI-pemK genes of plasmid R100, the phd-doc genes of phage P1, and the ccdA-ccdB genes, of plasmid F. Several toxin-antitoxin encoding gene analogues have been identified on the *E. coli* K-12 chromosome, such as mazE-mazF.

In numerous cases where TA systems were studied experimentally, cloning of the toxin was nearly impossible in the absence of the cognate antitoxin. Based on this concept the present inventors reasoned that data derived from Sanger-based whole genome shotgun sequencing can experimentally and systematically reveal active TA pairs. In such a genome sequencing process, randomly fragmented DNA pieces of the genome are serially cloned and propagated within *E. coli* prior to sequencing. The ends of the cloned fragments are then sequenced, and overlapping sequences are used for genome assembly (FIG. 1A). It has been shown that analysis of clone distribution patterns can reveal genes toxic to bacteria, which are uncloneable and cause gaps (Kimelman et al., 2012; Sorek et al., 2007). However, the toxin in a TA pair is not expected to cause a gap, since the adjacent antitoxin will sometimes be found on the same clone, neutralizing the toxic effect. Nevertheless, random fragments that contain the toxin but not the antitoxin will cause cell death and will be absent from the set of clones covering the genome (FIG. 1B).

Figure 5A:
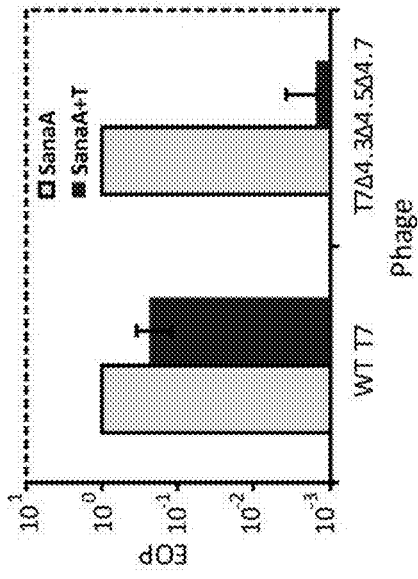
Figure 5B:
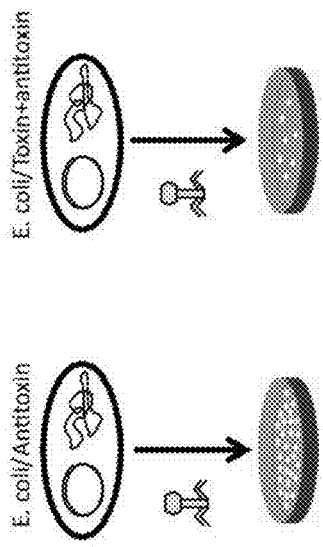

The present inventors took advantage of this typical biased cloning pattern to systematically detect toxin-antitoxin gene pairs within hundreds of microbial genomes. The analyses, while retrieving many known TA systems, also exposed 9 novel families of TA modules widespread in numerous bacterial species. These systems were subsequently experimentally validated as TA systems (FIGS. 3A-C). By engineering these systems into new bacteria, the present inventors showed that the toxin-antitoxin pairs can protect the engineered bacteria from phage attacks (FIGS. 5A-B). Such engineered bacteria can be utilized in the dairy industry, where phages cause serious annual losses, as well as in other industries that rely on large-scale bacterial fermentation for biotechnological production. Infection experiments with T7 phage and multiple T7 phage deletion mutants further showed that two of these new TA pairs provide resistance against T7, and also revealed a general anti-TA mechanism encoded by the phage (FIGS. 5C-F). Specifically, the present inventors discovered a phage peptide that inhibits toxin-antitoxin systems by inhibiting Lon protease. This peptide was further shown to inhibit the formation of bacterial persistence, thus active as a mechanism to reduce antibiotics resistance among bacteria.

Thus, according to one aspect of the present invention there is provided an isolated polypeptide comprising an amino acid sequence at least 90% homologous to a sequence selected from the group consisting of SEQ ID NOs: 2773-5544 and 11089-11094, wherein the polypeptide has antimicrobial activity.

The phrase "antimicrobial activity" as used herein, refers to an ability to suppress, control, inhibit or kill microorganisms, such as bacteria, archaea and fungi. Thus for example the antimicrobial activity may comprise bactericidal or bacteriostatic activity, or both.

According to a preferred embodiment, the isolated polypeptide comprises an amino acid sequence at least 60%, at least 70%, at least 80%, at least 90% or at least 95% homologous to SEQ ID NOs: 2773-5544.

According to a preferred embodiment, the isolated polypeptide comprises an amino acid sequence at least 60%, at least 70%, at least 80%, at least 90% or at least 95% homologous to SEQ ID NOs: 2773-3117.

According to a preferred embodiment, the isolated polypeptide comprises an amino acid sequence at least 60%, at least 70%, at least 80%, at least 90% or at least 95% homologous to SEQ ID NOs: 11089-11094. Such polypeptides are capable of inhibiting (decreasing activity by more than 10%, 20%, 30%, 40%, 50%, 60%, 70%, 80% or 90%) a member of the Lon protease family. Lon proteases are ATP-dependent serine peptidases belonging to the MEROPS peptidase family S16 (lon protease family, clan SF).

According to another aspect of the present invention there is provided an isolated polypeptide comprising an amino acid sequence at least 60%, at least 70%, at least 80%, at least 90% or at least 95% homologous to any one of SEQ ID NOs: 8317-11088, wherein the polypeptide protects a microbe from an activity of a toxin. Such polypeptides may be expressed in microbial populations thereby protecting the microbial population from the toxic effect of the toxin. Methods of expressing polypeptides are described herein below.

Polypeptides which protect microbes from an activity of a toxin (i.e. antitoxin) may have a Ki of $1 \times 10^{(-5)}$ M-$1 \times 10^{(-10)}$ M for the toxin.

According to another embodiment, the sequence selected from the group consisting of SEQ ID NOs. 8317-8661.

According to still another embodiment, the peptides of the present invention consist of the amino acid sequences selected from the group consisting of SEQ ID NOs: 2773-5544 or SEQ ID NO:8317-11088 or SEQ ID NOs: 11089-11094.

Homology may be determined using BlastP software of the National Center of Biotechnology Information (NCBI) using default parameters). The homolog may also refer to an ortholog, a deletion, insertion, or substitution variant, including an amino acid substitution.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, to by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2, 3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc.).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |

TABLE 2-continued

| Non-conventional amino acid | Code | Non-conventional amino acid | Code |
|---|---|---|---|
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl)carbamylmethyl-glycine | Nnbhm |
| N-(3,3-diphenylpropyl)glycine | Nbhe | N-(N-(3,3-diphenylpropyl)carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

The peptides of the present invention may be attached (either covalently or non-covalently) to a penetrating agent.

As used herein the phrase "penetrating agent" refers to an agent which enhances translocation of any of the attached peptide across a cell membrane.

According to one embodiment, the penetrating agent is a peptide and is attached to the antimicrobial peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

The peptides of the present invention can be biochemically synthesized such as by using standard solid phase techniques. These methods include exclusive solid phase synthesis, partial solid phase synthesis methods, fragment condensation, to classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

A variety of prokaryotic or eukaryotic cells can be used as host-expression systems to express the polypeptides of some embodiments of the invention. These include, but are not limited to; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors [Studier et al. (1990) Methods in Enzymol. 185:60-89).

Other than containing the necessary elements for the transcription and translation of the inserted coding sequence, the expression construct of some embodiments of the invention can also include sequences engineered to enhance stability, production, purification, yield or toxicity of the expressed antimicrobial peptide. For example, the expression of a fusion protein or a cleavable fusion protein to comprising the antimicrobial peptides of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the antimicrobial and the heterologous protein, the antimicrobial can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

Recovery of the recombinant peptide is effected following an appropriate time in culture. The phrase "recovering the recombinant peptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In addition to being synthesizable in host cells, the peptides of the present invention can also be synthesized using in vitro expression systems. These methods are well known in the art and the components of the system are commercially available.

The peptides disclosed herein, which comprise anti-microbial properties may be used to kill microbes.

Thus, according to another aspect of the present invention there is provided a method of killing a microbe, the method comprising contacting the microbe with the isolated peptides comprising an amino acid sequence selected from the group consisting of SEQ ID NOs: 2773-5544 and 11089-11094.

According to a particular embodiment, the peptide used for killing a microbe comprises the sequence 11089-11094.

The microbe may be for example a gram-positive or gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium complex*, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, to *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, *Yersinia pestis*.

As used herein the term "contacting" refers to the positioning of the peptides of the present invention such that they are in direct or indirect contact with the bacterial cells. Thus, the present invention contemplates both applying the peptides of the present invention to a desirable surface and/or directly to the bacterial cells.

According to another embodiment the surface is comprised in a biological tissue, such as for example, mammalian tissues e.g. the skin.

It will be appreciated that the microbes may be comprised inside a particular organism, (e.g. intracellularly or extracellularly) for example inside a mammalian body or inside a plant. In this case, the contacting may be effected by administering the peptides per se or by transfecting the cells of the organism with a nucleic acid construct which comprises a nucleic acid sequence which encodes the peptides of the present invention.

Thus, the present invention contemplates polynucleotide sequences encoding the antimicrobial polypeptides disclosed herein. Such polynucleotide sequences are set forth in SEQ ID NOs: 1-2772.

Such a nucleic acid construct includes a promoter sequence for directing transcription of the polynucleotide sequence in the cell in a constitutive or inducible manner.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804) or pathogen-inducible promoters. Such promoters include those from pathogenesis-related proteins (PR proteins), which are induced following infection by a pathogen.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

The nucleic acid constructs described herein will have a plurality of restriction sites for insertion of the sequence of the invention so that it is under transcriptional regulation of the regulatory regions. Selectable marker genes that ensure maintenance of the vector in the cell can also be included in the expression vector. Preferred selectable markers include those which confer resistance to drugs such as ampicillin, chloramphenicol, erythromycin, kanamycin (neomycin), and tetracycline (Davies et al. (1978) Annu. Rev. Microbiol. 32:469). Selectable markers can also allow a cell to grow on minimal medium, or in the presence of toxic metabolite and can include biosynthetic genes, such as those in the histidine, tryptophan, and leucine biosynthetic pathways.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], to lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Recombinant viral vectors are useful for in vivo expression of the antimicrobial peptides of the invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, to electroporation and infection with recombinant viral vectors. In addition, see U.S. Pat. Nos. 5,464,764 and 5,487,992 for positive-negative selection methods.

Exemplary methods of introducing expression vectors into bacterial cells include for example conventional transformation or transfection techniques, or by phage-mediated infection. As used herein, the terms "transformation," "transduction," "conjugation," and "protoplast fusion" are intended to refer to a variety of art-recognized techniques for introducing foreign nucleic acid (e.g., DNA) into a cell, including calcium phosphate or calcium chloride co-precipitation, DEAE-dextran-mediated transfection, lipofection, or electroporation.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Where appropriate, the polynucleotides may be optimized for increased expression in the transformed organism. For example, the polynucleotides can be synthesized using preferred codons for improved expression. For optimal expression in plants or fungi, the pre- and propeptide sequences may be needed. The propeptide segments may play a role in aiding correct peptide folding.

Since the polypeptides comprising an amino acid sequence selected from the group consisting of SEQ ID NOs: 2773-5544 and 11089-11094 have antimicrobial activity, the present invention contemplates use thereof for treating infection in a mammalian subject.

According to one embodiment, the peptides are used to treat a topical infection (i.e. infection of the skin) and are provided in a topical formulation.

According to another embodiment, the peptides are used to treat an infection inside the body. In this case, the peptides (or polynucleotides encoding same) may be provided ex vivo or in vivo.

Accordingly, the present invention contemplates contacting cells with the polypeptides comprising an amino acid sequence selected from the group consisting of SEQ ID NOs: 2773-5544 and 11089-11094 (or with expression constructs that encode the peptides) per se or as part of a pharmaceutical composition.

According to a particular embodiment, the peptide used in the pharmaceutical composition comprises the sequence 11089-11094.

The peptides may be used alone or together with additional antimicrobial agents (e.g. antibiotic and/or additional antimicrobial peptides).

Exemplary antibiotics include, but are not limited to aminoglycoside antibiotics, cephalosporins, quinolone antibiotics, macrolide antibiotics, penicillins, sulfonamides, tetracyclines and carbapenems. It will be appreciated that since the peptides of embodiments of this invention enhance the antibacterial effect of the antibiotic, doses of the antibiotic may be lower (e.g. 20% lower, 30% lower, 40% lower, 50% lower, 60% lower, 70% lower, 80% lower or even 90% lower than those currently in use.

The pharmaceutical compositions of the present invention are administered to a subject in need thereof in order to prevent or treat a bacterial infection.

As used herein, the term "subject in need thereof" refers to a mammal, preferably a human subject.

As used herein, the term "treating" refers to curing, reversing, attenuating, alleviating, minimizing, suppressing or halting the deleterious effects of a pathogen infection.

The phrase "pharmaceutical composition", as used herein refers to a preparation of one or more of the active ingredients described herein with other chemical components such as physiologically suitable carriers and excipients. The purpose of a pharmaceutical composition is to facilitate administration of a compound to an organism.

As used herein the term "active ingredient" refers to peptides of the present invention accountable for the intended biological effect. It will be appreciated that a polynucleotide encoding a peptide of the present invention may be administered directly into a subject (as is, or part of a pharmaceutical composition) where it is translated in the target cells i.e. by gene therapy. Accordingly, the phrase "active ingredient" also includes such polynucleotides.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference and are further described herein below.

It will be appreciated that the peptides of the present invention can be provided to the individual with additional active agents to achieve an improved therapeutic effect as compared to treatment with each agent by itself.

Exemplary additional agents include antibiotics (e.g. rifampicin, chloramphenicol and spectinomycin).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, to such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain to formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The preparation of the present invention may also be formulated as a topical composition, such as a spray, a cream, a mouthwash, a wipe, a foam, a soap, an oil, a solution, a lotion, an ointment, a paste and a gel.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can to be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned, the peptides described herein which comprise antitoxin activity may be expressed in microbial populations, thereby protecting the microbial population from the toxic effect of a toxin.

Thus, the present invention further contemplates polynucleotide sequences encoding the antitoxin polypeptides disclosed herein. Such polynucleotide sequences are set forth in SEQ ID NOs: 5548-8316.

The present inventors have further discovered novel toxin antitoxin pairs that may be expressed in bacterial populations. Expression therein may serve to protect the bacterial population from the lytic effect of a bacteriophage (i.e. impart resistance to the bacteriophage).

Such pairs are summarized in Table 3 herein below.

TABLE 3

| Toxin polypeptide sequences | | Antitoxin polypeptide sequences | |
|---|---|---|---|
| SEQ ID NO: | designation | SEQ ID NO: | designation |
| 2773 | >Toxin: Lferr_1303 | 8317 | >Antitoxin: Lferr_1302 |
| 2774 | >Toxin: Adeg_2177 | 8318 | >Antitoxin: Adeg_2178 |
| 2775 | >Toxin: BLD_0338 | 8319 | >Antitoxin: BLD_0339 |
| 2776 | >Toxin: HMPREF0175_1783 | 8320 | >Antitoxin: HMPREF0175_1782 |
| 2777 | >Toxin: BIL_08340 | 8321 | >Antitoxin: BIL_08350 |
| 2778 | >Toxin: BL1460 | 8322 | >Antitoxin: BL1461 |
| 2779 | >Toxin: HMPREF0177_01212 | 8323 | >Antitoxin: HMPREF0177_01213 |
| 2780 | >Toxin: CJA_3634 | 8324 | >Antitoxin: CJA_3633 |
| 2781 | >Toxin: MldDRAFT_1473 | 8325 | >Antitoxin: MldDRAFT_1471 |
| 2782 | >Toxin: MldDRAFT_0420 | 8326 | >Antitoxin: MldDRAFT_0418 |
| 2783 | >Toxin: MldDRAFT_4398 | 8327 | >Antitoxin: MldDRAFT_4397 |
| 2784 | >Toxin: MldDRAFT_1876 | 8328 | >Antitoxin: MldDRAFT_1875 |
| 2785 | >Toxin: DaAHT2_0326 | 8329 | >Antitoxin: DaAHT2_0325 |
| 2786 | >Toxin: Elen_0846 | 8330 | >Antitoxin: Elen_0847 |
| 2787 | >Toxin: HCAN_1210 | 8331 | >Antitoxin: HCAN_1209 |
| 2788 | >Toxin: MELB17_24172 | 8332 | >Antitoxin: MELB17_24167 |
| 2789 | >Toxin: Mmwyl1_3205 | 8333 | >Antitoxin: Mmwyl1_3204 |
| 2790 | >Toxin: Pat9b_4701 | 8334 | >Antitoxin: Pat9b_4700 |
| 2791 | >Toxin: HMPREF06201504_1504 | 8335 | >Antitoxin: HMPREF0620_1505 |
| 2792 | >Toxin: Pecwa_0953 | 8336 | >Antitoxin: Pecwa_0952 |
| 2793 | >Toxin: plu0453 | 8337 | >Antitoxin: plu0454 |
| 2794 | >Toxin: plu3932 | 8338 | >Antitoxin: plu3931 |
| 2795 | >Toxin: HMPREF0693_2530 | 8339 | >Antitoxin: HMPREF0693_2531 |
| 2796 | >Toxin: PMI2316 | 8340 | >Antitoxin: PMI2317 |
| 2797 | >Toxin: PMI2493 | 8341 | >Antitoxin: PMI2492 |
| 2798 | >Toxin: Sden_0300 | 8342 | >Antitoxin: Sden_0299 |
| 2799 | >Toxin: Veis_2844 | 8343 | >Antitoxin: Veis_2845 |
| 2800 | >Toxin: XNC1_4222 | 8344 | >Antitoxin: XNC1_4221 |
| 2801 | >Toxin: BloniC5_010100004089 | 8345 | >Antitoxin: BloniC5_010100004094 |
| 2802 | >Toxin: BloniC5_010100007713 | 8346 | >Antitoxin: BloniC5_010100007718 |
| 2803 | >Toxin: HcanM9_010100006460 | 8347 | >Antitoxin: PROVRUST_02882 |
| 2804 | >Toxin: PROVRUST_02881 | 8348 | >Antitoxin: HcanM9_010100006455 |
| 2805 | >Toxin: AcdelDRAFT_0026 | 8349 | >Antitoxin: AcdelDRAFT_0025 |
| 2806 | >Toxin: Ajs_0911 | 8350 | >Antitoxin: Ajs_0912 |
| 2807 | >Toxin: A20C1_10775 | 8351 | >Antitoxin: A20C1_10770 |
| 2808 | >Toxin: Astex_0661 | 8352 | >Antitoxin: Astex_0662 |
| 2809 | >Toxin: bll1927 | 8353 | >Antitoxin: bll1928 |
| 2810 | >Toxin: HMPREF0183_2010 | 8354 | >Antitoxin: HMPREF0183_2009 |
| 2811 | >Toxin: CAP2UW1_0236 | 8355 | >Antitoxin: CAP2UW1_0235 |
| 2812 | >Toxin: pc2001 | 8356 | >Antitoxin: pc2002 |
| 2813 | >Toxin: Clim_1931 | 8357 | >Antitoxin: Clim_1932 |

TABLE 3-continued

| | Toxin polypeptide sequences | | Antitoxin polypeptide sequences |
|---|---|---|---|
| SEQ ID NO: | designation | SEQ ID NO: | designation |
| 2814 | >Toxin: Cpha266__0654 | 8358 | >Antitoxin: Cpha266__0653 |
| 2815 | >Toxin: Cvib__0668 | 8359 | >Antitoxin: Cvib__0667 |
| 2816 | >Toxin: Cwoe__5578 | 8360 | >Antitoxin: Cwoe__5577 |
| 2817 | >Toxin: cgR__0545 | 8361 | >Antitoxin: cgR__0546 |
| 2818 | >Toxin: Daci__0082 | 8362 | >Antitoxin: Daci__0083 |
| 2819 | >Toxin: Dole__3139 | 8363 | >Antitoxin: Dole__3138 |
| 2820 | >Toxin: Dbac__1303 | 8364 | >Antitoxin: Dbac__1304 |
| 2821 | >Toxin: Elen__3086 | 8365 | >Antitoxin: Elen__3085 |
| 2822 | >Toxin: HMPREF1023__01420 | 8366 | >Antitoxin: HMPREF1023__01419 |
| 2823 | >Toxin: Smed__6434 | 8367 | >Antitoxin: Smed__6433 |
| 2824 | >Toxin: Smed__5454 | 8368 | >Antitoxin: Smed__5453 |
| 2825 | >Toxin: Smed__6434 | 8369 | >Antitoxin: Smed__6433 |
| 2826 | >Toxin: GobsU__010100024456 | 8370 | >Antitoxin: GobsU__010100024461 |
| 2827 | >Toxin: gsr2662 | 8371 | >Antitoxin: glr2661 |
| 2828 | >Toxin: Gbro__4918 | 8372 | >Antitoxin: Gbro__4917 |
| 2829 | >Toxin: GPA__34760 | 8373 | >Antitoxin: GPA__34770 |
| 2830 | >Toxin: Intca__2903 | 8374 | >Antitoxin: Intca__2902 |
| 2831 | >Toxin: LLO__0649 | 8375 | >Antitoxin: LLO__0650 |
| 2832 | >Toxin: LLO__2898 | 8376 | >Antitoxin: LLO__2899 |
| 2833 | >Toxin: LNTAR__09414 | 8377 | >Antitoxin: LNTAR__09419 |
| 2834 | >Toxin: LNTAR__09681 | 8378 | >Antitoxin: LNTAR__09686 |
| 2835 | >Toxin: SPV1__04688 | 8379 | >Antitoxin: SPV1__04693 |
| 2836 | >Toxin: MexAM1__META2p1274 | 8380 | >Antitoxin: MexAM1__META2p1275 |
| 2837 | >Toxin: HMPREF0580__0585 | 8381 | >Antitoxin: HMPREF0580__0584 |
| 2838 | >Toxin: HMPREF0577__2238 | 8382 | >Antitoxin: HMPREF0577__2237 |
| 2839 | >Toxin: HMPREF9278__0956 | 8383 | >Antitoxin: HMPREF9278__0957 |
| 2840 | >Toxin: MLBr__02284 | 8384 | >Antitoxin: MLBr__02283 |
| 2841 | >Toxin: ML2284 | 8385 | >Antitoxin: ML2283 |
| 2842 | >Toxin: MMAR__3595 | 8386 | >Antitoxin: MMAR__3594 |
| 2843 | >Toxin: Namu__4516 | 8387 | >Antitoxin: Namu__4515 |
| 2844 | >Toxin: Nhal__3749 | 8388 | >Antitoxin: Nhal__3750 |
| 2845 | >Toxin: Olsu__1425 | 8389 | >Antitoxin: Olsu__1426 |
| 2846 | >Toxin: Plut__0508 | 8390 | >Antitoxin: Plut__0507 |
| 2847 | >Toxin: Ppha__0787 | 8391 | >Antitoxin: Ppha__0786 |
| 2848 | >Toxin: PHZ__p0168 | 8392 | >Antitoxin: PHZ__p0169 |
| 2849 | >Toxin: Pnap__4573 | 8393 | >Antitoxin: Pnap__4574 |
| 2850 | >Toxin: Bpro__1527 | 8394 | >Antitoxin: Bpro__1528 |
| 2851 | >Toxin: PFREUD__01930 | 8395 | >Antitoxin: PFREUD__01920 |
| 2852 | >Toxin: CRD__00786 | 8396 | >Antitoxin: CRD__00785 |
| 2853 | >Toxin: Rleg__6339 | 8397 | >Antitoxin: Rleg__6340 |
| 2854 | >Toxin: Rleg__6554 | 8398 | >Antitoxin: Rleg__6555 |
| 2855 | >Toxin: pRL100221 | 8399 | >Antitoxin: pRL100220 |
| 2856 | >Toxin: Arad__0082 | 8400 | >Antitoxin: Arad__0081 |
| 2857 | >Toxin: NGR__b00520 | 8401 | >Antitoxin: NGR__b00510 |
| 2858 | >Toxin: Rvan__1799 | 8402 | >Antitoxin: Rvan__1798 |
| 2859 | >Toxin: Rpdx1__0873 | 8403 | >Antitoxin: Rpdx1__0874 |
| 2860 | >Toxin: Rpdx1__1938 | 8404 | >Antitoxin: Rpdx1__1937 |
| 2861 | >Toxin: Shel__25040 | 8405 | >Antitoxin: Shel__25030 |
| 2862 | >Toxin: RS9917__04250 | 8406 | >Antitoxin: RS9917__04255 |
| 2863 | >Toxin: Sfum__2054 | 8407 | >Antitoxin: Sfum__2055 |
| 2864 | >Toxin: Vapar__5649 | 8408 | >Antitoxin: Vapar__5648 |
| 2865 | >Toxin: VDG1235__790 | 8409 | >Antitoxin: VDG1235__4870 |
| 2866 | >Toxin: XOO__2997 | 8410 | >Antitoxin: XOO__2998 |
| 2867 | >Toxin: Xoryp__010100009970 | 8411 | >Antitoxin: Xoryp__010100009965 |
| 2868 | >Toxin: XOO3154 | 8412 | >Antitoxin: XOO3155 |
| 2869 | >Toxin: PXO__01415 | 8413 | >Antitoxin: PXO__01414 |
| 2870 | >Toxin: Xcel__2876 | 8414 | >Antitoxin: Xcel__2875 |
| 2871 | >Toxin: ObacDRAFT__3823 | 8415 | >Antitoxin: ObacDRAFT__3824 |
| 2872 | >Toxin: HMPREF0016__02714 | 8416 | >Antitoxin: HMPREF0016__02713 |
| 2873 | >Toxin: NIES39__A02090 | 8417 | >Antitoxin: NIES39__A02080 |
| 2874 | >Toxin: Cpha266__1126 | 8418 | >Antitoxin: Cpha266__1127 |
| 2875 | >Toxin: PCC8801__1532 | 8419 | >Antitoxin: PCC8801__1533 |
| 2876 | >Toxin: Dehly__0318 | 8420 | >Antitoxin: Dehly__0317 |
| 2877 | >Toxin: Dhaf__0673 | 8421 | >Antitoxin: Dhaf__0674 |
| 2878 | >Toxin: DSY0713 | 8422 | >Antitoxin: DSY0714 |
| 2879 | >Toxin: DP0406 | 8423 | >Antitoxin: DP0407 |
| 2880 | >Toxin: Dtox__1318 | 8424 | >Antitoxin: Dtox__1319 |
| 2881 | >Toxin: HMPREF0358__0171 | 8425 | >Antitoxin: HMPREF0358__0170 |
| 2882 | >Toxin: ECABU__c38650 | 8426 | >Antitoxin: ECABU__c38640 |
| 2883 | >Toxin: ECCG__03832 | 8427 | >Antitoxin: ECCG__03831 |
| 2884 | >Toxin: ECDG__04005 | 8428 | >Antitoxin: ECDG__04004 |
| 2885 | >Toxin: ECIAI39__3917 | 8429 | >Antitoxin: ECIAI39__3916 |
| 2886 | >Toxin: HMPREF9549__04273 | 8430 | >Antitoxin: HMPREF9549__04274 |
| 2887 | >Toxin: HMPREF9553__03184 | 8431 | >Antitoxin: HMPREF9553__03183 |
| 2888 | >Toxin: HMPREF9530__02209 | 8432 | >Antitoxin: HMPREF9530__02210 |
| 2889 | >Toxin: HMPREF9531__03250 | 8433 | >Antitoxin: HMPREF9531__03251 |
| 2890 | >Toxin: HMPREF9534__00693 | 8434 | >Antitoxin: HMPREF9534__00692 |

TABLE 3-continued

| SEQ ID NO: | Toxin polypeptide sequences designation | SEQ ID NO: | Antitoxin polypeptide sequences designation |
|---|---|---|---|
| 2891 | >Toxin: ECO103_4157 | 8435 | >Antitoxin: ECO103_4156 |
| 2892 | >Toxin: ECSF_3257 | 8436 | >Antitoxin: ECSF_3256 |
| 2893 | >Toxin: EscoliO157_010100006036 | 8437 | >Antitoxin: EscoliO157_010100006031 |
| 2894 | >Toxin: EsccoliO157_010100001300 | 8438 | >Antitoxin: EsccoliO157_010100001305 |
| 2895 | >Toxin: EschcoliO157_010100002315 | 8439 | >Antitoxin: EshcoliO157_010100002320 |
| 2896 | >Toxin: EcoliO157_010100000650 | 8440 | >Antitoxin: EcoliO157_010100000645 |
| 2897 | >Toxin: EcoliO157_010100000480 | 8441 | >Antitoxin: EcolO157_010100000475 |
| 2898 | >Toxin: EcolO15_010100000460 | 8442 | >Antitoxin: EcolO15_010100000455 |
| 2899 | >Toxin: EcolO_010100000490 | 8443 | >Antitoxin: EcolO_010100000485 |
| 2900 | >Toxin: EcolO1_010100003356 | 8444 | >Antitoxin: EcolO1_010100003351 |
| 2901 | >Toxin: Z4801 | 8445 | >Antitoxin: Z4799 |
| 2902 | >Toxin: ESCCO14588_0146 | 8446 | >Antitoxin: ESCCO14588_0145 |
| 2903 | >Toxin: ECP_3530 | 8447 | >Antitoxin: ECP_3529 |
| 2904 | >Toxin: c4223 | 8448 | >Antitoxin: c4222 |
| 2905 | >Toxin: EcSMS35_3718 | 8449 | >Antitoxin: EcSMS35_3717 |
| 2906 | >Toxin: HMPREF9098_1123 | 8450 | >Antitoxin: HMPREF9098_1124 |
| 2907 | >Toxin: L8106_27027 | 8451 | >Antitoxin: L8106_27022 |
| 2908 | >Toxin: FB2170_11841 | 8452 | >Antitoxin: FB2170_11846 |
| 2909 | >Toxin: Maqu_0559 | 8453 | >Antitoxin: Maqu_0560 |
| 2910 | >Toxin: MC7420_773 | 8454 | >Antitoxin: MC7420_724 |
| 2911 | >Toxin: NB231_14358 | 8455 | >Antitoxin: NB231_14363 |
| 2912 | >Toxin: NE2520 | 8456 | >Antitoxin: NE2521 |
| 2913 | >Toxin: alr3451 | 8457 | >Antitoxin: alr3452 |
| 2914 | >Toxin: OSCT_2233 | 8458 | >Antitoxin: OSCT_2234 |
| 2915 | >Toxin: Ppha_1436 | 8459 | >Antitoxin: Ppha_1435 |
| 2916 | >Toxin: plu4452 | 8460 | >Antitoxin: plu4453 |
| 2917 | >Toxin: Pnap_2963 | 8461 | >Antitoxin: Pnap_2962 |
| 2918 | >Toxin: PstuA_020100002503 | 8462 | >Antitoxin: PstuA_020100002498 |
| 2919 | >Toxin: PA39016_001140007 | 8463 | >Antitoxin: PA39016_001140006 |
| 2920 | >Toxin: Psyr_3804 | 8464 | >Antitoxin: Psyr_3805 |
| 2921 | >Toxin: Rcas_2468 | 8465 | >Antitoxin: Rcas_2467 |
| 2922 | >Toxin: Sbal_4347 | 8466 | >Antitoxin: Sbal_4346 |
| 2923 | >Toxin: SD1617_2224 | 8467 | >Antitoxin: SD1617_2223 |
| 2924 | >Toxin: SDY_3582 | 8468 | >Antitoxin: SDY_3581 |
| 2925 | >Toxin: TERTU_3911 | 8469 | >Antitoxin: TERTU_3910 |
| 2926 | >Toxin: Tery_1571 | 8470 | >Antitoxin: Tery_1570 |
| 2927 | >Toxin: VFA_000662 | 8471 | >Antitoxin: VFA_000663 |
| 2928 | >Toxin: EcolE2_01000162 | 8472 | >Antitoxin: EcolE2_01000163 |
| 2929 | >Toxin: EcolM6_010100020382 | 8473 | >Antitoxin: EcolM6_010100020377 |
| 2930 | >Toxin: EcolM_010100020768 | 8474 | >Antitoxin: EcolM_010100020763 |
| 2931 | >Toxin: EcolB_01001160 | 8475 | >Antitoxin: EcolB_01001159 |
| 2932 | >Toxin: EcolF_01001475 | 8476 | >Antitoxin: EcolF_01001476 |
| 2933 | >Toxin: EschercoliO157_010100002920 | 8477 | >Antitoxin: EschercoliO157_010100002925 |
| 2934 | >Toxin: EschericoliO157_010100015347 | 8478 | >Antitoxin: EschericoliO157_010100015342 |
| 2935 | >Toxin: EschericcoliO157_010100003780 | 8479 | >Antitoxin: EschericcoliO157_010100003785 |
| 2936 | >Toxin: Aave_0160 | 8480 | >Antitoxin: Aave_0161 |
| 2937 | >Toxin: Amir_6975 | 8481 | >Antitoxin: Amir_6976 |
| 2938 | >Toxin: VSAL_I0392 | 8482 | >Antitoxin: VSAL_I0391 |
| 2939 | >Toxin: Mlg_0502 | 8483 | >Antitoxin: Mlg_0503 |
| 2940 | >Toxin: AmaxDRAFT_5193 | 8484 | >Antitoxin: AmaxDRAFT_5192 |
| 2941 | >Toxin: AmaxDRAFT_5205 | 8485 | >Antitoxin: AmaxDRAFT_5204 |
| 2942 | >Toxin: NIES39_K04470 | 8486 | >Antitoxin: NIES39_K04480 |
| 2943 | >Toxin: AplaP_010100002817 | 8487 | >Antitoxin: AplaP_010100002812 |
| 2944 | >Toxin: SI859A1_01336 | 8488 | >Antitoxin: SI859A1_01337 |
| 2945 | >Toxin: bthur0013_57000 | 8489 | >Antitoxin: bthur0013_57010 |
| 2946 | >Toxin: BGP_2335 | 8490 | >Antitoxin: BGP_2336 |
| 2947 | >Toxin: BHWA1_01320 | 8491 | >Antitoxin: BHWA1_01319 |
| 2948 | >Toxin: CAP2UW1_4295 | 8492 | >Antitoxin: CAP2UW1_4296 |
| 2949 | >Toxin: Cyan7822_4726 | 8493 | >Antitoxin: Cyan7822_4725 |
| 2950 | >Toxin: HMPREF0321_1867 | 8494 | >Antitoxin: HMPREF0321_1868 |
| 2951 | >Toxin: HMPREF0326_02542 | 8495 | >Antitoxin: HMPREF0326_02543 |
| 2952 | >Toxin: Dd1591_0935 | 8496 | >Antitoxin: Dd1591_0936 |
| 2953 | >Toxin: NT01EI_3442 | 8497 | >Antitoxin: NT01EI_3441 |
| 2954 | >Toxin: ETAE_3072 | 8498 | >Antitoxin: ETAE_3073 |
| 2955 | >Toxin: ETAF_2777 | 8499 | >Antitoxin: ETAF_2776 |
| 2956 | >Toxin: ENHAE0001_1187 | 8500 | >Antitoxin: ENHAE0001_1188 |
| 2957 | >Toxin: E2348C_1093 | 8501 | >Antitoxin: E2348C_1092 |
| 2958 | >Toxin: E4_010100008678 | 8502 | >Antitoxin: E4_010100008683 |
| 2959 | >Toxin: HMPREF0381_2362 | 8503 | >Antitoxin: HMPREF0381_2361 |
| 2960 | >Toxin: Glov_2199 | 8504 | >Antitoxin: Glov_2198 |
| 2961 | >Toxin: glr3370 | 8505 | >Antitoxin: glr3371 |
| 2962 | >Toxin: GDI0970 | 8506 | >Antitoxin: GDI0971 |
| 2963 | >Toxin: KPK_4974 | 8507 | >Antitoxin: KPK_4973 |
| 2964 | >Toxin: HMPREF0554_2331 | 8508 | >Antitoxin: HMPREF0554_2332 |

TABLE 3-continued

| SEQ ID NO: | Toxin polypeptide sequences designation | SEQ ID NO: | Antitoxin polypeptide sequences designation |
|---|---|---|---|
| 2965 | >Toxin: L8106_04306 | 8509 | >Antitoxin: L8106_04311 |
| 2966 | >Toxin: MELB17_05794 | 8510 | >Antitoxin: MELB17_05789 |
| 2967 | >Toxin: Micau_0029 | 8511 | >Antitoxin: Micau_0028 |
| 2968 | >Toxin: Mb0060 | 8512 | >Antitoxin: Mb0061 |
| 2969 | >Toxin: BCG_0090 | 8513 | >Antitoxin: BCG_0091 |
| 2970 | >Toxin: JTY_0060 | 8514 | >Antitoxin: JTY_0061 |
| 2971 | >Toxin: Mtub2_010100014508 | 8515 | >Antitoxin: Mtub2_010100014513 |
| 2972 | >Toxin: Mtube_010100000751 | 8516 | >Antitoxin: Mtube_010100000756 |
| 2973 | >Toxin: MT0065 | 8517 | >Antitoxin: MT0066 |
| 2974 | >Toxin: TBFG_10058 | 8518 | >Antitoxin: TBFG_10059 |
| 2975 | >Toxin: MRA_0061 | 8519 | >Antitoxin: MRA_0062 |
| 2976 | >Toxin: Rv0059 | 8520 | >Antitoxin: Rv0060 |
| 2977 | >Toxin: TBMG_00058 | 8521 | >Antitoxin: TBMG_00059 |
| 2978 | >Toxin: MtubK4_020200000305 | 8522 | >Antitoxin: MtubK4_020200000310 |
| 2979 | >Toxin: MtubKR_020200000315 | 8523 | >Antitoxin: MtubKR_020200000320 |
| 2980 | >Toxin: MtubKV_020200000310 | 8524 | >Antitoxin: MtubKV_020200000315 |
| 2981 | >Toxin: TMAG_00729 | 8525 | >Antitoxin: TMAG_00730 |
| 2982 | >Toxin: MtubS_010100002549 | 8526 | >Antitoxin: MtubS_010100002554 |
| 2983 | >Toxin: MtubSUM_010100000319 | 8527 | >Antitoxin: MtubSUM_010100000324 |
| 2984 | >Toxin: MtubSUMu_010100000950 | 8528 | >Antitoxin: MtubSUMu_010100000955 |
| 2985 | >Toxin: MtubSUMu0_010100002539 | 8529 | >Antitoxin: MtubSUMu0_010100002544 |
| 2986 | >Toxin: MtubSUMu00_010100001797 | 8530 | >Antitoxin: MtubSUMu00_010100001802 |
| 2987 | >Toxin: MtubSUMu007_010100002479 | 8531 | >Antitoxin: MtubSUMu007_010100002484 |
| 2988 | >Toxin: MtubSUMu008_010100002534 | 8532 | >Antitoxin: MtubSUMu008_010100002539 |
| 2989 | >Toxin: MtubSUMu009_010100020343 | 8533 | >Antitoxin: MtubSUMu009_010100020348 |
| 2990 | >Toxin: MtubSUMu01_010100020402 | 8534 | >Antitoxin: MtubSUMu01_010100020407 |
| 2991 | >Toxin: MtubSUNMu011_010100020688 | 8535 | >Antitoxin: MtubSUMu011_010100020693 |
| 2992 | >Toxin: MtubSUMu012_010100000252 | 8536 | >Antitoxin: MtubSUMu012_010100000257 |
| 2993 | >Toxin: Nhal_3405 | 8537 | >Antitoxin: Nhal_3406 |
| 2994 | >Toxin: NE1363 | 8538 | >Antitoxin: NE1364 |
| 2995 | >Toxin: OSCI_3800101 | 8539 | >Antitoxin: OSCI_3800102 |
| 2996 | >Toxin: Plav_2928 | 8540 | >Antitoxin: Plav_2929 |
| 2997 | >Toxin: PC1_0863 | 8541 | >Antitoxin: PC1_0862 |
| 2998 | >Toxin: PBAL39_20435 | 8542 | >Antitoxin: PBAL39_20430 |
| 2999 | >Toxin: HMPREF9019_0398 | 8543 | >Antitoxin: HMPREF9019_0397 |
| 3000 | >Toxin: PSEEN0280 | 8544 | >Antitoxin: PSEEN0281 |
| 3001 | >Toxin: Pmen_0565 | 8545 | >Antitoxin: Pmen_0566 |
| 3002 | >Toxin: Rpal_2100 | 8546 | >Antitoxin: Rpal_2099 |
| 3003 | >Toxin: RoseRS_0296 | 8547 | >Antitoxin: RoseRS_0297 |
| 3004 | >Toxin: ISM_01070 | 8548 | >Antitoxin: ISM_01065 |
| 3005 | >Toxin: RflaF_010100007781 | 8549 | >Antitoxin: RflaF_010100007776 |
| 3006 | >Toxin: Sputcn32_3528 | 8550 | >Antitoxin: Sputcn32_3529 |
| 3007 | >Toxin: STAUR_1046 | 8551 | >Antitoxin: STAUR_1047 |
| 3008 | >Toxin: sll8002 | 8552 | >Antitoxin: sll8001 |
| 3009 | >Toxin: Slip_1960 | 8553 | >Antitoxin: Slip_1959 |
| 3010 | >Toxin: Tmz1t_3595 | 8554 | >Antitoxin: Tmz1t_3594 |
| 3011 | >Toxin: TaqDRAFT_4249 | 8555 | >Antitoxin: TaqDRAFT_4250 |
| 3012 | >Toxin: Tbd_1490 | 8556 | >Antitoxin: Tbd_1489 |
| 3013 | >Toxin: ZZM4_0145 | 8557 | >Antitoxin: ZZM4_0144 |
| 3014 | >Toxin: APCC8_010100024013 | 8558 | >Antitoxin: APCC8_010100024018 |
| 3015 | >Toxin: APCC8_010100024078 | 8559 | >Antitoxin: APCC8_010100024083 |
| 3016 | >Toxin: DthioDRAFT_0920 | 8560 | >Antitoxin: DthioDRAFT_0919 |
| 3017 | >Toxin: MettuDRAFT_1183 | 8561 | >Antitoxin: MettuDRAFT_1184 |
| 3018 | >Toxin: Mtub0_010100020641 | 8562 | >Antitoxin: Mtub0_010100020646 |
| 3019 | >Toxin: Mtub9_010100021293 | 8563 | >Antitoxin: Mtub9_010100021298 |
| 3020 | >Toxin: MtubC_01003315 | 8564 | >Antitoxin: MtubC_01003316 |
| 3021 | >Toxin: MtubCP_010100002512 | 8565 | >Antitoxin: MtubCP_010100002517 |
| 3022 | >Toxin: MtubE_010100020484 | 8566 | >Antitoxin: MtubE_010100020489 |
| 3023 | >Toxin: MtubG1_010100021149 | 8567 | >Antitoxin: MtubG1_010100021154 |
| 3024 | >Toxin: MtubH_010100021035 | 8568 | >Antitoxin: MtubH_010100021040 |
| 3025 | >Toxin: MtubK8_010100002630 | 8569 | >Antitoxin: MtubK8_010100002635 |
| 3026 | >Toxin: MtubKZN_010100019149 | 8570 | >Antitoxin: MtubKZN_010100019144 |
| 3027 | >Toxin: MtubT1_010100000475 | 8571 | >Antitoxin: MtubT1_010100000480 |
| 3028 | >Toxin: MtubT_010100021213 | 8572 | >Antitoxin: MtubT_010100021218 |
| 3029 | >Toxin: MtubT9_010100002236 | 8573 | >Antitoxin: MtubT9_010100002241 |
| 3030 | >Toxin: PROVRUST_01477 | 8574 | >Antitoxin: PROVRUST_01478 |
| 3031 | >Toxin: AcdelDRAFT_0253 | 8575 | >Antitoxin: AcdelDRAFT_0254 |
| 3032 | >Toxin: Ajs_1569 | 8576 | >Antitoxin: Ajs_1570 |
| 3033 | >Toxin: BURPS1106A_2452 | 8577 | >Antitoxin: BURPS1106A_2451 |
| 3034 | >Toxin: Bpse14_010100013779 | 8578 | >Antitoxin: Bpse14_010100013774 |
| 3035 | >Toxin: Bpseu9_010100040554 | 8579 | >Antitoxin: Bpseu9_010100040549 |
| 3036 | >Toxin: BpseB_010100013291 | 8580 | >Antitoxin: BpseB_010100013286 |

TABLE 3-continued

| SEQ ID NO: | Toxin polypeptide sequences designation | SEQ ID NO: | Antitoxin polypeptide sequences designation |
|---|---|---|---|
| 3037 | >Toxin: BUH_2443 | 8581 | >Antitoxin: BUH_2442 |
| 3038 | >Toxin: Clim_0213 | 8582 | >Antitoxin: Clim_0214 |
| 3039 | >Toxin: MldDRAFT_0262 | 8583 | >Antitoxin: MldDRAFT_0261 |
| 3040 | >Toxin: Dalk_1149 | 8584 | >Antitoxin: Dalk_1150 |
| 3041 | >Toxin: HMPREF0358_4229 | 8585 | >Antitoxin: HMPREF0358_4228 |
| 3042 | >Toxin: ECABU_c33410 | 8586 | >Antitoxin: ECABU_c33400 |
| 3043 | >Toxin: ECFG_02048 | 8587 | >Antitoxin: ECFG_02047 |
| 3044 | >Toxin: ECGG_01859 | 8588 | >Antitoxin: ECGG_01858 |
| 3045 | >Toxin: HMPREF9346_01205 | 8589 | >Antitoxin: HMPREF9346_01204 |
| 3046 | >Toxin: HMPREF9552_04316 | 8590 | >Antitoxin: HMPREF9552_04315 |
| 3047 | >Toxin: HMPREF9531_00622 | 8591 | >Antitoxin: HMPREF9531_00623 |
| 3048 | >Toxin: HMPREF9534_00156 | 8592 | >Antitoxin: HMPREF9534_00157 |
| 3049 | >Toxin: HMPREF9534_02242 | 8593 | >Antitoxin: HMPREF9534_02241 |
| 3050 | >Toxin: ECUMN_3416 | 8594 | >Antitoxin: ECUMN_3415 |
| 3051 | >Toxin: c3682 | 8595 | >Antitoxin: c3681 |
| 3052 | >Toxin: EschWDRAFT_2732 | 8596 | >Antitoxin: EschWDRAFT_2733 |
| 3053 | >Toxin: ECW_m4651 | 8597 | >Antitoxin: ECW_m4650 |
| 3054 | >Toxin: ESCG_00445 | 8598 | >Antitoxin: ESCG_00444 |
| 3055 | >Toxin: LDG_1702 | 8599 | >Antitoxin: LDG_1703 |
| 3056 | >Toxin: LPC_1887 | 8600 | >Antitoxin: LPC_1888 |
| 3057 | >Toxin: Ipl0200 | 8601 | >Antitoxin: Ipl0199 |
| 3058 | >Toxin: Ipp2408 | 8602 | >Antitoxin: Ipp2409 |
| 3059 | >Toxin: Mslp34_2080 | 8603 | >Antitoxin: Mslp34_2081 |
| 3060 | >Toxin: Plut_0717 | 8604 | >Antitoxin: Plut_0716 |
| 3061 | >Toxin: Ppha_1969 | 8605 | >Antitoxin: Ppha_1968 |
| 3062 | >Toxin: SKA34_21022 | 8606 | >Antitoxin: SKA34_21027 |
| 3063 | >Toxin: PAU_03952 | 8607 | >Antitoxin: PAU_03953 |
| 3064 | >Toxin: plu4270 | 8608 | >Antitoxin: plu4271 |
| 3065 | >Toxin: PSHAb0102 | 8609 | >Antitoxin: PSHAb0101 |
| 3066 | >Toxin: RC1_3156 | 8610 | >Antitoxin: RC1_3157 |
| 3067 | >Toxin: Sbal_4457 | 8611 | >Antitoxin: Sbal_4456 |
| 3068 | >Toxin: Shewana3_4161 | 8612 | >Antitoxin: Shewana3_4160 |
| 3069 | >Toxin: slr5102 | 8613 | >Antitoxin: slr5101 |
| 3070 | >Toxin: Vels_3691 | 8614 | >Antitoxin: Vels_3690 |
| 3071 | >Toxin: VIBHAR_06811 | 8615 | >Antitoxin: VIBHAR_06812 |
| 3072 | >Toxin: pVT1_52 | 8616 | >Antitoxin: pVT1_51 |
| 3073 | >Toxin: VV20181 | 8617 | >Antitoxin: VV20180 |
| 3074 | >Toxin: VVM_01405 | 8618 | >Antitoxin: VVM_01404 |
| 3075 | >Toxin: VSWAT3_18743 | 8619 | >Antitoxin: VSWAT3_18738 |
| 3076 | >Toxin: yaldo0001_40550 | 8620 | >Antitoxin: yaldo0001_40560 |
| 3077 | >Toxin: YE4109 | 8621 | >Antitoxin: YE4110 |
| 3078 | >Toxin: EcolH5_010100022792 | 8622 | >Antitoxin: EcolH5_010100022787 |
| 3079 | >Toxin: Nham_0582 | 8623 | >Antitoxin: Nham_0581 |
| 3080 | >Toxin: Swol_1548 | 8624 | >Antitoxin: Swol_1549 |
| 3081 | >Toxin: Ppro_0237 | 8625 | >Antitoxin: Ppro_0238 |
| 3082 | >Toxin: Aave_0159 | 8626 | >Antitoxin: Aave_0158 |
| 3083 | >Toxin: Cthe_0519 | 8627 | >Antitoxin: Cthe_0520 |
| 3084 | >Toxin: Daci_4205 | 8628 | >Antitoxin: Daci_4206 |
| 3085 | >Toxin: Nther_0364 | 8629 | >Antitoxin: Nther_0363 |
| 3086 | >Toxin: Ppha_1128 | 8630 | >Antitoxin: Ppha_1127 |
| 3087 | >Toxin: Afer_1394 | 8631 | >Antitoxin: Afer_1395 |
| 3088 | >Toxin: Mmar10_3055 | 8632 | >Antitoxin: Mmar10_3056 |
| 3089 | >Toxin: Hhal_0412 | 8633 | >Antitoxin: Hhal_0413 |
| 3090 | >Toxin: Rsph17029_3386 | 8634 | >Antitoxin: Rsph17029_3385 |
| 3091 | >Toxin: Acry_3581 | 8635 | >Antitoxin: Acry_3582 |
| 3092 | >Toxin: Spro_0571 | 8636 | >Antitoxin: Spro_0572 |
| 3093 | >Toxin: PputGB1_4746 | 8637 | >Antitoxin: PputGB1_4747 |
| 3094 | >Toxin: Glov_0294 | 8638 | >Antitoxin: Glov_0295 |
| 3095 | >Toxin: Psyr_1426 | 8639 | >Antitoxin: Psyr_1427 |
| 3096 | >Toxin: Bxe_A1177 | 8640 | >Antitoxin: Bxe_A1178 |
| 3097 | >Toxin: Rmet_2360 | 8641 | >Antitoxin: Rmet_2359 |
| 3098 | >Toxin: Ajs_1249 | 8642 | >Antitoxin: Ajs_1250 |
| 3099 | >Toxin: Ajs_1391 | 8643 | >Antitoxin: Ajs_1392 |
| 3100 | >Toxin: Ajs_2179 | 8644 | >Antitoxin: Ajs_2180 |
| 3101 | >Toxin: Mpe_A2401 | 8645 | >Antitoxin: Mpe_A2400 |
| 3102 | >Toxin: Plav_3431 | 8646 | >Antitoxin: Plav_3430 |
| 3103 | >Toxin: Spro_4161 | 8647 | >Antitoxin: Spro_4162 |
| 3104 | >Toxin: Daci_4186 | 8648 | >Antitoxin: Daci_4185 |
| 3105 | >Toxin: Tmz1t_0941 | 8649 | >Antitoxin: Tmz1t_0942 |
| 3106 | >Toxin: Tgr7_2866 | 8650 | >Antitoxin: Tgr7_2865 |
| 3107 | >Toxin: Avin_36380 | 8651 | >Antitoxin: Avin_36370 |
| 3108 | >Toxin: Rpic12D_0690 | 8652 | >Antitoxin: Rpic12D_0689 |
| 3109 | >Toxin: Dd1591_0428 | 8653 | >Antitoxin: Dd1591_0429 |
| 3110 | >Toxin: Mbar_A1358 | 8654 | >Antitoxin: Mbar_A1357 |
| 3111 | >Toxin: RoseRS_2587 | 8655 | >Antitoxin: RoseRS_2588 |
| 3112 | >Toxin: Rcas_4238 | 8656 | >Antitoxin: Rcas_4239 |
| 3113 | >Toxin: TRQ2_0318 | 8657 | >Antitoxin: TRQ2_0317 |

TABLE 3-continued

| SEQ ID NO: | Toxin polypeptide sequences designation | SEQ ID NO: | Antitoxin polypeptide sequences designation |
|---|---|---|---|
| 3114 | >Toxin: Clim_0935 | 8658 | >Antitoxin: Clim_0934 |
| 3115 | >Toxin: Paes_1991 | 8659 | >Antitoxin: Paes_1990 |
| 3116 | >Toxin: Cagg_3810 | 8660 | >Antitoxin: Cagg_3811 |
| 3117 | >Toxin: Cagg_3824 | 8661 | >Antitoxin: Cagg_3825 |
| 3118 | >Toxin: Ava_B0311 | 8662 | >Antitoxin: Ava_B0312 |
| 3119 | >Toxin: Sfri_2090 | 8663 | >Antitoxin: Sfri_2089 |
| 3120 | >Toxin: Pnap_4584 | 8664 | >Antitoxin: Pnap_4583 |
| 3121 | >Toxin: Mpe_B0172 | 8665 | >Antitoxin: Mpe_B0171 |
| 3122 | >Toxin: Fjoh_3012 | 8666 | >Antitoxin: Fjoh_3013 |
| 3123 | >Toxin: Swit_5328 | 8667 | >Antitoxin: Swit_5327 |
| 3124 | >Toxin: MADE_00121 | 8668 | >Antitoxin: MADE_00120 |
| 3125 | >Toxin: Tmz1t_2113 | 8669 | >Antitoxin: Tmz1t_2114 |
| 3126 | >Toxin: Mnod_0641 | 8670 | >Antitoxin: Mnod_0642 |
| 3127 | >Toxin: Amir_0591 | 8671 | >Antitoxin: Amir_0592 |
| 3128 | >Toxin: Mfl052 | 8672 | >Antitoxin: Mfl051 |
| 3129 | >Toxin: Bcep18194_B0245 | 8673 | >Antitoxin: Bcep18194_B0246 |
| 3130 | >Toxin: RPC_2242 | 8674 | >Antitoxin: RPC_2243 |
| 3131 | >Toxin: Pden_4165 | 8675 | >Antitoxin: Pden_4164 |
| 3132 | >Toxin: Swit_2282 | 8676 | >Antitoxin: Swit_2281 |
| 3133 | >Toxin: Mext_2035 | 8677 | >Antitoxin: Mext_2036 |
| 3134 | >Toxin: Mpop_1996 | 8678 | >Antitoxin: Mpop_1997 |
| 3135 | >Toxin: Gdia_2649 | 8679 | >Antitoxin: Gdia_2650 |
| 3136 | >Toxin: Msil_0447 | 8680 | >Antitoxin: Msil_0446 |
| 3137 | >Toxin: Mchl_2310 | 8681 | >Antitoxin: Mchl_2311 |
| 3138 | >Toxin: Avi_1240 | 8682 | >Antitoxin: Avi_1242 |
| 3139 | >Toxin: Caci_6778 | 8683 | >Antitoxin: Caci_6779 |
| 3140 | >Toxin: Tfu_0002 | 8684 | >Antitoxin: Tfu_0003 |
| 3141 | >Toxin: Mmcs_0002 | 8685 | >Antitoxin: Mmcs_0003 |
| 3142 | >Toxin: Arth_0002 | 8686 | >Antitoxin: Arth_0003 |
| 3143 | >Toxin: Noca_0002 | 8687 | >Antitoxin: Noca_0003 |
| 3144 | >Toxin: Mkms_0010 | 8688 | >Antitoxin: Mkms_0011 |
| 3145 | >Toxin: Mvan_0002 | 8689 | >Antitoxin: Mvan_0003 |
| 3146 | >Toxin: Mjls_0002 | 8690 | >Antitoxin: Mjls_0003 |
| 3147 | >Toxin: Mflv_0826 | 8691 | >Antitoxin: Mflv_0825 |
| 3148 | >Toxin: Strop_0003 | 8692 | >Antitoxin: Strop_0004 |
| 3149 | >Toxin: Sare_0002 | 8693 | >Antitoxin: Sare_0003 |
| 3150 | >Toxin: Achl_0002 | 8694 | >Antitoxin: Achl_0003 |
| 3151 | >Toxin: Amir_0002 | 8695 | >Antitoxin: Amir_0003 |
| 3152 | >Toxin: Bcav_0002 | 8696 | >Antitoxin: Bcav_0003 |
| 3153 | >Toxin: Ksed_00020 | 8697 | >Antitoxin: Ksed_00030 |
| 3154 | >Toxin: Caci_0002 | 8698 | >Antitoxin: Caci_0003 |
| 3155 | >Toxin: Svir_00020 | 8699 | >Antitoxin: Svir_00030 |
| 3156 | >Toxin: Namu_0002 | 8700 | >Antitoxin: Namu_0003 |
| 3157 | >Toxin: B21_04046 | 8701 | >Antitoxin: B21_04047 |
| 3158 | >Toxin: RS05352 | 8702 | >Antitoxin: RS05353 |
| 3159 | >Toxin: PSPTO_2507 | 8703 | >Antitoxin: PSPTO_2508 |
| 3160 | >Toxin: Psyr_2311 | 8704 | >Antitoxin: Psyr_2312 |
| 3161 | >Toxin: RPB_2618 | 8705 | >Antitoxin: RPB_2619 |
| 3162 | >Toxin: Rfer_0277 | 8706 | >Antitoxin: Rfer_0278 |
| 3163 | >Toxin: Pden_4294 | 8707 | >Antitoxin: Pden_4293 |
| 3164 | >Toxin: Noca_0421 | 8708 | >Antitoxin: Noca_0420 |
| 3165 | >Toxin: Aave_1295 | 8709 | >Antitoxin: Aave_1296 |
| 3166 | >Toxin: Pnap_0622 | 8710 | >Antitoxin: Pnap_0621 |
| 3167 | >Toxin: Ent638_0383 | 8711 | >Antitoxin: Ent638_0384 |
| 3168 | >Toxin: BBta_1616 | 8712 | >Antitoxin: BBta_1615 |
| 3169 | >Toxin: Smed_1972 | 8713 | >Antitoxin: Smed_1971 |
| 3170 | >Toxin: Mmwyl1_0005 | 8714 | >Antitoxin: Mmwyl1_0006 |
| 3171 | >Toxin: YpsIP31758_1619 | 8715 | >Antitoxin: YpsIP31758_1620 |
| 3172 | >Toxin: Xaut_0312 | 8716 | >Antitoxin: Xaut_0313 |
| 3173 | >Toxin: EcHS_A4466 | 8717 | >Antitoxin: EcHS_A4465 |
| 3174 | >Toxin: EcE24377A_4780 | 8718 | >Antitoxin: EcE24377A_4782 |
| 3175 | >Toxin: Franean1_3622 | 8719 | >Antitoxin: Franean1_3621 |
| 3176 | >Toxin: YpAngola_A2844 | 8720 | >Antitoxin: YpAngola_A2843 |
| 3177 | >Toxin: Mext_4022 | 8721 | >Antitoxin: Mext_4023 |
| 3178 | >Toxin: EcolC_3795 | 8722 | >Antitoxin: EcolC_3794 |
| 3179 | >Toxin: YPK_1727 | 8723 | >Antitoxin: YPK_1728 |
| 3180 | >Toxin: Xfasm12_0209 | 8724 | >Antitoxin: Xfasm12_0208 |
| 3181 | >Toxin: EcSMS35_4690 | 8725 | >Antitoxin: EcSMS35_4691 |
| 3182 | >Toxin: Lcho_1439 | 8726 | >Antitoxin: Lcho_1440 |
| 3183 | >Toxin: Mrad2831_0164 | 8727 | >Antitoxin: Mrad2831_0163 |
| 3184 | >Toxin: Mrad2831_5255 | 8728 | >Antitoxin: Mrad2831_5256 |
| 3185 | >Toxin: XfasM23_0185 | 8729 | >Antitoxin: XfasM23_0184 |
| 3186 | >Toxin: PXO_03749 | 8730 | >Antitoxin: PXO_03748 |
| 3187 | >Toxin: SbBS512_E4752 | 8731 | >Antitoxin: SbBS512_E4753 |
| 3188 | >Toxin: Rpal_2976 | 8732 | >Antitoxin: Rpal_2977 |
| 3189 | >Toxin: Gbem_2877 | 8733 | >Antitoxin: Gbem_2876 |
| 3190 | >Toxin: M446_0617 | 8734 | >Antitoxin: M446_0618 |

TABLE 3-continued

| | Toxin polypeptide sequences | | Antitoxin polypeptide sequences |
|---|---|---|---|
| SEQ ID NO: | designation | SEQ ID NO: | designation |
| 3191 | >Toxin: ECH74115_5728 | 8735 | >Antitoxin: ECH74115_5729 |
| 3192 | >Toxin: Rleg2_2511 | 8736 | >Antitoxin: Rleg2_2510 |
| 3193 | >Toxin: Rleg2_6179 | 8737 | >Antitoxin: Rleg2_6178 |
| 3194 | >Toxin: Mchl_4391 | 8738 | >Antitoxin: Mchl_4392 |
| 3195 | >Toxin: Achl_0581 | 8739 | >Antitoxin: Achl_0580 |
| 3196 | >Toxin: A2cp1_3290 | 8740 | >Antitoxin: A2cp1_3289 |
| 3197 | >Toxin: Avi_2793 | 8741 | >Antitoxin: Avi_2792 |
| 3198 | >Toxin: Amir_0551 | 8742 | >Antitoxin: Amir_0552 |
| 3199 | >Toxin: Rleg_2766 | 8743 | >Antitoxin: Rleg_2765 |
| 3200 | >Toxin: PC1_4290 | 8744 | >Antitoxin: PC1_4289 |
| 3201 | >Toxin: Cpin_0640 | 8745 | >Antitoxin: Cpin_0639 |
| 3202 | >Toxin: Caci_0025 | 8746 | >Antitoxin: Caci_0026 |
| 3203 | >Toxin: CPR_1661 | 8747 | >Antitoxin: CPR_1660 |
| 3204 | >Toxin: SAG0378 | 8748 | >Antitoxin: SAG0379 |
| 3205 | >Toxin: BCE_3854 | 8749 | >Antitoxin: BCE_3853 |
| 3206 | >Toxin: LMOf2365_1339 | 8750 | >Antitoxin: LMOf2365_1340 |
| 3207 | >Toxin: GBAA_3953 | 8751 | >Antitoxin: GBAA_3952 |
| 3208 | >Toxin: BAS3667 | 8752 | >Antitoxin: BAS3666 |
| 3209 | >Toxin: BT9727_3557 | 8753 | >Antitoxin: BT9727_3556 |
| 3210 | >Toxin: Mfl292 | 8754 | >Antitoxin: Mfl293 |
| 3211 | >Toxin: BCZK3575 | 8755 | >Antitoxin: BCZK3574 |
| 3212 | >Toxin: DET0985 | 8756 | >Antitoxin: DET0984 |
| 3213 | >Toxin: SACOL1285 | 8757 | >Antitoxin: SACOL1286 |
| 3214 | >Toxin: SERP0833 | 8758 | >Antitoxin: SERP0834 |
| 3215 | >Toxin: PMN2A_1023 | 8759 | >Antitoxin: PMN2A_1024 |
| 3216 | >Toxin: Ava_1870 | 8760 | >Antitoxin: Ava_1869 |
| 3217 | >Toxin: Syncc9902_0594 | 8761 | >Antitoxin: Syncc9902_0593 |
| 3218 | >Toxin: Syncc9605_2079 | 8762 | >Antitoxin: Syncc9605_2080 |
| 3219 | >Toxin: PMT9312_1585 | 8763 | >Antitoxin: PMT9312_1586 |
| 3220 | >Toxin: Synpcc7942_2022 | 8764 | >Antitoxin: Synpcc7942_2021 |
| 3221 | >Toxin: Dgeo_1234 | 8765 | >Antitoxin: Dgeo_1235 |
| 3222 | >Toxin: Moth_1047 | 8766 | >Antitoxin: Moth_1048 |
| 3223 | >Toxin: Tery_3978 | 8767 | >Antitoxin: Tery_3977 |
| 3224 | >Toxin: CPF_1943 | 8768 | >Antitoxin: CPF_1942 |
| 3225 | >Toxin: Swol_0897 | 8769 | >Antitoxin: Swol_0898 |
| 3226 | >Toxin: OEOE_0430 | 8770 | >Antitoxin: OEOE_0431 |
| 3227 | >Toxin: LEUM_1358 | 8771 | >Antitoxin: LEUM_1357 |
| 3228 | >Toxin: LGAS_0811 | 8772 | >Antitoxin: LGAS_0812 |
| 3229 | >Toxin: LACR_0814 | 8773 | >Antitoxin: LACR_0815 |
| 3230 | >Toxin: STER_0380 | 8774 | >Antitoxin: STER_0381 |
| 3231 | >Toxin: Dvul_2431 | 8775 | >Antitoxin: Dvul_2432 |
| 3232 | >Toxin: P9515_16721 | 8776 | >Antitoxin: P9515_16731 |
| 3233 | >Toxin: A9601_16961 | 8777 | >Antitoxin: A9601_16971 |
| 3234 | >Toxin: P9303_04151 | 8778 | >Antitoxin: P9303_04141 |
| 3235 | >Toxin: NATL1_18931 | 8779 | >Antitoxin: NATL1_18941 |
| 3236 | >Toxin: Cthe_0994 | 8780 | >Antitoxin: Cthe_0993 |
| 3237 | >Toxin: P9301_16831 | 8781 | >Antitoxin: P9301_16841 |
| 3238 | >Toxin: Dred_1960 | 8782 | >Antitoxin: Dred_1959 |
| 3239 | >Toxin: DehaBAV1_0876 | 8783 | >Antitoxin: DehaBAV1_0875 |
| 3240 | >Toxin: SaurJH9_1326 | 8784 | >Antitoxin: SaurJH9_1327 |
| 3241 | >Toxin: Lreu_0696 | 8785 | >Antitoxin: Lreu_0697 |
| 3242 | >Toxin: RoseRS_3749 | 8786 | >Antitoxin: RoseRS_3750 |
| 3243 | >Toxin: SaurJH1_1352 | 8787 | >Antitoxin: SaurJH1_1353 |
| 3244 | >Toxin: Bcer98_2468 | 8788 | >Antitoxin: Bcer98_2467 |
| 3245 | >Toxin: Rcas_1134 | 8789 | >Antitoxin: Rcas_1133 |
| 3246 | >Toxin: Haur_0473 | 8790 | >Antitoxin: Haur_0474 |
| 3247 | >Toxin: P9211_16141 | 8791 | >Antitoxin: P9211_16151 |
| 3248 | >Toxin: Cphy_2777 | 8792 | >Antitoxin: Cphy_2776 |
| 3249 | >Toxin: BcerKBAB4_3638 | 8793 | >Antitoxin: BcerKBAB4_3637 |
| 3250 | >Toxin: Teth514_1648 | 8794 | >Antitoxin: Teth514_1647 |
| 3251 | >Toxin: Daud_0923 | 8795 | >Antitoxin: Daud_0924 |
| 3252 | >Toxin: Nther_1441 | 8796 | >Antitoxin: Nther_1442 |
| 3253 | >Toxin: MARTH_orf784 | 8797 | >Antitoxin: MARTH_orf786 |
| 3254 | >Toxin: BCAH187_A3863 | 8798 | >Antitoxin: BCAH187_A3862 |
| 3255 | >Toxin: Dtur_1206 | 8799 | >Antitoxin: Dtur_1207 |
| 3256 | >Toxin: BCB4264_A3914 | 8800 | >Antitoxin: BCB4264_A3913 |
| 3257 | >Toxin: PCC7424_2359 | 8801 | >Antitoxin: PCC7424_2358 |
| 3258 | >Toxin: PCC8801_2712 | 8802 | >Antitoxin: PCC8801_2711 |
| 3259 | >Toxin: BCG9842_B1330 | 8803 | >Antitoxin: BCG9842_B1331 |
| 3260 | >Toxin: DvMF_2515 | 8804 | >Antitoxin: DvMF_2514 |
| 3261 | >Toxin: BCAH820_3828 | 8805 | >Antitoxin: BCAH820_3827 |
| 3262 | >Toxin: Dhaf_3679 | 8806 | >Antitoxin: Dhaf_3678 |
| 3263 | >Toxin: Hore_07820 | 8807 | >Antitoxin: Hore_07830 |
| 3264 | >Toxin: Ccel_0454 | 8808 | >Antitoxin: Ccel_0455 |
| 3265 | >Toxin: Ddes_0061 | 8809 | >Antitoxin: Ddes_0060 |
| 3266 | >Toxin: Cyan7425_2089 | 8810 | >Antitoxin: Cyan7425_2090 |
| 3267 | >Toxin: Athe_1049 | 8811 | >Antitoxin: Athe_1050 |

TABLE 3-continued

| Toxin polypeptide sequences | | Antitoxin polypeptide sequences | |
|---|---|---|---|
| SEQ ID NO: | designation | SEQ ID NO: | designation |
| 3268 | >Toxin: Afer_0636 | 8812 | >Antitoxin: Afer_0637 |
| 3269 | >Toxin: Dbac_2412 | 8813 | >Antitoxin: Dbac_2413 |
| 3270 | >Toxin: GWCH70_1152 | 8814 | >Antitoxin: GWCH70_1153 |
| 3271 | >Toxin: Elen_1812 | 8815 | >Antitoxin: Elen_1811 |
| 3272 | >Toxin: Cagg_3683 | 8816 | >Antitoxin: Cagg_3682 |
| 3273 | >Toxin: Ccur_08060 | 8817 | >Antitoxin: Ccur_08050 |
| 3274 | >Toxin: Apre_0607 | 8818 | >Antitoxin: Apre_0608 |
| 3275 | >Toxin: Cyan8802_3391 | 8819 | >Antitoxin: Cyan8802_3392 |
| 3276 | >Toxin: Dtox_3191 | 8820 | >Antitoxin: Dtox_3190 |
| 3277 | >Toxin: Aaci_1432 | 8821 | >Antitoxin: Aaci_1433 |
| 3278 | >Toxin: Dret_0497 | 8822 | >Antitoxin: Dret_0496 |
| 3279 | >Toxin: Ent638_3663 | 8823 | >Antitoxin: Ent638_3662 |
| 3280 | >Toxin: SbBS512_E3548 | 8824 | >Antitoxin: SbBS512_E3550 |
| 3281 | >Toxin: SNSL254_A3604 | 8825 | >Antitoxin: SNSL254_A3603 |
| 3282 | >Toxin: SeHA_C3639 | 8826 | >Antitoxin: SeHA_C3638 |
| 3283 | >Toxin: SeSA_A3534 | 8827 | >Antitoxin: SeSA_A3533 |
| 3284 | >Toxin: SeAg_B3532 | 8828 | >Antitoxin: SeAg_B3531 |
| 3285 | >Toxin: SeD_A3701 | 8829 | >Antitoxin: SeD_A3700 |
| 3286 | >Toxin: ECH74115_4545 | 8830 | >Antitoxin: ECH74115_4543 |
| 3287 | >Toxin: Patl_0700 | 8831 | >Antitoxin: Patl_0699 |
| 3288 | >Toxin: Shewmr7_0726 | 8832 | >Antitoxin: Shewmr7_0725 |
| 3289 | >Toxin: Dvul_2762 | 8833 | >Antitoxin: Dvul_2763 |
| 3290 | >Toxin: Sbal_1288 | 8834 | >Antitoxin: Sbal_1287 |
| 3291 | >Toxin: VC0395_1052 | 8835 | >Antitoxin: VC0395_1053 |
| 3292 | >Toxin: PSPA7_0699 | 8836 | >Antitoxin: PSPA7_0700 |
| 3293 | >Toxin: PSPA7_5057 | 8837 | >Antitoxin: PSPA7_5056 |
| 3294 | >Toxin: Mmwyl1_0582 | 8838 | >Antitoxin: Mmwyl1_0583 |
| 3295 | >Toxin: VIBHAR_05030 | 8839 | >Antitoxin: VIBHAR_05029 |
| 3296 | >Toxin: YPK_0902 | 8840 | >Antitoxin: YPK_0901 |
| 3297 | >Toxin: SNSL254_A2931 | 8841 | >Antitoxin: SNSL254_A2932 |
| 3298 | >Toxin: SeHA_C3487 | 8842 | >Antitoxin: SeHA_C3488 |
| 3299 | >Toxin: SeAg_B2795 | 8843 | >Antitoxin: SeAg_B2796 |
| 3300 | >Toxin: VSAL_I1032 | 8844 | >Antitoxin: VSAL_I1031 |
| 3301 | >Toxin: Dde_0244 | 8845 | >Antitoxin: Dde_0243 |
| 3302 | >Toxin: RSc2303 | 8846 | >Antitoxin: RSc2304 |
| 3303 | >Toxin: RS02977 | 8847 | >Antitoxin: RS02976 |
| 3304 | >Toxin: Tbd_1300 | 8848 | >Antitoxin: Tbd_1299 |
| 3305 | >Toxin: Tbd_1439 | 8849 | >Antitoxin: Tbd_1438 |
| 3306 | >Toxin: Nmul_A2583 | 8850 | >Antitoxin: Nmul_A2584 |
| 3307 | >Toxin: Mfla_1336 | 8851 | >Antitoxin: Mfla_1337 |
| 3308 | >Toxin: Rmet_4706 | 8852 | >Antitoxin: Rmet_4707 |
| 3309 | >Toxin: Pput_2293 | 8853 | >Antitoxin: Pput_2292 |
| 3310 | >Toxin: PputGB1_2459 | 8854 | >Antitoxin: PputGB1_2458 |
| 3311 | >Toxin: PputW619_2468 | 8855 | >Antitoxin: PputW619_2467 |
| 3312 | >Toxin: Lcho_3884 | 8856 | >Antitoxin: Lcho_3883 |
| 3313 | >Toxin: Avin_29100 | 8857 | >Antitoxin: Avin_29110 |
| 3314 | >Toxin: GBAA_2803 | 8858 | >Antitoxin: GBAA_2804 |
| 3315 | >Toxin: BAS2613 | 8859 | >Antitoxin: BAS2614 |
| 3316 | >Toxin: BCZK2530 | 8860 | >Antitoxin: BCZK2531 |
| 3317 | >Toxin: Moth_1254 | 8861 | >Antitoxin: Moth_1255 |
| 3318 | >Toxin: Cthe_2752 | 8862 | >Antitoxin: Cthe_2753 |
| 3319 | >Toxin: Haur_2771 | 8863 | >Antitoxin: Haur_2772 |
| 3320 | >Toxin: Cphy_3555 | 8864 | >Antitoxin: Cphy_3554 |
| 3321 | >Toxin: Teth514_2351 | 8865 | >Antitoxin: Teth514_2352 |
| 3322 | >Toxin: BCAH187_A2853 | 8866 | >Antitoxin: BCAH187_A2854 |
| 3323 | >Toxin: BCAH820_2811 | 8867 | >Antitoxin: BCAH820_2812 |
| 3324 | >Toxin: Dhaf_1135 | 8868 | >Antitoxin: Dhaf_1136 |
| 3325 | >Toxin: Hore_14040 | 8869 | >Antitoxin: Hore_14050 |
| 3326 | >Toxin: Apar_1232 | 8870 | >Antitoxin: Apar_1233 |
| 3327 | >Toxin: Dtox_2072 | 8871 | >Antitoxin: Dtox_2071 |
| 3328 | >Toxin: SO_1986 | 8872 | >Antitoxin: SO_1985 |
| 3329 | >Toxin: PSPTO_1043 | 8873 | >Antitoxin: PSPTO_1042 |
| 3330 | >Toxin: Psyr_0892 | 8874 | >Antitoxin: Psyr_0891 |
| 3331 | >Toxin: CPS_1377 | 8875 | >Antitoxin: CPS_1378 |
| 3332 | >Toxin: RPB_0486 | 8876 | >Antitoxin: RPB_0487 |
| 3333 | >Toxin: Jann_4021 | 8877 | >Antitoxin: Jann_4022 |
| 3334 | >Toxin: Sde_2471 | 8878 | >Antitoxin: Sde_2472 |
| 3335 | >Toxin: Sden_3374 | 8879 | >Antitoxin: Sden_3373 |
| 3336 | >Toxin: RPD_0340 | 8880 | >Antitoxin: RPD_0339 |
| 3337 | >Toxin: TM1040_0415 | 8881 | >Antitoxin: TM1040_0416 |
| 3338 | >Toxin: Patl_1332 | 8882 | >Antitoxin: Patl_1333 |
| 3339 | >Toxin: Rru_A0722 | 8883 | >Antitoxin: Rru_A0721 |
| 3340 | >Toxin: Shewmr7_2347 | 8884 | >Antitoxin: Shewmr7_2348 |
| 3341 | >Toxin: RSP_1092 | 8885 | >Antitoxin: RSP_1093 |
| 3342 | >Toxin: Shewmr4_2275 | 8886 | >Antitoxin: Shewmr4_2276 |
| 3343 | >Toxin: Mmar10_0274 | 8887 | >Antitoxin: Mmar10_0275 |
| 3344 | >Toxin: Sfri_2318 | 8888 | >Antitoxin: Sfri_2319 |

TABLE 3-continued

| | Toxin polypeptide sequences | | Antitoxin polypeptide sequences |
|---|---|---|---|
| SEQ ID NO: | designation | SEQ ID NO: | designation |
| 3345 | >Toxin: Shewana3_2465 | 8889 | >Antitoxin: Shewana3_2466 |
| 3346 | >Toxin: Sama_2036 | 8890 | >Antitoxin: Sama_2037 |
| 3347 | >Toxin: Ping_0995 | 8891 | >Antitoxin: Ping_0996 |
| 3348 | >Toxin: Aave_3570 | 8892 | >Antitoxin: Aave_3569 |
| 3349 | >Toxin: Maqu_0518 | 8893 | >Antitoxin: Maqu_0517 |
| 3350 | >Toxin: Sbal_2597 | 8894 | >Antitoxin: Sbal_2598 |
| 3351 | >Toxin: Rsph17029_2755 | 8895 | >Antitoxin: Rsph17029_2756 |
| 3352 | >Toxin: Shew_1476 | 8896 | >Antitoxin: Shew_1477 |
| 3353 | >Toxin: Sputcn32_2322 | 8897 | >Antitoxin: Sputcn32_2323 |
| 3354 | >Toxin: Rsph17025_2936 | 8898 | >Antitoxin: Rsph17025_2935 |
| 3355 | >Toxin: VC0395_A1891 | 8899 | >Antitoxin: VC0395_A1890 |
| 3356 | >Toxin: BBta_2959 | 8900 | >Antitoxin: BBta_2958 |
| 3357 | >Toxin: Mmwyl1_4075 | 8901 | >Antitoxin: Mmwyl1_4076 |
| 3358 | >Toxin: Shew185_2636 | 8902 | >Antitoxin: Shew185_2637 |
| 3359 | >Toxin: Plav_1868 | 8903 | >Antitoxin: Plav_1867 |
| 3360 | >Toxin: Xaut_1629 | 8904 | >Antitoxin: Xaut_1630 |
| 3361 | >Toxin: VIBHAR_03284 | 8905 | >Antitoxin: VIBHAR_03283 |
| 3362 | >Toxin: Dshi_0366 | 8906 | >Antitoxin: Dshi_0365 |
| 3363 | >Toxin: Sbal195_2711 | 8907 | >Antitoxin: Sbal195_2712 |
| 3364 | >Toxin: Caul_1554 | 8908 | >Antitoxin: Caul_1553 |
| 3365 | >Toxin: Swoo_2780 | 8909 | >Antitoxin: Swoo_2779 |
| 3366 | >Toxin: Rpal_0551 | 8910 | >Antitoxin: Rpal_0550 |
| 3367 | >Toxin: Smal_1959 | 8911 | >Antitoxin: Smal_1960 |
| 3368 | >Toxin: MADE_01437 | 8912 | >Antitoxin: MADE_01438 |
| 3369 | >Toxin: Sbal223_1749 | 8913 | >Antitoxin: Sbal223_1748 |
| 3370 | >Toxin: Avi_0089 | 8914 | >Antitoxin: Avi_0090 |
| 3371 | >Toxin: CPR_1140 | 8915 | >Antitoxin: CPR_1139 |
| 3372 | >Toxin: SAG0350 | 8916 | >Antitoxin: SAG0349 |
| 3373 | >Toxin: CPF_1328 | 8917 | >Antitoxin: CPF_1327 |
| 3374 | >Toxin: OEOE_1587 | 8918 | >Antitoxin: OEOE_1588 |
| 3375 | >Toxin: LEUM_0315 | 8919 | >Antitoxin: LEUM_0314 |
| 3376 | >Toxin: LACR_0826 | 8920 | >Antitoxin: LACR_0825 |
| 3377 | >Toxin: STER_0435 | 8921 | >Antitoxin: STER_0434 |
| 3378 | >Toxin: Lreu_0986 | 8922 | >Antitoxin: Lreu_0987 |
| 3379 | >Toxin: Cphy_0519 | 8923 | >Antitoxin: Cphy_0518 |
| 3380 | >Toxin: Shel_01090 | 8924 | >Antitoxin: Shel_01080 |
| 3381 | >Toxin: Jann_0512 | 8925 | >Antitoxin: Jann_0513 |
| 3382 | >Toxin: TM1040_2567 | 8926 | >Antitoxin: TM1040_2566 |
| 3383 | >Toxin: Rru_A1858 | 8927 | >Antitoxin: Rru_A1857 |
| 3384 | >Toxin: RSP_1668 | 8928 | >Antitoxin: RSP_1669 |
| 3385 | >Toxin: Mmar10_1577 | 8929 | >Antitoxin: Mmar10_1576 |
| 3386 | >Toxin: Pden_1402 | 8930 | >Antitoxin: Pden_1401 |
| 3387 | >Toxin: Rsph17029_0301 | 8931 | >Antitoxin: Rsph17029_0302 |
| 3388 | >Toxin: Rsph17025_2578 | 8932 | >Antitoxin: Rsph17025_2577 |
| 3389 | >Toxin: Acry_0529 | 8933 | >Antitoxin: Acry_0530 |
| 3390 | >Toxin: Plav_2866 | 8934 | >Antitoxin: Plav_2867 |
| 3391 | >Toxin: Dshi_0192 | 8935 | >Antitoxin: Dshi_0193 |
| 3392 | >Toxin: Gdia_0378 | 8936 | >Antitoxin: Gdia_0377 |
| 3393 | >Toxin: B21_03041 | 8937 | >Antitoxin: B21_03040 |
| 3394 | >Toxin: PSPTO_4425 | 8938 | >Antitoxin: PSPTO_4424 |
| 3395 | >Toxin: Psyr_4119 | 8939 | >Antitoxin: Psyr_4118 |
| 3396 | >Toxin: Csal_2206 | 8940 | >Antitoxin: Csal_2205 |
| 3397 | >Toxin: HS_0753 | 8941 | >Antitoxin: HS_0754 |
| 3398 | >Toxin: Ent638_3665 | 8942 | >Antitoxin: Ent638_3664 |
| 3399 | >Toxin: Mmwyl1_2399 | 8943 | >Antitoxin: Mmwyl1_2398 |
| 3400 | >Toxin: EcHS_A3419 | 8944 | >Antitoxin: EcHS_A3418 |
| 3401 | >Toxin: EcE24377A_3713 | 8945 | >Antitoxin: EcE24377A_3712 |
| 3402 | >Toxin: Spro_4348 | 8946 | >Antitoxin: Spro_4347 |
| 3403 | >Toxin: COXBURSA331_A1940 | 8947 | >Antitoxin: COXBURSA331_A1939 |
| 3404 | >Toxin: YpAngola_A1133 | 8948 | >Antitoxin: YpAngola_A1132 |
| 3405 | >Toxin: EcolC_0476 | 8949 | >Antitoxin: EcolC_0477 |
| 3406 | >Toxin: YPK_0525 | 8950 | >Antitoxin: YPK_0526 |
| 3407 | >Toxin: SbBS512_E3546 | 8951 | >Antitoxin: SbBS512_E3547 |
| 3408 | >Toxin: SNSL254_A3607 | 8952 | >Antitoxin: SNSL254_A3605 |
| 3409 | >Toxin: SeSA_A3536 | 8953 | >Antitoxin: SeSA_A3535 |
| 3410 | >Toxin: SeD_A3704 | 8954 | >Antitoxin: SeD_A3702 |
| 3411 | >Toxin: ECH74115_4547 | 8955 | >Antitoxin: ECH74115_4546 |
| 3412 | >Toxin: Dd703_3638 | 8956 | >Antitoxin: Dd703_3637 |
| 3413 | >Toxin: Dd1591_3796 | 8957 | >Antitoxin: Dd1591_3795 |
| 3414 | >Toxin: PC1_0293 | 8958 | >Antitoxin: PC1_0294 |
| 3415 | >Toxin: B21_03060 | 8959 | >Antitoxin: B21_03059 |
| 3416 | >Toxin: SO_4097 | 8960 | >Antitoxin: SO_4096 |
| 3417 | >Toxin: PP_0934 | 8961 | >Antitoxin: PP_0935 |
| 3418 | >Toxin: PSPTO_4471 | 8962 | >Antitoxin: PSPTO_4470 |
| 3419 | >Toxin: MCA0101 | 8963 | >Antitoxin: MCA0102 |
| 3420 | >Toxin: Psyr_4162 | 8964 | >Antitoxin: Psyr_4161 |
| 3421 | >Toxin: Psyc_0484 | 8965 | >Antitoxin: Psyc_0485 |

TABLE 3-continued

| SEQ ID NO: | Toxin polypeptide sequences designation | SEQ ID NO: | Antitoxin polypeptide sequences designation |
|---|---|---|---|
| 3422 | >Toxin: CPS_4559 | 8966 | >Antitoxin: CPS_4558 |
| 3423 | >Toxin: Daro_0115 | 8967 | >Antitoxin: Daro_0114 |
| 3424 | >Toxin: Tbd_0261 | 8968 | >Antitoxin: Tbd_0262 |
| 3425 | >Toxin: Tcr_1631 | 8969 | >Antitoxin: Tcr_1632 |
| 3426 | >Toxin: Nmul_A0319 | 8970 | >Antitoxin: Nmul_A0318 |
| 3427 | >Toxin: Sde_3191 | 8971 | >Antitoxin: Sde_3190 |
| 3428 | >Toxin: Mfla_2492 | 8972 | >Antitoxin: Mfla_2493 |
| 3429 | >Toxin: Sden_3333 | 8973 | >Antitoxin: Sden_3332 |
| 3430 | >Toxin: Csal_2239 | 8974 | >Antitoxin: Csal_2238 |
| 3431 | >Toxin: Pcryo_0479 | 8975 | >Antitoxin: Pcryo_0480 |
| 3432 | >Toxin: Rmet_0052 | 8976 | >Antitoxin: Rmet_0053 |
| 3433 | >Toxin: BCI_0048 | 8977 | >Antitoxin: BCI_0047 |
| 3434 | >Toxin: Patl_0184 | 8978 | >Antitoxin: Patl_0185 |
| 3435 | >Toxin: Rru_A0471 | 8979 | >Antitoxin: Rru_A0472 |
| 3436 | >Toxin: HS_1126 | 8980 | >Antitoxin: HS_1125 |
| 3437 | >Toxin: Shewmr7_0480 | 8981 | >Antitoxin: Shewmr7_0481 |
| 3438 | >Toxin: Shewmr4_3471 | 8982 | >Antitoxin: Shewmr4_3470 |
| 3439 | >Toxin: Mlg_0170 | 8983 | >Antitoxin: Mlg_0171 |
| 3440 | >Toxin: Sfri_3737 | 8984 | >Antitoxin: Sfri_3736 |
| 3441 | >Toxin: PA14_58130 | 8985 | >Antitoxin: PA14_58120 |
| 3442 | >Toxin: Mmc1_1413 | 8986 | >Antitoxin: Mmc1_1414 |
| 3443 | >Toxin: Shewana3_3647 | 8987 | >Antitoxin: Shewana3_3646 |
| 3444 | >Toxin: Sama_0468 | 8988 | >Antitoxin: Sama_0469 |
| 3445 | >Toxin: Ping_1123 | 8989 | >Antitoxin: Ping_1124 |
| 3446 | >Toxin: Aave_0295 | 8990 | >Antitoxin: Aave_0296 |
| 3447 | >Toxin: Ajs_0240 | 8991 | >Antitoxin: Ajs_0241 |
| 3448 | >Toxin: Veis_1609 | 8992 | >Antitoxin: Veis_1608 |
| 3449 | >Toxin: Hhal_1006 | 8993 | >Antitoxin: Hhal_1007 |
| 3450 | >Toxin: Maqu_2727 | 8994 | >Antitoxin: Maqu_2726 |
| 3451 | >Toxin: Sbal_3821 | 8995 | >Antitoxin: Sbal_3820 |
| 3452 | >Toxin: Shew_0404 | 8996 | >Antitoxin: Shew_0405 |
| 3453 | >Toxin: Pnuc_2022 | 8997 | >Antitoxin: Pnuc_2023 |
| 3454 | >Toxin: Ent638_3686 | 8998 | >Antitoxin: Ent638_3685 |
| 3455 | >Toxin: Pmen_0857 | 8999 | >Antitoxin: Pmen_0858 |
| 3456 | >Toxin: Sputcn32_0575 | 9000 | >Antitoxin: Sputcn32_0576 |
| 3457 | >Toxin: VC0395_A2835 | 9001 | >Antitoxin: VC0395_A2836 |
| 3458 | >Toxin: Pput_0974 | 9002 | >Antitoxin: Pput_0975 |
| 3459 | >Toxin: PsycPRwf_0421 | 9003 | >Antitoxin: PsycPRwf_0422 |
| 3460 | >Toxin: PSPA7_5094 | 9004 | >Antitoxin: PSPA7_5093 |
| 3461 | >Toxin: Mmwyl1_1938 | 9005 | >Antitoxin: Mmwyl1_1939 |
| 3462 | >Toxin: Shew185_0498 | 9006 | >Antitoxin: Shew185_0499 |
| 3463 | >Toxin: YpsIP31758_0399 | 9007 | >Antitoxin: YpsIP31758_0400 |
| 3464 | >Toxin: VIBHAR_03684 | 9008 | >Antitoxin: VIBHAR_03683 |
| 3465 | >Toxin: EcHS_A3439 | 9009 | >Antitoxin: EcHS_A3438 |
| 3466 | >Toxin: EcE24377A_3733 | 9010 | >Antitoxin: EcE24377A_3731 |
| 3467 | >Toxin: Ssed_0559 | 9011 | >Antitoxin: Ssed_0560 |
| 3468 | >Toxin: Spro_4410 | 9012 | >Antitoxin: Spro_4409 |
| 3469 | >Toxin: Spea_3753 | 9013 | >Antitoxin: Spea_3752 |
| 3470 | >Toxin: Sbal195_0519 | 9014 | >Antitoxin: Sbal195_0520 |
| 3471 | >Toxin: COXBURSA331_A1647 | 9015 | >Antitoxin: COXBURSA331_A1646 |
| 3472 | >Toxin: YpAngola_A1197 | 9016 | >Antitoxin: YpAngola_A1196 |
| 3473 | >Toxin: PputGB1_0941 | 9017 | >Antitoxin: PputGB1_0942 |
| 3474 | >Toxin: EcolC_0457 | 9018 | >Antitoxin: EcolC_0458 |
| 3475 | >Toxin: PputW619_4281 | 9019 | >Antitoxin: PputW619_4280 |
| 3476 | >Toxin: YPK_0466 | 9020 | >Antitoxin: YPK_0467 |
| 3477 | >Toxin: Swoo_4401 | 9021 | >Antitoxin: Swoo_4400 |
| 3478 | >Toxin: Xfasm12_0669 | 9022 | >Antitoxin: Xfasm12_0670 |
| 3479 | >Toxin: EcSMS35_3545 | 9023 | >Antitoxin: EcSMS35_3544 |
| 3480 | >Toxin: Lcho_0503 | 9024 | >Antitoxin: Lcho_0502 |
| 3481 | >Toxin: Pnec_1739 | 9025 | >Antitoxin: Pnec_1740 |
| 3482 | >Toxin: XfasM23_0588 | 9026 | >Antitoxin: XfasM23_0589 |
| 3483 | >Toxin: SbBS512_E3281 | 9027 | >Antitoxin: SbBS512_E3280 |
| 3484 | >Toxin: Smal_3453 | 9028 | >Antitoxin: Smal_3452 |
| 3485 | >Toxin: SNSL254_A3636 | 9029 | >Antitoxin: SNSL254_A3635 |
| 3486 | >Toxin: SeHA_C3671 | 9030 | >Antitoxin: SeHA_C3670 |
| 3487 | >Toxin: SeSA_A3565 | 9031 | >Antitoxin: SeSA_A3564 |
| 3488 | >Toxin: MADE_00265 | 9032 | >Antitoxin: MADE_00266 |
| 3489 | >Toxin: SeAg_B3564 | 9033 | >Antitoxin: SeAg_B3563 |
| 3490 | >Toxin: Lferr_2193 | 9034 | >Antitoxin: Lferr_2194 |
| 3491 | >Toxin: SeD_A3733 | 9035 | >Antitoxin: SeD_A3732 |
| 3492 | >Toxin: VSAL_I0484 | 9036 | >Antitoxin: VSAL_I0485 |
| 3493 | >Toxin: ECH74115_4566 | 9037 | >Antitoxin: ECH74115_4565 |
| 3494 | >Toxin: Tmz1t_0237 | 9038 | >Antitoxin: Tmz1t_0238 |
| 3495 | >Toxin: Sbal223_0523 | 9039 | >Antitoxin: Sbal223_0524 |
| 3496 | >Toxin: AFE_2563 | 9040 | >Antitoxin: AFE_2564 |
| 3497 | >Toxin: Tgr7_0513 | 9041 | >Antitoxin: Tgr7_0512 |
| 3498 | >Toxin: Dtpsy_0234 | 9042 | >Antitoxin: Dtpsy_0235 |

TABLE 3-continued

| | Toxin polypeptide sequences | | Antitoxin polypeptide sequences |
|---|---|---|---|
| SEQ ID NO: | designation | SEQ ID NO: | designation |
| 3499 | >Toxin: Avin__12660 | 9043 | >Antitoxin: Avin__12670 |
| 3500 | >Toxin: Dd703__3676 | 9044 | >Antitoxin: Dd703__3675 |
| 3501 | >Toxin: Dd1591__3834 | 9045 | >Antitoxin: Dd1591__3833 |
| 3502 | >Toxin: PC1__0253 | 9046 | >Antitoxin: PC1__0254 |
| 3503 | >Toxin: Nwi__1700 | 9047 | >Antitoxin: Nwi__1701 |
| 3504 | >Toxin: Noc__2148 | 9048 | >Antitoxin: Noc__2149 |
| 3505 | >Toxin: RPB__2392 | 9049 | >Antitoxin: RPB__2391 |
| 3506 | >Toxin: RPC__3329 | 9050 | >Antitoxin: RPC__3330 |
| 3507 | >Toxin: RPD__3059 | 9051 | >Antitoxin: RPD__3060 |
| 3508 | >Toxin: Nham__2421 | 9052 | >Antitoxin: Nham__2422 |
| 3509 | >Toxin: Meso__1370 | 9053 | >Antitoxin: Meso__1369 |
| 3510 | >Toxin: Ping__2499 | 9054 | >Antitoxin: Ping__2498 |
| 3511 | >Toxin: BBta__4778 | 9055 | >Antitoxin: BBta__4779 |
| 3512 | >Toxin: Xaut__4540 | 9056 | >Antitoxin: Xaut__4541 |
| 3513 | >Toxin: Rpal__3560 | 9057 | >Antitoxin: Rpal__3561 |
| 3514 | >Toxin: M446__2256 | 9058 | >Antitoxin: M446__2255 |
| 3515 | >Toxin: Msil__0751 | 9059 | >Antitoxin: Msil__0752 |
| 3516 | >Toxin: Mnod__0353 | 9060 | >Antitoxin: Mnod__0354 |
| 3517 | >Toxin: Francci3__0679 | 9061 | >Antitoxin: Francci3__0680 |
| 3518 | >Toxin: Dgeo__0887 | 9062 | >Antitoxin: Dgeo__0888 |
| 3519 | >Toxin: Mmcs__1228 | 9063 | >Antitoxin: Mmcs__1229 |
| 3520 | >Toxin: Arth__1129 | 9064 | >Antitoxin: Arth__1130 |
| 3521 | >Toxin: Mkms__1245 | 9065 | >Antitoxin: Mkms__1246 |
| 3522 | >Toxin: Mvan__1587 | 9066 | >Antitoxin: Mvan__1588 |
| 3523 | >Toxin: Mjls__1254 | 9067 | >Antitoxin: Mjls__1255 |
| 3524 | >Toxin: Mflv__4846 | 9068 | >Antitoxin: Mflv__4845 |
| 3525 | >Toxin: TBFG__13349 | 9069 | >Antitoxin: TBFG__13348 |
| 3526 | >Toxin: Cphamn1__2514 | 9070 | >Antitoxin: Cphamn1__2515 |
| 3527 | >Toxin: Paes__2255 | 9071 | >Antitoxin: Paes__2256 |
| 3528 | >Toxin: Achl__1202 | 9072 | >Antitoxin: Achl__1203 |
| 3529 | >Toxin: Amir__6464 | 9073 | >Antitoxin: Amir__6463 |
| 3530 | >Toxin: Bcav__2952 | 9074 | >Antitoxin: Bcav__2951 |
| 3531 | >Toxin: Bfae__21330 | 9075 | >Antitoxin: Bfae__21320 |
| 3532 | >Toxin: Mlut__04830 | 9076 | >Antitoxin: Mlut__04840 |
| 3533 | >Toxin: Caci__0770 | 9077 | >Antitoxin: Caci__0771 |
| 3534 | >Toxin: Svir__05360 | 9078 | >Antitoxin: Svir__05370 |
| 3535 | >Toxin: Jden__0819 | 9079 | >Antitoxin: Jden__0820 |
| 3536 | >Toxin: Namu__1309 | 9080 | >Antitoxin: Namu__1310 |
| 3537 | >Toxin: SERP2170 | 9081 | >Antitoxin: SERP2169 |
| 3538 | >Toxin: Moth__0607 | 9082 | >Antitoxin: Moth__0606 |
| 3539 | >Toxin: Swol__1512 | 9083 | >Antitoxin: Swol__1513 |
| 3540 | >Toxin: Dred__2469 | 9084 | >Antitoxin: Dred__2470 |
| 3541 | >Toxin: Gdia__2026 | 9085 | >Antitoxin: Gdia__2027 |
| 3542 | >Toxin: Ksed__17560 | 9086 | >Antitoxin: Ksed__17550 |
| 3543 | >Toxin: Elen__1387 | 9087 | >Antitoxin: Elen__1386 |
| 3544 | >Toxin: Ccur__00390 | 9088 | >Antitoxin: Ccur__00380 |
| 3545 | >Toxin: Apre__1243 | 9089 | >Antitoxin: Apre__1242 |
| 3546 | >Toxin: Shel__11050 | 9090 | >Antitoxin: Shel__11040 |
| 3547 | >Toxin: Apar__0696 | 9091 | >Antitoxin: Apar__0695 |
| 3548 | >Toxin: Dtox__3044 | 9092 | >Antitoxin: Dtox__3045 |
| 3549 | >Toxin: PG0071 | 9093 | >Antitoxin: PG0070 |
| 3550 | >Toxin: CHU__1037 | 9094 | >Antitoxin: CHU__1036 |
| 3551 | >Toxin: Fjoh__2903 | 9095 | >Antitoxin: Fjoh__2902 |
| 3552 | >Toxin: Oter__2576 | 9096 | >Antitoxin: Oter__2577 |
| 3553 | >Toxin: Aasi__0289 | 9097 | >Antitoxin: Aasi__0288 |
| 3554 | >Toxin: Coch__1756 | 9098 | >Antitoxin: Coch__1757 |
| 3555 | >Toxin: Phep__4279 | 9099 | >Antitoxin: Phep__4278 |
| 3556 | >Toxin: Dfer__3015 | 9100 | >Antitoxin: Dfer__3014 |
| 3557 | >Toxin: Cpin__1279 | 9101 | >Antitoxin: Cpin__1278 |
| 3558 | >Toxin: CPR__2094 | 9102 | >Antitoxin: CPR__2093 |
| 3559 | >Toxin: CPF__2382 | 9103 | >Antitoxin: CPF__2381 |
| 3560 | >Toxin: Cthe__0163 | 9104 | >Antitoxin: Cthe__0164 |
| 3561 | >Toxin: Cphy__2548 | 9105 | >Antitoxin: Cphy__2547 |
| 3562 | >Toxin: Dhaf__4334 | 9106 | >Antitoxin: Dhaf__4333 |
| 3563 | >Toxin: Hore__14100 | 9107 | >Antitoxin: Hore__14090 |
| 3564 | >Toxin: Ccel__1323 | 9108 | >Antitoxin: Ccel__1324 |
| 3565 | >Toxin: Apre__0929 | 9109 | >Antitoxin: Apre__0930 |
| 3566 | >Toxin: PSPTO__5284 | 9110 | >Antitoxin: PSPTO__5283 |
| 3567 | >Toxin: Psyr__4842 | 9111 | >Antitoxin: Psyr__4841 |
| 3568 | >Toxin: Sde__0348 | 9112 | >Antitoxin: Sde__0349 |
| 3569 | >Toxin: Spro__3823 | 9113 | >Antitoxin: Spro__3822 |
| 3570 | >Toxin: COXBURSA331__A1734 | 9114 | >Antitoxin: COXBURSA331__A1733 |
| 3571 | >Toxin: YpAngola__A3240 | 9115 | >Antitoxin: YpAngola__A3239 |
| 3572 | >Toxin: YPK__1034 | 9116 | >Antitoxin: YPK__1035 |
| 3573 | >Toxin: SeHA__C3216 | 9117 | >Antitoxin: SeHA__C3215 |
| 3574 | >Toxin: SeSA__A3167 | 9118 | >Antitoxin: SeSA__A3166 |
| 3575 | >Toxin: SeAg__B3150 | 9119 | >Antitoxin: SeAg__B3149 |

TABLE 3-continued

| Toxin polypeptide sequences | | Antitoxin polypeptide sequences | |
|---|---|---|---|
| SEQ ID NO: | designation | SEQ ID NO: | designation |
| 3576 | >Toxin: SeD_A3330 | 9120 | >Antitoxin: SeD_A3329 |
| 3577 | >Toxin: Dd703_3016 | 9121 | >Antitoxin: Dd703_3015 |
| 3578 | >Toxin: PC1_0905 | 9122 | >Antitoxin: PC1_0906 |
| 3579 | >Toxin: Rfer_3786 | 9123 | >Antitoxin: Rfer_3785 |
| 3580 | >Toxin: Bpro_0265 | 9124 | >Antitoxin: Bpro_0266 |
| 3581 | >Toxin: Aave_0347 | 9125 | >Antitoxin: Aave_0348 |
| 3582 | >Toxin: Ajs_0287 | 9126 | >Antitoxin: Ajs_0288 |
| 3583 | >Toxin: Pnap_0212 | 9127 | >Antitoxin: Pnap_0213 |
| 3584 | >Toxin: Veis_1273 | 9128 | >Antitoxin: Veis_1274 |
| 3585 | >Toxin: Mpe_A3434 | 9129 | >Antitoxin: Mpe_A3433 |
| 3586 | >Toxin: Daci_0400 | 9130 | >Antitoxin: Daci_0401 |
| 3587 | >Toxin: Lcho_3990 | 9131 | >Antitoxin: Lcho_3989 |
| 3588 | >Toxin: Dtpsy_0282 | 9132 | >Antitoxin: Dtpsy_0283 |
| 3589 | >Toxin: Vapar_4904 | 9133 | >Antitoxin: Vapar_4903 |
| 3590 | >Toxin: Csal_1644 | 9134 | >Antitoxin: Csal_1645 |
| 3591 | >Toxin: Patl_1767 | 9135 | >Antitoxin: Patl_1766 |
| 3592 | >Toxin: CHU_1081 | 9136 | >Antitoxin: CHU_1080 |
| 3593 | >Toxin: Sfri_1851 | 9137 | >Antitoxin: Sfri_1850 |
| 3594 | >Toxin: Fjoh_2211 | 9138 | >Antitoxin: Fjoh_2212 |
| 3595 | >Toxin: Spro_3043 | 9139 | >Antitoxin: Spro_3042 |
| 3596 | >Toxin: Caul_4167 | 9140 | >Antitoxin: Caul_4168 |
| 3597 | >Toxin: MADE_01800 | 9141 | >Antitoxin: MADE_01799 |
| 3598 | >Toxin: Phep_2288 | 9142 | >Antitoxin: Phep_2287 |
| 3599 | >Toxin: Dfer_5124 | 9143 | >Antitoxin: Dfer_5125 |
| 3600 | >Toxin: Mpal_0372 | 9144 | >Antitoxin: Mpal_0371 |
| 3601 | >Toxin: Shewmr7_0701 | 9145 | >Antitoxin: Shewmr7_0702 |
| 3602 | >Toxin: Sbal_1270 | 9146 | >Antitoxin: Sbal_1271 |
| 3603 | >Toxin: Ent638_1343 | 9147 | >Antitoxin: Ent638_1344 |
| 3604 | >Toxin: VC0395_1075 | 9148 | >Antitoxin: VC0395_1074 |
| 3605 | >Toxin: EcHS_A0912 | 9149 | >Antitoxin: EcHS_A0913 |
| 3606 | >Toxin: EcolC_2792 | 9150 | >Antitoxin: EcolC_2791 |
| 3607 | >Toxin: YPK_0884 | 9151 | >Antitoxin: YPK_0885 |
| 3608 | >Toxin: Mbar_A3105 | 9152 | >Antitoxin: Mbar_A3104 |
| 3609 | >Toxin: BURPS1710b_A1055 | 9153 | >Antitoxin: BURPS1710b_A1054 |
| 3610 | >Toxin: Pcar_2990 | 9154 | >Antitoxin: Pcar_2991 |
| 3611 | >Toxin: Plut_1064 | 9155 | >Antitoxin: Plut_1065 |
| 3612 | >Toxin: Nmul_A1660 | 9156 | >Antitoxin: Nmul_A1659 |
| 3613 | >Toxin: BTH_II0420 | 9157 | >Antitoxin: BTH_II0421 |
| 3614 | >Toxin: Rfer_1162 | 9158 | >Antitoxin: Rfer_1163 |
| 3615 | >Toxin: Bxe_A1880 | 9159 | >Antitoxin: Bxe_A1881 |
| 3616 | >Toxin: Bxe_C0048 | 9160 | >Antitoxin: Bxe_C0047 |
| 3617 | >Toxin: Patl_2669 | 9161 | >Antitoxin: Patl_2670 |
| 3618 | >Toxin: RSP_3930 | 9162 | >Antitoxin: RSP_3931 |
| 3619 | >Toxin: Sfri_3050 | 9163 | >Antitoxin: Sfri_3051 |
| 3620 | >Toxin: Ping_0464 | 9164 | >Antitoxin: Ping_0465 |
| 3621 | >Toxin: Pnap_2335 | 9165 | >Antitoxin: Pnap_2334 |
| 3622 | >Toxin: Rsph17029_4098 | 9166 | >Antitoxin: Rsph17029_4099 |
| 3623 | >Toxin: BMA10247_A0148 | 9167 | >Antitoxin: BMA10247_A0149 |
| 3624 | >Toxin: BURPS668_A2793 | 9168 | >Antitoxin: BURPS668_A2792 |
| 3625 | >Toxin: BURPS1106A_A2651 | 9169 | >Antitoxin: BURPS1106A_A2650 |
| 3626 | >Toxin: BBta_1439 | 9170 | >Antitoxin: BBta_1438 |
| 3627 | >Toxin: Mmwyl1_1955 | 9171 | >Antitoxin: Mmwyl1_1956 |
| 3628 | >Toxin: Dshi_0436 | 9172 | >Antitoxin: Dshi_0437 |
| 3629 | >Toxin: Bind_2774 | 9173 | >Antitoxin: Bind_2775 |
| 3630 | >Toxin: Bphy_1128 | 9174 | >Antitoxin: Bphy_1127 |
| 3631 | >Toxin: Bphyt_5559 | 9175 | >Antitoxin: Bphyt_5558 |
| 3632 | >Toxin: Rpal_1056 | 9176 | >Antitoxin: Rpal_1055 |
| 3633 | >Toxin: Paes_0889 | 9177 | >Antitoxin: Paes_0890 |
| 3634 | >Toxin: Avin_19680 | 9178 | >Antitoxin: Avin_19690 |
| 3635 | >Toxin: Dbac_0951 | 9179 | >Antitoxin: Dbac_0950 |
| 3636 | >Toxin: Fjoh_2893 | 9180 | >Antitoxin: Fjoh_2892 |
| 3637 | >Toxin: Coch_1073 | 9181 | >Antitoxin: Coch_1072 |
| 3638 | >Toxin: Phep_0306 | 9182 | >Antitoxin: Phep_0307 |
| 3639 | >Toxin: Dfer_4782 | 9183 | >Antitoxin: Dfer_4783 |
| 3640 | >Toxin: Cpin_0735 | 9184 | >Antitoxin: Cpin_1736 |
| 3641 | >Toxin: Cpin_2192 | 9185 | >Antitoxin: Cpin_2193 |
| 3642 | >Toxin: Cpin_3748 | 9186 | >Antitoxin: Cpin_3747 |
| 3643 | >Toxin: DET1408 | 9187 | >Antitoxin: DET1409 |
| 3644 | >Toxin: Dgeo_1103 | 9188 | >Antitoxin: Dgeo_1102 |
| 3645 | >Toxin: Moth_2402 | 9189 | >Antitoxin: Moth_2403 |
| 3646 | >Toxin: Dred_3174 | 9190 | >Antitoxin: Dred_3175 |
| 3647 | >Toxin: DehaBAV1_1215 | 9191 | >Antitoxin: DehaBAV1_1216 |
| 3648 | >Toxin: Daud_2173 | 9192 | >Antitoxin: Daud_2174 |
| 3649 | >Toxin: Elen_1088 | 9193 | >Antitoxin: Elen_1087 |
| 3650 | >Toxin: Ccur_09300 | 9194 | >Antitoxin: Ccur_09310 |
| 3651 | >Toxin: Shel_23670 | 9195 | >Antitoxin: Shel_23680 |
| 3652 | >Toxin: Dtox_0059 | 9196 | >Antitoxin: Dtox_0058 |

TABLE 3-continued

| SEQ ID NO: | Toxin polypeptide sequences designation | SEQ ID NO: | Antitoxin polypeptide sequences designation |
|---|---|---|---|
| 3653 | >Toxin: Aacl_2782 | 9197 | >Antitoxin: Aacl_2783 |
| 3654 | >Toxin: RSc0621 | 9198 | >Antitoxin: RSc0620 |
| 3655 | >Toxin: Daro_2593 | 9199 | >Antitoxin: Daro_2592 |
| 3656 | >Toxin: Bpro_0540 | 9200 | >Antitoxin: Bpro_0541 |
| 3657 | >Toxin: Bpro_2731 | 9201 | >Antitoxin: Bpro_2730 |
| 3658 | >Toxin: Spro_1511 | 9202 | >Antitoxin: Spro_1510 |
| 3659 | >Toxin: Dacl_3133 | 9203 | >Antitoxin: Dacl_3134 |
| 3660 | >Toxin: Bphy_5021 | 9204 | >Antitoxin: Bphy_5020 |
| 3661 | >Toxin: Gdia_1698 | 9205 | >Antitoxin: Gdia_1697 |
| 3662 | >Toxin: Gdia_2752 | 9206 | >Antitoxin: Gdia_2751 |
| 3663 | >Toxin: Vapar_2991 | 9207 | >Antitoxin: Vapar_2990 |
| 3664 | >Toxin: Ajs_3305 | 9208 | >Antitoxin: Ajs_3304 |
| 3665 | >Toxin: TBFG_12339 | 9209 | >Antitoxin: TBFG_12340 |
| 3666 | >Toxin: Oter_4149 | 9210 | >Antitoxin: Oter_4150 |
| 3667 | >Toxin: M446_6662 | 9211 | >Antitoxin: M446_6663 |
| 3668 | >Toxin: Dtpsy_2658 | 9212 | >Antitoxin: Dtpsy_2657 |
| 3669 | >Toxin: Bcav_0146 | 9213 | >Antitoxin: Bcav_0145 |
| 3670 | >Toxin: Bfae_28370 | 9214 | >Antitoxin: Bfae_28380 |
| 3671 | >Toxin: RSc1117 | 9215 | >Antitoxin: RSc1118 |
| 3672 | >Toxin: Reut_A1076 | 9216 | >Antitoxin: Reut_A1077 |
| 3673 | >Toxin: Rmet_1040 | 9217 | >Antitoxin: Rmet_1041 |
| 3674 | >Toxin: TM1040_1846 | 9218 | >Antitoxin: TM1040_1845 |
| 3675 | >Toxin: RSP_0777 | 9219 | >Antitoxin: RSP_0776 |
| 3676 | >Toxin: Pden_1840 | 9220 | >Antitoxin: Pden_1839 |
| 3677 | >Toxin: BMASAVP1_A2201 | 9221 | >Antitoxin: BMASAVP1_A2200 |
| 3678 | >Toxin: Rsph17029_2433 | 9222 | >Antitoxin: Rsph17029_2432 |
| 3679 | >Toxin: BMA10247_1474 | 9223 | >Antitoxin: BMA10247_1473 |
| 3680 | >Toxin: BURPS668_2584 | 9224 | >Antitoxin: BURPS668_2583 |
| 3681 | >Toxin: BURPS1106A_2639 | 9225 | >Antitoxin: BURPS1106A_2638 |
| 3682 | >Toxin: Rsph17025_0402 | 9226 | >Antitoxin: Rsph17025_0403 |
| 3683 | >Toxin: Glov_0758 | 9227 | >Antitoxin: Glov_0759 |
| 3684 | >Toxin: PSPTO_0935 | 9228 | >Antitoxin: PSPTO_0936 |
| 3685 | >Toxin: Psyr_0803 | 9229 | >Antitoxin: Psyr_0804 |
| 3686 | >Toxin: Psyc_0758 | 9230 | >Antitoxin: Psyc_0757 |
| 3687 | >Toxin: Noc_1003 | 9231 | >Antitoxin: Noc_1004 |
| 3688 | >Toxin: Bcep18194_B0278 | 9232 | >Antitoxin: Bcep18194_B0277 |
| 3689 | >Toxin: Rru_A0901 | 9233 | >Antitoxin: Rru_A0900 |
| 3690 | >Toxin: Ping_1268 | 9234 | >Antitoxin: Ping_1269 |
| 3691 | >Toxin: Pnap_4659 | 9235 | >Antitoxin: Pnap_4660 |
| 3692 | >Toxin: PsycPRwf_0082 | 9236 | >Antitoxin: PsycPRwf_0083 |
| 3693 | >Toxin: YpsIP31758_3791 | 9237 | >Antitoxin: YpsIP31758_3792 |
| 3694 | >Toxin: YpAngola_A0660 | 9238 | >Antitoxin: YpAngola_A0659 |
| 3695 | >Toxin: YPK_3879 | 9239 | >Antitoxin: YPK_3880 |
| 3696 | >Toxin: ECH74115_1348 | 9240 | >Antitoxin: ECH74115_1347 |
| 3697 | >Toxin: Tbd_0567 | 9241 | >Antitoxin: Tbd_0566 |
| 3698 | >Toxin: Mmc1_3717 | 9242 | >Antitoxin: Mmc1_3716 |
| 3699 | >Toxin: Pden_4150 | 9243 | >Antitoxin: Pden_4151 |
| 3700 | >Toxin: Pnuc_1157 | 9244 | >Antitoxin: Pnuc_1156 |
| 3701 | >Toxin: Rsph17025_3918 | 9245 | >Antitoxin: Rsph17025_3917 |
| 3702 | >Toxin: BBta_3671 | 9246 | >Antitoxin: BBta_3672 |
| 3703 | >Toxin: Dshi_2807 | 9247 | >Antitoxin: Dshi_2806 |
| 3704 | >Toxin: Mpop_4156 | 9248 | >Antitoxin: Mpop_4157 |
| 3705 | >Toxin: Mnod_7668 | 9249 | >Antitoxin: Mnod_7669 |
| 3706 | >Toxin: YpsIP31758_1279 | 9250 | >Antitoxin: YpsIP31758_1280 |
| 3707 | >Toxin: Spro_3465 | 9251 | >Antitoxin: Spro_3464 |
| 3708 | >Toxin: YpAngola_A2785 | 9252 | >Antitoxin: YpAngola_A2784 |
| 3709 | >Toxin: YPK_1392 | 9253 | >Antitoxin: YPK_1393 |
| 3710 | >Toxin: Dd703_3212 | 9254 | >Antitoxin: Dd703_3211 |
| 3711 | >Toxin: Dd1591_3291 | 9255 | >Antitoxin: Dd1591_3290 |
| 3712 | >Toxin: PC1_0756 | 9256 | >Antitoxin: PC1_0757 |
| 3713 | >Toxin: Dde_0128 | 9257 | >Antitoxin: Dde_0127 |
| 3714 | >Toxin: Rfer_3566 | 9258 | >Antitoxin: Rfer_3565 |
| 3715 | >Toxin: RPC_4427 | 9259 | >Antitoxin: RPC_4426 |
| 3716 | >Toxin: Rmet_2589 | 9260 | >Antitoxin: Rmet_2590 |
| 3717 | >Toxin: Bcen_1535 | 9261 | >Antitoxin: Bcen_1534 |
| 3718 | >Toxin: Rxyl_2989 | 9262 | >Antitoxin: Rxyl_2988 |
| 3719 | >Toxin: Moth_0726 | 9263 | >Antitoxin: Moth_0727 |
| 3720 | >Toxin: Bcen2424_6294 | 9264 | >Antitoxin: Bcen2424_6295 |
| 3721 | >Toxin: Bmul_6106 | 9265 | >Antitoxin: Bmul_6107 |
| 3722 | >Toxin: Bcenmc03_6953 | 9266 | >Antitoxin: Bcenmc03_6954 |
| 3723 | >Toxin: BamMC406_5964 | 9267 | >Antitoxin: BamMC406_5963 |
| 3724 | >Toxin: Oter_2151 | 9268 | >Antitoxin: Oter_2150 |
| 3725 | >Toxin: Bphy_5836 | 9269 | >Antitoxin: Bphy_5837 |
| 3726 | >Toxin: SNSL254_A0178 | 9270 | >Antitoxin: SNSL254_A0179 |
| 3727 | >Toxin: SeSA_A0181 | 9271 | >Antitoxin: SeSA_A0182 |
| 3728 | >Toxin: SeAg_B0194 | 9272 | >Antitoxin: SeAg_B0195 |
| 3729 | >Toxin: SeD_A0177 | 9273 | >Antitoxin: SeD_A0178 |

TABLE 3-continued

| SEQ ID NO: | Toxin polypeptide sequences designation | SEQ ID NO: | Antitoxin polypeptide sequences designation |
|---|---|---|---|
| 3730 | >Toxin: Mnod_8221 | 9274 | >Antitoxin: Mnod_8220 |
| 3731 | >Toxin: Phep_0524 | 9275 | >Antitoxin: Phep_0523 |
| 3732 | >Toxin: Dd703_0691 | 9276 | >Antitoxin: Dd703_0692 |
| 3733 | >Toxin: Dd1591_0648 | 9277 | >Antitoxin: Dd1591_0649 |
| 3734 | >Toxin: PC1_3536 | 9278 | >Antitoxin: PC1_3535 |
| 3735 | >Toxin: SO_0666 | 9279 | >Antitoxin: SO_0665 |
| 3736 | >Toxin: Mfla_2701 | 9280 | >Antitoxin: Mfla_2702 |
| 3737 | >Toxin: Bpro_3782 | 9281 | >Antitoxin: Bpro_3781 |
| 3738 | >Toxin: VC0395_A0764 | 9282 | >Antitoxin: VC0395_A0765 |
| 3739 | >Toxin: Shew185_2088 | 9283 | >Antitoxin: Shew185_2087 |
| 3740 | >Toxin: Sbal195_2135 | 9284 | >Antitoxin: Sbal195_2134 |
| 3741 | >Toxin: Tgr7_1642 | 9285 | >Antitoxin: Tgr7_1643 |
| 3742 | >Toxin: Avi_3008 | 9286 | >Antitoxin: Avi_3009 |
| 3743 | >Toxin: Dde_0309 | 9287 | >Antitoxin: Dde_0308 |
| 3744 | >Toxin: YpsIP31758_2058 | 9288 | >Antitoxin: YpsIP31758_2057 |
| 3745 | >Toxin: YpAngola_A2450 | 9289 | >Antitoxin: YpAngola_A2449 |
| 3746 | >Toxin: YPK_2170 | 9290 | >Antitoxin: YPK_2169 |
| 3747 | >Toxin: DvMF_2349 | 9291 | >Antitoxin: DvMF_2348 |
| 3748 | >Toxin: Avi_2178 | 9292 | >Antitoxin: Avi_2179 |
| 3749 | >Toxin: Dd703_1873 | 9293 | >Antitoxin: Dd703_1872 |
| 3750 | >Toxin: Dd1591_2093 | 9294 | >Antitoxin: Dd1591_2092 |
| 3751 | >Toxin: Dret_2124 | 9295 | >Antitoxin: Dret_2123 |
| 3752 | >Toxin: Ent638_0215 | 9296 | >Antitoxin: Ent638_0214 |
| 3753 | >Toxin: YpsIP31758_3844 | 9297 | >Antitoxin: YpsIP31758_3845 |
| 3754 | >Toxin: Spro_0292 | 9298 | >Antitoxin: Spro_0291 |
| 3755 | >Toxin: YpAngola_A0464 | 9299 | >Antitoxin: YpAngola_A0463 |
| 3756 | >Toxin: YPK_0356 | 9300 | >Antitoxin: YPK_0355 |
| 3757 | >Toxin: Dd703_3708 | 9301 | >Antitoxin: Dd703_3709 |
| 3758 | >Toxin: Dd1591_3862 | 9302 | >Antitoxin: Dd1591_3863 |
| 3759 | >Toxin: PC1_0224 | 9303 | >Antitoxin: PC1_0223 |
| 3760 | >Toxin: CPS_3479 | 9304 | >Antitoxin: CPS_3478 |
| 3761 | >Toxin: Sden_1676 | 9305 | >Antitoxin: Sden_1677 |
| 3762 | >Toxin: BCl_0426 | 9306 | >Antitoxin: BCl_0425 |
| 3763 | >Toxin: Sbal_2404 | 9307 | >Antitoxin: Sbal_2403 |
| 3764 | >Toxin: Ent638_1631 | 9308 | >Antitoxin: Ent638_1632 |
| 3765 | >Toxin: Sputcn32_2156 | 9309 | >Antitoxin: Sputcn32_2155 |
| 3766 | >Toxin: Shew185_2393 | 9310 | >Antitoxin: Shew185_2392 |
| 3767 | >Toxin: Spea_1545 | 9311 | >Antitoxin: Spea_1546 |
| 3768 | >Toxin: Sbal195_2509 | 9312 | >Antitoxin: Sbal195_2508 |
| 3769 | >Toxin: Sbal223_1954 | 9313 | >Antitoxin: Sbal223_1955 |
| 3770 | >Toxin: Dd1591_1648 | 9314 | >Antitoxin: Dd1591_1649 |
| 3771 | >Toxin: PC1_2477 | 9315 | >Antitoxin: PC1_2476 |
| 3772 | >Toxin: B21_02512 | 9316 | >Antitoxin: B21_02513 |
| 3773 | >Toxin: SO_3428 | 9317 | >Antitoxin: SO_3429 |
| 3774 | >Toxin: GSU0148 | 9318 | >Antitoxin: GSU0147 |
| 3775 | >Toxin: MCA0389 | 9319 | >Antitoxin: MCA0388 |
| 3776 | >Toxin: Noc_0926 | 9320 | >Antitoxin: Noc_0925 |
| 3777 | >Toxin: Pcar_2408 | 9321 | >Antitoxin: Pcar_2407 |
| 3778 | >Toxin: Gmet_0201 | 9322 | >Antitoxin: Gmet_0200 |
| 3779 | >Toxin: Tcr_1590 | 9323 | >Antitoxin: Tcr_1591 |
| 3780 | >Toxin: Mfla_0568 | 9324 | >Antitoxin: Mfla_0569 |
| 3781 | >Toxin: Csal_0625 | 9325 | >Antitoxin: Csal_0624 |
| 3782 | >Toxin: Patl_3015 | 9326 | >Antitoxin: Patl_3016 |
| 3783 | >Toxin: Shewmr7_1198 | 9327 | >Antitoxin: Shewmr7_1197 |
| 3784 | >Toxin: Shewmr4_1127 | 9328 | >Antitoxin: Shewmr4_1126 |
| 3785 | >Toxin: Mlg_1481 | 9329 | >Antitoxin: Mlg_1482 |
| 3786 | >Toxin: Mmc1_0013 | 9330 | >Antitoxin: Mmc1_0012 |
| 3787 | >Toxin: Shewana3_1128 | 9331 | >Antitoxin: Shewana3_1127 |
| 3788 | >Toxin: Ppro_3176 | 9332 | >Antitoxin: Ppro_3177 |
| 3789 | >Toxin: Sama_1048 | 9333 | >Antitoxin: Sama_1047 |
| 3790 | >Toxin: Hhal_1653 | 9334 | >Antitoxin: Hhal_1654 |
| 3791 | >Toxin: Sbal_3115 | 9335 | >Antitoxin: Sbal_3116 |
| 3792 | >Toxin: Shew_1217 | 9336 | >Antitoxin: Shew_1216 |
| 3793 | >Toxin: Ent638_3172 | 9337 | >Antitoxin: Ent638_3173 |
| 3794 | >Toxin: Sputcn32_2745 | 9338 | >Antitoxin: Sputcn32_2746 |
| 3795 | >Toxin: VC0395_A0072 | 9339 | >Antitoxin: VC0395_A0071 |
| 3796 | >Toxin: Gura_0222 | 9340 | >Antitoxin: Gura_0221 |
| 3797 | >Toxin: Shew185_3124 | 9341 | >Antitoxin: Shew185_3125 |
| 3798 | >Toxin: YpsIP31758_3238 | 9342 | >Antitoxin: YpsIP31758_3239 |
| 3799 | >Toxin: VIBHAR_03511 | 9343 | >Antitoxin: VIBHAR_03512 |
| 3800 | >Toxin: EcHS_A2833 | 9344 | >Antitoxin: EcHS_A2834 |
| 3801 | >Toxin: Spro_0843 | 9345 | >Antitoxin: Spro_0842 |
| 3802 | >Toxin: Sbal195_3267 | 9346 | >Antitoxin: Sbal195_3268 |
| 3803 | >Toxin: COXBURSA331_A0883 | 9347 | >Antitoxin: COXBURSA331_A0882 |
| 3804 | >Toxin: EcolC_1015 | 9348 | >Antitoxin: EcolC_1014 |
| 3805 | >Toxin: YPK_3373 | 9349 | >Antitoxin: YPK_3374 |
| 3806 | >Toxin: EcSMS35_2820 | 9350 | >Antitoxin: EcSMS35_2821 |

TABLE 3-continued

| Toxin polypeptide sequences | | Antitoxin polypeptide sequences | |
|---|---|---|---|
| SEQ ID NO: | designation | SEQ ID NO: | designation |
| 3807 | >Toxin: PXO_00147 | 9351 | >Antitoxin: PXO_00148 |
| 3808 | >Toxin: SbBS512_E3180 | 9352 | >Antitoxin: SbBS512_E3179 |
| 3809 | >Toxin: Smal_1478 | 9353 | >Antitoxin: Smal_1477 |
| 3810 | >Toxin: SNSL254_A3029 | 9354 | >Antitoxin: SNSL254_A3030 |
| 3811 | >Toxin: SeHA_C3013 | 9355 | >Antitoxin: SeHA_C3014 |
| 3812 | >Toxin: SeSA_A2978 | 9356 | >Antitoxin: SeSA_A2979 |
| 3813 | >Toxin: MADE_02846 | 9357 | >Antitoxin: MADE_02847 |
| 3814 | >Toxin: Gbem_3633 | 9358 | >Antitoxin: Gbem_3632 |
| 3815 | >Toxin: SeAg_B2946 | 9359 | >Antitoxin: SeAg_B2947 |
| 3816 | >Toxin: Lferr_1052 | 9360 | >Antitoxin: Lferr_1051 |
| 3817 | >Toxin: SeD_A3136 | 9361 | >Antitoxin: SeD_A3137 |
| 3818 | >Toxin: ECH74115_3944 | 9362 | >Antitoxin: ECH74115_3945 |
| 3819 | >Toxin: Sbal223_1250 | 9363 | >Antitoxin: Sbal223_1249 |
| 3820 | >Toxin: AFE_0934 | 9364 | >Antitoxin: AFE_0933 |
| 3821 | >Toxin: Tgr7_1289 | 9365 | >Antitoxin: Tgr7_1288 |
| 3822 | >Toxin: Dd703_0998 | 9366 | >Antitoxin: Dd703_0997 |
| 3823 | >Toxin: Dd1591_0983 | 9367 | >Antitoxin: Dd1591_0982 |
| 3824 | >Toxin: PC1_3211 | 9368 | >Antitoxin: PC1_3212 |
| 3825 | >Toxin: GM21_3738 | 9369 | >Antitoxin: GM21_3737 |
| 3826 | >Toxin: Bpro_1133 | 9370 | >Antitoxin: Bpro_1134 |
| 3827 | >Toxin: Aave_0898 | 9371 | >Antitoxin: Aave_0899 |
| 3828 | >Toxin: Ajs_3581 | 9372 | >Antitoxin: Ajs_3580 |
| 3829 | >Toxin: Pnap_3357 | 9373 | >Antitoxin: Pnap_3356 |
| 3830 | >Toxin: Veis_3024 | 9374 | >Antitoxin: Veis_3023 |
| 3831 | >Toxin: Mpe_A3193 | 9375 | >Antitoxin: Mpe_A3192 |
| 3832 | >Toxin: Dacl_1569 | 9376 | >Antitoxin: Dacl_1570 |
| 3833 | >Toxin: Lcho_3974 | 9377 | >Antitoxin: Lcho_3973 |
| 3834 | >Toxin: Dtpsy_2904 | 9378 | >Antitoxin: Dtpsy_2903 |
| 3835 | >Toxin: Vapar_4629 | 9379 | >Antitoxin: Vapar_4628 |
| 3836 | >Toxin: RSc0670 | 9380 | >Antitoxin: RSc0669 |
| 3837 | >Toxin: PP_4990 | 9381 | >Antitoxin: PP_4991 |
| 3838 | >Toxin: PSPTO_5032 | 9382 | >Antitoxin: PSPTO_5033 |
| 3839 | >Toxin: Psyr_0490 | 9383 | >Antitoxin: Psyr_0489 |
| 3840 | >Toxin: Psyc_1816 | 9384 | >Antitoxin: Psyc_1817 |
| 3841 | >Toxin: Daro_3897 | 9385 | >Antitoxin: Daro_3898 |
| 3842 | >Toxin: Reut_A2621 | 9386 | >Antitoxin: Reut_A2622 |
| 3843 | >Toxin: Tbd_2550 | 9387 | >Antitoxin: Tbd_2551 |
| 3844 | >Toxin: Noc_0129 | 9388 | >Antitoxin: Noc_0130 |
| 3845 | >Toxin: Rfer_1373 | 9389 | >Antitoxin: Rfer_1372 |
| 3846 | >Toxin: Sde_3632 | 9390 | >Antitoxin: Sde_3633 |
| 3847 | >Toxin: Mfla_1244 | 9391 | >Antitoxin: Mfla_1243 |
| 3848 | >Toxin: Bpro_1138 | 9392 | >Antitoxin: Bpro_1137 |
| 3849 | >Toxin: Pcryo_2099 | 9393 | >Antitoxin: Pcryo_2100 |
| 3850 | >Toxin: Rmet_0671 | 9394 | >Antitoxin: Rmet_0670 |
| 3851 | >Toxin: Mlg_0357 | 9395 | >Antitoxin: Mlg_0356 |
| 3852 | >Toxin: PA14_05340 | 9396 | >Antitoxin: PA14_05330 |
| 3853 | >Toxin: Aave_0903 | 9397 | >Antitoxin: Aave_0902 |
| 3854 | >Toxin: Ajs_3576 | 9398 | >Antitoxin: Ajs_3577 |
| 3855 | >Toxin: Pnap_3352 | 9399 | >Antitoxin: Pnap_3353 |
| 3856 | >Toxin: Veis_3019 | 9400 | >Antitoxin: Veis_3020 |
| 3857 | >Toxin: Mpe_A3188 | 9401 | >Antitoxin: Mpe_A3189 |
| 3858 | >Toxin: Maqu_3769 | 9402 | >Antitoxin: Maqu_3768 |
| 3859 | >Toxin: Pmen_0405 | 9403 | >Antitoxin: Pmen_0404 |
| 3860 | >Toxin: Pput_4864 | 9404 | >Antitoxin: Pput_4865 |
| 3861 | >Toxin: PsycPRwf_2157 | 9405 | >Antitoxin: PsycPRwf_2158 |
| 3862 | >Toxin: PSPA7_0510 | 9406 | >Antitoxin: PSPA7_0509 |
| 3863 | >Toxin: Dacl_1574 | 9407 | >Antitoxin: Dacl_1573 |
| 3864 | >Toxin: PputGB1_5040 | 9408 | >Antitoxin: PputGB1_5041 |
| 3865 | >Toxin: PputW619_0474 | 9409 | >Antitoxin: PputW619_0473 |
| 3866 | >Toxin: Lcho_3969 | 9410 | >Antitoxin: Lcho_3970 |
| 3867 | >Toxin: PXO_01604 | 9411 | >Antitoxin: PXO_01603 |
| 3868 | >Toxin: Rpic_0614 | 9412 | >Antitoxin: Rpic_0613 |
| 3869 | >Toxin: Smal_3087 | 9413 | >Antitoxin: Smal_3088 |
| 3870 | >Toxin: Tmz1t_3690 | 9414 | >Antitoxin: Tmz1t_3689 |
| 3871 | >Toxin: Tgr7_2902 | 9415 | >Antitoxin: Tgr7_2903 |
| 3872 | >Toxin: Dtpsy_2899 | 9416 | >Antitoxin: Dtpsy_2900 |
| 3873 | >Toxin: Vapar_4624 | 9417 | >Antitoxin: Vapar_4625 |
| 3874 | >Toxin: Rpic12D_0562 | 9418 | >Antitoxin: Rpic12D_0561 |
| 3875 | >Toxin: Jann_2718 | 9419 | >Antitoxin: Jann_2719 |
| 3876 | >Toxin: TM1040_1520 | 9420 | >Antitoxin: TM1040_1521 |
| 3877 | >Toxin: Rru_A2437 | 9421 | >Antitoxin: Rru_A2438 |
| 3878 | >Toxin: RSP_0193 | 9422 | >Antitoxin: RSP_0194 |
| 3879 | >Toxin: Pden_1269 | 9423 | >Antitoxin: Pden_1268 |
| 3880 | >Toxin: Rsph17029_1826 | 9424 | >Antitoxin: Rsph17029_1827 |
| 3881 | >Toxin: Rsph17025_1452 | 9425 | >Antitoxin: Rsph17025_1451 |
| 3882 | >Toxin: Acry_0172 | 9426 | >Antitoxin: Acry_0171 |
| 3883 | >Toxin: Swit_2553 | 9427 | >Antitoxin: Swit_2554 |

TABLE 3-continued

| Toxin polypeptide sequences | | Antitoxin polypeptide sequences | |
|---|---|---|---|
| SEQ ID NO: | designation | SEQ ID NO: | designation |
| 3884 | >Toxin: Plav__3295 | 9428 | >Antitoxin: Plav__3296 |
| 3885 | >Toxin: Dshi__1392 | 9429 | >Antitoxin: Dshi__1391 |
| 3886 | >Toxin: RSc2588 | 9430 | >Antitoxin: RSc2587 |
| 3887 | >Toxin: BTH_I0808 | 9431 | >Antitoxin: BTH_I0809 |
| 3888 | >Toxin: Rmet__1336 | 9432 | >Antitoxin: Rmet__1337 |
| 3889 | >Toxin: Rmet__1546 | 9433 | >Antitoxin: Rmet__1547 |
| 3890 | >Toxin: Bamb__2000 | 9434 | >Antitoxin: Bamb__2001 |
| 3891 | >Toxin: Shewana3__1278 | 9435 | >Antitoxin: Shewana3__1279 |
| 3892 | >Toxin: Aave__0722 | 9436 | >Antitoxin: Aave__0723 |
| 3893 | >Toxin: Pnap__4191 | 9437 | >Antitoxin: Pnap__4192 |
| 3894 | >Toxin: PSPA7__3710 | 9438 | >Antitoxin: PSPA7__3709 |
| 3895 | >Toxin: PSPA7__3723 | 9439 | >Antitoxin: PSPA7__3722 |
| 3896 | >Toxin: Daci__0442 | 9440 | >Antitoxin: Daci__0441 |
| 3897 | >Toxin: Bmul__2346 | 9441 | >Antitoxin: Bmul__2347 |
| 3898 | >Toxin: Rpic__2641 | 9442 | >Antitoxin: Rpic__2642 |
| 3899 | >Toxin: Tmz1t__2064 | 9443 | >Antitoxin: Tmz1t__2063 |
| 3900 | >Toxin: Tgr7__1891 | 9444 | >Antitoxin: Tgr7__1892 |
| 3901 | >Toxin: Dtpsy__1314 | 9445 | >Antitoxin: Dtpsy__1315 |
| 3902 | >Toxin: Dtpsy__3510 | 9446 | >Antitoxin: Dtpsy__3509 |
| 3903 | >Toxin: Avin__35760 | 9447 | >Antitoxin: Avin__35750 |
| 3904 | >Toxin: Avin__35850 | 9448 | >Antitoxin: Avin__35840 |
| 3905 | >Toxin: CPR__1601 | 9449 | >Antitoxin: CPR__1602 |
| 3906 | >Toxin: Ent638__4115 | 9450 | >Antitoxin: Ent638__4116 |
| 3907 | >Toxin: VC0395__0010 | 9451 | >Antitoxin: VC0395__0011 |
| 3908 | >Toxin: EcHS_A3965 | 9452 | >Antitoxin: EcHS_A3964 |
| 3909 | >Toxin: EcE24377A__4265 | 9453 | >Antitoxin: EcE24377A__4264 |
| 3910 | >Toxin: Spro__4900 | 9454 | >Antitoxin: Spro__4901 |
| 3911 | >Toxin: EcolC__4245 | 9455 | >Antitoxin: EcolC__4246 |
| 3912 | >Toxin: EcSMS35__4117 | 9456 | >Antitoxin: EcSMS35__4116 |
| 3913 | >Toxin: Nther__2687 | 9457 | >Antitoxin: Nther__2688 |
| 3914 | >Toxin: SNSL254_A4165 | 9458 | >Antitoxin: SNSL254_A4164 |
| 3915 | >Toxin: SeSA_A4094 | 9459 | >Antitoxin: SeSA_A4093 |
| 3916 | >Toxin: SeAg_B4109 | 9460 | >Antitoxin: SeAg_B4108 |
| 3917 | >Toxin: SeD_A4274 | 9461 | >Antitoxin: SeD_A4273 |
| 3918 | >Toxin: ECH74115__5185 | 9462 | >Antitoxin: ECH74115__5184 |
| 3919 | >Toxin: Aaci__2279 | 9463 | >Antitoxin: Aaci__2280 |
| 3920 | >Toxin: Adeh__0013 | 9464 | >Antitoxin: Adeh__0014 |
| 3921 | >Toxin: Anae109__0014 | 9465 | >Antitoxin: Anae109__0015 |
| 3922 | >Toxin: Dole__1190 | 9466 | >Antitoxin: Dole__1189 |
| 3923 | >Toxin: AnaeK__0013 | 9467 | >Antitoxin: AnaeK__0014 |
| 3924 | >Toxin: Dtur__0950 | 9468 | >Antitoxin: Dtur__0951 |
| 3925 | >Toxin: A2cp1__0013 | 9469 | >Antitoxin: A2cp1__0014 |
| 3926 | >Toxin: Dbac__0487 | 9470 | >Antitoxin: Dbac__0486 |
| 3927 | >Toxin: Dret__1117 | 9471 | >Antitoxin: Dret__1116 |
| 3928 | >Toxin: Reut_B4429 | 9472 | >Antitoxin: Reut_B4430 |
| 3929 | >Toxin: Noc__1239 | 9473 | >Antitoxin: Noc__1240 |
| 3930 | >Toxin: Pcar__2552 | 9474 | >Antitoxin: Pcar__2553 |
| 3931 | >Toxin: Adeh__0797 | 9475 | >Antitoxin: Adeh__0798 |
| 3932 | >Toxin: Nham__4186 | 9476 | >Antitoxin: Nham__4185 |
| 3933 | >Toxin: Acid345__3002 | 9477 | >Antitoxin: Acid345__3001 |
| 3934 | >Toxin: CHU__2211 | 9478 | >Antitoxin: CHU__2210 |
| 3935 | >Toxin: Fjoh__1636 | 9479 | >Antitoxin: Fjoh__1637 |
| 3936 | >Toxin: RoseRS__4141 | 9480 | >Antitoxin: RoseRS__4142 |
| 3937 | >Toxin: Anae109__0842 | 9481 | >Antitoxin: Anae109__0843 |
| 3938 | >Toxin: Rcas__1464 | 9482 | >Antitoxin: Rcas__1465 |
| 3939 | >Toxin: Mext__0217 | 9483 | >Antitoxin: Mext__0218 |
| 3940 | >Toxin: Mrad2831__6224 | 9484 | >Antitoxin: Mrad2831__6225 |
| 3941 | >Toxin: Oter__3933 | 9485 | >Antitoxin: Oter__3932 |
| 3942 | >Toxin: Mpop__0019 | 9486 | >Antitoxin: Mpop__0020 |
| 3943 | >Toxin: Amuc__1872 | 9487 | >Antitoxin: Amuc__1873 |
| 3944 | >Toxin: AnaeK__0845 | 9488 | >Antitoxin: AnaeK__0846 |
| 3945 | >Toxin: M446__5823 | 9489 | >Antitoxin: M446__5822 |
| 3946 | >Toxin: Gdia__0834 | 9490 | >Antitoxin: Gdia__0833 |
| 3947 | >Toxin: Mchl__0161 | 9491 | >Antitoxin: Mchl__0162 |
| 3948 | >Toxin: A2cp1__0849 | 9492 | >Antitoxin: A2cp1__0850 |
| 3949 | >Toxin: Mnod__6892 | 9493 | >Antitoxin: Mnod__6891 |
| 3950 | >Toxin: Rleg__5954 | 9494 | >Antitoxin: Rleg__5953 |
| 3951 | >Toxin: Phep__0290 | 9495 | >Antitoxin: Phep__0291 |
| 3952 | >Toxin: Dfer__3475 | 9496 | >Antitoxin: Dfer__3474 |
| 3953 | >Toxin: Cagg__3385 | 9497 | >Antitoxin: Cagg__3384 |
| 3954 | >Toxin: Cpin__0527 | 9498 | >Antitoxin: Cpin__0526 |
| 3955 | >Toxin: Arth__2706 | 9499 | >Antitoxin: Arth__2705 |
| 3956 | >Toxin: Noca__1440 | 9500 | >Antitoxin: Noca__1441 |
| 3957 | >Toxin: Strop__0973 | 9501 | >Antitoxin: Strop__0974 |
| 3958 | >Toxin: Franean1__5838 | 9502 | >Antitoxin: Franean1__5837 |
| 3959 | >Toxin: Sare__0910 | 9503 | >Antitoxin: Sare__0911 |
| 3960 | >Toxin: Achl__2437 | 9504 | >Antitoxin: Achl__2436 |

TABLE 3-continued

| Toxin polypeptide sequences | | Antitoxin polypeptide sequences | |
|---|---|---|---|
| SEQ ID NO: | designation | SEQ ID NO: | designation |
| 3961 | >Toxin: Bfae_20600 | 9505 | >Antitoxin: Bfae_20590 |
| 3962 | >Toxin: Mlut_14700 | 9506 | >Antitoxin: Mlut_14690 |
| 3963 | >Toxin: Ksed_08660 | 9507 | >Antitoxin: Ksed_08670 |
| 3964 | >Toxin: Caci_7585 | 9508 | >Antitoxin: Caci_7584 |
| 3965 | >Toxin: Svir_30890 | 9509 | >Antitoxin: Svir_30880 |
| 3966 | >Toxin: Jden_1822 | 9510 | >Antitoxin: Jden_1821 |
| 3967 | >Toxin: Rfer_2071 | 9511 | >Antitoxin: Rfer_2070 |
| 3968 | >Toxin: Bpro_2703 | 9512 | >Antitoxin: Bpro_2704 |
| 3969 | >Toxin: Aave_1588 | 9513 | >Antitoxin: Aave_1587 |
| 3970 | >Toxin: Ajs_3149 | 9514 | >Antitoxin: Ajs_3150 |
| 3971 | >Toxin: Pnap_2537 | 9515 | >Antitoxin: Pnap_2538 |
| 3972 | >Toxin: Veis_4366 | 9516 | >Antitoxin: Veis_4365 |
| 3973 | >Toxin: Mpe_A1578 | 9517 | >Antitoxin: Mpe_A1577 |
| 3974 | >Toxin: Pnuc_0828 | 9518 | >Antitoxin: Pnuc_0827 |
| 3975 | >Toxin: Daci_2856 | 9519 | >Antitoxin: Daci_2855 |
| 3976 | >Toxin: Lcho_1899 | 9520 | >Antitoxin: Lcho_1898 |
| 3977 | >Toxin: Pnec_1011 | 9521 | >Antitoxin: Pnec_1012 |
| 3978 | >Toxin: Dtpsy_2496 | 9522 | >Antitoxin: Dtpsy_2497 |
| 3979 | >Toxin: Vapar_2587 | 9523 | >Antitoxin: Vapar_2586 |
| 3980 | >Toxin: Daro_0008 | 9524 | >Antitoxin: Daro_0007 |
| 3981 | >Toxin: Nmul_A2694 | 9525 | >Antitoxin: Nmul_A2693 |
| 3982 | >Toxin: Sama_2952 | 9526 | >Antitoxin: Sama_2951 |
| 3983 | >Toxin: Hhal_0366 | 9527 | >Antitoxin: Hhal_0365 |
| 3984 | >Toxin: Swoo_3314 | 9528 | >Antitoxin: Swoo_3313 |
| 3985 | >Toxin: DvMF_1096 | 9529 | >Antitoxin: DvMF_1097 |
| 3986 | >Toxin: Tgr7_0082 | 9530 | >Antitoxin: Tgr7_0081 |
| 3987 | >Toxin: Avin_50630 | 9531 | >Antitoxin: Avin_50640 |
| 3988 | >Toxin: BR0817 | 9532 | >Antitoxin: BR0818 |
| 3989 | >Toxin: Nwi_1872 | 9533 | >Antitoxin: Nwi_1871 |
| 3990 | >Toxin: RPB_2589 | 9534 | >Antitoxin: RPB_2590 |
| 3991 | >Toxin: RPC_2419 | 9535 | >Antitoxin: RPC_2420 |
| 3992 | >Toxin: RPD_2870 | 9536 | >Antitoxin: RPD_2869 |
| 3993 | >Toxin: Nham_2205 | 9537 | >Antitoxin: Nham_2204 |
| 3994 | >Toxin: Rru_A1571 | 9538 | >Antitoxin: Rru_A1572 |
| 3995 | >Toxin: Meso_1037 | 9539 | >Antitoxin: Meso_1038 |
| 3996 | >Toxin: Mmar10_1371 | 9540 | >Antitoxin: Mmar10_1372 |
| 3997 | >Toxin: BBta_4546 | 9541 | >Antitoxin: BBta_4545 |
| 3998 | >Toxin: BOV_0812 | 9542 | >Antitoxin: BOV_0813 |
| 3999 | >Toxin: Smed_0905 | 9543 | >Antitoxin: Smed_0906 |
| 4000 | >Toxin: Oant_2408 | 9544 | >Antitoxin: Oant_2407 |
| 4001 | >Toxin: Plav_3211 | 9545 | >Antitoxin: Plav_3210 |
| 4002 | >Toxin: Xaut_4618 | 9546 | >Antitoxin: Xaut_4617 |
| 4003 | >Toxin: Mext_1070 | 9547 | >Antitoxin: Mext_1069 |
| 4004 | >Toxin: Mrad2831_2044 | 9548 | >Antitoxin: Mrad2831_2043 |
| 4005 | >Toxin: Mpop_1004 | 9549 | >Antitoxin: Mpop_1003 |
| 4006 | >Toxin: Rpal_3283 | 9550 | >Antitoxin: Rpal_3282 |
| 4007 | >Toxin: M446_4405 | 9551 | >Antitoxin: M446_4406 |
| 4008 | >Toxin: Rleg2_1276 | 9552 | >Antitoxin: Rleg2_1277 |
| 4009 | >Toxin: Msil_2933 | 9553 | >Antitoxin: Msil_2934 |
| 4010 | >Toxin: Mchl_1199 | 9554 | >Antitoxin: Mchl_1198 |
| 4011 | >Toxin: Mnod_4141 | 9555 | >Antitoxin: Mnod_4142 |
| 4012 | >Toxin: Avi_1731 | 9556 | >Antitoxin: Avi_1733 |
| 4013 | >Toxin: Rleg_1368 | 9557 | >Antitoxin: Rleg_1369 |
| 4014 | >Toxin: PMN2A_1141 | 9558 | >Antitoxin: PMN2A_1140 |
| 4015 | >Toxin: Ava_0994 | 9559 | >Antitoxin: Ava_0993 |
| 4016 | >Toxin: Noc_0362 | 9560 | >Antitoxin: Noc_0361 |
| 4017 | >Toxin: Syncc9902_1940 | 9561 | >Antitoxin: Syncc9902_1941 |
| 4018 | >Toxin: Syncc9605_0390 | 9562 | >Antitoxin: Syncc9605_0389 |
| 4019 | >Toxin: Gmet_1568 | 9563 | >Antitoxin: Gmet_1569 |
| 4020 | >Toxin: Synpcc7942_0158 | 9564 | >Antitoxin: Synpcc7942_0159 |
| 4021 | >Toxin: Nmul_A0972 | 9565 | >Antitoxin: Nmul_A0971 |
| 4022 | >Toxin: Tery_1108 | 9566 | >Antitoxin: Tery_1109 |
| 4023 | >Toxin: Mlg_1160 | 9567 | >Antitoxin: Mlg_1159 |
| 4024 | >Toxin: P9303_22891 | 9568 | >Antitoxin: P9303_22901 |
| 4025 | >Toxin: NATL1_20151 | 9569 | >Antitoxin: NATL1_20141 |
| 4026 | >Toxin: Cthe_2539 | 9570 | >Antitoxin: Cthe_2540 |
| 4027 | >Toxin: Gura_3943 | 9571 | >Antitoxin: Gura_3942 |
| 4028 | >Toxin: P9211_16891 | 9572 | >Antitoxin: P9211_16881 |
| 4029 | >Toxin: Nther_1092 | 9573 | >Antitoxin: Nther_1093 |
| 4030 | >Toxin: Cphamn1_0645 | 9574 | >Antitoxin: Cphamn1_0646 |
| 4031 | >Toxin: Gbem_1980 | 9575 | >Antitoxin: Gbem_1979 |
| 4032 | >Toxin: Dhaf_4109 | 9576 | >Antitoxin: Dhaf_4108 |
| 4033 | >Toxin: Athe_1186 | 9577 | >Antitoxin: Athe_1187 |
| 4034 | >Toxin: GM21_2240 | 9578 | >Antitoxin: GM21_2241 |
| 4035 | >Toxin: Mpal_1141 | 9579 | >Antitoxin: Mpal_1140 |
| 4036 | >Toxin: BCE_3851 | 9580 | >Antitoxin: BCE_3850 |
| 4037 | >Toxin: LMOf2365_1342 | 9581 | >Antitoxin: LMOf2365_1343 |

TABLE 3-continued

| Toxin polypeptide sequences | | Antitoxin polypeptide sequences | |
|---|---|---|---|
| SEQ ID NO: | designation | SEQ ID NO: | designation |
| 4038 | >Toxin: GBAA_3950 | 9582 | >Antitoxin: GBAA_3949 |
| 4039 | >Toxin: BAS3664 | 9583 | >Antitoxin: BAS3663 |
| 4040 | >Toxin: BT9727_3554 | 9584 | >Antitoxin: BT9727_3553 |
| 4041 | >Toxin: BCZK3572 | 9585 | >Antitoxin: BCZK3571 |
| 4042 | >Toxin: Tfu_0778 | 9586 | >Antitoxin: Tfu_0779 |
| 4043 | >Toxin: Pcar_1555 | 9587 | >Antitoxin: Pcar_1556 |
| 4044 | >Toxin: Adeh_1102 | 9588 | >Antitoxin: Adeh_1103 |
| 4045 | >Toxin: Francci3_3562 | 9589 | >Antitoxin: Francci3_3561 |
| 4046 | >Toxin: Acid345_4217 | 9590 | >Antitoxin: Acid345_4216 |
| 4047 | >Toxin: Rxyl_1411 | 9591 | >Antitoxin: Rxyl_1412 |
| 4048 | >Toxin: Sfum_1228 | 9592 | >Antitoxin: Sfum_1229 |
| 4049 | >Toxin: Acel_1515 | 9593 | >Antitoxin: Acel_1514 |
| 4050 | >Toxin: Dvul_2433 | 9594 | >Antitoxin: Dvul_2434 |
| 4051 | >Toxin: Bcer98_2465 | 9595 | >Antitoxin: Bcer98_2464 |
| 4052 | >Toxin: Franean1_1182 | 9596 | >Antitoxin: Franean1_1183 |
| 4053 | >Toxin: Dole_3035 | 9597 | >Antitoxin: Dole_3034 |
| 4054 | >Toxin: Sare_1327 | 9598 | >Antitoxin: Sare_1328 |
| 4055 | >Toxin: BcerKBAB4_3635 | 9599 | >Antitoxin: BcerKBAB4_3634 |
| 4056 | >Toxin: BCAH187_A3860 | 9600 | >Antitoxin: BCAH187_A3859 |
| 4057 | >Toxin: Dtur_1208 | 9601 | >Antitoxin: Dtur_1209 |
| 4058 | >Toxin: BCB4264_A3911 | 9602 | >Antitoxin: BCB4264_A3910 |
| 4059 | >Toxin: BCG9842_B1333 | 9603 | >Antitoxin: BCG9842_B1334 |
| 4060 | >Toxin: DvMF_2513 | 9604 | >Antitoxin: DvMF_2512 |
| 4061 | >Toxin: A2cp1_1230 | 9605 | >Antitoxin: A2cp1_1231 |
| 4062 | >Toxin: Amir_5834 | 9606 | >Antitoxin: Amir_5833 |
| 4063 | >Toxin: Dbac_2414 | 9607 | >Antitoxin: Dbac_2415 |
| 4064 | >Toxin: GWCH70_1155 | 9608 | >Antitoxin: GWCH70_1156 |
| 4065 | >Toxin: Caci_7742 | 9609 | >Antitoxin: Caci_7741 |
| 4066 | >Toxin: Svir_14570 | 9610 | >Antitoxin: Svir_14580 |
| 4067 | >Toxin: Dret_0495 | 9611 | >Antitoxin: Dret_0494 |
| 4068 | >Toxin: Namu_2207 | 9612 | >Antitoxin: Namu_2208 |
| 4069 | >Toxin: Nwi_0373 | 9613 | >Antitoxin: Nwi_0372 |
| 4070 | >Toxin: RPB_0069 | 9614 | >Antitoxin: RPB_0068 |
| 4071 | >Toxin: RPC_0508 | 9615 | >Antitoxin: RPC_0507 |
| 4072 | >Toxin: RPD_0093 | 9616 | >Antitoxin: RPD_0092 |
| 4073 | >Toxin: Nham_0466 | 9617 | >Antitoxin: Nham_0465 |
| 4074 | >Toxin: Mmar10_2381 | 9618 | >Antitoxin: Mmar10_2382 |
| 4075 | >Toxin: BBta_7609 | 9619 | >Antitoxin: BBta_7610 |
| 4076 | >Toxin: Smed_2552 | 9620 | >Antitoxin: Smed_2553 |
| 4077 | >Toxin: Plav_1578 | 9621 | >Antitoxin: Plav_1577 |
| 4078 | >Toxin: Xaut_2019 | 9622 | >Antitoxin: Xaut_2020 |
| 4079 | >Toxin: Caul_0378 | 9623 | >Antitoxin: Caul_0377 |
| 4080 | >Toxin: Bind_0430 | 9624 | >Antitoxin: Bind_0429 |
| 4081 | >Toxin: Rpal_0614 | 9625 | >Antitoxin: Rpal_0615 |
| 4082 | >Toxin: M446_2063 | 9626 | >Antitoxin: M446_2062 |
| 4083 | >Toxin: Rleg2_3582 | 9627 | >Antitoxin: Rleg2_3583 |
| 4084 | >Toxin: Msil_1898 | 9628 | >Antitoxin: Msil_1897 |
| 4085 | >Toxin: Mnod_0448 | 9629 | >Antitoxin: Mnod_0449 |
| 4086 | >Toxin: Avi_4036 | 9630 | >Antitoxin: Avi_4037 |
| 4087 | >Toxin: Rleg_3875 | 9631 | >Antitoxin: Rleg_3876 |
| 4088 | >Toxin: Arth_1982 | 9632 | >Antitoxin: Arth_1981 |
| 4089 | >Toxin: Shew185_0950 | 9633 | >Antitoxin: Shew185_0949 |
| 4090 | >Toxin: Bcer98_2848 | 9634 | >Antitoxin: Bcer98_2847 |
| 4091 | >Toxin: CHAB381_0432 | 9635 | >Antitoxin: CHAB381_0433 |
| 4092 | >Toxin: Sbal195_0985 | 9636 | >Antitoxin: Sbal195_0984 |
| 4093 | >Toxin: Cphy_0848 | 9637 | >Antitoxin: Cphy_0849 |
| 4094 | >Toxin: Sbal223_0971 | 9638 | >Antitoxin: Sbal223_0970 |
| 4095 | >Toxin: Caci_2776 | 9639 | >Antitoxin: Caci_2777 |
| 4096 | >Toxin: Rfer_0220 | 9640 | >Antitoxin: Rfer_0219 |
| 4097 | >Toxin: Bxe_A1422 | 9641 | >Antitoxin: Bxe_A1421 |
| 4098 | >Toxin: Bpro_1628 | 9642 | >Antitoxin: Bpro_1627 |
| 4099 | >Toxin: Pnap_2944 | 9643 | >Antitoxin: Pnap_2945 |
| 4100 | >Toxin: Veis_0732 | 9644 | >Antitoxin: Veis_0731 |
| 4101 | >Toxin: BBta_6640 | 9645 | >Antitoxin: BBta_6641 |
| 4102 | >Toxin: Daci_0074 | 9646 | >Antitoxin: Daci_0075 |
| 4103 | >Toxin: Bphy_1540 | 9647 | >Antitoxin: Bphy_1541 |
| 4104 | >Toxin: Bphyt_2696 | 9648 | >Antitoxin: Bphyt_2697 |
| 4105 | >Toxin: Vapar_0093 | 9649 | >Antitoxin: Vapar_0092 |
| 4106 | >Toxin: Jann_2733 | 9650 | >Antitoxin: Jann_2732 |
| 4107 | >Toxin: TM1040_2312 | 9651 | >Antitoxin: TM1040_2311 |
| 4108 | >Toxin: RSP_1856 | 9652 | >Antitoxin: RSP_1857 |
| 4109 | >Toxin: Pden_0538 | 9653 | >Antitoxin: Pden_0539 |
| 4110 | >Toxin: Rsph17029_0505 | 9654 | >Antitoxin: Rsph17029_0506 |
| 4111 | >Toxin: Rsph17025_0642 | 9655 | >Antitoxin: Rsph17025_0643 |
| 4112 | >Toxin: Dshi_2404 | 9656 | >Antitoxin: Dshi_2403 |
| 4113 | >Toxin: Bpro_3279 | 9657 | >Antitoxin: Bpro_3280 |
| 4114 | >Toxin: Aave_2105 | 9658 | >Antitoxin: Aave_2104 |

TABLE 3-continued

| | Toxin polypeptide sequences | | Antitoxin polypeptide sequences |
|---|---|---|---|
| SEQ ID NO: | designation | SEQ ID NO: | designation |
| 4115 | >Toxin: Ajs_2841 | 9659 | >Antitoxin: Ajs_2842 |
| 4116 | >Toxin: Pnap_1404 | 9660 | >Antitoxin: Pnap_1403 |
| 4117 | >Toxin: Mpe_A2319 | 9661 | >Antitoxin: Mpe_A2320 |
| 4118 | >Toxin: BMA10247_2917 | 9662 | >Antitoxin: BMA10247_2916 |
| 4119 | >Toxin: BURPS668_0556 | 9663 | >Antitoxin: BURPS668_0555 |
| 4120 | >Toxin: BURPS1106A_0571 | 9664 | >Antitoxin: BURPS1106A_0570 |
| 4121 | >Toxin: Pnuc_1002 | 9665 | >Antitoxin: Pnuc_1003 |
| 4122 | >Toxin: Dshi_1669 | 9666 | >Antitoxin: Dshi_1670 |
| 4123 | >Toxin: Daci_2370 | 9667 | >Antitoxin: Daci_2369 |
| 4124 | >Toxin: Dtpsy_2330 | 9668 | >Antitoxin: Dtpsy_2331 |
| 4125 | >Toxin: Vapar_3530 | 9669 | >Antitoxin: Vapar_3531 |
| 4126 | >Toxin: BR0659 | 9670 | >Antitoxin: BR0658 |
| 4127 | >Toxin: Meso_0948 | 9671 | >Antitoxin: Meso_0947 |
| 4128 | >Toxin: BARBAKC583_0471 | 9672 | >Antitoxin: BARBAKC583_0470 |
| 4129 | >Toxin: BOV_0652 | 9673 | >Antitoxin: BOV_0651 |
| 4130 | >Toxin: Smed_0680 | 9674 | >Antitoxin: Smed_0679 |
| 4131 | >Toxin: Oant_2629 | 9675 | >Antitoxin: Oant_2630 |
| 4132 | >Toxin: Rleg2_0996 | 9676 | >Antitoxin: Rleg2_0995 |
| 4133 | >Toxin: Rleg_1149 | 9677 | >Antitoxin: Rleg_1148 |
| 4134 | >Toxin: Reut_A3273 | 9678 | >Antitoxin: Reut_A3274 |
| 4135 | >Toxin: Bcep18194_B3076 | 9679 | >Antitoxin: Bcep18194_B3075 |
| 4136 | >Toxin: Rmet_3438 | 9680 | >Antitoxin: Rmet_3439 |
| 4137 | >Toxin: PputW619_3105 | 9681 | >Antitoxin: PputW619_3106 |
| 4138 | >Toxin: Rpic_3958 | 9682 | >Antitoxin: Rpic_3957 |
| 4139 | >Toxin: Bphyt_4351 | 9683 | >Antitoxin: Bphyt_4352 |
| 4140 | >Toxin: Rpic12D_4071 | 9684 | >Antitoxin: Rpic12D_4070 |
| 4141 | >Toxin: Ent638_2196 | 9685 | >Antitoxin: Ent638_2197 |
| 4142 | >Toxin: VC0395_A1332 | 9686 | >Antitoxin: VC0395_A1333 |
| 4143 | >Toxin: VIBHAR_01574 | 9687 | >Antitoxin: VIBHAR_01573 |
| 4144 | >Toxin: Spro_2657 | 9688 | >Antitoxin: Spro_2658 |
| 4145 | >Toxin: YpAngola_A2304 | 9689 | >Antitoxin: YpAngola_A2305 |
| 4146 | >Toxin: SNSL254_A1841 | 9690 | >Antitoxin: SNSL254_A1842 |
| 4147 | >Toxin: SeHA_C1904 | 9691 | >Antitoxin: SeHA_C1905 |
| 4148 | >Toxin: SeSA_A1846 | 9692 | >Antitoxin: SeSA_A1847 |
| 4149 | >Toxin: SeAg_B1432 | 9693 | >Antitoxin: SeAg_B1431 |
| 4150 | >Toxin: SeD_A1614 | 9694 | >Antitoxin: SeD_A1613 |
| 4151 | >Toxin: Dd703_1924 | 9695 | >Antitoxin: Dd703_1925 |
| 4152 | >Toxin: Dd1591_2162 | 9696 | >Antitoxin: Dd1591_2163 |
| 4153 | >Toxin: PC1_2015 | 9697 | >Antitoxin: PC1_2014 |
| 4154 | >Toxin: B21_03000 | 9698 | >Antitoxin: B21_02999 |
| 4155 | >Toxin: HS_0247 | 9699 | >Antitoxin: HS_0248 |
| 4156 | >Toxin: Ent638_3620 | 9700 | >Antitoxin: Ent638_3619 |
| 4157 | >Toxin: YpsIP31758_3610 | 9701 | >Antitoxin: YpsIP31758_3609 |
| 4158 | >Toxin: EcHS_A3377 | 9702 | >Antitoxin: EcHS_A3376 |
| 4159 | >Toxin: EcE24377A_3669 | 9703 | >Antitoxin: EcE24377A_3668 |
| 4160 | >Toxin: Spro_0475 | 9704 | >Antitoxin: Spro_0476 |
| 4161 | >Toxin: EcolC_0516 | 9705 | >Antitoxin: EcolC_0517 |
| 4162 | >Toxin: EcSMS35_3480 | 9706 | >Antitoxin: EcSMS35_3479 |
| 4163 | >Toxin: SbBS512_E3586 | 9707 | >Antitoxin: SbBS512_E3587 |
| 4164 | >Toxin: SNSL254_A3563 | 9708 | >Antitoxin: SNSL254_A3562 |
| 4165 | >Toxin: SeHA_C3599 | 9709 | >Antitoxin: SeHA_C3598 |
| 4166 | >Toxin: SeSA_A3494 | 9710 | >Antitoxin: SeSA_A3493 |
| 4167 | >Toxin: SeAg_B3492 | 9711 | >Antitoxin: SeAg_B3491 |
| 4168 | >Toxin: ECH74115_4506 | 9712 | >Antitoxin: ECH74115_4505 |
| 4169 | >Toxin: Dd703_3358 | 9713 | >Antitoxin: Dd703_3357 |
| 4170 | >Toxin: Dd1591_3477 | 9714 | >Antitoxin: Dd1591_3476 |
| 4171 | >Toxin: PC1_0560 | 9715 | >Antitoxin: PC1_0561 |
| 4172 | >Toxin: B21_03043 | 9716 | >Antitoxin: B21_03044 |
| 4173 | >Toxin: CPS_4344 | 9717 | >Antitoxin: CPS_4345 |
| 4174 | >Toxin: Sde_3165 | 9718 | >Antitoxin: Sde_3166 |
| 4175 | >Toxin: Csal_2208 | 9719 | >Antitoxin: Csal_2209 |
| 4176 | >Toxin: Maqu_2697 | 9720 | >Antitoxin: Maqu_2698 |
| 4177 | >Toxin: Ent638_3667 | 9721 | >Antitoxin: Ent638_3668 |
| 4178 | >Toxin: VC0395_A0102 | 9722 | >Antitoxin: VC0395_A0101 |
| 4179 | >Toxin: Mmwyl1_2401 | 9723 | >Antitoxin: Mmwyl1_2402 |
| 4180 | >Toxin: YpsIP31758_0458 | 9724 | >Antitoxin: YpsIP31758_0457 |
| 4181 | >Toxin: VIBHAR_00880 | 9725 | >Antitoxin: VIBHAR_00879 |
| 4182 | >Toxin: EcHS_A3421 | 9726 | >Antitoxin: EcHS_A3422 |
| 4183 | >Toxin: EcE24377A_3715 | 9727 | >Antitoxin: EcE24377A_3716 |
| 4184 | >Toxin: Spro_4350 | 9728 | >Antitoxin: Spro_4351 |
| 4185 | >Toxin: YpAngola_A1135 | 9729 | >Antitoxin: YpAngola_A1136 |
| 4186 | >Toxin: EcolC_0474 | 9730 | >Antitoxin: EcolC_0473 |
| 4187 | >Toxin: EcSMS35_3528 | 9731 | >Antitoxin: EcSMS35_3529 |
| 4188 | >Toxin: SbBS512_E3544 | 9732 | >Antitoxin: SbBS512_E3543 |
| 4189 | >Toxin: SNSL254_A3609 | 9733 | >Antitoxin: SNSL254_A3610 |
| 4190 | >Toxin: SeHA_C3644 | 9734 | >Antitoxin: SeHA_C3645 |
| 4191 | >Toxin: SeSA_A3538 | 9735 | >Antitoxin: SeSA_A3539 |

TABLE 3-continued

| SEQ ID NO: | Toxin polypeptide sequences designation | SEQ ID NO: | Antitoxin polypeptide sequences designation |
|---|---|---|---|
| 4192 | >Toxin: SeAg_B3537 | 9736 | >Antitoxin: SeAg_B3538 |
| 4193 | >Toxin: SeD_A3706 | 9737 | >Antitoxin: SeD_A3707 |
| 4194 | >Toxin: VSAL_I2665 | 9738 | >Antitoxin: VSAL_I2666 |
| 4195 | >Toxin: ECH74115_4549 | 9739 | >Antitoxin: ECH74115_4550 |
| 4196 | >Toxin: Dd703_3640 | 9740 | >Antitoxin: Dd703_3641 |
| 4197 | >Toxin: Dd1591_3798 | 9741 | >Antitoxin: Dd1591_3799 |
| 4198 | >Toxin: PC1_0291 | 9742 | >Antitoxin: PC1_0290 |
| 4199 | >Toxin: YpsIP31758_3940 | 9743 | >Antitoxin: YpsIP31758_3939 |
| 4200 | >Toxin: Spro_4576 | 9744 | >Antitoxin: Spro_4575 |
| 4201 | >Toxin: YpAngola_A3697 | 9745 | >Antitoxin: YpAngola_A3696 |
| 4202 | >Toxin: YPK_0256 | 9746 | >Antitoxin: YPK_0257 |
| 4203 | >Toxin: Dd703_0373 | 9747 | >Antitoxin: Dd703_0374 |
| 4204 | >Toxin: Dd1591_0297 | 9748 | >Antitoxin: Dd1591_0298 |
| 4205 | >Toxin: PC1_3849 | 9749 | >Antitoxin: PC1_3848 |
| 4206 | >Toxin: GBAA_2146 | 9750 | >Antitoxin: GBAA_2145 |
| 4207 | >Toxin: BAS1997 | 9751 | >Antitoxin: BAS1996 |
| 4208 | >Toxin: BT9727_1970 | 9752 | >Antitoxin: BT9727_1969 |
| 4209 | >Toxin: BCZK1949 | 9753 | >Antitoxin: BCZK1948 |
| 4210 | >Toxin: Daro_0816 | 9754 | >Antitoxin: Daro_0817 |
| 4211 | >Toxin: Ajs_2839 | 9755 | >Antitoxin: Ajs_2840 |
| 4212 | >Toxin: Veis_2593 | 9756 | >Antitoxin: Veis_2594 |
| 4213 | >Toxin: GSU2198 | 9757 | >Antitoxin: GSU2197 |
| 4214 | >Toxin: Gmet_2296 | 9758 | >Antitoxin: Gmet_2295 |
| 4215 | >Toxin: Dde_2378 | 9759 | >Antitoxin: Dde_2379 |
| 4216 | >Toxin: Acid345_1874 | 9760 | >Antitoxin: Acid345_1875 |
| 4217 | >Toxin: Moth_1112 | 9761 | >Antitoxin: Moth_1111 |
| 4218 | >Toxin: Sfum_0419 | 9762 | >Antitoxin: Sfum_0418 |
| 4219 | >Toxin: Dvul_2004 | 9763 | >Antitoxin: Dvul_2005 |
| 4220 | >Toxin: Gura_3127 | 9764 | >Antitoxin: Gura_3126 |
| 4221 | >Toxin: Dole_2355 | 9765 | >Antitoxin: Dole_2354 |
| 4222 | >Toxin: SYO3AOP1_0820 | 9766 | >Antitoxin: SYO3AOP1_0821 |
| 4223 | >Toxin: Gbem_0761 | 9767 | >Antitoxin: Gbem_0762 |
| 4224 | >Toxin: DvMF_1330 | 9768 | >Antitoxin: DvMF_1331 |
| 4225 | >Toxin: Ddes_1273 | 9769 | >Antitoxin: Ddes_1274 |
| 4226 | >Toxin: Dbac_0582 | 9770 | >Antitoxin: Dbac_0583 |
| 4227 | >Toxin: GM21_0777 | 9771 | >Antitoxin: GM21_0778 |
| 4228 | >Toxin: Dret_1591 | 9772 | >Antitoxin: Dret_1590 |
| 4229 | >Toxin: BR1724 | 9773 | >Antitoxin: BR1725 |
| 4230 | >Toxin: Nwi_2732 | 9774 | >Antitoxin: Nwi_2733 |
| 4231 | >Toxin: RPB_4464 | 9775 | >Antitoxin: RPB_4465 |
| 4232 | >Toxin: RPC_4764 | 9776 | >Antitoxin: RPC_4765 |
| 4233 | >Toxin: RPD_4310 | 9777 | >Antitoxin: RPD_4311 |
| 4234 | >Toxin: Nham_3529 | 9778 | >Antitoxin: Nham_3530 |
| 4235 | >Toxin: Meso_3442 | 9779 | >Antitoxin: Meso_3441 |
| 4236 | >Toxin: Mmar10_2444 | 9780 | >Antitoxin: Mmar10_2445 |
| 4237 | >Toxin: BARBAKC583_0135 | 9781 | >Antitoxin: BARBAKC583_0136 |
| 4238 | >Toxin: BBta_6921 | 9782 | >Antitoxin: BBta_6922 |
| 4239 | >Toxin: BOV_1667 | 9783 | >Antitoxin: BOV_1668 |
| 4240 | >Toxin: Smed_2648 | 9784 | >Antitoxin: Smed_2649 |
| 4241 | >Toxin: Oant_1192 | 9785 | >Antitoxin: Oant_1191 |
| 4242 | >Toxin: Plav_2110 | 9786 | >Antitoxin: Plav_2109 |
| 4243 | >Toxin: Mext_2364 | 9787 | >Antitoxin: Mext_2365 |
| 4244 | >Toxin: Mrad2831_0162 | 9788 | >Antitoxin: Mrad2831_0161 |
| 4245 | >Toxin: Bind_3470 | 9789 | >Antitoxin: Bind_3469 |
| 4246 | >Toxin: Mpop_2320 | 9790 | >Antitoxin: Mpop_2321 |
| 4247 | >Toxin: Rpal_1017 | 9791 | >Antitoxin: Rpal_1016 |
| 4248 | >Toxin: M446_5999 | 9792 | >Antitoxin: M446_6000 |
| 4249 | >Toxin: Rleg2_3234 | 9793 | >Antitoxin: Rleg2_3235 |
| 4250 | >Toxin: Msil_2280 | 9794 | >Antitoxin: Msil_2281 |
| 4251 | >Toxin: Mchl_2641 | 9795 | >Antitoxin: Mchl_2642 |
| 4252 | >Toxin: Mnod_7288 | 9796 | >Antitoxin: Mnod_7287 |
| 4253 | >Toxin: Avi_3642 | 9797 | >Antitoxin: Avi_3640 |
| 4254 | >Toxin: Rleg_3530 | 9798 | >Antitoxin: Rleg_3531 |
| 4255 | >Toxin: Sala_1670 | 9799 | >Antitoxin: Sala_1671 |
| 4256 | >Toxin: Rru_A3324 | 9800 | >Antitoxin: Rru_A3325 |
| 4257 | >Toxin: RSP_0690 | 9801 | >Antitoxin: RSP_0691 |
| 4258 | >Toxin: Rsph17029_2345 | 9802 | >Antitoxin: Rsph17029_2346 |
| 4259 | >Toxin: Smed_5929 | 9803 | >Antitoxin: Smed_5930 |
| 4260 | >Toxin: Oant_0463 | 9804 | >Antitoxin: Oant_0464 |
| 4261 | >Toxin: Xaut_0465 | 9805 | >Antitoxin: Xaut_0464 |
| 4262 | >Toxin: Dshi_0667 | 9806 | >Antitoxin: Dshi_0666 |
| 4263 | >Toxin: Rpal_0014 | 9807 | >Antitoxin: Rpal_0015 |
| 4264 | >Toxin: M446_6713 | 9808 | >Antitoxin: M446_6712 |
| 4265 | >Toxin: Msil_3665 | 9809 | >Antitoxin: Msil_3664 |
| 4266 | >Toxin: Avi_2393 | 9810 | >Antitoxin: Avi_2391 |
| 4267 | >Toxin: Rleg_4956 | 9811 | >Antitoxin: Rleg_4957 |
| 4268 | >Toxin: Mbar_A0098 | 9812 | >Antitoxin: Mbar_A0099 |

TABLE 3-continued

| Toxin polypeptide sequences | | Antitoxin polypeptide sequences | |
|---|---|---|---|
| SEQ ID NO: | designation | SEQ ID NO: | designation |
| 4269 | >Toxin: Mhun_2241 | 9813 | >Antitoxin: Mhun_2242 |
| 4270 | >Toxin: Mbur_0013 | 9814 | >Antitoxin: Mbur_0012 |
| 4271 | >Toxin: Mthe_1716 | 9815 | >Antitoxin: Mthe_1717 |
| 4272 | >Toxin: Tpen_0243 | 9816 | >Antitoxin: Tpen_0244 |
| 4273 | >Toxin: Pisl_0560 | 9817 | >Antitoxin: Pisl_0559 |
| 4274 | >Toxin: Mlab_0093 | 9818 | >Antitoxin: Mlab_0092 |
| 4275 | >Toxin: Memar_0576 | 9819 | >Antitoxin: Memar_0575 |
| 4276 | >Toxin: Pcal_1747 | 9820 | >Antitoxin: Pcal_1748 |
| 4277 | >Toxin: MmarC5_0167 | 9821 | >Antitoxin: MmarC5_0168 |
| 4278 | >Toxin: Pars_1730 | 9822 | >Antitoxin: Pars_1729 |
| 4279 | >Toxin: Msed_0103 | 9823 | >Antitoxin: Msed_0102 |
| 4280 | >Toxin: Mevan_0722 | 9824 | >Antitoxin: Mevan_0721 |
| 4281 | >Toxin: Maeo_1396 | 9825 | >Antitoxin: Maeo_1395 |
| 4282 | >Toxin: MmarC7_0656 | 9826 | >Antitoxin: MmarC7_0655 |
| 4283 | >Toxin: Mboo_0544 | 9827 | >Antitoxin: Mboo_0543 |
| 4284 | >Toxin: Cmaq_1832 | 9828 | >Antitoxin: Cmaq_1833 |
| 4285 | >Toxin: MmarC6_1262 | 9829 | >Antitoxin: MmarC6_1263 |
| 4286 | >Toxin: Nmar_0798 | 9830 | >Antitoxin: Nmar_0799 |
| 4287 | >Toxin: Tneu_1550 | 9831 | >Antitoxin: Tneu_1549 |
| 4288 | >Toxin: Hlac_2437 | 9832 | >Antitoxin: Hlac_2438 |
| 4289 | >Toxin: Huta_2304 | 9833 | >Antitoxin: Huta_2303 |
| 4290 | >Toxin: Mpal_0454 | 9834 | >Antitoxin: Mpal_0453 |
| 4291 | >Toxin: Hmuk_1840 | 9835 | >Antitoxin: Hmuk_1839 |
| 4292 | >Toxin: Moth_1750 | 9836 | >Antitoxin: Moth_1749 |
| 4293 | >Toxin: Daud_1377 | 9837 | >Antitoxin: Daud_1376 |
| 4294 | >Toxin: Nther_1816 | 9838 | >Antitoxin: Nther_1815 |
| 4295 | >Toxin: Dhaf_0220 | 9839 | >Antitoxin: Dhaf_0221 |
| 4296 | >Toxin: Hore_05640 | 9840 | >Antitoxin: Hore_05650 |
| 4297 | >Toxin: Dtox_2395 | 9841 | >Antitoxin: Dtox_2394 |
| 4298 | >Toxin: Aaci_2129 | 9842 | >Antitoxin: Aaci_2128 |
| 4299 | >Toxin: Swol_0491 | 9843 | >Antitoxin: Swol_0492 |
| 4300 | >Toxin: Sfum_0261 | 9844 | >Antitoxin: Sfum_0262 |
| 4301 | >Toxin: Franean1_1571 | 9845 | >Antitoxin: Franean1_1572 |
| 4302 | >Toxin: Glov_0185 | 9846 | >Antitoxin: Glov_0186 |
| 4303 | >Toxin: Mlut_00580 | 9847 | >Antitoxin: Mlut_00590 |
| 4304 | >Toxin: Caci_6429 | 9848 | >Antitoxin: Caci_6430 |
| 4305 | >Toxin: Namu_3589 | 9849 | >Antitoxin: Namu_3588 |
| 4306 | >Toxin: Swol_0979 | 9850 | >Antitoxin: Swol_0978 |
| 4307 | >Toxin: Dred_1882 | 9851 | >Antitoxin: Dred_1883 |
| 4308 | >Toxin: Tpet_0396 | 9852 | >Antitoxin: Tpet_0397 |
| 4309 | >Toxin: Pmob_1380 | 9853 | >Antitoxin: Pmob_1379 |
| 4310 | >Toxin: Daud_0556 | 9854 | >Antitoxin: Daud_0555 |
| 4311 | >Toxin: TRQ2_0412 | 9855 | >Antitoxin: TRQ2_0413 |
| 4312 | >Toxin: Dhaf_2730 | 9856 | >Antitoxin: Dhaf_2731 |
| 4313 | >Toxin: Dtox_2130 | 9857 | >Antitoxin: Dtox_2129 |
| 4314 | >Toxin: Aaci_1489 | 9858 | >Antitoxin: Aaci_1488 |
| 4315 | >Toxin: Rfer_2867 | 9859 | >Antitoxin: Rfer_2868 |
| 4316 | >Toxin: Meso_2435 | 9860 | >Antitoxin: Meso_2436 |
| 4317 | >Toxin: Mlg_2738 | 9861 | >Antitoxin: Mlg_2739 |
| 4318 | >Toxin: Ajs_3127 | 9862 | >Antitoxin: Ajs_3128 |
| 4319 | >Toxin: Mpe_A2221 | 9863 | >Antitoxin: Mpe_A2222 |
| 4320 | >Toxin: Smed_5505 | 9864 | >Antitoxin: Smed_5504 |
| 4321 | >Toxin: Dshi_0628 | 9865 | >Antitoxin: Dshi_0627 |
| 4322 | >Toxin: Mext_2852 | 9866 | >Antitoxin: Mext_2851 |
| 4323 | >Toxin: Mrad2831_6165 | 9867 | >Antitoxin: Mrad2831_6166 |
| 4324 | >Toxin: Mpop_2970 | 9868 | >Antitoxin: Mpop_2969 |
| 4325 | >Toxin: M446_3944 | 9869 | >Antitoxin: M446_3943 |
| 4326 | >Toxin: Mchl_3078 | 9870 | >Antitoxin: Mchl_3077 |
| 4327 | >Toxin: Mnod_3623 | 9871 | >Antitoxin: Mnod_3624 |
| 4328 | >Toxin: Dtpsy_2474 | 9872 | >Antitoxin: Dtpsy_2475 |
| 4329 | >Toxin: Vapar_1590 | 9873 | >Antitoxin: Vapar_1589 |
| 4330 | >Toxin: Mmcs_2235 | 9874 | >Antitoxin: Mmcs_2236 |
| 4331 | >Toxin: Noca_0933 | 9875 | >Antitoxin: Noca_0932 |
| 4332 | >Toxin: Mkms_2282 | 9876 | >Antitoxin: Mkms_2283 |
| 4333 | >Toxin: Mvan_0335 | 9877 | >Antitoxin: Mvan_0334 |
| 4334 | >Toxin: Mjls_2274 | 9878 | >Antitoxin: Mjls_2275 |
| 4335 | >Toxin: Strop_1773 | 9879 | >Antitoxin: Strop_1772 |
| 4336 | >Toxin: Sare_1760 | 9880 | >Antitoxin: Sare_1759 |
| 4337 | >Toxin: Amir_1992 | 9881 | >Antitoxin: Amir_1993 |
| 4338 | >Toxin: Bfae_27580 | 9882 | >Antitoxin: Bfae_27570 |
| 4339 | >Toxin: Caci_4842 | 9883 | >Antitoxin: Caci_4843 |
| 4340 | >Toxin: Svir_11380 | 9884 | >Antitoxin: Svir_11370 |
| 4341 | >Toxin: B21_02992 | 9885 | >Antitoxin: B21_02991 |
| 4342 | >Toxin: BCl_0636 | 9886 | >Antitoxin: BCl_0635 |
| 4343 | >Toxin: Ping_0813 | 9887 | >Antitoxin: Ping_0814 |
| 4344 | >Toxin: Ent638_3610 | 9888 | >Antitoxin: Ent638_3609 |
| 4345 | >Toxin: VC0395_A0168 | 9889 | >Antitoxin: VC0395_A0169 |

TABLE 3-continued

| | Toxin polypeptide sequences | | Antitoxin polypeptide sequences |
|---|---|---|---|
| SEQ ID NO: | designation | SEQ ID NO: | designation |
| 4346 | >Toxin: YpsIP31758__3600 | 9890 | >Antitoxin: YpsIP31758__3599 |
| 4347 | >Toxin: VIBHAR__03402 | 9891 | >Antitoxin: VIBHAR__03401 |
| 4348 | >Toxin: EcHS__A3368 | 9892 | >Antitoxin: EcHS__A3367 |
| 4349 | >Toxin: EcE24377A__3661 | 9893 | >Antitoxin: EcE24377A__3660 |
| 4350 | >Toxin: Spro__0485 | 9894 | >Antitoxin: Spro__0486 |
| 4351 | >Toxin: YpAngola__A3987 | 9895 | >Antitoxin: YpAngola__A3988 |
| 4352 | >Toxin: EcolC__0524 | 9896 | >Antitoxin: EcolC__0525 |
| 4353 | >Toxin: YPK__3734 | 9897 | >Antitoxin: YPK__3733 |
| 4354 | >Toxin: EcSMS35__3472 | 9898 | >Antitoxin: EcSMS35__3471 |
| 4355 | >Toxin: SbBS512__E3594 | 9899 | >Antitoxin: SbBS512__E3595 |
| 4356 | >Toxin: SNSL254__A3553 | 9900 | >Antitoxin: SNSL254__A3552 |
| 4357 | >Toxin: SeHA__C3589 | 9901 | >Antitoxin: SeHA__C3588 |
| 4358 | >Toxin: SeSA__A3483 | 9902 | >Antitoxin: SeSA__A3482 |
| 4359 | >Toxin: SeAg__B3483 | 9903 | >Antitoxin: SeAg__B3482 |
| 4360 | >Toxin: SeD__A3651 | 9904 | >Antitoxin: SeD__A3650 |
| 4361 | >Toxin: VSAL__I0594 | 9905 | >Antitoxin: VSAL__I0595 |
| 4362 | >Toxin: ECH74115__4498 | 9906 | >Antitoxin: ECH74115__4497 |
| 4363 | >Toxin: Avin__42860 | 9907 | >Antitoxin: Avin__42850 |
| 4364 | >Toxin: Dd703__3350 | 9908 | >Antitoxin: Dd703__3349 |
| 4365 | >Toxin: Dd1591__3469 | 9909 | >Antitoxin: Dd1591__3468 |
| 4366 | >Toxin: PC1__0568 | 9910 | >Antitoxin: PC1__0569 |
| 4367 | >Toxin: BCE__0330 | 9911 | >Antitoxin: BCE__0329 |
| 4368 | >Toxin: GBAA__0301 | 9912 | >Antitoxin: GBAA__0300 |
| 4369 | >Toxin: BAS0288 | 9913 | >Antitoxin: BAS0287 |
| 4370 | >Toxin: CPS__3456 | 9914 | >Antitoxin: CPS__3455 |
| 4371 | >Toxin: Tfu__1437 | 9915 | >Antitoxin: Tfu__1438 |
| 4372 | >Toxin: Saro__3197 | 9916 | >Antitoxin: Saro__3196 |
| 4373 | >Toxin: Dgeo__2423 | 9917 | >Antitoxin: Dgeo__2422 |
| 4374 | >Toxin: Sala__0217 | 9918 | >Antitoxin: Sala__0218 |
| 4375 | >Toxin: Sama__2874 | 9919 | >Antitoxin: Sama__2873 |
| 4376 | >Toxin: Swit__2131 | 9920 | >Antitoxin: Swit__2130 |
| 4377 | >Toxin: Bcer98__0282 | 9921 | >Antitoxin: Bcer98__0281 |
| 4378 | >Toxin: Franean1__0106 | 9922 | >Antitoxin: Franean1__0105 |
| 4379 | >Toxin: BcerKBAB4__0282 | 9923 | >Antitoxin: BcerKBAB4__0281 |
| 4380 | >Toxin: Caul__2841 | 9924 | >Antitoxin: Caul__2840 |
| 4381 | >Toxin: Oter__2237 | 9925 | >Antitoxin: Oter__2236 |
| 4382 | >Toxin: Smal__1106 | 9926 | >Antitoxin: Smal__1105 |
| 4383 | >Toxin: MADE__01581 | 9927 | >Antitoxin: MADE__01582 |
| 4384 | >Toxin: BCAH187__A0374 | 9928 | >Antitoxin: BCAH187__A0373 |
| 4385 | >Toxin: BCB4264__A0347 | 9929 | >Antitoxin: BCB4264__A0346 |
| 4386 | >Toxin: BCG9842__B4973 | 9930 | >Antitoxin: BCG9842__B4974 |
| 4387 | >Toxin: BCAH820__0333 | 9931 | >Antitoxin: BCAH820__0332 |
| 4388 | >Toxin: Dhaf__0786 | 9932 | >Antitoxin: Dhaf__0785 |
| 4389 | >Toxin: Ccel__1361 | 9933 | >Antitoxin: Ccel__1362 |
| 4390 | >Toxin: Amir__1211 | 9934 | >Antitoxin: Amir__1210 |
| 4391 | >Toxin: GWCH70__0387 | 9935 | >Antitoxin: GWCH70__0386 |
| 4392 | >Toxin: Elen__2127 | 9936 | >Antitoxin: Elen__2126 |
| 4393 | >Toxin: Dfer__3657 | 9937 | >Antitoxin: Dfer__3656 |
| 4394 | >Toxin: Cpin__1882 | 9938 | >Antitoxin: Cpin__1881 |
| 4395 | >Toxin: Caci__1922 | 9939 | >Antitoxin: Caci__1923 |
| 4396 | >Toxin: Apre__0211 | 9940 | >Antitoxin: Apre__0210 |
| 4397 | >Toxin: Apar__0055 | 9941 | >Antitoxin: Apar__0056 |
| 4398 | >Toxin: Dtox__2916 | 9942 | >Antitoxin: Dtox__2917 |
| 4399 | >Toxin: Tfu__2052 | 9943 | >Antitoxin: Tfu__2053 |
| 4400 | >Toxin: Cag__0777 | 9944 | >Antitoxin: Cag__0776 |
| 4401 | >Toxin: Francci3__3169 | 9945 | >Antitoxin: Francci3__3170 |
| 4402 | >Toxin: Acel__1257 | 9946 | >Antitoxin: Acel__1258 |
| 4403 | >Toxin: Mflv__3524 | 9947 | >Antitoxin: Mflv__3525 |
| 4404 | >Toxin: Strop__1894 | 9948 | >Antitoxin: Strop__1893 |
| 4405 | >Toxin: TBFG__11676 | 9949 | >Antitoxin: TBFG__11675 |
| 4406 | >Toxin: Franean1__1743 | 9950 | >Antitoxin: Franean1__1742 |
| 4407 | >Toxin: Cphamn1__1332 | 9951 | >Antitoxin: Cphamn1__1333 |
| 4408 | >Toxin: Bcav__2367 | 9952 | >Antitoxin: Bcav__2368 |
| 4409 | >Toxin: Elen__2339 | 9953 | >Antitoxin: Elen__2340 |
| 4410 | >Toxin: Svir__25570 | 9954 | >Antitoxin: Svir__25580 |
| 4411 | >Toxin: Jden__1117 | 9955 | >Antitoxin: Jden__1116 |
| 4412 | >Toxin: Mbar__A3694 | 9956 | >Antitoxin: Mbar__A3695 |
| 4413 | >Toxin: Mhun__0050 | 9957 | >Antitoxin: Mhun__0049 |
| 4414 | >Toxin: Mbur__1179 | 9958 | >Antitoxin: Mbur__1180 |
| 4415 | >Toxin: Mthe__0027 | 9959 | >Antitoxin: Mthe__0026 |
| 4416 | >Toxin: Tpen__0286 | 9960 | >Antitoxin: Tpen__0287 |
| 4417 | >Toxin: Pisl__0703 | 9961 | >Antitoxin: Pisl__0704 |
| 4418 | >Toxin: Mlab__1163 | 9962 | >Antitoxin: Mlab__1164 |
| 4419 | >Toxin: Memar__0312 | 9963 | >Antitoxin: Memar__0311 |
| 4420 | >Toxin: Pcal__2091 | 9964 | >Antitoxin: Pcal__2090 |
| 4421 | >Toxin: MmarC5__0217 | 9965 | >Antitoxin: MmarC5__0218 |
| 4422 | >Toxin: Pars__2321 | 9966 | >Antitoxin: Pars__2320 |

TABLE 3-continued

| | Toxin polypeptide sequences | | Antitoxin polypeptide sequences |
|---|---|---|---|
| SEQ ID NO: | designation | SEQ ID NO: | designation |
| 4423 | >Toxin: Msed_0033 | 9967 | >Antitoxin: Msed_0032 |
| 4424 | >Toxin: Mevan_0671 | 9968 | >Antitoxin: Mevan_0670 |
| 4425 | >Toxin: Maeo_0791 | 9969 | >Antitoxin: Maeo_0792 |
| 4426 | >Toxin: MmarC7_0606 | 9970 | >Antitoxin: MmarC7_0605 |
| 4427 | >Toxin: Mboo_1934 | 9971 | >Antitoxin: Mboo_1935 |
| 4428 | >Toxin: MmarC6_1312 | 9972 | >Antitoxin: MmarC6_1313 |
| 4429 | >Toxin: Nmar_0347 | 9973 | >Antitoxin: Nmar_0346 |
| 4430 | >Toxin: Tneu_1963 | 9974 | >Antitoxin: Tneu_1962 |
| 4431 | >Toxin: Hlac_0107 | 9975 | >Antitoxin: Hlac_0108 |
| 4432 | >Toxin: Huta_0784 | 9976 | >Antitoxin: Huta_0785 |
| 4433 | >Toxin: Mpal_2159 | 9977 | >Antitoxin: Mpal_2158 |
| 4434 | >Toxin: Hmuk_0515 | 9978 | >Antitoxin: Hmuk_0516 |
| 4435 | >Toxin: Daro_2618 | 9979 | >Antitoxin: Daro_2619 |
| 4436 | >Toxin: Ajs_1330 | 9980 | >Antitoxin: Ajs_1331 |
| 4437 | >Toxin: Pnap_4568 | 9981 | >Antitoxin: Pnap_4567 |
| 4438 | >Toxin: Mpe_A1650 | 9982 | >Antitoxin: Mpe_A1651 |
| 4439 | >Toxin: Mpe_A2673 | 9983 | >Antitoxin: Mpe_A2672 |
| 4440 | >Toxin: Daci_1741 | 9984 | >Antitoxin: Daci_1740 |
| 4441 | >Toxin: Lcho_0143 | 9985 | >Antitoxin: Lcho_0142 |
| 4442 | >Toxin: Tmz1t_2383 | 9986 | >Antitoxin: Tmz1t_2384 |
| 4443 | >Toxin: Dtpsy_1143 | 9987 | >Antitoxin: Dtpsy_1144 |
| 4444 | >Toxin: Avin_18560 | 9988 | >Antitoxin: Avin_18550 |
| 4445 | >Toxin: Tfu_2917 | 9989 | >Antitoxin: Tfu_2916 |
| 4446 | >Toxin: Francci3_0254 | 9990 | >Antitoxin: Francci3_0255 |
| 4447 | >Toxin: Mmcs_2811 | 9991 | >Antitoxin: Mmcs_2810 |
| 4448 | >Toxin: Arth_1620 | 9992 | >Antitoxin: Arth_1621 |
| 4449 | >Toxin: Mkms_2855 | 9993 | >Antitoxin: Mkms_2854 |
| 4450 | >Toxin: Mvan_3088 | 9994 | >Antitoxin: Mvan_3087 |
| 4451 | >Toxin: Mjls_2838 | 9995 | >Antitoxin: Mjls_2837 |
| 4452 | >Toxin: Mflv_3358 | 9996 | >Antitoxin: Mflv_3357 |
| 4453 | >Toxin: Strop_0824 | 9997 | >Antitoxin: Strop_0825 |
| 4454 | >Toxin: TBFG_11873 | 9998 | >Antitoxin: TBFG_11874 |
| 4455 | >Toxin: Franean1_6582 | 9999 | >Antitoxin: Franean1_6581 |
| 4456 | >Toxin: Sare_0768 | 10000 | >Antitoxin: Sare_0769 |
| 4457 | >Toxin: Achl_1614 | 10001 | >Antitoxin: Achl_1615 |
| 4458 | >Toxin: Ksed_01850 | 10002 | >Antitoxin: Ksed_01860 |
| 4459 | >Toxin: Caci_0306 | 10003 | >Antitoxin: Caci_0305 |
| 4460 | >Toxin: Svir_37270 | 10004 | >Antitoxin: Svir_37280 |
| 4461 | >Toxin: Namu_3765 | 10005 | >Antitoxin: Namu_3766 |
| 4462 | >Toxin: Syncc9605_2124 | 10006 | >Antitoxin: Syncc9605_2125 |
| 4463 | >Toxin: Rru_A3295 | 10007 | >Antitoxin: Rru_A3294 |
| 4464 | >Toxin: P9515_15031 | 10008 | >Antitoxin: P9515_15041 |
| 4465 | >Toxin: P9301_15281 | 10009 | >Antitoxin: P9301_15291 |
| 4466 | >Toxin: RoseRS_3359 | 10010 | >Antitoxin: RoseRS_3358 |
| 4467 | >Toxin: Mboo_1484 | 10011 | >Antitoxin: Mboo_1485 |
| 4468 | >Toxin: Rcas_4148 | 10012 | >Antitoxin: Rcas_4149 |
| 4469 | >Toxin: Shewana3_2170 | 10013 | >Antitoxin: Shewana3_2169 |
| 4470 | >Toxin: Veis_0272 | 10014 | >Antitoxin: Veis_0273 |
| 4471 | >Toxin: Shew185_2063 | 10015 | >Antitoxin: Shew185_2064 |
| 4472 | >Toxin: VIBHAR_02966 | 10016 | >Antitoxin: VIBHAR_02965 |
| 4473 | >Toxin: Sbal195_2110 | 10017 | >Antitoxin: Sbal195_2111 |
| 4474 | >Toxin: SeHA_C1627 | 10018 | >Antitoxin: SeHA_C1628 |
| 4475 | >Toxin: SeSA_A1555 | 10019 | >Antitoxin: SeSA_A1556 |
| 4476 | >Toxin: SeD_A1885 | 10020 | >Antitoxin: SeD_A1884 |
| 4477 | >Toxin: SO_0503 | 10021 | >Antitoxin: SO_0502 |
| 4478 | >Toxin: CPS_2452 | 10022 | >Antitoxin: CPS_2453 |
| 4479 | >Toxin: Jann_3654 | 10023 | >Antitoxin: Jann_3653 |
| 4480 | >Toxin: TM1040_0158 | 10024 | >Antitoxin: TM1040_0157 |
| 4481 | >Toxin: Sfri_2516 | 10025 | >Antitoxin: Sfri_2515 |
| 4482 | >Toxin: Shewana3_2338 | 10026 | >Antitoxin: Shewana3_2337 |
| 4483 | >Toxin: Sputcn32_3823 | 10027 | >Antitoxin: Sputcn32_3822 |
| 4484 | >Toxin: VIBHAR_05267 | 10028 | >Antitoxin: VIBHAR_05266 |
| 4485 | >Toxin: EcE24377A_3989 | 10029 | >Antitoxin: EcE24377A_3987 |
| 4486 | >Toxin: Dshi_0586 | 10030 | >Antitoxin: Dshi_0587 |
| 4487 | >Toxin: Swoo_1498 | 10031 | >Antitoxin: Swoo_1499 |
| 4488 | >Toxin: EcSMS35_A0147 | 10032 | >Antitoxin: EcSMS35_A0148 |
| 4489 | >Toxin: EcSMS35_3797 | 10033 | >Antitoxin: EcSMS35_3796 |
| 4490 | >Toxin: BR0925 | 10034 | >Antitoxin: BR0924 |
| 4491 | >Toxin: Nwi_1669 | 10035 | >Antitoxin: Nwi_1670 |
| 4492 | >Toxin: RPB_3001 | 10036 | >Antitoxin: RPB_3002 |
| 4493 | >Toxin: Jann_1716 | 10037 | >Antitoxin: Jann_1715 |
| 4494 | >Toxin: RPC_2847 | 10038 | >Antitoxin: RPC_2848 |
| 4495 | >Toxin: RPD_2449 | 10039 | >Antitoxin: RPD_2448 |
| 4496 | >Toxin: Nham_2333 | 10040 | >Antitoxin: Nham_2334 |
| 4497 | >Toxin: TM1040_1092 | 10041 | >Antitoxin: TM1040_1091 |
| 4498 | >Toxin: Meso_1786 | 10042 | >Antitoxin: Meso_1787 |
| 4499 | >Toxin: RSP_2972 | 10043 | >Antitoxin: RSP_2973 |

TABLE 3-continued

| Toxin polypeptide sequences | | Antitoxin polypeptide sequences | |
|---|---|---|---|
| SEQ ID NO: | designation | SEQ ID NO: | designation |
| 4500 | >Toxin: Mmar10_1307 | 10044 | >Antitoxin: Mmar10_1306 |
| 4501 | >Toxin: Rsph17029_1618 | 10045 | >Antitoxin: Rsph17029_1619 |
| 4502 | >Toxin: Rsph17025_1851 | 10046 | >Antitoxin: Rsph17025_1852 |
| 4503 | >Toxin: BBta_3957 | 10047 | >Antitoxin: BBta_3956 |
| 4504 | >Toxin: BOV_0919 | 10048 | >Antitoxin: BOV_0918 |
| 4505 | >Toxin: Smed_1474 | 10049 | >Antitoxin: Smed_1475 |
| 4506 | >Toxin: Oant_2261 | 10050 | >Antitoxin: Oant_2262 |
| 4507 | >Toxin: Plav_3269 | 10051 | >Antitoxin: Plav_3270 |
| 4508 | >Toxin: Xaut_4196 | 10052 | >Antitoxin: Xaut_4195 |
| 4509 | >Toxin: Dshi_1179 | 10053 | >Antitoxin: Dshi_1178 |
| 4510 | >Toxin: Mext_2985 | 10054 | >Antitoxin: Mext_2984 |
| 4511 | >Toxin: Mrad2831_1807 | 10055 | >Antitoxin: Mrad2831_1808 |
| 4512 | >Toxin: Bind_0013 | 10056 | >Antitoxin: Bind_0012 |
| 4513 | >Toxin: Mpop_3169 | 10057 | >Antitoxin: Mpop_3168 |
| 4514 | >Toxin: Rpal_2735 | 10058 | >Antitoxin: Rpal_2734 |
| 4515 | >Toxin: M446_5848 | 10059 | >Antitoxin: M446_5847 |
| 4516 | >Toxin: Rleg2_1909 | 10060 | >Antitoxin: Rleg2_1910 |
| 4517 | >Toxin: Msil_1618 | 10061 | >Antitoxin: Msil_1619 |
| 4518 | >Toxin: Mchl_3211 | 10062 | >Antitoxin: Mchl_3210 |
| 4519 | >Toxin: Mnod_6053 | 10063 | >Antitoxin: Mnod_6052 |
| 4520 | >Toxin: Avi_1887 | 10064 | >Antitoxin: Avi_1886 |
| 4521 | >Toxin: Rleg_2116 | 10065 | >Antitoxin: Rleg_2117 |
| 4522 | >Toxin: Tfu_2015 | 10066 | >Antitoxin: Tfu_2014 |
| 4523 | >Toxin: Franccl3_1639 | 10067 | >Antitoxin: Franccl3_1640 |
| 4524 | >Toxin: Mmcs_2406 | 10068 | >Antitoxin: Mmcs_2407 |
| 4525 | >Toxin: Rxyl_2003 | 10069 | >Antitoxin: Rxyl_2002 |
| 4526 | >Toxin: Arth_2089 | 10070 | >Antitoxin: Arth_2090 |
| 4527 | >Toxin: Noca_2532 | 10071 | >Antitoxin: Noca_2533 |
| 4528 | >Toxin: Mkms_2452 | 10072 | >Antitoxin: Mkms_2453 |
| 4529 | >Toxin: Mvan_2705 | 10073 | >Antitoxin: Mvan_2706 |
| 4530 | >Toxin: Mjls_2446 | 10074 | >Antitoxin: Mjls_2447 |
| 4531 | >Toxin: Mflv_3708 | 10075 | >Antitoxin: Mflv_3707 |
| 4532 | >Toxin: Strop_3096 | 10076 | >Antitoxin: Strop_3095 |
| 4533 | >Toxin: Franean1_2065 | 10077 | >Antitoxin: Franean1_2066 |
| 4534 | >Toxin: Sare_3323 | 10078 | >Antitoxin: Sare_3322 |
| 4535 | >Toxin: BLD_0433 | 10079 | >Antitoxin: BLD_0434 |
| 4536 | >Toxin: Achl_1830 | 10080 | >Antitoxin: Achl_1831 |
| 4537 | >Toxin: Afer_0851 | 10081 | >Antitoxin: Afer_0852 |
| 4538 | >Toxin: Amir_5197 | 10082 | >Antitoxin: Amir_5196 |
| 4539 | >Toxin: Bcav_2169 | 10083 | >Antitoxin: Bcav_2168 |
| 4540 | >Toxin: Bfae_15220 | 10084 | >Antitoxin: Bfae_15230 |
| 4541 | >Toxin: Mlut_11370 | 10085 | >Antitoxin: Mlut_11380 |
| 4542 | >Toxin: Ksed_13130 | 10086 | >Antitoxin: Ksed_13140 |
| 4543 | >Toxin: Caci_5606 | 10087 | >Antitoxin: Caci_5605 |
| 4544 | >Toxin: Svir_15890 | 10088 | >Antitoxin: Svir_15900 |
| 4545 | >Toxin: Jden_1258 | 10089 | >Antitoxin: Jden_1259 |
| 4546 | >Toxin: Apar_0922 | 10090 | >Antitoxin: Apar_0921 |
| 4547 | >Toxin: Namu_2802 | 10091 | >Antitoxin: Namu_2803 |
| 4548 | >Toxin: BRA0605 | 10092 | >Antitoxin: BRA0606 |
| 4549 | >Toxin: Nwi_1713 | 10093 | >Antitoxin: Nwi_1714 |
| 4550 | >Toxin: RPB_2418 | 10094 | >Antitoxin: RPB_2417 |
| 4551 | >Toxin: RPC_2238 | 10095 | >Antitoxin: RPC_2237 |
| 4552 | >Toxin: RPD_3034 | 10096 | >Antitoxin: RPD_3035 |
| 4553 | >Toxin: Nham_2438 | 10097 | >Antitoxin: Nham_2439 |
| 4554 | >Toxin: Meso_1353 | 10098 | >Antitoxin: Meso_1352 |
| 4555 | >Toxin: BBta_4734 | 10099 | >Antitoxin: BBta_4735 |
| 4556 | >Toxin: BOV_A0570 | 10100 | >Antitoxin: BOV_A0571 |
| 4557 | >Toxin: Smed_0931 | 10101 | >Antitoxin: Smed_0930 |
| 4558 | >Toxin: Oant_3672 | 10102 | >Antitoxin: Oant_3673 |
| 4559 | >Toxin: Plav_2830 | 10103 | >Antitoxin: Plav_2829 |
| 4560 | >Toxin: Xaut_3864 | 10104 | >Antitoxin: Xaut_3863 |
| 4561 | >Toxin: Mext_2380 | 10105 | >Antitoxin: Mext_2381 |
| 4562 | >Toxin: Mrad2831_3572 | 10106 | >Antitoxin: Mrad2831_3573 |
| 4563 | >Toxin: Mpop_2337 | 10107 | >Antitoxin: Mpop_2338 |
| 4564 | >Toxin: Rpal_3536 | 10108 | >Antitoxin: Rpal_3537 |
| 4565 | >Toxin: M446_6672 | 10109 | >Antitoxin: M446_6673 |
| 4566 | >Toxin: Rleg2_1294 | 10110 | >Antitoxin: Rleg2_1293 |
| 4567 | >Toxin: Mchl_2657 | 10111 | >Antitoxin: Mchl_2658 |
| 4568 | >Toxin: Mnod_7411 | 10112 | >Antitoxin: Mnod_7412 |
| 4569 | >Toxin: Avi_1755 | 10113 | >Antitoxin: Avi_1754 |
| 4570 | >Toxin: Rleg_1386 | 10114 | >Antitoxin: Rleg_1385 |
| 4571 | >Toxin: Tery_4376 | 10115 | >Antitoxin: Tery_4375 |
| 4572 | >Toxin: Dtur_0871 | 10116 | >Antitoxin: Dtur_0872 |
| 4573 | >Toxin: Cyan7425_2516 | 10117 | >Antitoxin: Cyan7425_2517 |
| 4574 | >Toxin: Elen_2553 | 10118 | >Antitoxin: Elen_2552 |
| 4575 | >Toxin: Ccur_05120 | 10119 | >Antitoxin: Ccur_05130 |
| 4576 | >Toxin: Shel_07820 | 10120 | >Antitoxin: Shel_07830 |

TABLE 3-continued

| SEQ ID NO: | Toxin polypeptide sequences designation | SEQ ID NO: | Antitoxin polypeptide sequences designation |
|---|---|---|---|
| 4577 | >Toxin: Apar_0459 | 10121 | >Antitoxin: Apar_0460 |
| 4578 | >Toxin: Moth_1329 | 10122 | >Antitoxin: Moth_1330 |
| 4579 | >Toxin: Swol_1344 | 10123 | >Antitoxin: Swol_1345 |
| 4580 | >Toxin: Cthe_0714 | 10124 | >Antitoxin: Cthe_0713 |
| 4581 | >Toxin: Dred_1154 | 10125 | >Antitoxin: Dred_1153 |
| 4582 | >Toxin: Daud_1178 | 10126 | >Antitoxin: Daud_1179 |
| 4583 | >Toxin: Nther_1638 | 10127 | >Antitoxin: Nther_1639 |
| 4584 | >Toxin: Emin_0546 | 10128 | >Antitoxin: Emin_0545 |
| 4585 | >Toxin: Dhaf_3385 | 10129 | >Antitoxin: Dhaf_3386 |
| 4586 | >Toxin: GWCH70_2169 | 10130 | >Antitoxin: GWCH70_2170 |
| 4587 | >Toxin: Apre_1019 | 10131 | >Antitoxin: Apre_1020 |
| 4588 | >Toxin: Dtox_2102 | 10132 | >Antitoxin: Dtox_2101 |
| 4589 | >Toxin: Aaci_1703 | 10133 | >Antitoxin: Aaci_1704 |
| 4590 | >Toxin: Dde_1453 | 10134 | >Antitoxin: Dde_1452 |
| 4591 | >Toxin: Sfum_2116 | 10135 | >Antitoxin: Sfum_2117 |
| 4592 | >Toxin: Dvul_1964 | 10136 | >Antitoxin: Dvul_1965 |
| 4593 | >Toxin: Anae109_2310 | 10137 | >Antitoxin: Anae109_2309 |
| 4594 | >Toxin: Dole_1983 | 10138 | >Antitoxin: Dole_1982 |
| 4595 | >Toxin: DvMF_0908 | 10139 | >Antitoxin: DvMF_0909 |
| 4596 | >Toxin: Ddes_0761 | 10140 | >Antitoxin: Ddes_0760 |
| 4597 | >Toxin: Dbac_0507 | 10141 | >Antitoxin: Dbac_0508 |
| 4598 | >Toxin: Dret_2197 | 10142 | >Antitoxin: Dret_2196 |
| 4599 | >Toxin: RSp1366 | 10143 | >Antitoxin: RS02091 |
| 4600 | >Toxin: Rfer_3196 | 10144 | >Antitoxin: Rfer_3197 |
| 4601 | >Toxin: Rmet_4919 | 10145 | >Antitoxin: Rmet_4918 |
| 4602 | >Toxin: Ajs_1142 | 10146 | >Antitoxin: Ajs_1141 |
| 4603 | >Toxin: Rpic_4057 | 10147 | >Antitoxin: Rpic_4058 |
| 4604 | >Toxin: Dtpsy_1063 | 10148 | >Antitoxin: Dtpsy_1062 |
| 4605 | >Toxin: Rpic12D_4169 | 10149 | >Antitoxin: Rpic12D_4170 |
| 4606 | >Toxin: Nham_4673 | 10150 | >Antitoxin: Nham_4674 |
| 4607 | >Toxin: Smed_5395 | 10151 | >Antitoxin: Smed_5394 |
| 4608 | >Toxin: Mrad2831_6101 | 10152 | >Antitoxin: Mrad2831_6102 |
| 4609 | >Toxin: Mchl_5573 | 10153 | >Antitoxin: Mchl_5574 |
| 4610 | >Toxin: Avi_8129 | 10154 | >Antitoxin: Avi_8130 |
| 4611 | >Toxin: Avi_9187 | 10155 | >Antitoxin: Avi_9188 |
| 4612 | >Toxin: Rleg_5516 | 10156 | >Antitoxin: Rleg_5515 |
| 4613 | >Toxin: Bpro_4159 | 10157 | >Antitoxin: Bpro_4158 |
| 4614 | >Toxin: Aave_4353 | 10158 | >Antitoxin: Aave_4352 |
| 4615 | >Toxin: Ajs_3761 | 10159 | >Antitoxin: Ajs_3760 |
| 4616 | >Toxin: Pnap_0473 | 10160 | >Antitoxin: Pnap_0474 |
| 4617 | >Toxin: Mpe_A3358 | 10161 | >Antitoxin: Mpe_A3357 |
| 4618 | >Toxin: Daci_5972 | 10162 | >Antitoxin: Daci_5971 |
| 4619 | >Toxin: Dtpsy_3042 | 10163 | >Antitoxin: Dtpsy_3041 |
| 4620 | >Toxin: Vapar_4721 | 10164 | >Antitoxin: Vapar_4720 |
| 4621 | >Toxin: Nwi_1134 | 10165 | >Antitoxin: Nwi_1135 |
| 4622 | >Toxin: RPB_3775 | 10166 | >Antitoxin: RPB_3774 |
| 4623 | >Toxin: Jann_4196 | 10167 | >Antitoxin: Jann_4195 |
| 4624 | >Toxin: RPD_1695 | 10168 | >Antitoxin: RPD_1696 |
| 4625 | >Toxin: Nham_1394 | 10169 | >Antitoxin: Nham_1395 |
| 4626 | >Toxin: TM1040_2963 | 10170 | >Antitoxin: TM1040_2962 |
| 4627 | >Toxin: Rru_A2824 | 10171 | >Antitoxin: Rru_A2823 |
| 4628 | >Toxin: RSP_1329 | 10172 | >Antitoxin: RSP_1328 |
| 4629 | >Toxin: Pden_2112 | 10173 | >Antitoxin: Pden_2113 |
| 4630 | >Toxin: Rsph17029_2990 | 10174 | >Antitoxin: Rsph17029_2989 |
| 4631 | >Toxin: Rsph17025_2602 | 10175 | >Antitoxin: Rsph17025_2603 |
| 4632 | >Toxin: Acry_2132 | 10176 | >Antitoxin: Acry_2131 |
| 4633 | >Toxin: BBta_5495 | 10177 | >Antitoxin: BBta_5494 |
| 4634 | >Toxin: Plav_2572 | 10178 | >Antitoxin: Plav_2573 |
| 4635 | >Toxin: Dshi_3249 | 10179 | >Antitoxin: Dshi_3250 |
| 4636 | >Toxin: Rpal_4409 | 10180 | >Antitoxin: Rpal_4408 |
| 4637 | >Toxin: Gdia_3440 | 10181 | >Antitoxin: Gdia_3441 |
| 4638 | >Toxin: Mnod_5536 | 10182 | >Antitoxin: Mnod_5535 |
| 4639 | >Toxin: Moth_0849 | 10183 | >Antitoxin: Moth_0848 |
| 4640 | >Toxin: Swol_0832 | 10184 | >Antitoxin: Swol_0831 |
| 4641 | >Toxin: Cthe_0444 | 10185 | >Antitoxin: Cthe_0443 |
| 4642 | >Toxin: Dred_0683 | 10186 | >Antitoxin: Dred_0682 |
| 4643 | >Toxin: Haur_3503 | 10187 | >Antitoxin: Haur_3504 |
| 4644 | >Toxin: Teth514_2004 | 10188 | >Antitoxin: Teth514_2005 |
| 4645 | >Toxin: Ccel_2065 | 10189 | >Antitoxin: Ccel_2066 |
| 4646 | >Toxin: GWCH70_1027 | 10190 | >Antitoxin: GWCH70_1026 |
| 4647 | >Toxin: Dtox_1063 | 10191 | >Antitoxin: Dtox_1062 |
| 4648 | >Toxin: Aaci_1287 | 10192 | >Antitoxin: Aaci_1286 |
| 4649 | >Toxin: Teth514_1606 | 10193 | >Antitoxin: Teth514_1605 |
| 4650 | >Toxin: SYO3AOP1_1148 | 10194 | >Antitoxin: SYO3AOP1_1147 |
| 4651 | >Toxin: Dtur_1158 | 10195 | >Antitoxin: Dtur_1157 |
| 4652 | >Toxin: Athe_1327 | 10196 | >Antitoxin: Athe_1326 |
| 4653 | >Toxin: Afer_1349 | 10197 | >Antitoxin: Afer_1350 |

TABLE 3-continued

| | Toxin polypeptide sequences | | Antitoxin polypeptide sequences |
|---|---|---|---|
| SEQ ID NO: | designation | SEQ ID NO: | designation |
| 4654 | >Toxin: Elen__1335 | 10198 | >Antitoxin: Elen__1334 |
| 4655 | >Toxin: Ccur__06870 | 10199 | >Antitoxin: Ccur__06860 |
| 4656 | >Toxin: Shel__09680 | 10200 | >Antitoxin: Shel__09670 |
| 4657 | >Toxin: Pcar__1442 | 10201 | >Antitoxin: Pcar__1443 |
| 4658 | >Toxin: Dde__2432 | 10202 | >Antitoxin: Dde__2433 |
| 4659 | >Toxin: Moth__2390 | 10203 | >Antitoxin: Moth__2389 |
| 4660 | >Toxin: Swol 2392 | 10204 | >Antitoxin: Swol__2391 |
| 4661 | >Toxin: Dvul__1854 | 10205 | >Antitoxin: Dvul__1855 |
| 4662 | >Toxin: Dred__3162 | 10206 | >Antitoxin: Dred__3161 |
| 4663 | >Toxin: Dole__2082 | 10207 | >Antitoxin: Dole__2081 |
| 4664 | >Toxin: DvMF__3097 | 10208 | >Antitoxin: DvMF__3096 |
| 4665 | >Toxin: Ddes__1617 | 10209 | >Antitoxin: Ddes__1618 |
| 4666 | >Toxin: Dbac__0064 | 10210 | >Antitoxin: Dbac__0063 |
| 4667 | >Toxin: Dtox__4177 | 10211 | >Antitoxin: Dtox__4176 |
| 4668 | >Toxin: Dret__1418 | 10212 | >Antitoxin: Dret__1419 |
| 4669 | >Toxin: RSc2583 | 10213 | >Antitoxin: RSc2582 |
| 4670 | >Toxin: Saro__0317 | 10214 | >Antitoxin: Saro__0316 |
| 4671 | >Toxin: RPC__3540 | 10215 | >Antitoxin: RPC__3539 |
| 4672 | >Toxin: RPC__3900 | 10216 | >Antitoxin: RPC__3899 |
| 4673 | >Toxin: Rmet__1342 | 10217 | >Antitoxin: Rmet__1343 |
| 4674 | >Toxin: Rmet__1551 | 10218 | >Antitoxin: Rmet__1552 |
| 4675 | >Toxin: Sala__2613 | 10219 | >Antitoxin: Sala__2612 |
| 4676 | >Toxin: Rru__A0807 | 10220 | >Antitoxin: Rru__A0806 |
| 4677 | >Toxin: Meso__0508 | 10221 | >Antitoxin: Meso__0507 |
| 4678 | >Toxin: Meso__2323 | 10222 | >Antitoxin: Meso__2322 |
| 4679 | >Toxin: Meso__3852 | 10223 | >Antitoxin: Meso__3853 |
| 4680 | >Toxin: Bamb__2005 | 10224 | >Antitoxin: Bamb__2006 |
| 4681 | >Toxin: Shewana3__1283 | 10225 | >Antitoxin: Shewana3__1284 |
| 4682 | >Toxin: Pden__1483 | 10226 | >Antitoxin: Pden__1482 |
| 4683 | >Toxin: Pden__3195 | 10227 | >Antitoxin: Pden__3196 |
| 4684 | >Toxin: Aave__0727 | 10228 | >Antitoxin: Aave__0728 |
| 4685 | >Toxin: Ajs__2910 | 10229 | >Antitoxin: Ajs__2909 |
| 4686 | >Toxin: Pnap__4196 | 10230 | >Antitoxin: Pnap__4197 |
| 4687 | >Toxin: BBta__1501 | 10231 | >Antitoxin: BBta__1502 |
| 4688 | >Toxin: BBta__7441 | 10232 | >Antitoxin: BBta__7442 |
| 4689 | >Toxin: BBta__7742 | 10233 | >Antitoxin: BBta__7743 |
| 4690 | >Toxin: Swit__3692 | 10234 | >Antitoxin: Swit__3693 |
| 4691 | >Toxin: PSPA7__3705 | 10235 | >Antitoxin: PSPA7__3704 |
| 4692 | >Toxin: Oant__3213 | 10236 | >Antitoxin: Oant__3214 |
| 4693 | >Toxin: Plav__3542 | 10237 | >Antitoxin: Plav__3543 |
| 4694 | >Toxin: Xaut__0596 | 10238 | >Antitoxin: Xaut__0597 |
| 4695 | >Toxin: Xaut__0748 | 10239 | >Antitoxin: Xaut__0747 |
| 4696 | >Toxin: Xaut__2879 | 10240 | >Antitoxin: Xaut__2880 |
| 4697 | >Toxin: Xaut__3003 | 10241 | >Antitoxin: Xaut__3002 |
| 4698 | >Toxin: Xaut__3999 | 10242 | >Antitoxin: Xaut__3998 |
| 4699 | >Toxin: Daci__0437 | 10243 | >Antitoxin: Daci__0436 |
| 4700 | >Toxin: Daci__2698 | 10244 | >Antitoxin: Daci__2697 |
| 4701 | >Toxin: Bmul__2351 | 10245 | >Antitoxin: Bmul__2352 |
| 4702 | >Toxin: Caul__2028 | 10246 | >Antitoxin: Caul__2029 |
| 4703 | >Toxin: Caul__3828 | 10247 | >Antitoxin: Caul__3829 |
| 4704 | >Toxin: Mpop__3087 | 10248 | >Antitoxin: Mpop__3088 |
| 4705 | >Toxin: Rpic__2646 | 10249 | >Antitoxin: Rpic__2647 |
| 4706 | >Toxin: Paes__2347 | 10250 | >Antitoxin: Paes__2348 |
| 4707 | >Toxin: Gdia__1012 | 10251 | >Antitoxin: Gdia__1011 |
| 4708 | >Toxin: Gdia__2825 | 10252 | >Antitoxin: Gdia__2826 |
| 4709 | >Toxin: Tgr7__1896 | 10253 | >Antitoxin: Tgr7__1897 |
| 4710 | >Toxin: Avi__9659 | 10254 | >Antitoxin: Avi__9658 |
| 4711 | >Toxin: Dtpsy__3505 | 10255 | >Antitoxin: Dtpsy__3504 |
| 4712 | >Toxin: Avin__35710 | 10256 | >Antitoxin: Avin__35700 |
| 4713 | >Toxin: GM21__2350 | 10257 | >Antitoxin: GM21__2349 |
| 4714 | >Toxin: BCE__A0182 | 10258 | >Antitoxin: BCE__A0183 |
| 4715 | >Toxin: GBAA__3860 | 10259 | >Antitoxin: GBAA__3861 |
| 4716 | >Toxin: BAS3576 | 10260 | >Antitoxin: BAS3577 |
| 4717 | >Toxin: BT9727__3476 | 10261 | >Antitoxin: BT9727__3477 |
| 4718 | >Toxin: BCZK3488 | 10262 | >Antitoxin: BCZK3489 |
| 4719 | >Toxin: Tfu__0951 | 10263 | >Antitoxin: Tfu__0952 |
| 4720 | >Toxin: Nmul__A2277 | 10264 | >Antitoxin: Nmul__42278 |
| 4721 | >Toxin: Adeh__3496 | 10265 | >Antitoxin: Adeh__3495 |
| 4722 | >Toxin: Rxyl__0131 | 10266 | >Antitoxin: Rxyl__0132 |
| 4723 | >Toxin: Mlg__0323 | 10267 | >Antitoxin: Mlg__0324 |
| 4724 | >Toxin: Mlg__0325 | 10268 | >Antitoxin: Mlg__0324 |
| 4725 | >Toxin: Arth__4098 | 10269 | >Antitoxin: Arth__4097 |
| 4726 | >Toxin: Acel__1651 | 10270 | >Antitoxin: Acel__1650 |
| 4727 | >Toxin: Mvan__3669 | 10271 | >Antitoxin: Mvan__3668 |
| 4728 | >Toxin: Dred__2140 | 10272 | >Antitoxin: Dred__2141 |
| 4729 | >Toxin: Strop__0446 | 10273 | >Antitoxin: Strop__0445 |
| 4730 | >Toxin: Krad__4588 | 10274 | >Antitoxin: Krad__4587 |

TABLE 3-continued

| SEQ ID NO: | Toxin polypeptide sequences designation | SEQ ID NO: | Antitoxin polypeptide sequences designation |
|---|---|---|---|
| 4731 | >Toxin: Bcer98_0518 | 10275 | >Antitoxin: Bcer98_0517 |
| 4732 | >Toxin: Sare_0534 | 10276 | >Antitoxin: Sare_0533 |
| 4733 | >Toxin: BcerKBAB4_3497 | 10277 | >Antitoxin: BcerKBAB4_3498 |
| 4734 | >Toxin: AnaeK_3584 | 10278 | >Antitoxin: AnaeK_3583 |
| 4735 | >Toxin: BCAH187_A3780 | 10279 | >Antitoxin: BCAH187_A3781 |
| 4736 | >Toxin: BCB4264_A3830 | 10280 | >Antitoxin: BCB4264_A3831 |
| 4737 | >Toxin: BCG9842_B1471 | 10281 | >Antitoxin: BCG9842_B1470 |
| 4738 | >Toxin: BCAH820_3742 | 10282 | >Antitoxin: BCAH820_3743 |
| 4739 | >Toxin: BCAH820_B0280 | 10283 | >Antitoxin: BCAH820_B0279 |
| 4740 | >Toxin: Achl_3872 | 10284 | >Antitoxin: Achl_3871 |
| 4741 | >Toxin: A2cp1_3653 | 10285 | >Antitoxin: A2cp1_3652 |
| 4742 | >Toxin: Bcav_4020 | 10286 | >Antitoxin: Bcav_4021 |
| 4743 | >Toxin: Bcav_4022 | 10287 | >Antitoxin: Bcav_4021 |
| 4744 | >Toxin: GWCH70_1801 | 10288 | >Antitoxin: GWCH70_1802 |
| 4745 | >Toxin: Mlut_21360 | 10289 | >Antitoxin: Mlut_21350 |
| 4746 | >Toxin: Ksed_10590 | 10290 | >Antitoxin: Ksed_10580 |
| 4747 | >Toxin: Elen_1553 | 10291 | >Antitoxin: Elen_1552 |
| 4748 | >Toxin: Cagg_3412 | 10292 | >Antitoxin: Cagg_3411 |
| 4749 | >Toxin: Ccur_11220 | 10293 | >Antitoxin: Ccur_11230 |
| 4750 | >Toxin: Svir_36750 | 10294 | >Antitoxin: Svir_36760 |
| 4751 | >Toxin: Apre_0987 | 10295 | >Antitoxin: Apre_0988 |
| 4752 | >Toxin: Jden_2500 | 10296 | >Antitoxin: Jden_2499 |
| 4753 | >Toxin: Shel_01260 | 10297 | >Antitoxin: Shel_01250 |
| 4754 | >Toxin: Apar_0439 | 10298 | >Antitoxin: Apar_0438 |
| 4755 | >Toxin: Dtox_2078 | 10299 | >Antitoxin: Dtox_2077 |
| 4756 | >Toxin: Aaci_1113 | 10300 | >Antitoxin: Aaci_1112 |
| 4757 | >Toxin: Aaci_2657 | 10301 | >Antitoxin: Aaci_2658 |
| 4758 | >Toxin: Moth_0866 | 10302 | >Antitoxin: Moth_0865 |
| 4759 | >Toxin: Swol_0964 | 10303 | >Antitoxin: Swol_0963 |
| 4760 | >Toxin: Teth514_1858 | 10304 | >Antitoxin: Teth514_1859 |
| 4761 | >Toxin: Daud_1351 | 10305 | >Antitoxin: Daud_1352 |
| 4762 | >Toxin: Nther_1322 | 10306 | >Antitoxin: Nther_1321 |
| 4763 | >Toxin: Dhaf_4024 | 10307 | >Antitoxin: Dhaf_4025 |
| 4764 | >Toxin: Hore_09300 | 10308 | >Antitoxin: Hore_09290 |
| 4765 | >Toxin: Ccel_1852 | 10309 | >Antitoxin: Ccel_1853 |
| 4766 | >Toxin: Athe_1363 | 10310 | >Antitoxin: Athe_1362 |
| 4767 | >Toxin: Dtox_1126 | 10311 | >Antitoxin: Dtox_1125 |
| 4768 | >Toxin: Aaci_1300 | 10312 | >Antitoxin: Aaci_1299 |
| 4769 | >Toxin: Francci3_0449 | 10313 | >Antitoxin: Francci3_0448 |
| 4770 | >Toxin: Mmcs_4529 | 10314 | >Antitoxin: Mmcs_4528 |
| 4771 | >Toxin: Noca_4230 | 10315 | >Antitoxin: Noca_4231 |
| 4772 | >Toxin: Mkms_4616 | 10316 | >Antitoxin: Mkms_4615 |
| 4773 | >Toxin: Mvan_5101 | 10317 | >Antitoxin: Mvan_5100 |
| 4774 | >Toxin: Mjls_4912 | 10318 | >Antitoxin: Mjls_4911 |
| 4775 | >Toxin: Mflv_1646 | 10319 | >Antitoxin: Mflv_1647 |
| 4776 | >Toxin: Franean1_6169 | 10320 | >Antitoxin: Franean1_6170 |
| 4777 | >Toxin: Amir_6828 | 10321 | >Antitoxin: Amir_6827 |
| 4778 | >Toxin: Svir_37710 | 10322 | >Antitoxin: Svir_37700 |
| 4779 | >Toxin: Cthe_0333 | 10323 | >Antitoxin: Cthe_0334 |
| 4780 | >Toxin: Tpet_1428 | 10324 | >Antitoxin: Tpet_1429 |
| 4781 | >Toxin: Cphy_3800 | 10325 | >Antitoxin: Cphy_3799 |
| 4782 | >Toxin: Teth514_2147 | 10326 | >Antitoxin: Teth514_2146 |
| 4783 | >Toxin: TRQ2_1474 | 10327 | >Antitoxin: TRQ2_1475 |
| 4784 | >Toxin: Nther_0091 | 10328 | >Antitoxin: Nther_0092 |
| 4785 | >Toxin: Dtur_0910 | 10329 | >Antitoxin: Dtur_0911 |
| 4786 | >Toxin: Athe_1290 | 10330 | >Antitoxin: Athe_1291 |
| 4787 | >Toxin: Dtox_0180 | 10331 | >Antitoxin: Dtox_0179 |
| 4788 | >Toxin: BRA0158 | 10332 | >Antitoxin: BRA0159 |
| 4789 | >Toxin: RPC_1101 | 10333 | >Antitoxin: RPC_1102 |
| 4790 | >Toxin: Meso_0291 | 10334 | >Antitoxin: Meso_0290 |
| 4791 | >Toxin: BARBAKC583_1137 | 10335 | >Antitoxin: BARBAKC583_1136 |
| 4792 | >Toxin: BOV_A0142 | 10336 | >Antitoxin: BOV_A0143 |
| 4793 | >Toxin: Smed_0262 | 10337 | >Antitoxin: Smed_0263 |
| 4794 | >Toxin: Oant_4205 | 10338 | >Antitoxin: Oant_4204 |
| 4795 | >Toxin: Mext_0625 | 10339 | >Antitoxin: Mext_0626 |
| 4796 | >Toxin: Mrad2831_1685 | 10340 | >Antitoxin: Mrad2831_1684 |
| 4797 | >Toxin: Bind_3649 | 10341 | >Antitoxin: Bind_3648 |
| 4798 | >Toxin: Mpop_0603 | 10342 | >Antitoxin: Mpop_0604 |
| 4799 | >Toxin: Rleg2_0324 | 10343 | >Antitoxin: Rleg2_0325 |
| 4800 | >Toxin: Msil_0031 | 10344 | >Antitoxin: Msil_0032 |
| 4801 | >Toxin: Mchl_0636 | 10345 | >Antitoxin: Mchl_0637 |
| 4802 | >Toxin: Avi_0744 | 10346 | >Antitoxin: Avi_0745 |
| 4803 | >Toxin: Rleg_0356 | 10347 | >Antitoxin: Rleg_0357 |
| 4804 | >Toxin: Rfer_0565 | 10348 | >Antitoxin: Rfer_0566 |
| 4805 | >Toxin: Aave_4380 | 10349 | >Antitoxin: Aave_4379 |
| 4806 | >Toxin: Ajs_3792 | 10350 | >Antitoxin: Ajs_3791 |
| 4807 | >Toxin: Veis_2178 | 10351 | >Antitoxin: Veis_2177 |

TABLE 3-continued

| SEQ ID NO: | Toxin polypeptide sequences designation | SEQ ID NO: | Antitoxin polypeptide sequences designation |
|---|---|---|---|
| 4808 | >Toxin: Mpe_A0583 | 10352 | >Antitoxin: Mpe_A0584 |
| 4809 | >Toxin: Daci_0653 | 10353 | >Antitoxin: Daci_0654 |
| 4810 | >Toxin: Lcho_1597 | 10354 | >Antitoxin: Lcho_1598 |
| 4811 | >Toxin: Dtpsy_3066 | 10355 | >Antitoxin: Dtpsy_3065 |
| 4812 | >Toxin: BMAA0399 | 10356 | >Antitoxin: BMAA0400 |
| 4813 | >Toxin: BURPS1710b_A1204 | 10357 | >Antitoxin: BURPS1710b_A1203 |
| 4814 | >Toxin: Bcep18194_B1592 | 10358 | >Antitoxin: Bcep18194_B1591 |
| 4815 | >Toxin: BTH_II0254 | 10359 | >Antitoxin: BTH_II0255 |
| 4816 | >Toxin: Jann_3035 | 10360 | >Antitoxin: Jann_3036 |
| 4817 | >Toxin: Sde_1522 | 10361 | >Antitoxin: Sde_1521 |
| 4818 | >Toxin: RSP_3487 | 10362 | >Antitoxin: RSP_3488 |
| 4819 | >Toxin: Sfri_2373 | 10363 | >Antitoxin: Sfri_2372 |
| 4820 | >Toxin: PA14_00910 | 10364 | >Antitoxin: PA14_00900 |
| 4821 | >Toxin: Pden_2453 | 10365 | >Antitoxin: Pden_2454 |
| 4822 | >Toxin: Aave_1473 | 10366 | >Antitoxin: Aave_1474 |
| 4823 | >Toxin: BMASAVP1_1593 | 10367 | >Antitoxin: BMASAVP1_1594 |
| 4824 | >Toxin: Rsph17029_3131 | 10368 | >Antitoxin: Rsph17029_3132 |
| 4825 | >Toxin: BMA10247_A0448 | 10369 | >Antitoxin: BMA10247_A0450 |
| 4826 | >Toxin: BURPS668_A2965 | 10370 | >Antitoxin: BURPS668_A2963 |
| 4827 | >Toxin: BURPS1106A_A2840 | 10371 | >Antitoxin: BURPS1106A_A2838 |
| 4828 | >Toxin: Pmen_2316 | 10372 | >Antitoxin: Pmen_2315 |
| 4829 | >Toxin: Acry_2088 | 10373 | >Antitoxin: Acry_2087 |
| 4830 | >Toxin: PSPA7_0148 | 10374 | >Antitoxin: PSPA7_0147 |
| 4831 | >Toxin: Spro_3000 | 10375 | >Antitoxin: Spro_3001 |
| 4832 | >Toxin: Daci_3846 | 10376 | >Antitoxin: Daci_3847 |
| 4833 | >Toxin: Lcho_4057 | 10377 | >Antitoxin: Lcho_4058 |
| 4834 | >Toxin: PXO_00250 | 10378 | >Antitoxin: PXO_00249 |
| 4835 | >Toxin: Msil_2352 | 10379 | >Antitoxin: Msil_2351 |
| 4836 | >Toxin: Mnod_3048 | 10380 | >Antitoxin: Mnod_3049 |
| 4837 | >Toxin: Avi_6041 | 10381 | >Antitoxin: Avi_6040 |
| 4838 | >Toxin: Avin_26710 | 10382 | >Antitoxin: Avin_26700 |
| 4839 | >Toxin: Vapar_0213 | 10383 | >Antitoxin: Vapar_0214 |
| 4840 | >Toxin: Vapar_0516 | 10384 | >Antitoxin: Vapar_0517 |
| 4841 | >Toxin: CPS_4227 | 10385 | >Antitoxin: CPS_4226 |
| 4842 | >Toxin: Reut_B5017 | 10386 | >Antitoxin: Reut_B5016 |
| 4843 | >Toxin: Tbd_0071 | 10387 | >Antitoxin: Tbd_0072 |
| 4844 | >Toxin: PA14_06670 | 10388 | >Antitoxin: PA14_06680 |
| 4845 | >Toxin: Pden_2494 | 10389 | >Antitoxin: Pden_2493 |
| 4846 | >Toxin: Ajs_1906 | 10390 | >Antitoxin: Ajs_1907 |
| 4847 | >Toxin: Maqu_3130 | 10391 | >Antitoxin: Maqu_3129 |
| 4848 | >Toxin: Memar_0876 | 10392 | >Antitoxin: Memar_0877 |
| 4849 | >Toxin: PSPA7_0612 | 10393 | >Antitoxin: PSPA7_0613 |
| 4850 | >Toxin: Mboo_0955 | 10394 | >Antitoxin: Mboo_0956 |
| 4851 | >Toxin: Dshi_3173 | 10395 | >Antitoxin: Dshi_3174 |
| 4852 | >Toxin: Lcho_1448 | 10396 | >Antitoxin: Lcho_1447 |
| 4853 | >Toxin: Tmz1t_2609 | 10397 | >Antitoxin: Tmz1t_2610 |
| 4854 | >Toxin: Dtpsy_1711 | 10398 | >Antitoxin: Dtpsy_1712 |
| 4855 | >Toxin: Mpal_2629 | 10399 | >Antitoxin: Mpal_2628 |
| 4856 | >Toxin: Jann_1701 | 10400 | >Antitoxin: Jann_1702 |
| 4857 | >Toxin: TM1040_1114 | 10401 | >Antitoxin: TM1040_1115 |
| 4858 | >Toxin: RSP_2955 | 10402 | >Antitoxin: RSP_2954 |
| 4859 | >Toxin: Pden_1882 | 10403 | >Antitoxin: Pden_1881 |
| 4860 | >Toxin: Rsph17029_1600 | 10404 | >Antitoxin: Rsph17029_1599 |
| 4861 | >Toxin: Rsph17025_0890 | 10405 | >Antitoxin: Rsph17025_0891 |
| 4862 | >Toxin: Dshi_1737 | 10406 | >Antitoxin: Dshi_1736 |
| 4863 | >Toxin: Tfu_0674 | 10407 | >Antitoxin: Tfu_0675 |
| 4864 | >Toxin: Francci3_3583 | 10408 | >Antitoxin: Francci3_3582 |
| 4865 | >Toxin: Noca_3245 | 10409 | >Antitoxin: Noca_3244 |
| 4866 | >Toxin: Mvan_2207 | 10410 | >Antitoxin: Mvan_2208 |
| 4867 | >Toxin: Mflv_4135 | 10411 | >Antitoxin: Mflv_4134 |
| 4868 | >Toxin: Franean1_1159 | 10412 | >Antitoxin: Franean1_1160 |
| 4869 | >Toxin: Bcav_2509 | 10413 | >Antitoxin: Bcav_2508 |
| 4870 | >Toxin: Bfae_10100 | 10414 | >Antitoxin: Bfae_10110 |
| 4871 | >Toxin: Ksed_11170 | 10415 | >Antitoxin: Ksed_11180 |
| 4872 | >Toxin: Namu_3115 | 10416 | >Antitoxin: Namu_3114 |
| 4873 | >Toxin: SAG1651 | 10417 | >Antitoxin: SAG1652 |
| 4874 | >Toxin: LMOf2365_2675 | 10418 | >Antitoxin: LMOf2365_2676 |
| 4875 | >Toxin: SACOL0708 | 10419 | >Antitoxin: SACOL0709 |
| 4876 | >Toxin: SERP2344 | 10420 | >Antitoxin: SERP2343 |
| 4877 | >Toxin: MCAP_0235 | 10421 | >Antitoxin: MCAP_0236 |
| 4878 | >Toxin: Rxyl_1067 | 10422 | >Antitoxin: Rxyl_1068 |
| 4879 | >Toxin: SaurJH9_0674 | 10423 | >Antitoxin: SaurJH9_0675 |
| 4880 | >Toxin: SaurJH1_0689 | 10424 | >Antitoxin: SaurJH1_0690 |
| 4881 | >Toxin: Teth514_1026 | 10425 | >Antitoxin: Teth514_1027 |
| 4882 | >Toxin: Hlac_1459 | 10426 | >Antitoxin: Hlac_1460 |
| 4883 | >Toxin: Afer_0878 | 10427 | >Antitoxin: Afer_0879 |
| 4884 | >Toxin: Amir_6113 | 10428 | >Antitoxin: Amir_6112 |

TABLE 3-continued

| Toxin polypeptide sequences | | Antitoxin polypeptide sequences | |
|---|---|---|---|
| SEQ ID NO: | designation | SEQ ID NO: | designation |
| 4885 | >Toxin: GWCH70_1343 | 10429 | >Antitoxin: GWCH70_1344 |
| 4886 | >Toxin: Rleg_2433 | 10430 | >Antitoxin: Rleg_2434 |
| 4887 | >Toxin: Cagg_2004 | 10431 | >Antitoxin: Cagg_2005 |
| 4888 | >Toxin: Apre_1081 | 10432 | >Antitoxin: Apre_1082 |
| 4889 | >Toxin: Namu_1660 | 10433 | >Antitoxin: Namu_1661 |
| 4890 | >Toxin: RSc2444 | 10434 | >Antitoxin: RSc2443 |
| 4891 | >Toxin: Ajs_3450 | 10435 | >Antitoxin: Ajs_3449 |
| 4892 | >Toxin: Pnap_3339 | 10436 | >Antitoxin: Pnap_3338 |
| 4893 | >Toxin: Veis_1654 | 10437 | >Antitoxin: Veis_1653 |
| 4894 | >Toxin: Mpe_A2695 | 10438 | >Antitoxin: Mpe_A2694 |
| 4895 | >Toxin: Pnuc_1733 | 10439 | >Antitoxin: Pnuc_1732 |
| 4896 | >Toxin: Daci_1904 | 10440 | >Antitoxin: Daci_1905 |
| 4897 | >Toxin: Lcho_0695 | 10441 | >Antitoxin: Lcho_0694 |
| 4898 | >Toxin: Dtpsy_2777 | 10442 | >Antitoxin: Dtpsy_2776 |
| 4899 | >Toxin: Vapar_4033 | 10443 | >Antitoxin: Vapar_4032 |
| 4900 | >Toxin: Plut_1586 | 10444 | >Antitoxin: Plut_1587 |
| 4901 | >Toxin: Cag_0551 | 10445 | >Antitoxin: Cag_0550 |
| 4902 | >Toxin: CHU_2016 | 10446 | >Antitoxin: CHU_2017 |
| 4903 | >Toxin: Cpha266_0605 | 10447 | >Antitoxin: Cpha266_0604 |
| 4904 | >Toxin: Fjoh_0491 | 10448 | >Antitoxin: Fjoh_0492 |
| 4905 | >Toxin: Clim_1961 | 10449 | >Antitoxin: Clim_1962 |
| 4906 | >Toxin: Cphamn1_0635 | 10450 | >Antitoxin: Cphamn1_0634 |
| 4907 | >Toxin: Ppha_0731 | 10451 | >Antitoxin: Ppha_0730 |
| 4908 | >Toxin: Paes_0590 | 10452 | >Antitoxin: Paes_0589 |
| 4909 | >Toxin: Phep_4088 | 10453 | >Antitoxin: Phep_4089 |
| 4910 | >Toxin: Dfer_4057 | 10454 | >Antitoxin: Dfer_4056 |
| 4911 | >Toxin: Cpin_1428 | 10455 | >Antitoxin: Cpin_1427 |
| 4912 | >Toxin: TM1040_1251 | 10456 | >Antitoxin: TM1040_1250 |
| 4913 | >Toxin: Meso_0178 | 10457 | >Antitoxin: Meso_0179 |
| 4914 | >Toxin: RSP_1412 | 10458 | >Antitoxin: RSP_3802 |
| 4915 | >Toxin: Rsph17029_3482 | 10459 | >Antitoxin: Rsph17029_3481 |
| 4916 | >Toxin: Rsph17025_3687 | 10460 | >Antitoxin: Rsph17025_3686 |
| 4917 | >Toxin: VC0395_A2847 | 10461 | >Antitoxin: VC0395_A2846 |
| 4918 | >Toxin: VIBHAR_00792 | 10462 | >Antitoxin: VIBHAR_00791 |
| 4919 | >Toxin: VSAL_I0355 | 10463 | >Antitoxin: VSAL_I0354 |
| 4920 | >Toxin: Dbac_0032 | 10464 | >Antitoxin: Dbac_0031 |
| 4921 | >Toxin: BR1365 | 10465 | >Antitoxin: BR1366 |
| 4922 | >Toxin: Dde_1190 | 10466 | >Antitoxin: Dde_1191 |
| 4923 | >Toxin: RPC_1951 | 10467 | >Antitoxin: RPC_1950 |
| 4924 | >Toxin: RPC_1959 | 10468 | >Antitoxin: RPC_1960 |
| 4925 | >Toxin: Rru_A3500 | 10469 | >Antitoxin: Rru_A3499 |
| 4926 | >Toxin: RSP_3207 | 10470 | >Antitoxin: RSP_3208 |
| 4927 | >Toxin: Rsph17029_3947 | 10471 | >Antitoxin: Rsph17029_3948 |
| 4928 | >Toxin: Rsph17025_3436 | 10472 | >Antitoxin: Rsph17025_3435 |
| 4929 | >Toxin: BOV_1321 | 10473 | >Antitoxin: BOV_1322 |
| 4930 | >Toxin: Ssed_2093 | 10474 | >Antitoxin: Ssed_2094 |
| 4931 | >Toxin: Dole_2022 | 10475 | >Antitoxin: Dole_2021 |
| 4932 | >Toxin: Ddes_1471 | 10476 | >Antitoxin: Ddes_1472 |
| 4933 | >Toxin: Dbac_3138 | 10477 | >Antitoxin: Dbac_3137 |
| 4934 | >Toxin: Dret_0756 | 10478 | >Antitoxin: Dret_0757 |
| 4935 | >Toxin: Mbar_A3104 | 10479 | >Antitoxin: Mbar_A3103 |
| 4936 | >Toxin: Pcar_2991 | 10480 | >Antitoxin: Pcar_2992 |
| 4937 | >Toxin: Plut_1065 | 10481 | >Antitoxin: Plut_1066 |
| 4938 | >Toxin: Nmul_A1659 | 10482 | >Antitoxin: Nmul_A1658 |
| 4939 | >Toxin: Rfer_1163 | 10483 | >Antitoxin: Rfer_1164 |
| 4940 | >Toxin: Patl_2670 | 10484 | >Antitoxin: Patl_2671 |
| 4941 | >Toxin: Sfri_3051 | 10485 | >Antitoxin: Sfri_3052 |
| 4942 | >Toxin: Ping_0465 | 10486 | >Antitoxin: Ping_0466 |
| 4943 | >Toxin: Pnap_2334 | 10487 | >Antitoxin: Pnap_2333 |
| 4944 | >Toxin: Mmwyl1_1956 | 10488 | >Antitoxin: Mmwyl1_1957 |
| 4945 | >Toxin: Paes_0890 | 10489 | >Antitoxin: Paes_0891 |
| 4946 | >Toxin: Dbac_0950 | 10490 | >Antitoxin: Dbac_0949 |
| 4947 | >Toxin: Reut_B4434 | 10491 | >Antitoxin: Reut_B4433 |
| 4948 | >Toxin: Nham_4181 | 10492 | >Antitoxin: Nham_4182 |
| 4949 | >Toxin: Acid345_2997 | 10493 | >Antitoxin: Acid345_2998 |
| 4950 | >Toxin: M446_5818 | 10494 | >Antitoxin: M446_5819 |
| 4951 | >Toxin: Gdia_0829 | 10495 | >Antitoxin: Gdia_0830 |
| 4952 | >Toxin: Mnod_6887 | 10496 | >Antitoxin: Mnod_6888 |
| 4953 | >Toxin: Cagg_1523 | 10497 | >Antitoxin: Cagg_1524 |
| 4954 | >Toxin: Pcar_0845 | 10498 | >Antitoxin: Pcar_0846 |
| 4955 | >Toxin: Dde_2156 | 10499 | >Antitoxin: Dde_2155 |
| 4956 | >Toxin: Csal_1619 | 10500 | >Antitoxin: Csal_1618 |
| 4957 | >Toxin: CFF8240_0849 | 10501 | >Antitoxin: CFF8240_0848 |
| 4958 | >Toxin: Ping_3346 | 10502 | >Antitoxin: Ping_3345 |
| 4959 | >Toxin: Anae109_0871 | 10503 | >Antitoxin: Anae109_0872 |
| 4960 | >Toxin: Dole_1735 | 10504 | >Antitoxin: Dole_1736 |
| 4961 | >Toxin: AnaeK_1509 | 10505 | >Antitoxin: AnaeK_1510 |

TABLE 3-continued

| | Toxin polypeptide sequences | | Antitoxin polypeptide sequences |
|---|---|---|---|
| SEQ ID NO: | designation | SEQ ID NO: | designation |
| 4962 | >Toxin: A2cp1_1604 | 10506 | >Antitoxin: A2cp1_1605 |
| 4963 | >Toxin: Dret_1657 | 10507 | >Antitoxin: Dret_1656 |
| 4964 | >Toxin: Noc_2709 | 10508 | >Antitoxin: Noc_2708 |
| 4965 | >Toxin: RPC_1184 | 10509 | >Antitoxin: RPC_1183 |
| 4966 | >Toxin: Mvan_1183 | 10510 | >Antitoxin: Mvan_1182 |
| 4967 | >Toxin: Mflv_5149 | 10511 | >Antitoxin: Mflv_5150 |
| 4968 | >Toxin: Franean1_1484 | 10512 | >Antitoxin: Franean1_1485 |
| 4969 | >Toxin: M446_5114 | 10513 | >Antitoxin: M446_5113 |
| 4970 | >Toxin: Amir_5089 | 10514 | >Antitoxin: Amir_5088 |
| 4971 | >Toxin: Nwi_1704 | 10515 | >Antitoxin: Nwi_1703 |
| 4972 | >Toxin: RPB_2386 | 10516 | >Antitoxin: RPB_2387 |
| 4973 | >Toxin: RPC_3334 | 10517 | >Antitoxin: RPC_3333 |
| 4974 | >Toxin: RPD_3068 | 10518 | >Antitoxin: RPD_3067 |
| 4975 | >Toxin: Nham_2426 | 10519 | >Antitoxin: Nham_2425 |
| 4976 | >Toxin: BBta_4785 | 10520 | >Antitoxin: BBta_4784 |
| 4977 | >Toxin: Xaut_4457 | 10521 | >Antitoxin: Xaut_4456 |
| 4978 | >Toxin: Rpal_3566 | 10522 | >Antitoxin: Rpal_3565 |
| 4979 | >Toxin: Nwi_2202 | 10523 | >Antitoxin: Nwi_2201 |
| 4980 | >Toxin: RPB_3675 | 10524 | >Antitoxin: RPB_3674 |
| 4981 | >Toxin: RPC_1634 | 10525 | >Antitoxin: RPC_1635 |
| 4982 | >Toxin: RPD_1785 | 10526 | >Antitoxin: RPD_1786 |
| 4983 | >Toxin: Nham_2604 | 10527 | >Antitoxin: Nham_2603 |
| 4984 | >Toxin: Rxyl_0115 | 10528 | >Antitoxin: Rxyl_0116 |
| 4985 | >Toxin: Meso_1291 | 10529 | >Antitoxin: Meso_1292 |
| 4986 | >Toxin: Acry_0472 | 10530 | >Antitoxin: Acry_0473 |
| 4987 | >Toxin: BBta_5315 | 10531 | >Antitoxin: BBta_5314 |
| 4988 | >Toxin: Smed_1484 | 10532 | >Antitoxin: Smed_1483 |
| 4989 | >Toxin: Plav_2958 | 10533 | >Antitoxin: Plav_2957 |
| 4990 | >Toxin: Rpal_4323 | 10534 | >Antitoxin: Rpal_4322 |
| 4991 | >Toxin: M446_5446 | 10535 | >Antitoxin: M446_5447 |
| 4992 | >Toxin: Mnod_1753 | 10536 | >Antitoxin: Mnod_1754 |
| 4993 | >Toxin: BR0896 | 10537 | >Antitoxin: BR0897 |
| 4994 | >Toxin: BOV_0892 | 10538 | >Antitoxin: BOV_0893 |
| 4995 | >Toxin: Oant_2331 | 10539 | >Antitoxin: Oant_2330 |
| 4996 | >Toxin: CCV52592_1895 | 10540 | >Antitoxin: CCV52592_1894 |
| 4997 | >Toxin: Plav_2660 | 10541 | >Antitoxin: Plav_2659 |
| 4998 | >Toxin: CCC13826_1098 | 10542 | >Antitoxin: CCC13826_1097 |
| 4999 | >Toxin: Ssed_2356 | 10543 | >Antitoxin: Ssed_2355 |
| 5000 | >Toxin: Swoo_2229 | 10544 | >Antitoxin: Swoo_2230 |
| 5001 | >Toxin: M446_2238 | 10545 | >Antitoxin: M446_2239 |
| 5002 | >Toxin: Rleg2_1503 | 10546 | >Antitoxin: Rleg2_1504 |
| 5003 | >Toxin: Mnod_0371 | 10547 | >Antitoxin: Mnod_0370 |
| 5004 | >Toxin: Avi_2480 | 10548 | >Antitoxin: Avi_2479 |
| 5005 | >Toxin: Rleg_1701 | 10549 | >Antitoxin: Rleg_1702 |
| 5006 | >Toxin: DET0050 | 10550 | >Antitoxin: DET0051 |
| 5007 | >Toxin: Tfu_2070 | 10551 | >Antitoxin: Tfu_2069 |
| 5008 | >Toxin: Francci3_3214 | 10552 | >Antitoxin: Francci3_3213 |
| 5009 | >Toxin: Mmcs_2346 | 10553 | >Antitoxin: Mmcs_2347 |
| 5010 | >Toxin: Rxyl_1359 | 10554 | >Antitoxin: Rxyl_1360 |
| 5011 | >Toxin: Arth_2278 | 10555 | >Antitoxin: Arth_2277 |
| 5012 | >Toxin: Acel_1330 | 10556 | >Antitoxin: Acel_1329 |
| 5013 | >Toxin: Noca_2407 | 10557 | >Antitoxin: Noca_2408 |
| 5014 | >Toxin: Mkms_2393 | 10558 | >Antitoxin: Mkms_2394 |
| 5015 | >Toxin: Mvan_2640 | 10559 | >Antitoxin: Mvan_2641 |
| 5016 | >Toxin: Mjls_2387 | 10560 | >Antitoxin: Mjls_2388 |
| 5017 | >Toxin: Mflv_3763 | 10561 | >Antitoxin: Mflv_3762 |
| 5018 | >Toxin: Strop_1828 | 10562 | >Antitoxin: Strop_1829 |
| 5019 | >Toxin: DehaBAV1_0047 | 10563 | >Antitoxin: DehaBAV1_0048 |
| 5020 | >Toxin: TBFG_12576 | 10564 | >Antitoxin: TBFG_12575 |
| 5021 | >Toxin: Franean1_1694 | 10565 | >Antitoxin: Franean1_1695 |
| 5022 | >Toxin: Sare_1819 | 10566 | >Antitoxin: Sare_1820 |
| 5023 | >Toxin: BLD_0616 | 10567 | >Antitoxin: BLD_0615 |
| 5024 | >Toxin: MARTH_orf202 | 10568 | >Antitoxin: MARTH_orf203 |
| 5025 | >Toxin: UUR10_0378 | 10569 | >Antitoxin: UUR10_0379 |
| 5026 | >Toxin: Dtur_1023 | 10570 | >Antitoxin: Dtur_1024 |
| 5027 | >Toxin: Achl_2015 | 10571 | >Antitoxin: Achl_2014 |
| 5028 | >Toxin: Afer_0951 | 10572 | >Antitoxin: Afer_0952 |
| 5029 | >Toxin: Amir_5265 | 10573 | >Antitoxin: Amir_5264 |
| 5030 | >Toxin: Bcav_2014 | 10574 | >Antitoxin: Bcav_2015 |
| 5031 | >Toxin: Bfae_16360 | 10575 | >Antitoxin: Bfae_16350 |
| 5032 | >Toxin: Mlut_12720 | 10576 | >Antitoxin: Mlut_12710 |
| 5033 | >Toxin: Ksed_12510 | 10577 | >Antitoxin: Ksed_12520 |
| 5034 | >Toxin: Elen_2555 | 10578 | >Antitoxin: Elen_2554 |
| 5035 | >Toxin: Caci_2378 | 10579 | >Antitoxin: Caci_2379 |
| 5036 | >Toxin: Ccur_05100 | 10580 | >Antitoxin: Ccur_05110 |
| 5037 | >Toxin: Svir_15270 | 10581 | >Antitoxin: Svir_15280 |
| 5038 | >Toxin: Jden_1351 | 10582 | >Antitoxin: Jden_1350 |

TABLE 3-continued

| | Toxin polypeptide sequences | | Antitoxin polypeptide sequences |
|---|---|---|---|
| SEQ ID NO: | designation | SEQ ID NO: | designation |
| 5039 | >Toxin: Shel_07800 | 10583 | >Antitoxin: Shel_07810 |
| 5040 | >Toxin: Apar_0457 | 10584 | >Antitoxin: Apar_0458 |
| 5041 | >Toxin: Namu_3297 | 10585 | >Antitoxin: Namu_3296 |
| 5042 | >Toxin: BR0669 | 10586 | >Antitoxin: BR0670 |
| 5043 | >Toxin: Meso_0960 | 10587 | >Antitoxin: Meso_0961 |
| 5044 | >Toxin: Smed_0707 | 10588 | >Antitoxin: Smed_0708 |
| 5045 | >Toxin: Oant_2617 | 10589 | >Antitoxin: Oant_2616 |
| 5046 | >Toxin: Rleg2_1014 | 10590 | >Antitoxin: Rleg2_1015 |
| 5047 | >Toxin: Avi_1463 | 10591 | >Antitoxin: Avi_1464 |
| 5048 | >Toxin: Rleg_1166 | 10592 | >Antitoxin: Rleg_1167 |
| 5049 | >Toxin: Reut_B5756 | 10593 | >Antitoxin: Reut_B5755 |
| 5050 | >Toxin: Bcep18194_C6667 | 10594 | >Antitoxin: Bcep18194_C6668 |
| 5051 | >Toxin: Bcep18194_C7628 | 10595 | >Antitoxin: Bcep18194_C7629 |
| 5052 | >Toxin: Rmet_3558 | 10596 | >Antitoxin: Rmet_3557 |
| 5053 | >Toxin: Daci_1984 | 10597 | >Antitoxin: Daci_1983 |
| 5054 | >Toxin: Bmul_6053 | 10598 | >Antitoxin: Bmul_6054 |
| 5055 | >Toxin: Bphyt_4360 | 10599 | >Antitoxin: Bphyt_4361 |
| 5056 | >Toxin: Gdia_0758 | 10600 | >Antitoxin: Gdia_0759 |
| 5057 | >Toxin: Rfer_1402 | 10601 | >Antitoxin: Rfer_1401 |
| 5058 | >Toxin: Bpro_1690 | 10602 | >Antitoxin: Bpro_1689 |
| 5059 | >Toxin: Aave_1884 | 10603 | >Antitoxin: Aave_1883 |
| 5060 | >Toxin: Ajs_3355 | 10604 | >Antitoxin: Ajs_3356 |
| 5061 | >Toxin: Pnap_1461 | 10605 | >Antitoxin: Pnap_1460 |
| 5062 | >Toxin: Veis_3939 | 10606 | >Antitoxin: Veis_3938 |
| 5063 | >Toxin: Mpe_A1104 | 10607 | >Antitoxin: Mpe_A1103 |
| 5064 | >Toxin: Daci_5345 | 10608 | >Antitoxin: Daci_5346 |
| 5065 | >Toxin: Lcho_0681 | 10609 | >Antitoxin: Lcho_0680 |
| 5066 | >Toxin: Dtpsy_2703 | 10610 | >Antitoxin: Dtpsy_2704 |
| 5067 | >Toxin: Vapar_1473 | 10611 | >Antitoxin: Vapar_1472 |
| 5068 | >Toxin: DET0199 | 10612 | >Antitoxin: DET0198 |
| 5069 | >Toxin: Mbar_A2432 | 10613 | >Antitoxin: Mbar_A2431 |
| 5070 | >Toxin: Dde_2738 | 10614 | >Antitoxin: Dde_2739 |
| 5071 | >Toxin: Mhun_0927 | 10615 | >Antitoxin: Mhun_0928 |
| 5072 | >Toxin: Mthe_0907 | 10616 | >Antitoxin: Mthe_0908 |
| 5073 | >Toxin: Sfum_0349 | 10617 | >Antitoxin: Sfum_0348 |
| 5074 | >Toxin: Dvul_2100 | 10618 | >Antitoxin: Dvul_2101 |
| 5075 | >Toxin: Memar_2454 | 10619 | >Antitoxin: Memar_2455 |
| 5076 | >Toxin: DehaBAV1_0154 | 10620 | >Antitoxin: DehaBAV1_0155 |
| 5077 | >Toxin: Mboo_0831 | 10621 | >Antitoxin: Mboo_0832 |
| 5078 | >Toxin: Dole_2967 | 10622 | >Antitoxin: Dole_2968 |
| 5079 | >Toxin: DvMF_2934 | 10623 | >Antitoxin: DvMF_2933 |
| 5080 | >Toxin: Dbac_0077 | 10624 | >Antitoxin: Dbac_0078 |
| 5081 | >Toxin: Mpal_0502 | 10625 | >Antitoxin: Mpal_0501 |
| 5082 | >Toxin: Dret_1407 | 10626 | >Antitoxin: Dret_1406 |
| 5083 | >Toxin: Mbar_A0388 | 10627 | >Antitoxin: Mbar_A0387 |
| 5084 | >Toxin: Mhun_1181 | 10628 | >Antitoxin: Mhun_1182 |
| 5085 | >Toxin: Mbur_1241 | 10629 | >Antitoxin: Mbur_1242 |
| 5086 | >Toxin: Mthe_1611 | 10630 | >Antitoxin: Mthe_1610 |
| 5087 | >Toxin: Mlab_1220 | 10631 | >Antitoxin: Mlab_1221 |
| 5088 | >Toxin: Memar_0285 | 10632 | >Antitoxin: Memar_0286 |
| 5089 | >Toxin: MmarC7_0296 | 10633 | >Antitoxin: MmarC7_0297 |
| 5090 | >Toxin: Mboo_2347 | 10634 | >Antitoxin: Mboo_2346 |
| 5091 | >Toxin: Hlac_0279 | 10635 | >Antitoxin: Hlac_0280 |
| 5092 | >Toxin: Huta_1435 | 10636 | >Antitoxin: Huta_1436 |
| 5093 | >Toxin: Mpal_2679 | 10637 | >Antitoxin: Mpal_2678 |
| 5094 | >Toxin: Hmuk_1279 | 10638 | >Antitoxin: Hmuk_1280 |
| 5095 | >Toxin: Jann_1095 | 10639 | >Antitoxin: Jann_1094 |
| 5096 | >Toxin: TM1040_1726 | 10640 | >Antitoxin: TM1040_1727 |
| 5097 | >Toxin: RSP_0387 | 10641 | >Antitoxin: RSP_0386 |
| 5098 | >Toxin: Rsph17029_2041 | 10642 | >Antitoxin: Rsph17029_2040 |
| 5099 | >Toxin: Rsph17025_0849 | 10643 | >Antitoxin: Rsph17025_0850 |
| 5100 | >Toxin: Dshi_0770 | 10644 | >Antitoxin: Dshi_0769 |
| 5101 | >Toxin: Dd1591_2975 | 10645 | >Antitoxin: Dd1591_2974 |
| 5102 | >Toxin: RPB_3184 | 10646 | >Antitoxin: RPB_3183 |
| 5103 | >Toxin: Saro_0334 | 10647 | >Antitoxin: Saro_0335 |
| 5104 | >Toxin: Jann_2923 | 10648 | >Antitoxin: Jann_2924 |
| 5105 | >Toxin: RPC_1882 | 10649 | >Antitoxin: RPC_1883 |
| 5106 | >Toxin: RPD_2314 | 10650 | >Antitoxin: RPD_2315 |
| 5107 | >Toxin: TM1040_2218 | 10651 | >Antitoxin: TM1040_2217 |
| 5108 | >Toxin: RSP_2821 | 10652 | >Antitoxin: RSP_2822 |
| 5109 | >Toxin: Pden_2540 | 10653 | >Antitoxin: Pden_2539 |
| 5110 | >Toxin: Rsph17029_1475 | 10654 | >Antitoxin: Rsph17029_1474 |
| 5111 | >Toxin: Rsph17025_1525 | 10655 | >Antitoxin: Rsph17025_1524 |
| 5112 | >Toxin: Daci_5844 | 10656 | >Antitoxin: Daci_5845 |
| 5113 | >Toxin: Rpal_2374 | 10657 | >Antitoxin: Rpal_2375 |
| 5114 | >Toxin: Mchl_5685 | 10658 | >Antitoxin: Mchl_5686 |
| 5115 | >Toxin: Rru_A0999 | 10659 | >Antitoxin: Rru_A0998 |

TABLE 3-continued

| Toxin polypeptide sequences | | Antitoxin polypeptide sequences | |
|---|---|---|---|
| SEQ ID NO: | designation | SEQ ID NO: | designation |
| 5116 | >Toxin: RSP_0542 | 10660 | >Antitoxin: RSP_0543 |
| 5117 | >Toxin: Rsph17029_2193 | 10661 | >Antitoxin: Rsph17029_2194 |
| 5118 | >Toxin: Rsph17025_1245 | 10662 | >Antitoxin: Rsph17025_1244 |
| 5119 | >Toxin: BBta_5905 | 10663 | >Antitoxin: BBta_5906 |
| 5120 | >Toxin: Xaut_0110 | 10664 | >Antitoxin: Xaut_0109 |
| 5121 | >Toxin: M446_3597 | 10665 | >Antitoxin: M446_3598 |
| 5122 | >Toxin: Gdia_1571 | 10666 | >Antitoxin: Gdia_1572 |
| 5123 | >Toxin: Mnod_4011 | 10667 | >Antitoxin: Mnod_4010 |
| 5124 | >Toxin: MCA0079 | 10668 | >Antitoxin: MCA0080 |
| 5125 | >Toxin: BTH_II1184 | 10669 | >Antitoxin: BTH_II1185 |
| 5126 | >Toxin: BBta_1297 | 10670 | >Antitoxin: BBta_1298 |
| 5127 | >Toxin: Mext_4520 | 10671 | >Antitoxin: Mext_4521 |
| 5128 | >Toxin: Mrad2831_3340 | 10672 | >Antitoxin: Mrad2831_3341 |
| 5129 | >Toxin: Mpop_5032 | 10673 | >Antitoxin: Mpop_5033 |
| 5130 | >Toxin: Mchl_4980 | 10674 | >Antitoxin: Mchl_4981 |
| 5131 | >Toxin: BRA0156 | 10675 | >Antitoxin: BRA0155 |
| 5132 | >Toxin: RPC_1099 | 10676 | >Antitoxin: RPC_1098 |
| 5133 | >Toxin: Meso_0293 | 10677 | >Antitoxin: Meso_0294 |
| 5134 | >Toxin: BARBAKC583_1139 | 10678 | >Antitoxin: BARBAKC583_1140 |
| 5135 | >Toxin: Smed_0260 | 10679 | >Antitoxin: Smed_0259 |
| 5136 | >Toxin: Oant_4207 | 10680 | >Antitoxin: Oant_4208 |
| 5137 | >Toxin: Mext_0623 | 10681 | >Antitoxin: Mext_0622 |
| 5138 | >Toxin: Mrad2831_1687 | 10682 | >Antitoxin: Mrad2831_1688 |
| 5139 | >Toxin: Bind_3651 | 10683 | >Antitoxin: Bind_3652 |
| 5140 | >Toxin: Mpop_0601 | 10684 | >Antitoxin: Mpop_0600 |
| 5141 | >Toxin: M446_3678 | 10685 | >Antitoxin: M446_3677 |
| 5142 | >Toxin: Rleg2_0322 | 10686 | >Antitoxin: Rleg2_0321 |
| 5143 | >Toxin: Msil_0029 | 10687 | >Antitoxin: Msil_0028 |
| 5144 | >Toxin: Mchl_0634 | 10688 | >Antitoxin: Mchl_0633 |
| 5145 | >Toxin: Avi_0742 | 10689 | >Antitoxin: Avi_0741 |
| 5146 | >Toxin: Rleg_0354 | 10690 | >Antitoxin: Rleg_0353 |
| 5147 | >Toxin: Nwi_0763 | 10691 | >Antitoxin: Nwi_0764 |
| 5148 | >Toxin: RPB_4586 | 10692 | >Antitoxin: RPB_4585 |
| 5149 | >Toxin: RPC_4789 | 10693 | >Antitoxin: RPC_4790 |
| 5150 | >Toxin: RPD_0816 | 10694 | >Antitoxin: RPD_0817 |
| 5151 | >Toxin: Nham_3461 | 10695 | >Antitoxin: Nham_3460 |
| 5152 | >Toxin: Mmar10_2232 | 10696 | >Antitoxin: Mmar10_2231 |
| 5153 | >Toxin: BBta_0830 | 10697 | >Antitoxin: BBta_0831 |
| 5154 | >Toxin: Smed_0520 | 10698 | >Antitoxin: Smed_0521 |
| 5155 | >Toxin: Plav_0671 | 10699 | >Antitoxin: Plav_0672 |
| 5156 | >Toxin: Xaut_4646 | 10700 | >Antitoxin: Xaut_4645 |
| 5157 | >Toxin: Mext_3261 | 10701 | >Antitoxin: Mext_3260 |
| 5158 | >Toxin: Mrad2831_0031 | 10702 | >Antitoxin: Mrad2831_0030 |
| 5159 | >Toxin: Bind_0728 | 10703 | >Antitoxin: Bind_0727 |
| 5160 | >Toxin: Mpop_3457 | 10704 | >Antitoxin: Mpop_3456 |
| 5161 | >Toxin: Rpal_0901 | 10705 | >Antitoxin: Rpal_0902 |
| 5162 | >Toxin: M446_2347 | 10706 | >Antitoxin: M446_2346 |
| 5163 | >Toxin: Rleg2_0604 | 10707 | >Antitoxin: Rleg2_0605 |
| 5164 | >Toxin: Msil_1239 | 10708 | >Antitoxin: Msil_1240 |
| 5165 | >Toxin: Mchl_3585 | 10709 | >Antitoxin: Mchl_3584 |
| 5166 | >Toxin: Mnod_0262 | 10710 | >Antitoxin: Mnod_0263 |
| 5167 | >Toxin: Avi_1042 | 10711 | >Antitoxin: Avi_1043 |
| 5168 | >Toxin: Rleg_0644 | 10712 | >Antitoxin: Rleg_0645 |
| 5169 | >Toxin: WD1300 | 10713 | >Antitoxin: WD1299 |
| 5170 | >Toxin: Tfu_0350 | 10714 | >Antitoxin: Tfu_0349 |
| 5171 | >Toxin: ECH_0468 | 10715 | >Antitoxin: ECH_0469 |
| 5172 | >Toxin: Ssed_3664 | 10716 | >Antitoxin: Ssed_3665 |
| 5173 | >Toxin: Spea_3282 | 10717 | >Antitoxin: Spea_3283 |
| 5174 | >Toxin: Swoo_3951 | 10718 | >Antitoxin: Swoo_3952 |
| 5175 | >Toxin: Dret_0793 | 10719 | >Antitoxin: Dret_0792 |
| 5176 | >Toxin: RSc2370 | 10720 | >Antitoxin: RSc2369 |
| 5177 | >Toxin: Reut_A0685 | 10721 | >Antitoxin: Reut_A0686 |
| 5178 | >Toxin: Bpro_0940 | 10722 | >Antitoxin: Bpro_0941 |
| 5179 | >Toxin: Ajs_3461 | 10723 | >Antitoxin: Ajs_3460 |
| 5180 | >Toxin: Pnap_0837 | 10724 | >Antitoxin: Pnap_0838 |
| 5181 | >Toxin: Mpe_A1173 | 10725 | >Antitoxin: Mpe_A1174 |
| 5182 | >Toxin: Pnuc_1395 | 10726 | >Antitoxin: Pnuc_1394 |
| 5183 | >Toxin: Lcho_3725 | 10727 | >Antitoxin: Lcho_3724 |
| 5184 | >Toxin: Rpic_2583 | 10728 | >Antitoxin: Rpic_2582 |
| 5185 | >Toxin: Dtpsy_2788 | 10729 | >Antitoxin: Dtpsy_2787 |
| 5186 | >Toxin: Vapar_4059 | 10730 | >Antitoxin: Vapar_4058 |
| 5187 | >Toxin: Rpic12D_2179 | 10731 | >Antitoxin: Rpic12D_2178 |
| 5188 | >Toxin: Mbar_A3386 | 10732 | >Antitoxin: Mbar_A3387 |
| 5189 | >Toxin: Mhun_1603 | 10733 | >Antitoxin: Mhun_1602 |
| 5190 | >Toxin: Mbur_0221 | 10734 | >Antitoxin: Mbur_0220 |
| 5191 | >Toxin: Mthe_0333 | 10735 | >Antitoxin: Mthe_0332 |
| 5192 | >Toxin: Pisl_0588 | 10736 | >Antitoxin: Pisl_0587 |

TABLE 3-continued

| Toxin polypeptide sequences | | Antitoxin polypeptide sequences | |
|---|---|---|---|
| SEQ ID NO: | designation | SEQ ID NO: | designation |
| 5193 | >Toxin: Mlab_1499 | 10737 | >Antitoxin: Mlab_1498 |
| 5194 | >Toxin: Memar_0719 | 10738 | >Antitoxin: Memar_0720 |
| 5195 | >Toxin: MmarC5_0965 | 10739 | >Antitoxin: MmarC5_0964 |
| 5196 | >Toxin: Pars_1758 | 10740 | >Antitoxin: Pars_1757 |
| 5197 | >Toxin: Msed_0028 | 10741 | >Antitoxin: Msed_0027 |
| 5198 | >Toxin: Mevan_1555 | 10742 | >Antitoxin: Mevan_1554 |
| 5199 | >Toxin: Maeo_0079 | 10743 | >Antitoxin: Maeo_0080 |
| 5200 | >Toxin: MmarC7_1663 | 10744 | >Antitoxin: MmarC7_1664 |
| 5201 | >Toxin: Mboo_0688 | 10745 | >Antitoxin: Mboo_0689 |
| 5202 | >Toxin: MmarC6_0250 | 10746 | >Antitoxin: MmarC6_0249 |
| 5203 | >Toxin: Nmar_0227 | 10747 | >Antitoxin: Nmar_0226 |
| 5204 | >Toxin: Tneu_1579 | 10748 | >Antitoxin: Tneu_1578 |
| 5205 | >Toxin: Hlac_1844 | 10749 | >Antitoxin: Hlac_1843 |
| 5206 | >Toxin: Huta_0752 | 10750 | >Antitoxin: Huta_0751 |
| 5207 | >Toxin: Mpal_0525 | 10751 | >Antitoxin: Mpal_0524 |
| 5208 | >Toxin: Hmuk_2623 | 10752 | >Antitoxin: Hmuk_2622 |
| 5209 | >Toxin: BR1407 | 10753 | >Antitoxin: BR1406 |
| 5210 | >Toxin: Nwi_2355 | 10754 | >Antitoxin: Nwi_2354 |
| 5211 | >Toxin: RPB_2028 | 10755 | >Antitoxin: RPB_2029 |
| 5212 | >Toxin: RPC_3273 | 10756 | >Antitoxin: RPC_3272 |
| 5213 | >Toxin: RPD_3362 | 10757 | >Antitoxin: RPD_3361 |
| 5214 | >Toxin: Nham_2734 | 10758 | >Antitoxin: Nham_2733 |
| 5215 | >Toxin: RSP_2135 | 10759 | >Antitoxin: RSP_2137 |
| 5216 | >Toxin: Pden_1906 | 10760 | >Antitoxin: Pden_1907 |
| 5217 | >Toxin: Rsph17029_0810 | 10761 | >Antitoxin: Rsph17029_0811 |
| 5218 | >Toxin: Rsph17025_0719 | 10762 | >Antitoxin: Rsph17025_0720 |
| 5219 | >Toxin: BBta_6108 | 10763 | >Antitoxin: BBta_6107 |
| 5220 | >Toxin: BOV_1364 | 10764 | >Antitoxin: BOV_1363 |
| 5221 | >Toxin: Smed_2029 | 10765 | >Antitoxin: Smed_2028 |
| 5222 | >Toxin: Oant_1770 | 10766 | >Antitoxin: Oant_1771 |
| 5223 | >Toxin: Mext_2666 | 10767 | >Antitoxin: Mext_2665 |
| 5224 | >Toxin: Mrad2831_4519 | 10768 | >Antitoxin: Mrad2831_4520 |
| 5225 | >Toxin: Bind_0773 | 10769 | >Antitoxin: Bind_0772 |
| 5226 | >Toxin: Mpop_2788 | 10770 | >Antitoxin: Mpop_2787 |
| 5227 | >Toxin: Rpal_4016 | 10771 | >Antitoxin: Rpal_4015 |
| 5228 | >Toxin: M446_1097 | 10772 | >Antitoxin: M446_1096 |
| 5229 | >Toxin: Rleg2_2546 | 10773 | >Antitoxin: Rleg2_2545 |
| 5230 | >Toxin: Msil_0597 | 10774 | >Antitoxin: Msil_0598 |
| 5231 | >Toxin: Mchl_2893 | 10775 | >Antitoxin: Mchl_2892 |
| 5232 | >Toxin: Mnod_0693 | 10776 | >Antitoxin: Mnod_0694 |
| 5233 | >Toxin: Avi_2826 | 10777 | >Antitoxin: Avi_2825 |
| 5234 | >Toxin: Rleg_2805 | 10778 | >Antitoxin: Rleg_2804 |
| 5235 | >Toxin: RPC_4221 | 10779 | >Antitoxin: RPC_4220 |
| 5236 | >Toxin: Ppro_3346 | 10780 | >Antitoxin: Ppro_3347 |
| 5237 | >Toxin: P9515_14121 | 10781 | >Antitoxin: P9515_14111 |
| 5238 | >Toxin: Mlab_1426 | 10782 | >Antitoxin: Mlab_1425 |
| 5239 | >Toxin: Mext_0850 | 10783 | >Antitoxin: Mext_0849 |
| 5240 | >Toxin: Mpop_0774 | 10784 | >Antitoxin: Mpop_0773 |
| 5241 | >Toxin: PCC8801_3331 | 10785 | >Antitoxin: PCC8801_3332 |
| 5242 | >Toxin: Mchl_0809 | 10786 | >Antitoxin: Mchl_0808 |
| 5243 | >Toxin: Dbac_1869 | 10787 | >Antitoxin: Dbac_1870 |
| 5244 | >Toxin: Cyan8802_2786 | 10788 | >Antitoxin: Cyan8802_2785 |
| 5245 | >Toxin: Jann_2651 | 10789 | >Antitoxin: Jann_2652 |
| 5246 | >Toxin: TM1040_1731 | 10790 | >Antitoxin: TM1040_1732 |
| 5247 | >Toxin: RSP_0760 | 10791 | >Antitoxin: RSP_0761 |
| 5248 | >Toxin: Pden_0936 | 10792 | >Antitoxin: Pden_0937 |
| 5249 | >Toxin: Rsph17029_2419 | 10793 | >Antitoxin: Rsph17029_2420 |
| 5250 | >Toxin: Rsph17025_0415 | 10794 | >Antitoxin: Rsph17025_0414 |
| 5251 | >Toxin: Dshi_0765 | 10795 | >Antitoxin: Dshi_0764 |
| 5252 | >Toxin: BR0096 | 10796 | >Antitoxin: BR0097 |
| 5253 | >Toxin: Nwi_0320 | 10797 | >Antitoxin: Nwi_0319 |
| 5254 | >Toxin: RPC_0207 | 10798 | >Antitoxin: RPC_0208 |
| 5255 | >Toxin: RPD_0522 | 10799 | >Antitoxin: RPD_0521 |
| 5256 | >Toxin: Nham_0411 | 10800 | >Antitoxin: Nham_0412 |
| 5257 | >Toxin: Meso_3360 | 10801 | >Antitoxin: Meso_3361 |
| 5258 | >Toxin: BBta_0379 | 10802 | >Antitoxin: BBta_0378 |
| 5259 | >Toxin: BOV_0094 | 10803 | >Antitoxin: BOV_0095 |
| 5260 | >Toxin: Smed_3086 | 10804 | >Antitoxin: Smed_3087 |
| 5261 | >Toxin: Oant_0108 | 10805 | >Antitoxin: Oant_0109 |
| 5262 | >Toxin: Rpal_0202 | 10806 | >Antitoxin: Rpal_0203 |
| 5263 | >Toxin: Rleg2_3741 | 10807 | >Antitoxin: Rleg2_3742 |
| 5264 | >Toxin: Avi_4191 | 10808 | >Antitoxin: Avi_4192 |
| 5265 | >Toxin: Rleg_4064 | 10809 | >Antitoxin: Rleg_4065 |
| 5266 | >Toxin: PP_4158 | 10810 | >Antitoxin: PP_4157 |
| 5267 | >Toxin: PSPTO_2245 | 10811 | >Antitoxin: PSPTO_2246 |
| 5268 | >Toxin: GSU2483 | 10812 | >Antitoxin: GSU2484 |
| 5269 | >Toxin: Psyr_2050 | 10813 | >Antitoxin: Psyr_2051 |

TABLE 3-continued

| Toxin polypeptide sequences | | Antitoxin polypeptide sequences | |
|---|---|---|---|
| SEQ ID NO: | designation | SEQ ID NO: | designation |
| 5270 | >Toxin: Reut_A2290 | 10814 | >Antitoxin: Reut_A2289 |
| 5271 | >Toxin: RPB_4648 | 10815 | >Antitoxin: RPB_4649 |
| 5272 | >Toxin: Nham_2991 | 10816 | >Antitoxin: Nham_2990 |
| 5273 | >Toxin: Rmet_0041 | 10817 | >Antitoxin: Rmet_0042 |
| 5274 | >Toxin: PA14_43350 | 10818 | >Antitoxin: PA14_43340 |
| 5275 | >Toxin: Pnap_3601 | 10819 | >Antitoxin: Pnap_3600 |
| 5276 | >Toxin: Spro_1245 | 10820 | >Antitoxin: Spro_1244 |
| 5277 | >Toxin: PputGB1_3730 | 10821 | >Antitoxin: PputGB1_3729 |
| 5278 | >Toxin: Avin_24520 | 10822 | >Antitoxin: Avin_24530 |
| 5279 | >Toxin: Vapar_4991 | 10823 | >Antitoxin: Vapar_4990 |
| 5280 | >Toxin: Jann_3967 | 10824 | >Antitoxin: Jann_3968 |
| 5281 | >Toxin: RSP_3149 | 10825 | >Antitoxin: RSP_3148 |
| 5282 | >Toxin: Veis_2514 | 10826 | >Antitoxin: Veis_2513 |
| 5283 | >Toxin: Rsph17029_3886 | 10827 | >Antitoxin: Rsph17029_3885 |
| 5284 | >Toxin: Mrad2831_5988 | 10828 | >Antitoxin: Mrad2831_5987 |
| 5285 | >Toxin: Mnod_8672 | 10829 | >Antitoxin: Mnod_8671 |
| 5286 | >Toxin: Vapar_5617 | 10830 | >Antitoxin: Vapar_5616 |
| 5287 | >Toxin: MCA1644 | 10831 | >Antitoxin: MCA1645 |
| 5288 | >Toxin: Daro_2905 | 10832 | >Antitoxin: Daro_2904 |
| 5289 | >Toxin: Tbd_1531 | 10833 | >Antitoxin: Tbd_1530 |
| 5290 | >Toxin: Noc_2387 | 10834 | >Antitoxin: Noc_2386 |
| 5291 | >Toxin: Nmul_A2113 | 10835 | >Antitoxin: Nmul_A2112 |
| 5292 | >Toxin: Mfla_1880 | 10836 | >Antitoxin: Mfla_1879 |
| 5293 | >Toxin: Mlg_0717 | 10837 | >Antitoxin: Mlg_0718 |
| 5294 | >Toxin: PXO_00875 | 10838 | >Antitoxin: PXO_00874 |
| 5295 | >Toxin: Smal_2687 | 10839 | >Antitoxin: Smal_2688 |
| 5296 | >Toxin: Lferr_0814 | 10840 | >Antitoxin: Lferr_0815 |
| 5297 | >Toxin: Tmz1t_2263 | 10841 | >Antitoxin: Tmz1t_2262 |
| 5298 | >Toxin: AFE_0665 | 10842 | >Antitoxin: AFE_0666 |
| 5299 | >Toxin: PSPTO_5226 | 10843 | >Antitoxin: PSPTO_5225 |
| 5300 | >Toxin: Psyr_0318 | 10844 | >Antitoxin: Psyr_0319 |
| 5301 | >Toxin: Noc_2576 | 10845 | >Antitoxin: Noc_2577 |
| 5302 | >Toxin: Sde_3516 | 10846 | >Antitoxin: Sde_3515 |
| 5303 | >Toxin: Mlg_2539 | 10847 | >Antitoxin: Mlg_2540 |
| 5304 | >Toxin: PA14_69030 | 10848 | >Antitoxin: PA14_69020 |
| 5305 | >Toxin: Hhal_1182 | 10849 | >Antitoxin: Hhal_1183 |
| 5306 | >Toxin: Maqu_3434 | 10850 | >Antitoxin: Maqu_3433 |
| 5307 | >Toxin: Pmen_0322 | 10851 | >Antitoxin: Pmen_0323 |
| 5308 | >Toxin: Pput_5110 | 10852 | >Antitoxin: Pput_5109 |
| 5309 | >Toxin: PSPA7_5970 | 10853 | >Antitoxin: PSPA7_5969 |
| 5310 | >Toxin: COXBURSA331_A0127 | 10854 | >Antitoxin: COXBURSA331_A0126 |
| 5311 | >Toxin: PputGB1_5263 | 10855 | >Antitoxin: PputGB1_5262 |
| 5312 | >Toxin: PputW619_5028 | 10856 | >Antitoxin: PputW619_5027 |
| 5313 | >Toxin: Xfasm12_0963 | 10857 | >Antitoxin: Xfasm12_0964 |
| 5314 | >Toxin: XfasM23_0845 | 10858 | >Antitoxin: XfasM23_0846 |
| 5315 | >Toxin: PXO_02381 | 10859 | >Antitoxin: PXO_02380 |
| 5316 | >Toxin: Smal_3280 | 10860 | >Antitoxin: Smal_3279 |
| 5317 | >Toxin: Tgr7_2768 | 10861 | >Antitoxin: Tgr7_2767 |
| 5318 | >Toxin: Avin_47360 | 10862 | >Antitoxin: Avin_47350 |
| 5319 | >Toxin: SO_2677 | 10863 | >Antitoxin: SO_2676 |
| 5320 | >Toxin: MCA2934 | 10864 | >Antitoxin: MCA2935 |
| 5321 | >Toxin: Mfla_2702 | 10865 | >Antitoxin: Mfla_2703 |
| 5322 | >Toxin: Rsph17025_2105 | 10866 | >Antitoxin: Rsph17025_2106 |
| 5323 | >Toxin: VC0395_A0765 | 10867 | >Antitoxin: VC0395_A0766 |
| 5324 | >Toxin: Shew185_2087 | 10868 | >Antitoxin: Shew185_2086 |
| 5325 | >Toxin: Xaut_4504 | 10869 | >Antitoxin: Xaut_4505 |
| 5326 | >Toxin: Sbal195_2134 | 10870 | >Antitoxin: Sbal195_2133 |
| 5327 | >Toxin: Lcho_2251 | 10871 | >Antitoxin: Lcho_2252 |
| 5328 | >Toxin: Rpal_0669 | 10872 | >Antitoxin: Rpal_0668 |
| 5329 | >Toxin: Rpal_3387 | 10873 | >Antitoxin: Rpal_3386 |
| 5330 | >Toxin: Tgr7_1643 | 10874 | >Antitoxin: Tgr7_1644 |
| 5331 | >Toxin: Avi_3009 | 10875 | >Antitoxin: Avi_3010 |
| 5332 | >Toxin: BR0179 | 10876 | >Antitoxin: BR0180 |
| 5333 | >Toxin: RPB_1399 | 10877 | >Antitoxin: RPB_1400 |
| 5334 | >Toxin: Saro_2556 | 10878 | >Antitoxin: Saro_2557 |
| 5335 | >Toxin: Rru_A1933 | 10879 | >Antitoxin: Rru_A1932 |
| 5336 | >Toxin: Meso_3989 | 10880 | >Antitoxin: Meso_3990 |
| 5337 | >Toxin: BOV_0173 | 10881 | >Antitoxin: BOV_0174 |
| 5338 | >Toxin: Smed_1099 | 10882 | >Antitoxin: Smed_1100 |
| 5339 | >Toxin: Oant_0188 | 10883 | >Antitoxin: Oant_0189 |
| 5340 | >Toxin: Caul_3269 | 10884 | >Antitoxin: Caul_3268 |
| 5341 | >Toxin: Rpal_4696 | 10885 | >Antitoxin: Rpal_4695 |
| 5342 | >Toxin: Rleg2_1636 | 10886 | >Antitoxin: Rleg2_1637 |
| 5343 | >Toxin: Avi_2146 | 10887 | >Antitoxin: Avi_2147 |
| 5344 | >Toxin: Rleg_1823 | 10888 | >Antitoxin: Rleg_1824 |
| 5345 | >Toxin: Jann_0425 | 10889 | >Antitoxin: Jann_0424 |
| 5346 | >Toxin: RPC_0267 | 10890 | >Antitoxin: RPC_0266 |

TABLE 3-continued

| SEQ ID NO: | Toxin polypeptide sequences designation | SEQ ID NO: | Antitoxin polypeptide sequences designation |
|---|---|---|---|
| 5347 | >Toxin: RPD_0453 | 10891 | >Antitoxin: RPD_0454 |
| 5348 | >Toxin: TM1040_0057 | 10892 | >Antitoxin: TM1040_0056 |
| 5349 | >Toxin: RSP_1492 | 10893 | >Antitoxin: RSP_1491 |
| 5350 | >Toxin: Rsph17029_0142 | 10894 | >Antitoxin: Rsph17029_0141 |
| 5351 | >Toxin: Rsph17025_2897 | 10895 | >Antitoxin: Rsph17025_2896 |
| 5352 | >Toxin: Swit_3664 | 10896 | >Antitoxin: Swit_3665 |
| 5353 | >Toxin: Smed_3048 | 10897 | >Antitoxin: Smed_3047 |
| 5354 | >Toxin: Xaut_2211 | 10898 | >Antitoxin: Xaut_2212 |
| 5355 | >Toxin: Caul_4587 | 10899 | >Antitoxin: Caul_4588 |
| 5356 | >Toxin: Rpal_0271 | 10900 | >Antitoxin: Rpal_0270 |
| 5357 | >Toxin: Rleg2_3772 | 10901 | >Antitoxin: Rleg2_3773 |
| 5358 | >Toxin: Avi_4242 | 10902 | >Antitoxin: Avi_4243 |
| 5359 | >Toxin: Rleg_4096 | 10903 | >Antitoxin: Rleg_4097 |
| 5360 | >Toxin: Pcar_2797 | 10904 | >Antitoxin: Pcar_2798 |
| 5361 | >Toxin: Plut_0583 | 10905 | >Antitoxin: Plut_0584 |
| 5362 | >Toxin: Francci3_3111 | 10906 | >Antitoxin: Francci3_3112 |
| 5363 | >Toxin: Ppro_1965 | 10907 | >Antitoxin: Ppro_1966 |
| 5364 | >Toxin: Dvul_0285 | 10908 | >Antitoxin: Dvul_0284 |
| 5365 | >Toxin: Fnod_0467 | 10909 | >Antitoxin: Fnod_0466 |
| 5366 | >Toxin: Franean1_1807 | 10910 | >Antitoxin: Franean1_1806 |
| 5367 | >Toxin: Cmaq_0059 | 10911 | >Antitoxin: Cmaq_0058 |
| 5368 | >Toxin: Emin_1036 | 10912 | >Antitoxin: Emin_1037 |
| 5369 | >Toxin: DvMF_2367 | 10913 | >Antitoxin: DvMF_2366 |
| 5370 | >Toxin: Tbd_0578 | 10914 | >Antitoxin: Tbd_0579 |
| 5371 | >Toxin: Rfer_2118 | 10915 | >Antitoxin: Rfer_2117 |
| 5372 | >Toxin: Bpro_2410 | 10916 | >Antitoxin: Bpro_2409 |
| 5373 | >Toxin: Aave_3160 | 10917 | >Antitoxin: Aave_3161 |
| 5374 | >Toxin: Ajs_1923 | 10918 | >Antitoxin: Ajs_1922 |
| 5375 | >Toxin: Pnap_2167 | 10919 | >Antitoxin: Pnap_2168 |
| 5376 | >Toxin: Veis_4920 | 10920 | >Antitoxin: Veis_4921 |
| 5377 | >Toxin: Lcho_2593 | 10921 | >Antitoxin: Lcho_2594 |
| 5378 | >Toxin: Dtpsy_1727 | 10922 | >Antitoxin: Dtpsy_1726 |
| 5379 | >Toxin: Vapar_2732 | 10923 | >Antitoxin: Vapar_2731 |
| 5380 | >Toxin: Francci3_3069 | 10924 | >Antitoxin: Francci3_3068 |
| 5381 | >Toxin: Mmcs_5077 | 10925 | >Antitoxin: Mmcs_5078 |
| 5382 | >Toxin: Mkms_5165 | 10926 | >Antitoxin: Mkms_5166 |
| 5383 | >Toxin: Mjls_5456 | 10927 | >Antitoxin: Mjls_5457 |
| 5384 | >Toxin: Franean1_1843 | 10928 | >Antitoxin: Franean1_1844 |
| 5385 | >Toxin: Afer_0480 | 10929 | >Antitoxin: Afer_0481 |
| 5386 | >Toxin: Amir_3816 | 10930 | >Antitoxin: Amir_3815 |
| 5387 | >Toxin: Svir_26430 | 10931 | >Antitoxin: Svir_26440 |
| 5388 | >Toxin: Namu_2498 | 10932 | >Antitoxin: Namu_2499 |
| 5389 | >Toxin: Adeh_2402 | 10933 | >Antitoxin: Adeh_2401 |
| 5390 | >Toxin: Anae109_0244 | 10934 | >Antitoxin: Anae109_0245 |
| 5391 | >Toxin: CCC13826_1729 | 10935 | >Antitoxin: CCC13826_1728 |
| 5392 | >Toxin: Oter_1803 | 10936 | >Antitoxin: Oter_1804 |
| 5393 | >Toxin: SYO3AOP1_0447 | 10937 | >Antitoxin: SYO3AOP1_0448 |
| 5394 | >Toxin: AnaeK_1461 | 10938 | >Antitoxin: AnaeK_1462 |
| 5395 | >Toxin: Dhaf_0209 | 10939 | >Antitoxin: Dhaf_0210 |
| 5396 | >Toxin: A2cp1_1556 | 10940 | >Antitoxin: A2cp1_1557 |
| 5397 | >Toxin: Hlac_1165 | 10941 | >Antitoxin: Hlac_1164 |
| 5398 | >Toxin: Daro_3986 | 10942 | >Antitoxin: Daro_3985 |
| 5399 | >Toxin: Rmet_1293 | 10943 | >Antitoxin: Rmet_1292 |
| 5400 | >Toxin: RSP_0499 | 10944 | >Antitoxin: RSP_0500 |
| 5401 | >Toxin: Mlg_2026 | 10945 | >Antitoxin: Mlg_2025 |
| 5402 | >Toxin: Pden_3101 | 10946 | >Antitoxin: Pden_3102 |
| 5403 | >Toxin: Pnap_1971 | 10947 | >Antitoxin: Pnap_1970 |
| 5404 | >Toxin: Mpe_A2822 | 10948 | >Antitoxin: Mpe_A2821 |
| 5405 | >Toxin: Rsph17029_2150 | 10949 | >Antitoxin: Rsph17029_2151 |
| 5406 | >Toxin: Rsph17025_3372 | 10950 | >Antitoxin: Rsph17025_3371 |
| 5407 | >Toxin: Xaut_2176 | 10951 | >Antitoxin: Xaut_2177 |
| 5408 | >Toxin: Bind_1153 | 10952 | >Antitoxin: Bind_1154 |
| 5409 | >Toxin: Bphy_7262 | 10953 | >Antitoxin: Bphy_7261 |
| 5410 | >Toxin: SNSL254_A1648 | 10954 | >Antitoxin: SNSL254_A1647 |
| 5411 | >Toxin: SeHA_C1707 | 10955 | >Antitoxin: SeHA_C1706 |
| 5412 | >Toxin: SeSA_A1640 | 10956 | >Antitoxin: SeSA_A1639 |
| 5413 | >Toxin: SeAg_B1635 | 10957 | >Antitoxin: SeAg_B1636 |
| 5414 | >Toxin: SeD_A1800 | 10958 | >Antitoxin: SeD_A1801 |
| 5415 | >Toxin: Avin_50560 | 10959 | >Antitoxin: Avin_50550 |
| 5416 | >Toxin: MCA0236 | 10960 | >Antitoxin: MCA0237 |
| 5417 | >Toxin: Ava_3935 | 10961 | >Antitoxin: Ava_3936 |
| 5418 | >Toxin: Ava_4253 | 10962 | >Antitoxin: Ava_4254 |
| 5419 | >Toxin: Francci3_4482 | 10963 | >Antitoxin: Francci3_4481 |
| 5420 | >Toxin: RPB_0975 | 10964 | >Antitoxin: RPB_0976 |
| 5421 | >Toxin: RPC_4457 | 10965 | >Antitoxin: RPC_4456 |
| 5422 | >Toxin: Bxe_B1473 | 10966 | >Antitoxin: Bxe_B1474 |
| 5423 | >Toxin: RPD_1079 | 10967 | >Antitoxin: RPD_1080 |

TABLE 3-continued

| Toxin polypeptide sequences | | Antitoxin polypeptide sequences | |
|---|---|---|---|
| SEQ ID NO: | designation | SEQ ID NO: | designation |
| 5424 | >Toxin: Pnap_2322 | 10968 | >Antitoxin: Pnap_2321 |
| 5425 | >Toxin: BBta_5919 | 10969 | >Antitoxin: BBta_5918 |
| 5426 | >Toxin: Xaut_0094 | 10970 | >Antitoxin: Xaut_0095 |
| 5427 | >Toxin: Franean1_6875 | 10971 | >Antitoxin: Franean1_6874 |
| 5428 | >Toxin: Lcho_1352 | 10972 | >Antitoxin: Lcho_1353 |
| 5429 | >Toxin: Bind_0479 | 10973 | >Antitoxin: Bind_0480 |
| 5430 | >Toxin: Rpal_5095 | 10974 | >Antitoxin: Rpal_5094 |
| 5431 | >Toxin: Lferr_1232 | 10975 | >Antitoxin: Lferr_1231 |
| 5432 | >Toxin: M446_3540 | 10976 | >Antitoxin: M446_3541 |
| 5433 | >Toxin: Gdia_1564 | 10977 | >Antitoxin: Gdia_1563 |
| 5434 | >Toxin: Msil_3626 | 10978 | >Antitoxin: Msil_3625 |
| 5435 | >Toxin: PCC7424_2113 | 10979 | >Antitoxin: PCC7424_2112 |
| 5436 | >Toxin: PCC8801_1791 | 10980 | >Antitoxin: PCC8801_1792 |
| 5437 | >Toxin: AFE_1514 | 10981 | >Antitoxin: AFE_1513 |
| 5438 | >Toxin: Cyan7425_4799 | 10982 | >Antitoxin: Cyan7425_4800 |
| 5439 | >Toxin: Mnod_3990 | 10983 | >Antitoxin: Mnod_3989 |
| 5440 | >Toxin: Cyan8802_1819 | 10984 | >Antitoxin: Cyan8802_1820 |
| 5441 | >Toxin: BR0572 | 10985 | >Antitoxin: BR0571 |
| 5442 | >Toxin: RPC_1776 | 10986 | >Antitoxin: RPC_1775 |
| 5443 | >Toxin: Meso_0874 | 10987 | >Antitoxin: Meso_0873 |
| 5444 | >Toxin: Mmar10_0895 | 10988 | >Antitoxin: Mmar10_0894 |
| 5445 | >Toxin: BOV_0573 | 10989 | >Antitoxin: BOV_0572 |
| 5446 | >Toxin: Oant_2687 | 10990 | >Antitoxin: Oant_2688 |
| 5447 | >Toxin: Plav_0876 | 10991 | >Antitoxin: Plav_0875 |
| 5448 | >Toxin: Xaut_0072 | 10992 | >Antitoxin: Xaut_0073 |
| 5449 | >Toxin: Caul_1204 | 10993 | >Antitoxin: Caul_1203 |
| 5450 | >Toxin: Avi_1289 | 10994 | >Antitoxin: Avi_1287 |
| 5451 | >Toxin: Ent638_3494 | 10995 | >Antitoxin: Ent638_3495 |
| 5452 | >Toxin: EcHS_A0931 | 10996 | >Antitoxin: EcHS_A0930 |
| 5453 | >Toxin: Spro_0871 | 10997 | >Antitoxin: Spro_0872 |
| 5454 | >Toxin: EcolC_2770 | 10998 | >Antitoxin: EcolC_2771 |
| 5455 | >Toxin: SNSL254_A4372 | 10999 | >Antitoxin: SNSL254_A4371 |
| 5456 | >Toxin: SeAg_B2861 | 11000 | >Antitoxin: SeAg_B2862 |
| 5457 | >Toxin: SeD_A3043 | 11001 | >Antitoxin: SeD_A3044 |
| 5458 | >Toxin: PC1_3178 | 11002 | >Antitoxin: PC1_3177 |
| 5459 | >Toxin: Nwi_3022 | 11003 | >Antitoxin: Nwi_3023 |
| 5460 | >Toxin: Nham_3394 | 11004 | >Antitoxin: Nham_3395 |
| 5461 | >Toxin: Dgeo_2838 | 11005 | >Antitoxin: Dgeo_2837 |
| 5462 | >Toxin: Pnap_2692 | 11006 | >Antitoxin: Pnap_2691 |
| 5463 | >Toxin: Pnuc_1487 | 11007 | >Antitoxin: Pnuc_1486 |
| 5464 | >Toxin: Acry_1978 | 11008 | >Antitoxin: Acry_1979 |
| 5465 | >Toxin: Swit_0949 | 11009 | >Antitoxin: Swit_0948 |
| 5466 | >Toxin: Xaut_1455 | 11010 | >Antitoxin: Xaut_1454 |
| 5467 | >Toxin: Xaut_2672 | 11011 | >Antitoxin: Xaut_2671 |
| 5468 | >Toxin: Mrad2831_4215 | 11012 | >Antitoxin: Mrad2831_4216 |
| 5469 | >Toxin: Mrad2831_5267 | 11013 | >Antitoxin: Mrad2831_5266 |
| 5470 | >Toxin: BamMC406_4627 | 11014 | >Antitoxin: BamMC406_4628 |
| 5471 | >Toxin: SYO3AOP1_0084 | 11015 | >Antitoxin: SYO3AOP1_0083 |
| 5472 | >Toxin: M446_6453 | 11016 | >Antitoxin: M446_6452 |
| 5473 | >Toxin: Mchl_5388 | 11017 | >Antitoxin: Mchl_5387 |
| 5474 | >Toxin: Mnod_8369 | 11018 | >Antitoxin: Mnod_8370 |
| 5475 | >Toxin: Mnod_8664 | 11019 | >Antitoxin: Mnod_8663 |
| 5476 | >Toxin: Mnod_2704 | 11020 | >Antitoxin: Mnod_2703 |
| 5477 | >Toxin: BR1550 | 11021 | >Antitoxin: BR1549 |
| 5478 | >Toxin: Meso_2169 | 11022 | >Antitoxin: Meso_2170 |
| 5479 | >Toxin: BOV_1498 | 11023 | >Antitoxin: BOV_1497 |
| 5480 | >Toxin: Smed_1549 | 11024 | >Antitoxin: Smed_1548 |
| 5481 | >Toxin: Oant_1616 | 11025 | >Antitoxin: Oant_1617 |
| 5482 | >Toxin: Rleg2_2786 | 11026 | >Antitoxin: Rleg2_2785 |
| 5483 | >Toxin: Avi_3221 | 11027 | >Antitoxin: Avi_3220 |
| 5484 | >Toxin: Rleg_3050 | 11028 | >Antitoxin: Rleg_3049 |
| 5485 | >Toxin: Swol_0189 | 11029 | >Antitoxin: Swol_0190 |
| 5486 | >Toxin: Cthe_2247 | 11030 | >Antitoxin: Cthe_2246 |
| 5487 | >Toxin: Teth514_0448 | 11031 | >Antitoxin: Teth514_0449 |
| 5488 | >Toxin: Nther_2239 | 11032 | >Antitoxin: Nther_2238 |
| 5489 | >Toxin: Hore_17170 | 11033 | >Antitoxin: Hore_17160 |
| 5490 | >Toxin: Ccel_0091 | 11034 | >Antitoxin: Ccel_0092 |
| 5491 | >Toxin: Athe_1678 | 11035 | >Antitoxin: Athe_1677 |
| 5492 | >Toxin: GWCH70_3034 | 11036 | >Antitoxin: GWCH70_3033 |
| 5493 | >Toxin: Rru_A0101 | 11037 | >Antitoxin: Rru_A0100 |
| 5494 | >Toxin: Smed_3679 | 11038 | >Antitoxin: Smed_3678 |
| 5495 | >Toxin: Anae109_0022 | 11039 | >Antitoxin: Anae109_0023 |
| 5496 | >Toxin: Rleg2_2305 | 11040 | >Antitoxin: Rleg2_2306 |
| 5497 | >Toxin: PCC7424_1520 | 11041 | >Antitoxin: PCC7424_1519 |
| 5498 | >Toxin: PCC8801_3755 | 11042 | >Antitoxin: PCC8801_3756 |
| 5499 | >Toxin: Cyan7425_0809 | 11043 | >Antitoxin: Cyan7425_0808 |
| 5500 | >Toxin: Tgr7_1598 | 11044 | >Antitoxin: Tgr7_1597 |

TABLE 3-continued

| SEQ ID NO: | Toxin polypeptide sequences designation | SEQ ID NO: | Antitoxin polypeptide sequences designation |
|---|---|---|---|
| 5501 | >Toxin: Rleg__2644 | 11045 | >Antitoxin: Rleg__2645 |
| 5502 | >Toxin: Cyan8802__3804 | 11046 | >Antitoxin: Cyan8802__3805 |
| 5503 | >Toxin: Shewmr7__0736 | 11047 | >Antitoxin: Shewmr7__0735 |
| 5504 | >Toxin: Mmwyl1__0574 | 11048 | >Antitoxin: Mmwyl1__0575 |
| 5505 | >Toxin: YPK__0910 | 11049 | >Antitoxin: YPK__0909 |
| 5506 | >Toxin: SNSL254__A2922 | 11050 | >Antitoxin: SNSL254__A2923 |
| 5507 | >Toxin: SeHA__C3478 | 11051 | >Antitoxin: SeHA__C347 |
| 5508 | >Toxin: SeAg__B2787 | 11052 | >Antitoxin: SeAg__B2788 |
| 5509 | >Toxin: VSAL__I1041 | 11053 | >Antitoxin: VSAL__I1040 |
| 5510 | >Toxin: RPB__3182 | 11054 | >Antitoxin: RPB__3183 |
| 5511 | >Toxin: Saro__0336 | 11055 | >Antitoxin: Saro__0335 |
| 5512 | >Toxin: Jann__2925 | 11056 | >Antitoxin: Jann__2924 |
| 5513 | >Toxin: RPC__1884 | 11057 | >Antitoxin: RPC__1883 |
| 5514 | >Toxin: RPD__2316 | 11058 | >Antitoxin: RPD__2315 |
| 5515 | >Toxin: RSP__2823 | 11059 | >Antitoxin: RSP__2822 |
| 5516 | >Toxin: Pden__2538 | 11060 | >Antitoxin: Pden__2539 |
| 5517 | >Toxin: Rsph17029__1473 | 11061 | >Antitoxin: Rsph17029__1474 |
| 5518 | >Toxin: Rpal__2376 | 11062 | >Antitoxin: Rpal__2375 |
| 5519 | >Toxin: Mchl__5687 | 11063 | >Antitoxin: Mchl__5686 |
| 5520 | >Toxin: Francci3__3214 | 11064 | >Antitoxin: Francci3__3215 |
| 5521 | >Toxin: Arth__2278 | 11065 | >Antitoxin: Arth__2279 |
| 5522 | >Toxin: Acel__1330 | 11066 | >Antitoxin: Acel__1331 |
| 5523 | >Toxin: Noca__2407 | 11067 | >Antitoxin: Noca__2406 |
| 5524 | >Toxin: Strop__1828 | 11068 | >Antitoxin: Strop__1827 |
| 5525 | >Toxin: Franean1__1694 | 11069 | >Antitoxin: Franean1__1693 |
| 5526 | >Toxin: Sare__1819 | 11070 | >Antitoxin: Sare__1818 |
| 5527 | >Toxin: Achl__2015 | 11071 | >Antitoxin: Achl__2016 |
| 5528 | >Toxin: Amir__5265 | 11072 | >Antitoxin: Amir__5266 |
| 5529 | >Toxin: Bcav__2014 | 11073 | >Antitoxin: Bcav__2013 |
| 5530 | >Toxin: Caci__2378 | 11074 | >Antitoxin: Caci__2377 |
| 5531 | >Toxin: Svir__15270 | 11075 | >Antitoxin: Svir__15260 |
| 5532 | >Toxin: Jden__1351 | 11076 | >Antitoxin: Jden__1352 |
| 5533 | >Toxin: Namu__3297 | 11077 | >Antitoxin: Namu__3298 |
| 5534 | >Toxin: Reut__C6182 | 11078 | >Antitoxin: Reut__C6181 |
| 5535 | >Toxin: Reut__C6338 | 11079 | >Antitoxin: Reut__C6339 |
| 5536 | >Toxin: Bxe__A1728 | 11080 | >Antitoxin: Bxe__A1729 |
| 5537 | >Toxin: Bxe__A0064 | 11081 | >Antitoxin: Bxe__A0063 |
| 5538 | >Toxin: Bpro__0341 | 11082 | >Antitoxin: Bpro__0340 |
| 5539 | >Toxin: Nham__3807 | 11083 | >Antitoxin: Nham__3806 |
| 5540 | >Toxin: Bcen2424__6839 | 11084 | >Antitoxin: Bcen2424__6838 |
| 5541 | >Toxin: Smed__6339 | 11085 | >Antitoxin: Smed__6338 |
| 5542 | >Toxin: Xaut__4609 | 11086 | >Antitoxin: Xaut__4610 |
| 5543 | >Toxin: Bphy__7465 | 11087 | >Antitoxin: Bphy__7466 |
| 5544 | >Toxin: Bphyt__6578 | 11088 | >Antitoxin: Bphyt__6579 |

According to yet another aspect of the present invention there is provided an isolated bacterial population genetically modified to express a toxin and a cognate antitoxin thereof, the bacterial population being resistant to a lytic activity of a bacteriophage, wherein said toxin comprises an amino acid sequence at least 90% homologous to a sequence as set forth in SEQ ID NOs: 2773-3117, wherein when said toxin comprises said amino acid sequence at least 90% homologous to SEQ ID NO: 2773-2804, said antitoxin comprises an amino acid sequence at least 90% homologous to the sequence as set forth in SEQ ID NO:8317-8348, wherein when said toxin comprises said amino acid sequence at least 90% homologous to SEQ ID to NO: 2805-2871, said antitoxin comprises an amino acid sequence at least 90% homologous to the sequence as set forth in SEQ ID NO:8349-8415, wherein when said toxin comprises said amino acid sequence at least 90% homologous to SEQ ID NO: 2872-2935, said antitoxin comprises an amino acid sequence at least 90% homologous to the sequence as set forth in SEQ ID NO:8416-8479, wherein when said toxin comprises said amino acid sequence at least 90% homologous to SEQ ID NO: 2936-3030, said antitoxin comprises an amino acid sequence at least 90% homologous to the sequence as set forth in SEQ ID NO:8480-8574, wherein when said toxin comprises said amino acid sequence at least 90% homologous to SEQ ID NO: 3031-3078, said antitoxin comprises an amino acid sequence at least 90% homologous to the sequence as set forth in SEQ ID NO: 8575-8622, wherein when said toxin comprises said amino acid sequence at least 90% homologous to SEQ ID NO: 3079-3087, said antitoxin comprises an amino acid sequence at least 90% homologous to the sequence as set forth in SEQ ID NO:8623-8631, wherein when said toxin comprises said amino acid sequence at least 90% homologous to SEQ ID NO: 3088-3094, said antitoxin comprises an amino acid sequence at least 90% homologous to the sequence as set forth in SEQ ID NO:8632-8638, wherein when said toxin comprises said amino acid sequence at least 90% homologous to SEQ ID NO: 3095-3109, said antitoxin comprises an amino acid sequence at least 90% homologous to the sequence as set forth in SEQ ID NO:8639-8653, wherein when said toxin comprises said amino acid sequence at least 90% homologous to SEQ ID NO: 3110-3117, said antitoxin comprises an amino acid sequence at least 90% homologous to the sequence as set forth in SEQ ID NO:8654-8661.

Thus for example, the present inventors have found that when the toxin comprises an amino acid sequence as set forth in SEQ ID NOs: 3031-3078, the bacterial population in which the toxin antitoxin system is expressed is protected from the lytic activity of the T7Δ4.3Δ4.5Δ4.7 bacteriophage.

Further, when the toxin comprises an amino acid sequence as set forth in SEQ ID NO: 2805-2871, the bacterial population in which the toxin antitoxin system is expressed is protected from the lytic activity of the WT T7 strain.

Methods of expressing polypeptides in microbial populations are known in the art and further described herein below.

Regulatory sequences include those that direct constitutive expression of a nucleotide sequence as well as those that direct inducible expression of the nucleotide sequence only under certain conditions. A bacterial promoter is any DNA sequence capable of binding bacterial RNA polymerase and initiating the downstream (3') transcription of a coding sequence into mRNA. A promoter can have a transcription initiation region, which is usually placed proximal to the 5' end of the coding sequence. This transcription initiation region typically includes an RNA polymerase binding site and a transcription initiation site. A bacterial promoter can also have a second domain called an operator, which can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence.

An example of a gene activator protein is the catabolite activator protein (CAP), which helps initiate transcription of the lac operon in *Escherichia coli* (Raibaud et al. (1984) Annu. Rev. Genet. 18:173). Regulated expression can therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, and a bacteriophage lambda promoter. Any suitable promoter can be used to carry out the present invention, including the native promoter or a heterologous promoter. Heterologous promoters can be constitutively active or inducible. A non-limiting example of a heterologous promoter is given in U.S. Pat. No. 6,242,194 to Kullen and Klaenhammer.

Sequences encoding metabolic pathway enzymes provide particularly useful promoter sequences. Examples include promoter sequences derived from sugar metabolizing enzymes, such as galactose, lactose (lac) (Chang et al. (1987) Nature 198:1056), and maltose. Additional examples include promoter sequences derived from biosynthetic enzymes such as tryptophan (trp) (Goeddel et al. (1980) Nucleic Acids Res. 8:4057; Yelverton et al. (1981) Nucleic Acids Res. 9:731; U.S. Pat. No. 4,738,921; EPO Publication Nos. 36,776 and 121,775). The beta-lactamase (bla) promoter system (Weissmann, (1981) "The Cloning of Interferon and Other Mistakes," in Interferon 3 (ed. I. Gresser); bacteriophage lambda PL (Shimatake et al. (1981) Nature 292:128); the arabinose-inducible araB promoter (U.S. Pat. No. 5,028,530); and T5 (U.S. Pat. No. 4,689,406) promoter systems also provide useful promoter sequences. See also Balbas (2001) Mol. Biotech. 19:251-267, where *E. coli* expression systems are discussed.

In addition, synthetic promoters that do not occur in nature also function as bacterial promoters. For example, transcription activation sequences of one bacterial or bacteriophage promoter can be joined with the operon sequences of another bacterial or bacteriophage promoter, creating a synthetic hybrid promoter (U.S. Pat. No. 4,551,433). For example, the tac (Amann et al. (1983) Gene 25:167; de Boer et al. (1983) Proc. Natl. Acad. Sci. 80:21) and trc (Brosius et al. (1985) J. Biol. Chem. 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-.beta.-D-galactoside (IPTG). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) J. Mol. Biol. 189:113; Tabor et al. (1985) Proc. Natl. Acad. Sci. 82:1074). In addition, a hybrid promoter can also be comprised of a bacteriophage promoter and an *E. coli* operator region (EPO Publication No. 267,851).

The vector can additionally contain a nucleotide sequence encoding the repressor (or inducer) for that promoter. For example, an inducible vector of the present invention can regulate transcription from the Lac operator (LacO) by expressing the nucleotide sequence encoding the LacI repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., lambda CI857, rendering lambda pL thermo-inducible, or lambda CI+, rendering lambda pL chemo-inducible) can be employed.

In addition to a functioning promoter sequence, an efficient ribosome-binding site is also useful for the expression of the fusion construct. In prokaryotes, the ribosome binding site is called the Shine-Dalgarno (SD) sequence and includes an initiation codon (ATG) and a sequence 3-9 nucleotides in length located 3-11 nucleotides upstream of the initiation codon (Shine et al. (1975) Nature 254:34). The SD sequence is thought to promote binding of mRNA to the ribosome by the pairing of bases between the SD sequence and the 3' end of bacterial 16S rRNA (Steitz et al. (1979) "Genetic Signals and Nucleotide Sequences in Messenger RNA," in Biological Regulation and Development: Gene Expression (ed. R. F. Goldberger, Plenum Press, NY).

The bacterial protecting peptides can also be secreted from the cell by creating chimeric DNA molecules that encode a protein comprising a signal peptide sequence fragment that provides for secretion of the two-component regulatory polypeptides in bacteria (U.S. Pat. No. 4,336,336). The signal sequence fragment typically encodes a signal peptide comprised of hydrophobic amino acids that direct the secretion of the protein from the cell. The protein is either secreted into the growth medium (Gram-positive bacteria) or into the periplasmic space, located between the inner and outer membrane of the cell (Gram-negative bacteria). Preferably there are processing sites, which can be cleaved either in vivo or in vitro, encoded between the signal peptide fragment and the protein of the invention.

DNA encoding suitable signal sequences can be derived from genes for secreted bacterial proteins, such as the *E. coli* outer membrane protein gene (ompA) (Masui et al. (1983) FEBS Lett. 151(1):159-164; Ghrayeb et al. (1984) EMBO J. 3:2437-2442) and the *E. coli* alkaline phosphatase signal sequence (phoA) (Oka et al. (1985) Proc. Natl. Acad. Sci.

82:7212). Other prokaryotic signals include, for example, the signal sequence from penicillinase, Ipp, or heat stable enterotoxin II leaders.

Typically, transcription termination sequences recognized by bacteria are regulatory regions located 3' to the translation stop codon and thus, together with the promoter, flank the coding sequence. These sequences direct the transcription of an mRNA that can be translated into the polypeptide encoded by the DNA. Transcription termination sequences frequently include DNA sequences (of about 50 nucleotides) that are capable of forming stem loop structures that aid in terminating transcription. Examples include transcription termination sequences derived from genes with strong promoters, such as the trp gene in *E. coli* as well as other biosynthetic genes.

Bacteria such as *Lactobacillus acidophilus* generally utilize the translation start codon ATG, which specifies the amino acid methionine (which is modified to N-formylmethionine in prokaryotic organisms). Bacteria also recognize alternative translation start codons, such as the codons GTG and TTG, which code for valine and leucine, respectively. However, when these alternative translation start codons are used as the initiation codon, these codons direct the incorporation of methionine rather than of the amino acid that they normally encode. *Lactobacillus acidophilus* NCFM recognizes these alternative translation start sites and incorporates methionine as the first amino acid.

It will be appreciated that for expressing toxin/antitoxin pairs in microbial populations the polynucleotide sequence encoding the toxin may be comprised in the same expression vector as that comprising the antitoxin or may be comprised on a separate expression vector from that of the antitoxin.

Exemplary microbial populations that may be protected from toxins and/or the lytic effect of bacteriophages according to this aspect of the present invention include those bacteria useful in dairy and fermentation processing. Thus, microorganisms in which the peptides described herein may be expressed are those that are useful in the manufacture of milk-derived products, such as cheeses, yogurt, fermented milk products, sour milks, and buttermilk. The microorganisms may be probiotic organisms.

According to one embodiment, the bacteria is a lactic acid bacteria.

As used herein the phrase "lactic acid bacteria" refers to a genus selected from the following: *Aerococcus, Carnobacterium, Enterococcus, Lactococcus, Lactobacillus, Leuconostoc, Oenococcus, Pediococcus, Streptococcus,* to *Melissococcus, Alloiococcus, Dolosigranulum, Lactosphaera, Tetragenococcus, Vagococcus,* and *Weissella* (Holzapfel et al. (2001) Am. J. Clin. Nutr. 73:365 S-373S; Bergey's Manual of Systematic Bacteriology, Vol. 2 (Williams and Wilkins, Baltimore (1986)) pp. 1075-1079).

The production of bacteria comprising the toxins and/or antitoxins of the present invention, the preparation of starter cultures of such bacteria, and methods of fermenting substrates, particularly food substrates such as milk, can be carried out in accordance with known techniques, including but not limited to those described in Mayra-Makinen and Bigret (1993) Lactic Acid Bacteria. Salminen and vonWright eds. Marcel Dekker, Inc. New York. 65-96; Sandine (1996) Dairy Starter Cultures Cogan and Accolas eds. VCH Publishers, New York. 191-206; Gilliland (1985) Bacterial Starter Cultures for Food. CRC Press, Boca Raton, Fla.

The term "fermenting" refers to the energy-yielding, metabolic breakdown of organic compounds by microorganisms that generally proceeds under anaerobic conditions and with the evolution of gas.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as to well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., to "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Coverage Analysis of Pairs of Genes:

Mapping of sequencing clones on 360 bacteria and 28 archaea for which raw clone sequencing data was available was performed as described in (Kimelman et al., 2012). Gene positions and annotations were downloaded as described (Kimelman et al., 2012). For each consecutive pair of genes in each genome, three numbers were recorded:

x=<number of clones fully spanning the first and not the second gene> y=<number of clones fully spanning the second gene but not the first gene> z=<number of clones fully spanning both genes>

A pair of genes conforming with {x=0; y>0; z>0} or {x>0; y=0; z>0} was declared as "following the TA cloning pattern". Pairs in which the putative toxin was identified as a 'hitchhiker' (Kimelman et al., 2012) were eliminated from further counts in order to avoid cases in which this clonability pattern was a byproduct of a nearby single, standalone toxic gene. Pairs residing in replicons lacking sufficient clone coverage were also ignored in further counts.

Aggregation of Pairs into Families:

Clustering of individual genes based on sequence homology was retrieved from IMG (worldwidewebimgdotjgidotdoedotgov/cgi-bin/w/maindotcgi) on November 2010 (based on the "IMG cluster" field). Cluster IDs were recorded for every consecutive pair of genes analyzed. Pairs containing a gene that lacked a cluster ID were discarded. All pairs having the same two cluster IDs (regardless of the order and the strand) were aggregated into a single "family of pairs". Families containing less than 7 pairs were ignored, to ensure statistical power in next steps of the analysis. This resulted in 21,417 families, containing at least 7 pairs of consecutive genes sharing to the same two cluster IDs, which were further analyzed. The following "TA cloning fraction" (F) parameters were calculated for each family:

F1=the fraction of family members that follow the TA cloning pattern {x=0; y>0; z>0}

F2=the fraction of family members that follow the TA cloning pattern {x>0; y=0; z>0}

Directionality of putative family (i.e., determining whether gene "x" is the putative toxin or the putative antitoxin) was determined using $F_{max}=\max\{F1,F2\}$, such that:

$F_{max}$=F1→x is the putative toxin $F_{max}$=F2→y is the putative toxin

For each family, the Genus names of all containing organisms were extracted. A "family diversity" (FD) measure was defined as the number of different genus names divided by the total number of family members (pairs). This measure was used to roughly assess the tendency of the family to undergo horizontal gene transfer (HGT) within a wide array of organisms, with higher FD corresponding to higher HGT tendency. For example, a 10-members family where all members are found in strains of *Escherichia coli* will receive a low FD of 0.1. Only families having FD>=0.5 were further analyzed, based on the empirical FD distribution among known families of TA systems (FIG. 9A=S3A).

A Statistical Framework to Detect TA Families:

Since a given pair of genes has the potential to follow the TA cloning pattern merely by chance (i.e., due to the random clone fragmentation) rather than reflecting a real toxin/antitoxin activity, clone distribution simulations were performed to assess statistical significance per family (FIG. 7=S1). For every pair of genes in each family, all clones covering its genome of origin were randomly distributed on the genome, shuffling clone positions but maintaining their number and sizes. Based on these random clone distributions, the x, y, and z values were measured for the gene pair, and a simulated "TA cloning fraction" ($F_{sim}$) was then calculated for the family. This procedure was repeated 1,000 times for each family, generating a distribution of $F_{sim\ (i)}$ (i=1..1000). The real $F_{max}$ of the family was then compared to the distribution of $F_{sim}$ values obtained from the simulations, generating an empirical p value for a family.

Since this procedure is computationally demanding to perform for >21000 families, only families where $F_{max}$>=0.3 (i.e., at least 30% of family members followed the TA cloning pattern) were thus analyzed. Families presenting p-value<=0.05 were considered as following the TA cloning pattern in a statistically significantly manner.

To identify families significantly localized to Defense Islands (DIs) (Makarova et al., 2011), a value of 'mean number of defense island genes in proximity' ($DI_{val}$) was calculated for each family based on a list of 132 COGs (DI genes) that were shown to be enriched in defense island regions (Makarova et al., 2011). For this, the average number of DI genes within a range of ±5 genes from each family member was calculated. Families having $DI_{val}>0.5$ were defined as DI associated (FIG. 2), based on the empirical $DI_{val}$ distribution among known families of TA systems (FIG. 9B). Families were further reviewed manually to remove transposon-containing families possibly associated with defense islands due to their transposition-related properties rather than being genuine TA systems.

Analysis of Known TA Systems within the Identified Set:

The locus tags of all genes from the 24 final families (FIG. 2) were checked against a previously compiled list of known TA systems (Makarova et al., 2009). For a given family, if at least one pair was found in the list of known TA systems, the family was declared as 'known'. Families that were not declared as 'known' were further similarly checked against a list of predicted TA genes downloaded from TADB (http://bioinfo-mmldotsjtudotedudotcn/TADB/) (Shao et al., 2011). Families in which at least one pair was found in this TADB list were declared as 'predicted'. Families found in neither list were declared as 'novel'.

Domain analysis of genes in the identified families was performed by searching their sequences against the Conserved Domain Database (CDD) (Marchler-Bauer et al., 2011) using rpsblast (ftp://ftpdotncbidotnihdotgov/blast/documents/rpsblastdothtml) with e-value threshold of 0.05.

For the Phylogenetic distribution analysis of families (FIG. 4), the IMG cluster ids (http://imgdotjgidotdoedotgov/cgi-bin/w/maindotcgi) of the toxin and to antitoxin for each family were used to retrieve all img adjacent pairs of genes that have the same two cluster ids. For each family, number and identity of organisms carrying members of the family were extracted (Tables 4 and 5, herein below; FIG. 4).

Experimental Evaluation of 'TA Cloning Pattern':

Toxin and antitoxin were amplified from their genomes of origin (in the case of sanaAT, psyrAT and sdenAT) or synthesized (GenScript) for the families pmenAT and rlegAT. The toxin was then directionally ligated into the pRSFDuet-1 vector (EMD Chemicals Inc.) and the antitoxin ligated into the pBAD/HisA plasmid (Invitrogen). Since transformation of the toxin gene alone resulted in mutations in the toxin due to toxicity, the two plasmids (carrying the toxin and antitoxin) were co-transformed into E. coli BL21(DE3)pLysS (Stratagene) in the presence of 0.3% arabinose to induce the antitoxin. The clones were verified by direct sequencing with primers on the pRSFduet-1 and pBAD/HisA vectors.

For the toxicity assay on plates, clones were cultured in LB medium with 100 µg/ml ampicillin, 50 µg/ml kanamycin, 34 µg/ml chloramphenicol and 0.3% arabinose overnight. The next day, a portion of each overnight culture was inoculated into fresh medium (10-fold dilution) and 10 µl were spotted on LB plates supplemented with 100 µg/ml ampicillin, 50 µg/ml kanamycin and 34 µg/ml chloramphenicol. Toxin, antitoxin or both were induced by 100 µM IPTG and 0.3% arabinose, respectively.

For the growth kinetics experiments 3 different colonies of each system were cultured in LB medium with 100 µg/ml ampicillin, 50 µg/ml kanamycin, 34 µg/ml chloramphenicol and 0.3% arabinose overnight. The next day cells were diluted 1:20 and measured for OD using 1 cm path cuvetts. Samples were equilibrated to the same OD and 5 µl of these samples were added to 175 µl LB medium supplemented with 100 µg/ml ampicillin, 50 µg/ml kanamycin, 34 µg/ml chloramphenicol in a 96-wells microplate. Cells were placed in Infinite M200 in a script employing a 60 cycles of ~5 min interval. Measurements were done using 486ex/516em bandwidth (Gain 95, 105 and 110) and OD at 600 nm overnight. For each of the colonies the following treatments were applied: No induction, induction of 100 µM IPTG and/or 0.3% arabinose after ~4 h, and induction of 100 µM IPTG after ~4 h and of 0.3% arabinose after another ~2.5 hours. The overnight growth replicate values were averaged and the measured OD values were plotted against time.

The viability assay (FIG. 3C) was performed as described by Pedersen et al (2002). Briefly, each strain was grown overnight at 37° C. in LB medium containing 100 µg/ml ampicillin, 50 µg/ml kanamycin, and 34 µg/ml chloramphenicol. In the next morning, cells were then diluted 1:1000 in the same medium as above and grown for 3 hours. At time zero cells were then washed once with LB, and then transcription of toxin was induced by 100 µM IPTG. At increasing time points after toxin induction (30, 60, 120, 180, 240 and 300 mins) cells were plated in several dilutions on LB-plates containing 100 µg/ml ampicillin, 50 µg/ml kanamycin, 34 µg/ml chloramphenicol and 0.3% arabinose. CFUs were determined in the next morning by colony counting.

Plaque Assays:

E. coli strains harboring the antitoxin only or the toxin-antitoxin of psyrAT, sanaAT, pmenAT, rlegAT, and sdenAT binary toxin-antitoxin systems were grown overnight in LB liquid medium supplemented with 35 µg/ml chloramphenicol, 100 µg/ml ampicillin and 0.3% L-arabinose with or without 50 µg/ml kanamycin, respectively. Overnight cultures were diluted 1:100 in fresh LB medium supplemented with inducers and antibiotics as above and aerated with shaking at 37° C. until reaching $O.D_{600}{\approx}0.5$. Cultures were then centrifuged for 10 min and re-suspended in LB to an $O.D_{600}$ of exactly 0.5. Volumes of 200 µl of culture and 10 µl of the indicated T7 phages were mixed in 3 ml of warm 0.8% agar LB supplemented with 35 µg/ml chloramphenicol, 100 µg/ml ampicillin and 0.3% L-arabinose or 35 µg/ml chloramphenicol, 100 µg/ml ampicillin, 50 µg/ml kanamycin, 0.3% L-arabinose, and 100 µM IPTG for the antitoxin only- or toxin-antitoxin-harboring cultures, respectively. The mixtures were immediately overlaid on LB plates supplemented with the above indicated inducers and antibiotics. Overlaid plates were incubated at 37° C. for 3 h and plaques were then counted. For a given TA pair, efficiency of plating (EOP) was calculated by dividing the number of plaque forming units (PFU) obtained for bacterial lawn expressing the toxin+antitoxin by the number of PFU obtained on the bacterial lawn expressing the antitoxin alone. For the rlegAT system, additional experiments were done with resuspension of cultures in LB to a higher $O.D_{600}$ of 2.5, to address the possibility that the observed smaller plaque sizes stemmed from lower lawn density resulting from partial toxicity of this system to E. coli when grown on plates.

Expression of Lon and 4.5 Proteins and Co-Immunoprecipitation Assay:

The 4.5 gene (3' His-tagged) and full-length Lon protease gene (5' Flag-tagged) were cloned into the $1^{st}$ and $2^{nd}$ expression cassettes, respectively, of the vector pRSFDuet-1 (EMD Chemicals, Inc.). DNA cloning was performed using the Restriction Free (RF) cloning procedure (Unger et al., 2010). Induction experiments were performed using E. coli BL21 (DE3) cells expressing only the Lon or the 4.5 proteins and cells expressing both Lon and 4.5 proteins. Induction was carried out at 37° C. for 3 hr by addition of 200 µM of IPTG. Cell pellets were lysed by sonication in a buffer containing 50 mM Tris-HCl, pH 7.4, 150 mM NaCl, 1 mM EDTA, 1% (v/v) Triton X-100, 1 mM phenylmethylsulfonyl fluoride (PMSF) and 1 μl/mL protease inhibitor cocktail (Set IV, EMD Chemicals, Inc.). Cell debris were removed by centrifugation at 4° C. for 15 minutes at 18,000 g. Clear supernatants were transferred to 1.5 ml tubes and incubated on a rotator shaker at 4° C. for 1 hr with 80 μl pre-washed anti-Flag M2-agarose beads (Sigma, #A2220). The beads were washed three times with the buffer described above and the Flag-tagged protein or protein complex were eluted using Flag-peptide (Sigma, #F3290) using the manufacturers' recommendations.

Example 1

Systematic Discovery of TA Families Based on Large-Scale Cloning Experiments 360 bacterial and 28 archaeal genomes that were sequenced using the clone-based Sanger approach, and for which the raw sequencing data was accessible and mapped to the assembled genome (Kimelman et al., 2012) were analyzed. For the sequencing of each genome, an average of 22,313 different randomly fragmented clones (typically sized between 3 kb-8 kb, thus typically spanning ~3 to ~8 genes) were inserted into $E.$ $coli.$ Cumulatively, the analyzed genomes span over 1.5 million genes to that were sequenced using over 8.5 million clones. The number of cloned DNA fragments that fully contain were recorded for each gene, and for each pair of consecutive genes.

To detect families of gene pairs in which one of the genes (putative toxin) is absent from clones unless the adjacent gene (putative antitoxin) is also present, the present inventors first searched for homologous gene pairs that repeatedly appear adjacent to each other in multiple genomes (at least 7 appearances) and aggregated them into families of pairs (Methods). To avoid the analysis of housekeeping genes that appear in conserved operons (e.g., ribosomal protein genes), the present inventors focused on families showing high tendency to undergo horizontal gene transfer (Methods). Each pair of genes (X and Y) in each family was considered as following the "TA cloning pattern" if the number of clones covering gene X (toxin) but not Y (antitoxin) was 0, the number of clones covering gene Y but not X was >0 and the number of clones covering both X and Y was >0 (FIGS. 1B-C).

Not all toxins are expected to manifest their toxicity when cloned in $E.$ $coli,$ because their expression depends on the ability of the $E.$ $coli$ host to recognize their native promoters and translate them using available tRNA pool (Sorek et al., 2007). Therefore, for a given toxin-antitoxin family of gene pairs, one may expect a significant fraction of pairs, but not necessarily all pairs, to follow the "TA cloning pattern" (FIG. 1C). To assign a statistical significance for a given family as possibly coding for a bona fide TA family, the present inventors performed, for each pair in each family, 1000 random simulations, where the clones used for sequencing of the relevant genome were randomly shuffled on the genome (Methods; FIG. 7). The results were then used to assign an empirical p-value per family, revealing families in which the fraction of pairs that follow the TA cloning pattern is significantly above the fraction expected by chance ($p<=0.05$). This yielded 188 candidate families (FIG. 2).

The identified families may include genes that follow the TA cloning pattern as a by-product of their functions, and not for reasons associated with classical TA systems. For example, a metabolic enzyme whose expression results in accumulation of toxic intermediates might be neutralized by an accompanying transcriptional repressor. This may be the case for the argininosuccinate synthase and the ArgR to repressor of the arginine regulon that obey the TA cloning patterns in 4 out of 12 homologous pairs. To identify TA systems more likely to play phage defense-related roles, the present inventors focused on those families that had high tendency to appear within bacterial "defense islands". It was recently shown that bacterial anti-phage immune systems such as restriction enzymes, CRISPR and Abi genes aggregate in such "defense island" loci in bacterial genomes (Makarova et al., 2011). Therefore, the present inventors selected those families in which the genomic neighborhood was enriched for defense genes (Methods). This analysis resulted in a set of 24 putative families of TA gene pairs, overall containing 400 pairs from 176 genomes (FIG. 2; Tables 4-5).

TABLE 4

Families of previously known and bioinformatically predicted toxin-antitoxin systems retrieved by the TA discovery algorithm

| | # pairs in family | Antitoxin superfamily | Toxin superfamily | COGs associated with antitoxin | COGs associated with toxin | P value for TA cloning pattern |
|---|---|---|---|---|---|---|
| 1 | 16 | RelB | RelE | COG3905 | COG3668 | $5.0 \times 10^{-3}$ |
| 2 | 25 | RelB | RelE | COG3077 | COG3041 | $3.0 \times 10^{-3}$ |
| 3 | 13 | RelB | RelE | n/a | n/a | $1.1 \times 10^{-2}$ |
| 4 | 33 | Xre | RelE | COG3620 | COG4679 | $2.5 \times 10^{-2}$ |
| 5 | 28 | Xre | RelE | n/a | COG2944 | $2.5 \times 10^{-2}$ |
| 6 | 32 | Xre | RelE | COG5499 | COG4680 | $7.0 \times 10^{-3}$ |
| 7 | 27 | Phd | RelE | COG2161 | COG2026 | $3.4 \times 10^{-2}$ |
| 8 | 9 | HicB | HicA | COG1598 | COG1724 | $9.0 \times 10^{-3}$ |
| 9 | 11 | HicB | HicA | n/a | COG1724 | $3.4 \times 10^{-2}$ |
| 10 | 12 | VapB | VapC | COG4456 | COG1487 | $4.0 \times 10^{-3}$ |
| 11 | 10 | HigA | HigB | COG3093 | COG3549 | $1.0 \times 10^{-3}$ |
| 12 | 22 | MosA | MosT | n/a | COG2253 | 0 |

TABLE 5

Novel families of toxin-antitoxin systems retrieved by the TA discovery algorithm

| # pairs in fam. | Antitoxin | Toxin | Antitoxin annotation | Toxin annotation | Domains associated with antitoxin | Domains associated with toxin | P value for TA cloning pattern |
|---|---|---|---|---|---|---|---|
| 11 | PsyrA SEQ ID NOs: 8416-8479 | PsyrT SEQ ID NOs: 2872-2935 | Nucleotide-binding protein | RecQ-family DNA helicase | COG0758 | COG0514 | 0 |

TABLE 5-continued

Novel families of toxin-antitoxin systems retrieved by the TA discovery algorithm

| # pairs in fam. | Antitoxin | Toxin | Antitoxin annotation | Toxin annotation | Domains associated with antitoxin | Domains associated with toxin | P value for TA cloning pattern |
|---|---|---|---|---|---|---|---|
| 10 | SanaA SEQ ID NO: 8575-8622 | SanaT SEQ ID NOs: 3031-3078 | S-adenosyl-homocysteine hydrolase | Hypothetical protein | n/a | DUF1814 | 0 |
| 10 | PmenA SEQ ID NO: 8480-8574 | PmenT SEQ ID NO: 2936-3030 | ADP-ribose binding domain protein | Hypothetical protein | COG2110 | n/a | 0 |
| 9 | SEQ ID NO: 8623-8631 | SEQ ID NOs: 3079-3087 | Hypothetical protein | Adenine specific DNA methylase | n/a | COG2189 | 0 |
| 7 | SEQ ID NO: 8632-8638 | SEQ ID NOs: 3088-3094 | T/G mismatch-specific endonuclease | Type II restriction endonuclease | COG3727 | PF09019 | 0 |
| 20 | RlegA SEQ ID NO: 8349-8415 | RlegT SEQ ID NOs: 2805-2871 | Predicted transcriptional regulator | Hypothetical protein | COG5340 | DUF1814 | 0 |
| 8 | SEQ ID NO: 8654-8661 | SEQ ID NOs: 3110-3117 | Hypothetical protein (associated with cas/cmr genes) | RAMP domain protein (Cmr6-like) | n/a | DUF324 | $2.9 \times 10^{-2}$ |
| 15 | SEQ ID NO: 8639-8653 | SEQ ID NO: 3095-3109 | Uncharacterized membrane protein | Membrane protein, TraG-like N-terminal domain | n/a | PF07916 | $2 \times 10^{-3}$ |
| 7 | SdenA SEQ ID NO: 8317-8348 | SdenT SEQ ID NOs: 2773-2804 | Hypothetical protein | Hypothetical protein | n/a | DUF1814 | $3 \times 10^{-3}$ |

*TA system that is part of a larger operon putatively involved in bacterial defense (FIG. 8).

Of the 24 identified families, 12 families (50%) were already described as TA systems, either experimentally (12 "known" families) or by earlier bioinformatic predictions (3 "predicted" families (Shao et al., 2011)), providing strong validation to the present cloning-based approach for TA discovery (Table 4). Although a diverse set of known TA families is represented in the set retrieved by the present algorithm, to due to limitations of the present approach not all known families were represented. For example, in the family consisting of HipAB gene pairs, 6 out of 19 pairs were found to obey the TA cloning pattern, but since the toxin is relatively large and the antitoxin is a short gene, such a pattern has high probability to occur by chance in the random simulations, and hence this family did not pass the present statistical threshold (p=0.43) (see Discussion).

Example 2

Experimental Validation of Novel TA Families

The present analysis retrieved 8 putative novel families of TA systems (Table 5). Six of these families, which appeared as "stand-alone" toxin-antitoxin pairs (see below), were selected for further experimental characterization (Table 6, herein below). A representative pair was selected from each family and co-transformed into E. coli BL21 (DE3) on a compatible two-vector system, so that the putative toxin was under the control of an IPTG-induced promoter, and the antitoxin was under the control of an arabinose-induced promoter (FIG. 3A). E. coli bacteria carrying these two plasmids were plated on agar plates containing IPTG, arabinose, or both IPTG and arabinose. In all six tested pairs, induction of toxin expression inhibited bacterial growth, while co-induction of the toxin and antitoxin resulted in bacterial survival (FIG. 3A). These results validate the genome-wide approach for discovery of novel TA systems.

The 6 novel validated families were named based on the species from which the validated system was taken: pmenAT (P. mendocina); sanaAT (S. sp. ana-3); rlegAT (R. leguminosarum); psyrAT (P. syringae); sdenAT (S. denitrificans); and hhalTA (H. halophila). The toxins in these new systems were further tested in order to analyze whether they have a bacteriocidic (cell-killing) or bacteriostatic (growth-inhibiting) effect. For this, IPTG was used to induce toxin expression for different time intervals (ranging from 30 to 300 mins) The cells were then plated on agar plates containing arabinose to activate antitoxin expression (FIG. 3C). For the rlegTA system, colony forming units dropped by 5 orders of magnitude following 120 minutes of toxin induction, implying that the rleg toxin has a bactericidal effect on the cells. These results were also supported by the kinetic assays, where induction of antitoxin expression 2.5 hours after toxin induction did not result in cell regrowth for rlegTA (FIG. 3B). A milder effect was observed for the remaining TA systems, with sdenTA and hhalTA showing almost no reduction in colony forming units following toxin induction, suggestive of a bacteriostatic effect for these systems (FIG. 3C).

Previous analyses have shown that toxin-antitoxin systems can be modular, such that members of one toxin family may be associated with several different types of antitoxin, and

TABLE 6

Gene pairs selected for experimental verification in a dual-plasmid arabinose/IPTG expression induction system

| Family | Antitoxin locus tag | A size (aa) | Toxin Locus tag | T size (aa) | Organism | # clones that cover antitoxin | # clones that cover toxin | # clones that cover both | Reversible toxicity? |
|---|---|---|---|---|---|---|---|---|---|
| sdenAT | Sden_0299 | 174 | Sden_0300 | 295 | *Shewanella denitrificans* OS217 | 8 | 0 | 31 | Yes |
| psyrAT | Psyr_3805 | 455 | Psyr_3804 | 698 | *Pseudomonas syringae* pv. *syringae* B728a | 13 | 0 | 1 | Partial |
| sanaAT | Shewana3_4160 | 136 | Shewana3_4161 | 313 | *Shewanella* sp. ANA-3 | 5 | 0 | 29 | Yes |
| pmenAT | Pmen_0566 | 360 | Pmen_0565 | 217 | *Pseudomonas mendocina* ymp | 3 | 0 | 10 | Yes |
| rlegAT | Rleg_6340 | 205 | Rleg_6339 | 289 | *Rhizobium leguminosarum* bv. *trifolii* WSM1325 | 11 | 0 | 31 | No |
| hhalTA | Hhal_0686 | 96 | Hhal_0685 | 119 | *Halorhodospira halophila* SL1 | 2 | 0 | 23 | Yes |

Example 4

Characteristics of Novel TA Families

Most type II TA modules described to date share several typical characteristics: the antitoxin appears upstream of the toxin; both the toxin and antitoxin are small proteins (typically ~100aa); and the antitoxin contains a DNA binding domain (Makarova et al., 2009). Since the present approach does not rely on such attributes for TA modules discovery it has the potential to expand the premises of TA modules properties. Indeed, some of the new families that were experimentally validated deviate significantly from the previously described characteristics. For example, the sizes of many new toxins and antitoxins are significantly larger than 100 aa, with a maximum of 698 aa in the toxin of the psyrAT system; in two families the toxin is located upstream of the antitoxin (FIG. 4A); and several antitoxins do not contain a known DNA binding domain (although the possibility cannot be ruled out that some antitoxins code for yet uncharacterized such domains) (FIG. 4A).

Although in most of the known TA systems the toxin is a ribonuclease, diverse domains within the new toxins detected, including DNA helicase, phosphoribosyl-transferase and nucleotidyl-transferase suggest novel mechanisms of toxicity (FIG. 4A). Similarly, the presence of an ADP-ribose-binding, S-adenosyl-homocysteine hydrolase and nucleotide-binding domains in some of the antitoxins suggest that these antitoxins perform a more complex function than simply masking the activity of the toxin by protein-protein interactions (FIG. 4A; Table 5). Finally, in four of the novel families, it seems that the TA system is part of a larger operon that is co-horizontally transferred between genomes in the context of defense islands, suggesting their involvement in more complex defense mechanisms (Table 5; FIG. 8).

vice versa (Leplae et al., 2011; Makarova et al., 2009). Indeed, the toxins of three of the present new families carry the same domain, DUF1814, with a different antitoxin associated with this domain in each of the three families (Table 2; FIG. 4A). One of these families, rlegAT, where the DUF1814 toxin is accompanied by COG5340 as an antitoxin, was previously shown to be enriched in defense islands in bacterial genomes and was suggested as a new TA system based on its two-gene nature (Makarova et al., 2011). The DUF1814 domain was recently classified as a nucleotidyl-transferase domain based on structural information, but its specific substrates are yet unknown (Kuchta et al., 2009). Interestingly, the DUF1814 domain was also documented in AbiG, a two-gene system involved in abortive infection in *Lactococcus lactis* via an unknown mechanism (Makarova et al., 2011; O'Connor et to al., 1996), although there is no direct homology between the AbiG system and any of the genes in the new TA systems that were presently detected. Therefore, the results point to DUF1814 domain-containing proteins as a widespread superfamily of toxins that might be involved in anti-phage defense (see below).

Overall, members of the novel systems that were detected appeared in 21% of the genomes analyzed, and in the vast majority of cases (93%) they appeared in the chromosomal DNA rather than on plasmids. These results suggest that such systems have important roles in bacterial physiology/defense rather than functioning as plasmid addiction molecules. The distribution of most families is spread across multiple bacterial phyla including several important human pathogens (Tables 4 and 5; FIGS. 4B-C). For example, the psyrAT, sanaAT, and pmenAT systems are abundant in enteropathogenic and uropathogenic *E. coli* strains; the pmenAT system also exists in many *Mycobacterium tuberculosis* isolates; psyrAT exists in *Shigella* and *Pseudomonas aeruginosa* strains; and the rlegAT and sanaAT systems exist in several pathogenic *Legionella* species. In addition, many resident bacteria of the human gut carry one or more of these TA modules, including bacteria belonging to the *Bifidobacterium* and *Prevotella* genera (Tables 7-11, herein below, FIG. 4C). This underscores the novel toxin-antitoxin families as potentially contributing to persistence, phage defense and stress responses of clinically important bacteria.

TABLE 7 pmenAT Family

| Organism name | Toxin IMG Gene Object ID | Antitoxin IMG Gene Object ID |
|---|---|---|
| *Acidovorax avenae citrulli* AAC00-1 | 639821371 | 639821372 |
| *Actinosynnema mirum* 101, DSM 43827 | 645948092 | 645948093 |
| *Aliivibrio salmonicida* LFI1238 | 643378769 | 643378768 |
| *Alkalilimnicola ehrlichei* MLHE-1 | 638125243 | 638125244 |
| *Arthrospira maxima* CS-328 | 643172840 | 643172839 |
| *Arthrospira maxima* CS-328 | 643172852 | 643172851 |
| *Arthrospira platensis* NIES-39 | 650387585 | 650387586 |
| *Arthrospira platensis* Paraca | 646128269 | 646128268 |
| *Arthrospira* sp. PCC 8005 | 648389866 | 648389867 |
| *Arthrospira* sp. PCC 8005 | 648389879 | 648389880 |
| *Aurantimonas manganoxydans* SI85-9A1 | 639105350 | 639105351 |
| *Bacillus thuringiensis* IBL200 | 644713531 | 644713532 |
| *Beggiatoa* sp. PS | 641099098 | 641099099 |
| *Brachyspira hyodysenteriae* WA1, ATCC 49526 | 643738127 | 643738126 |
| *Candidatus Accumulibacter phosphatis* Type IIA UW-1 | 645012050 | 645012051 |
| *Cyanothece* sp. PCC 7822 | 648189618 | 648189617 |
| *Dermacoccus* sp. Ellin185 | 650227082 | 650227083 |
| *Desulfonatronospira thiodismutans* ASO3-1 | 644404121 | 644404120 |
| *Desulfovibrio* sp. 3_1_syn3 | 648927836 | 648927837 |
| *Dickeya zeae* Ech1591 | 644851325 | 644851326 |
| *Edwardsiella ictaluri* 93-146 | 644783480 | 644783479 |
| *Edwardsiella tarda* EIB202 | 646417146 | 646417147 |
| *Edwardsiella tarda* FL6-60 | 648267250 | 648267249 |
| *Enhydrobacter aerosaccus* SK60 | 646169120 | 646169121 |
| *Escherichia coli* O127:H6 E2348/69 (EPEC) | 643442443 | 643442442 |
| *Escherichia* sp. 4_1_40B | 645350401 | 645350402 |
| *Eubacterium saburreum* DSM 3986 | 650308116 | 650308115 |
| *Geobacter lovleyi* SZ | 642677613 | 642677612 |
| *Gloeobacter violaceus* PCC 7421 | 637460780 | 637460781 |
| *Gluconacetobacter diazotrophicus* PAl 5, DSM 5601 | 641334933 | 641334934 |
| *Klebsiella pneumoniae* 342 | 643367815 | 643367814 |
| *Leptotrichia goodfellowii* F0264 | 647211994 | 647211995 |
| *Lyngbya* sp. CCY 8106 | 640014016 | 640014017 |
| *Marinobacter* sp. ELB17 | 640635553 | 640635552 |
| *Methylobacter tundripaludum* SV96 | 648842442 | 648842443 |
| *Micromonospora aurantiaca* ATCC 27029 | 648134607 | 648134606 |
| *Mycobacterium bovis* AF2122/97 | 637137397 | 637137398 |
| *Mycobacterium bovis* BCG Pasteur 1173P2 | 639828992 | 639828993 |
| *Mycobacterium bovis* BCG Tokyo 172 | 643732879 | 643732880 |
| *Mycobacterium tuberculosis* 02_1987 | 643025701 | 643025702 |
| *Mycobacterium tuberculosis* 210 | 647208652 | 647208653 |
| *Mycobacterium tuberculosis* 94_M4241A | 643021508 | 643021509 |
| *Mycobacterium tuberculosis* 98-R604 INH-RIF-EM | 645190033 | 645190034 |
| *Mycobacterium tuberculosis* C | 638728678 | 638728679 |
| *Mycobacterium tuberculosis* CDC1551 | 637094328 | 637094329 |
| *Mycobacterium tuberculosis* CPHL_A | 646012704 | 646012705 |
| *Mycobacterium tuberculosis* EAS054 | 643034220 | 643034221 |
| *Mycobacterium tuberculosis* F11 (ExPEC) | 640604798 | 640604799 |
| *Mycobacterium tuberculosis* GM 1503 | 643047494 | 643047495 |
| *Mycobacterium tuberculosis* H37Ra | 640600718 | 640600719 |
| *Mycobacterium tuberculosis* H37Rv (lab strain) | 637025228 | 637025229 |
| *Mycobacterium tuberculosis* Haarlem | 641785646 | 641785647 |
| *Mycobacterium tuberculosis* K85 | 646016919 | 646016920 |
| *Mycobacterium tuberculosis* KZN 1435 (MDR) | 644877737 | 644877738 |
| *Mycobacterium tuberculosis* KZN 4207 | 647084598 | 647084599 |
| *Mycobacterium tuberculosis* KZN 4207 (DS) | 645118109 | 645118108 |

TABLE 7-continued pmenAT Family

| Organism name | Toxin IMG Gene Object ID | Antitoxin IMG Gene Object ID |
|---|---|---|
| *Mycobacterium tuberculosis* KZN R506 | 648334260 | 648334261 |
| *Mycobacterium tuberculosis* KZN V2475 | 647088790 | 647088791 |
| *Mycobacterium tuberculosis* SUMu001 | 648445593 | 648445594 |
| *Mycobacterium tuberculosis* SUMu002 | 648446131 | 648446132 |
| *Mycobacterium tuberculosis* SUMu003 | 648449945 | 648449946 |
| *Mycobacterium tuberculosis* SUMu004 | 648454358 | 648454359 |
| *Mycobacterium tuberculosis* SUMu005 | 648458950 | 648458951 |
| *Mycobacterium tuberculosis* SUMu006 | 648463059 | 648463060 |
| *Mycobacterium tuberculosis* SUMu007 | 648467445 | 648467446 |
| *Mycobacterium tuberculosis* SUMu008 | 648471678 | 648471679 |
| *Mycobacterium tuberculosis* SUMu009 | 648479444 | 648479445 |
| *Mycobacterium tuberculosis* SUMu010 | 648483724 | 648483725 |
| *Mycobacterium tuberculosis* SUMu011 | 648487988 | 648487989 |
| *Mycobacterium tuberculosis* SUMu012 | 648488272 | 648488273 |
| *Mycobacterium tuberculosis* T17 | 643047830 | 643047831 |
| *Mycobacterium tuberculosis* T85 | 643038464 | 643038465 |
| *Mycobacterium tuberculosis* T92 | 643026422 | 643026423 |
| *Nitrosococcus halophilus* Nc4 | 646693941 | 646693942 |
| *Nitrosomonas europaea* ATCC 19718 | 637427715 | 637427716 |
| *Oscillatoria* sp. PCC 6506 | 648860075 | 648860076 |
| *Parvibaculum lavamentivorans* DS-1 | 640878511 | 640878512 |
| *Pectobacterium carotovorum carotovorum* PC1 | 644864144 | 644864143 |
| *Pedobacter* sp. BAL39 | 641137361 | 641137360 |
| *Prevotella timonensis* CRIS 5C-B1 | 647314799 | 647314798 |
| *Providencia rustigianii* DSM 4541 | 643141873 | 643141874 |
| *Pseudomonas entomophila* L48 | 637999408 | 637999409 |
| *Pseudomonas mendocina* ymp | 640501778 | 640501779 |
| *Rhodopseudomonas palustris* TIE-1 | 642711985 | 642711984 |
| *Roseiflexus* sp. RS-1 | 640593922 | 640593923 |
| *Roseovarius nubinhibens* ISM | 638835723 | 638835722 |
| *Ruminococcus flavefaciens* FD-1 | 646114893 | 646114892 |
| *Shewanella putrefaciens* CN-32 | 640500731 | 640500732 |
| *Stigmatella aurantiaca* DW4/3-1 | 649685957 | 649685958 |
| *Synechocystis* sp. PCC 6803 | 637472042 | 637472041 |
| *Syntrophothermus lipocalidus* DSM 12680 | 646854986 | 646854985 |
| *Thauera* sp. MZ1T | 643700535 | 643700534 |
| *Thermus aquaticus* Y51MC23 | 645188421 | 645188422 |
| *Thiobacillus denitrificans* ATCC 25259 | 637710175 | 637710174 |
| *Zymomonas mobilis* subsp. *mobilis* ZM4 ZM4 plasmid pZZM405 | 648935037 | 648935036 |

TABLE 8 psyrAT Family

| Organism name | Toxin IMG Gene Object ID | Antitoxin IMG Gene Object ID |
|---|---|---|
| *Acinetobacter johnsonii* SH046 | 646301838 | 646301837 |
| *Arthrospira platensis* NIES-39 | 650383509 | 650383508 |
| *Chlorobium phaeobacteroides* DSM 266 | 639765722 | 639765723 |
| *Cyanothece* sp. PCC 8801 | 643474605 | 643474606 |
| *Dehalogenimonas lykanthroporepellens* BL-DC-9 | 648069289 | 648069288 |
| *Desulfitobacterium hafniense* DCB-2 | 643560590 | 643560591 |
| *Desulfitobacterium hafniense* Y51 | 637910440 | 637910441 |
| *Desulfotalea psychrophila* LSv54 | 637527656 | 637527657 |
| *Desulfotomaculum acetoxidans* 5575, DSM 771 | 645033659 | 645033660 |
| *Escherichia coli* 83972 | 644299713 | 644299712 |
| *Escherichia coli* ABU 83972 | 648235458 | 648235457 |
| *Escherichia coli* B088 | 647955723 | 647955722 |
| *Escherichia coli* B185 | 647960289 | 647960288 |
| *Escherichia coli* E22 (EPEC) | 638663931 | 638663932 |
| *Escherichia coli* IAI39 | 643513743 | 643513742 |
| *Escherichia coli* M605 | 648348440 | 648348439 |
| *Escherichia coli* M718 | 648353998 | 648353997 |

TABLE 8-continued psyrAT Family

| Organism name | Toxin IMG Gene Object ID | Antitoxin IMG Gene Object ID |
|---|---|---|
| Escherichia coli MS 185-1 | 648599204 | 648599205 |
| Escherichia coli MS 200-1 | 648586960 | 648586959 |
| Escherichia coli MS 21-1 | 648564766 | 648564767 |
| Escherichia coli MS 45-1 | 648550266 | 648550267 |
| Escherichia coli MS 69-1 | 648553056 | 648553055 |
| Escherichia coli O103:H2 str. 12009 | 646343586 | 646343585 |
| Escherichia coli O111:NM B171 (EPEC2) | 638674448 | 638674447 |
| Escherichia coli O139:H28 F11 (ETEC) | 638660743 | 638660744 |
| Escherichia coli O150:H5 SE15 | 646872639 | 646872638 |
| Escherichia coli O157:H7 EC4042 | 642258307 | 642258308 |
| Escherichia coli O157:H7 EC4045 | 642254369 | 642254368 |
| Escherichia coli O157:H7 EC4076 | 642284244 | 642284243 |
| Escherichia coli O157:H7 EC4113 | 642276965 | 642276966 |
| Escherichia coli O157:H7 EC4196 | 642270878 | 642270879 |
| Escherichia coli O157:H7 EC4206 | 642245550 | 642245551 |
| Escherichia coli O157:H7 EC4401 | 642289554 | 642289553 |
| Escherichia coli O157:H7 EC4486 | 642295954 | 642295953 |
| Escherichia coli O157:H7 EC4501 | 642302598 | 642302597 |
| Escherichia coli O157:H7 EC508 | 642315404 | 642315403 |
| Escherichia coli O157:H7 EC869 | 642309592 | 642309591 |
| Escherichia coli O157:H7 EDL933 (EHEC) | 637066109 | 637066108 |
| Escherichia coli O157:H7 TW14588 | 643013921 | 643013922 |
| Escherichia coli O6:K15:H31 536 (UPEC) | 638064677 | 638064676 |
| Escherichia coli O6:K2:H1 CFT073 (UPEC) | 637358068 | 637358067 |
| Escherichia coli SECEC SMS-3-5 | 641618544 | 641618543 |
| Kingella denitrificans ATCC 33394 | 650370405 | 650370406 |
| Lyngbya sp. CCY 8106 | 640016567 | 640016566 |
| Maribacter sp. HTCC2170 | 648162921 | 648162922 |
| Marinobacter aquaeolei VT8 | 639810511 | 639810512 |
| Microcoleus chthonoplastes PCC 7420 | 647568262 | 647568263 |
| Nitrococcus mobilis Nb-231 | 639000572 | 639000573 |
| Nitrosomonas europaea ATCC 19718 | 637428828 | 637428829 |
| Nostoc sp. PCC 7120 | 637233840 | 637233841 |
| Oscillochloris trichoides DG6 | 650114297 | 650114298 |
| Pelodictyon phaeoclathratiforme BU-1 | 642727669 | 642727668 |
| Photorhabdus luminescens laumondii TTO1 | 637466171 | 637466172 |
| Polaromonas naphthalenivorans CJ2 | 639835976 | 639835975 |
| Providencia stuartii ATCC 25827 | 642341526 | 642341525 |
| Pseudomonas aeruginosa 39016 | 650201418 | 650201417 |
| Pseudomonas syringae pv. syringae B728a | 637654162 | 637654163 |
| Roseiflexus castenholzii HLO8, DSM 13941 | 640894598 | 640894597 |
| Shewanella baltica OS155 | 640121625 | 640121624 |
| Shigella dysenteriae 1617 | 650108289 | 650108288 |
| Shigella dysenteriae Sd197 | 640435823 | 640435822 |
| Sinorhizobium meliloti AK83, DSM 23913 | 648746639 | 648746638 |
| Teredinibacter turnerae T7901 | 644918750 | 644918749 |
| Trichodesmium erythraeum IMS101 | 638106714 | 638106713 |
| Vibrio furnissii CIP 102972 | 647177818 | 647177819 |

TABLE 9 rlegAT Family

| Organism name | Toxin IMG Gene Object ID | Antitoxin IMG Gene Object ID |
|---|---|---|
| Acidovorax delafieldii 2AN | 645555203 | 645555202 |
| Acidovorax sp. JS42 | 639838035 | 639838036 |
| Agreia sp. PHSC20C1 | 638988138 | 638988137 |
| Agrobacterium sp. H13-3 | 649987843 | 649987844 |
| Asticcacaulis excentricus CB 48 | 649817025 | 649817026 |
| Bradyrhizobium japonicum USDA 110 | 637369489 | 637369490 |
| Brevibacterium mcbrellneri ATCC 49030 | 647495830 | 647495829 |
| Candidatus Accumulibacter phosphatis Type IIA UW-1 | 645008063 | 645008062 |
| Candidatus Protochlamydia amoebophila UWE25 | 637502933 | 637502934 |
| Chlorobium limicola DSM 245 | 642669528 | 642669529 |
| Chlorobium phaeobacteroides DSM 266 | 639765252 | 639765251 |
| Chlorobium phaeovibrioides DSM 265 | 640453070 | 640453069 |
| Conexibacter woesei DSM 14684 | 646506209 | 646506208 |
| Corynebacterium glutamicum R | 640460410 | 640460411 |
| Delftia acidovorans SPH-1 | 641295145 | 641295146 |
| Desulfococcus oleovorans Hxd3 | 641265756 | 641265755 |
| Desulfomicrobium baculatum X, DSM 4028 | 645000532 | 645000533 |
| Eggerthella lenta VPI 0255, DSM 2243 | 645026066 | 645026065 |
| Eggerthella sp. 1_3_56FAA | 650045752 | 650045751 |
| Ensifer medicae WSM419 | 640743222 | 640743221 |
| Ensifer medicae WSM419 | 640777216 | 640777215 |
| Ensifer medicae WSM419 | 640743222 | 640743221 |
| Gemmata obscuriglobus UQM 2246 | 642225335 | 642225336 |
| Gloeobacter violaceus PCC 7421 | 637460064 | 637460063 |
| Gordonia bronchialis DSM 43247 | 646396290 | 646396289 |
| Gordonibacter pamelaeae 7-10-1-bT, DSM 19378 | 650562241 | 650562242 |
| Intrasporangium calvum 7KIP, DSM 43043 | 649830949 | 649830948 |
| Legionella longbeachae NSW150 | 648036627 | 648036628 |
| Legionella longbeachae NSW150 | 648038896 | 648038897 |
| Lentisphaera araneosa HTCC2155 | 641129191 | 641129192 |
| Lentisphaera araneosa HTCC2155 | 641132412 | 641132413 |
| Mariprofundus ferrooxydans PV-1 | 639879700 | 639879701 |
| Methylobacterium extorquens AM1 | 644816407 | 644816408 |
| Mobiluncus mulieris ATCC 35239 | 648832456 | 648832455 |
| Mobiluncus mulieris ATCC 35243 | 644432065 | 644432064 |
| Mobiluncus mulieris FB024-16 | 648839977 | 648839978 |
| Mycobacterium leprae Br4923 | 643606676 | 643606675 |
| Mycobacterium leprae TN | 637073074 | 637073073 |
| Mycobacterium marinum M, ATCC BAA-535 | 641718837 | 641718836 |
| Nakamurella multipartita Y-104, DSM 44233 | 645043556 | 645043555 |
| Nitrosococcus halophilus Nc4 | 646694275 | 646694276 |
| Olsenella uli VPI, DSM 7084 | 648106565 | 648106566 |
| Opitutaceae sp. TAV2 | 641180308 | 641180309 |
| Pelodictyon luteolum DSM 273 | 637768549 | 637768548 |
| Pelodictyon phaeoclathratiforme BU-1 | 642727042 | 642727041 |
| Phenylobacterium zucineum HLK1 | 642757721 | 642757722 |
| Polaromonas naphthalenivorans CJ2 | 639826420 | 639826421 |
| Polaromonas sp. JS666 | 639328971 | 639328972 |
| Polaromonas sp. JS666 | 639328971 | 639328972 |
| Propionibacterium freudenreichii shermanii CIRM-BIA1 | 649639912 | 649639911 |
| Raphidiopsis brookii D9 | 647110477 | 647110476 |
| Rhizobium leguminosarum bv. trifolii WSM1325 | 644828134 | 644828135 |
| Rhizobium leguminosarum bv. trifolii WSM1325 | 644828341 | 644828342 |
| Rhizobium leguminosarum bv. viciae 3841 | 639650816 | 639650815 |
| Rhizobium rhizogenes K84 | 643644497 | 643644496 |
| Rhizobium sp. NGR234 (ANU265) | 643821930 | 643821929 |
| Rhodomicrobium vannielii ATCC 17100 | 649745264 | 649745263 |
| Rhodopseudomonas palustris DX-1 | 649838192 | 649838193 |
| Rhodopseudomonas palustris DX-1 | 649839250 | 649839249 |
| Slackia heliotrinireducens RHS 1, DSM 20476 | 644987249 | 644987248 |
| Synechococcus sp. RS9917 | 638961153 | 638961154 |
| Syntrophobacter fumaroxidans MPOB | 639702820 | 639702821 |
| Variovorax paradoxus S110 | 644796233 | 644796232 |
| Verrucomicrobiales sp. DG1235 | 647600269 | 647600268 |
| Xanthomonas oryzae pv oryzae MAFF 311018 | 637850518 | 637850519 |
| Xanthomonas oryzae pv oryzicola BLS256 | 641737990 | 641737989 |
| Xanthomonas oryzae pv. oryzae KACC10331 | 637633303 | 637633304 |
| Xanthomonas oryzae pv. oryzae PXO99A | 642640643 | 642640644 |
| Xylanimonas cellulosilytica DSM 15894 | 646444306 | 646444305 |

TABLE 10 sdenAT Family

| Organism name | Toxin IMG Gene Object ID | Antitoxin IMG Gene Object ID |
|---|---|---|
| Acidithiobacillus ferrooxidans ATCC 53993 | 642789179 | 642789178 |
| Ammonifex degensii KC4 | 646360172 | 646360173 |
| Bifidobacterium longum DJO10A | 642679488 | 642679489 |
| Bifidobacterium longum longum ATCC 55813 | 644347132 | 644347131 |
| Bifidobacterium longum longum CCUG 52486 | 643912156 | 643912157 |
| Bifidobacterium longum longum CCUG 52486 | 643912885 | 643912886 |
| Bifidobacterium longum longum F8 | 650528372 | 650528373 |
| Bifidobacterium longum NCC2705 | 637327456 | 637327457 |
| Bifidobacterium sp. 12_1_47BFAA | 650054808 | 650054809 |
| Burkholderia rhizoxinica HKI 454 | 649762359 | 649762358 |
| Cellvibrio japonicus Ueda 107 | 642704960 | 642704959 |
| delta proteobacterium sp. MLMS-1 | 639152971 | 639152970 |
| delta proteobacterium sp. MLMS-1 | 639153350 | 639153349 |
| delta proteobacterium sp. MLMS-1 | 639155398 | 639155397 |
| delta proteobacterium sp. MLMS-1 | 639158034 | 639158033 |
| Desulfurivibrio alkaliphilus AHT2 | 646845548 | 646845547 |
| Eggerthella lenta VPI 0255, DSM 2243 | 645023812 | 645023813 |
| Helicobacter canadensis MIT 98-5491, ATCC 700968 | 643921049 | 643921048 |
| Helicobacter canadensis MIT 98-5491, ATCC 700968 | 647542139 | 647542138 |
| Marinobacter sp. ELB17 | 640637051 | 640637050 |
| Marinomonas sp. MWYL1 | 640805575 | 640805574 |
| Pantoea sp. At-9b | 649850365 | 649850364 |
| Parascardovia denticolens DSM 10105 | 650283875 | 650283876 |
| Pectobacterium wasabiae WPP 163 | 646378766 | 646378765 |
| Photorhabdus luminescens laumondii TTO1 | 637462283 | 637462284 |
| Photorhabdus luminescens laumondii TTO1 | 637465673 | 637465672 |
| Proteus mirabilis ATCC 29906 | 644443817 | 644443818 |
| Proteus mirabilis HI4320 | 642578705 | 642578706 |
| Proteus mirabilis HI4320 | 642578886 | 642578885 |
| Providencia rustigianii DSM 4541 | 643143270 | 643143271 |
| Shewanella denitrificans OS217 | 637954281 | 637954280 |
| Verminephrobacter eiseniae EF01-2 | 639850605 | 639850606 |
| Xenorhabdus nematophila ATCC 19061 | 649646151 | 649646150 |

TABLE 11 sanaAT Family

| Organism name | Toxin IMG Gene Object ID | Antitoxin IMG Gene Object ID |
|---|---|---|
| Acidovorax delafieldii 2AN | 645555430 | 645555431 |
| Acidovorax sp. JS42 | 639838656 | 639838657 |
| Burkholderia pseudomallei 1106a | 640135680 | 640135679 |
| Burkholderia pseudomallei 14 | 641944057 | 641944056 |
| Burkholderia pseudomallei 9 | 641966075 | 641966074 |
| Burkholderia pseudomallei B7210 | 641976418 | 641976417 |
| Burkholderia pseudomallei Pakistan 9 | 644419997 | 644419996 |
| Chlorobium limicola DSM 245 | 642667845 | 642667846 |
| delta proteobacterium sp. MLMS-1 | 639154553 | 639154552 |
| Desulfatibacillum alkenivorans AK-01 | 643534322 | 643534323 |
| Escherichia coli 83972 | 644303823 | 644303822 |
| Escherichia coli ABU 83972 | 648234949 | 648234948 |
| Escherichia coli FVEC1302 | 648901279 | 648901278 |
| Escherichia coli FVEC1412 | 647965363 | 647965362 |
| Escherichia coli H591 | 648379532 | 648379531 |
| Escherichia coli MS 119-7 | 648651653 | 648651652 |
| Escherichia coli MS 198-1 | 648524147 | 648524146 |
| Escherichia coli MS 45-1 | 648547640 | 648547641 |
| Escherichia coli MS 69-1 | 648552519 | 648552520 |
| Escherichia coli MS 69-1 | 648554605 | 648554604 |
| Escherichia coli O17:K52:H18 UMN026 | 644760974 | 644760973 |
| Escherichia coli O6:K2:H1 CFT073 (UPEC) | 637357531 | 637357530 |
| Escherichia coli W | 648733316 | 648733317 |
| Escherichia coli W, ATCC 9739 | 650430781 | 650430780 |
| Escherichia sp. 1_1_43 | 646267384 | 646267383 |
| Legionella drancourtii LLAP12 | 645590921 | 645590922 |
| Legionella pneumophila Corby | 640570188 | 640570189 |
| Legionella pneumophila Lens | 637581974 | 637581973 |
| Legionella pneumophila Paris | 637581109 | 637581110 |
| Methylovorus glucosetrophus SIP3-4 | 644899678 | 644899679 |
| Pelodictyon luteolum DSM 273 | 637768759 | 637768758 |
| Pelodictyon phaeoclathratiforme BU-1 | 642728170 | 642728169 |
| Photobacterium sp. SKA34 | 639052391 | 639052392 |
| Photorhabdus asymbiotica asymbiotica ATCC 43949 | 644890382 | 644890383 |
| Photorhabdus luminescens laumondii TTO1 | 637465992 | 637465993 |
| Pseudoalteromonas haloplanktis TAC125 | 637736049 | 637736048 |
| Rhodocista centenaria SW | 643414024 | 643414025 |
| Shewanella baltica OS155 | 640110446 | 640110445 |
| Shewanella sp. ANA-3 | 639720519 | 639720518 |
| Synechocystis sp. PCC 6803 | 637471904 | 637471903 |
| Verminephrobacter eiseniae EF01-2 | 639851447 | 639851446 |
| Vibrio harveyi BB120, ATCC BAA-1116 | 640911279 | 640911280 |
| Vibrio tapetis CECT4600; CIP104856; B1090 plasmid pVT1 | 642914607 | 642914606 |
| Vibrio vulnificus CMCP6 | 637363648 | 637363647 |
| Vibrio vulnificus M06-24/O | 649922394 | 649922393 |
| Vibrionales sp. SWAT-3 | 641059142 | 641059141 |
| Yersinia aldovae ATCC 35236 | 645336728 | 645336729 |
| Yersinia enterocolitica enterocolitica 8081 | 640077595 | 640077596 |

Example 5

Novel TA Systems Provide Phage Resistance

The present inventors next set out to explore whether any of the TA systems detected can provide defense against phage. For this, efficiency of plating assays of T7 phage on E. coli hosts were performed (FIG. 5A). Since these new TA systems to are widespread in E. coli strains (but are not found in the lab strains E. coli K-12 and E. coli BL21), it was hypothesized that a successful coliphage, such as T7, might hold anti-defense mechanisms that mitigate the defense conferred by the TA systems. The present inventors therefore tested, in addition to the wild-type (WT) T7 phage, 12 additional T7 mutants lacking genes that are not-essential for infection of E. coli K-12 (Table 12). Each of these T7 mutants was used to infect E. coli BL21 or K-12 expressing the five verified new TA systems, as well as control clones expressing only the antitoxin of each system (FIG. 5A). One of the tested systems, sanaAT, was found to provide E. coli with resistance against T7Δ4.3Δ4.5Δ4.7, reducing sensitivity to this phage strain by almost 3 orders of magnitude (FIG. 5B). A second system, rlegAT, resulted in opaque plaques with plaque diameters reduced more than fourfold for the WT T7 strain (diameters of 0.47 mm±0.06 for E. coli expressing both the toxin and the antitoxin, as compared to 1.77 mm±0.03 for bacteria expressing the antitoxin only).

TABLE 12

| | Genes deleted |
|---|---|
| WT T7 | none |
| T7Δ0.3 | 0.3 |
| T7Δ0.7Δ1.7 | 0.7, 1.7 |
| T7 LG3 | 1.1, 1.2, 1.3 |
| T7Δ1.2 | 1.2 |
| T7Δ1.2Δ1.7 | 1.2, 1.7 |
| T7Δ1.7 | 1.7 |
| T7Δ2.8 | 2.8 |
| T7Δ3.8 | 3.8 |
| T7 HS33 | 4.3, 4.5, 4.7 |
| T7Δ4.5 | 4.5 |
| T7Δ5.3-5.9 | 5.3-5.9 |
| T7Δ5.9 | 5.9 |

Figure 5C:
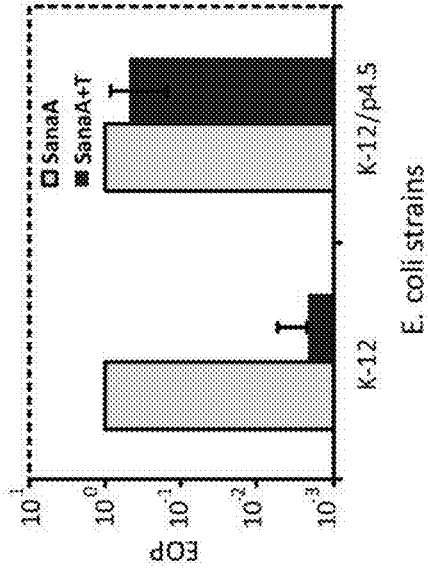

Since the sanaAT system provides resistance to a T7 phage lacking 3 non-essential genes (genes 4.3, 4.5 and 4.7) but not to the WT T7 phage, it was hypothesized that one of these genes codes for an anti-defense mechanism that overcomes the abortive infection imposed by the TA system. Complementation assays in E. coli K-12 expressing gene 4.5 from a plasmid marked this gene as encoding the anti-Abi mechanism (FIG. 5C). The 4.5 gene codes for a peptide (85aa) with no functional annotation.

The present inventors asked whether the defense provided by the sanaTA system against the phage is Lon-dependent. The Lon protease is one of the major proteolytic machineries in the bacterial cell (Gottesman, 2003), and was implicated in degradation ("destabilization") of many types of antitoxins in E. coli, thus enabling toxin activity (Christensen et al., 2001; Van Melderen et al., 1996; Wang et al., 2011). Indeed, T7 mutant growth on E. coli containing the sanaTA system was restored by two orders of magnitude when the E. coli also lacked ion (FIG. 5D), suggesting that the sanaTA protection from T7 phage depends on Lon activity.

Figure 5E:
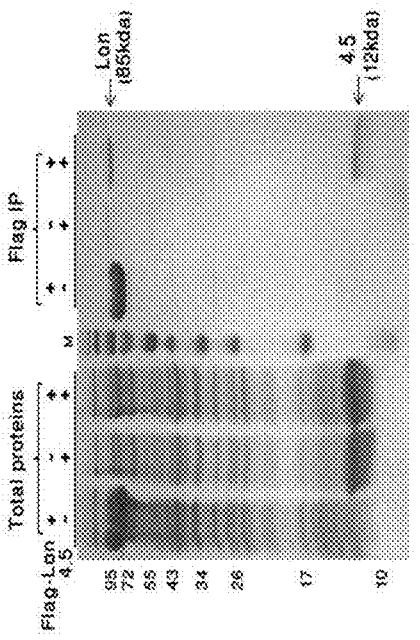
Figure 5D:
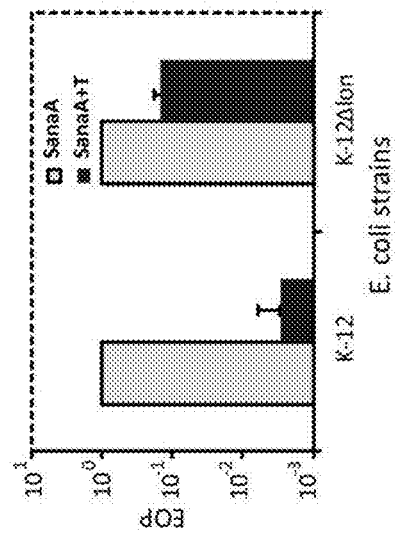
Figure 5F:
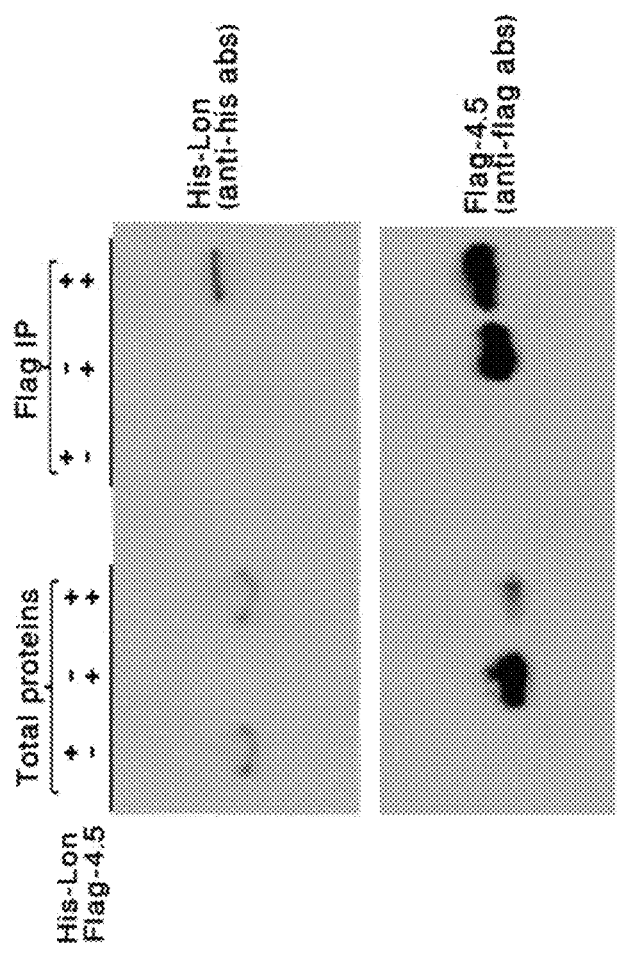

It was hypothesized that the phage gene product (Gp) 4.5 interacts with Lon to prevent antitoxin degradation and thus hinders the sanaTA abortive infection activity. To test this hypothesis we co-expressed Lon (Flag-tagged) and Gp4.5 within E. coli. Indeed, we found that Lon and Gp4.5 co-immuno-precipitate, indicating that 4.5 tightly binds Lon (FIG. 5E). A reciprocal co-immuno-precipitation assay, where pull-down was performed on flag-tagged Gp4.5 protein, produced similar co-immuno-precipitation patterns (FIG. 5F). Overall, these results suggest that the T7 Gp4.5 neutralizes TA-system-mediated abortive infection by inhibiting the Lon protease activity, thus preventing antitoxin degradation and toxin activation.

Example 6

Phage Anti-Abi Gene Inhibits Persistence-Mediated Resistance to Antibiotics

Toxin-antitoxin systems were shown to mediate bacterial resistance to antibiotics through promotion of persister cells (Maisonneuve et al., 2011; Rotem et al., 2010). Persisters are non-growing bacterial cells found in a dormant state and are thus resistant to many antibiotics and other stress conditions (Smith and Romesberg, 2007). Such persisters are stochastically found in bacterial populations as a small fraction of the population. It was recently shown that persistence in E. coli depends on resident type II TA systems as well as on the Lon protease. Indeed, deletion of Lon in E. coli was shown to mitigate TA-system-mediated persistence and resulted in higher sensitivity to antibiotics (Maisonneuve et al., 2011).

The present discovery of a T7-encoded peptide that generally alleviates TA systems activity via inhibition of the Lon protease raised the hypothesis that this peptide can also inhibit persister formation. To test this hypothesis persistence was measured as the fraction of surviving E. coli cells following 5 hr exposure to antibiotics (ampicillin) Bacteria expressing the 4.5 gene were 5-fold more sensitive to ampicillin as compared to WT bacteria (manifested in 5-fold less persister cells for ampicillin) (FIG. 6). These results suggest possible utility of phage-derived peptides as a means to tackle bacterial persistence.

To search for additional phage genes that may function as Lon inhibitors, the present inventors looked for all phage genomes for genes showing homology to the N-terminus of Lon, roughly where the 4.5 aligns (FIG. 5D). 6 such genes were found (including gene 4.5) in a diverse set of phages.

It may be predicted that these phage proteins inhibit Lon protease and can thus function as inhibitors of persistence.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Aizenman, E., Engelberg-Kulka, H., and Glaser, G. (1996). An Escherichia coli chromosomal "addiction module" regulated by guanosine [corrected] 3',5'-bispyrophosphate: a model for programmed bacterial cell death. Proc Natl Acad Sci USA 93, 6059-6063.

Amitai, S., Kolodkin-Gal, I., Hananya-Meltabashi, M., Sacher, A., and Engelberg-Kulka, H. (2009). Escherichia coli MazF leads to the simultaneous selective synthesis of both "death proteins" and "survival proteins". PLoS Genet. 5, e1000390.

Aoki, S. K., Diner, E. J., de Roodenbeke, C. T., Burgess, B. R., Poole, S. J., Braaten, B. A., Jones, A. M., Webb, J. S., Hayes, C. S., Cotter, P. A., et al. (2010). A widespread family of polymorphic contact-dependent toxin delivery systems in bacteria. Nature 468, 439-442.

Bernard, P., and Couturier, M. (1992). Cell killing by the F plasmid CcdB protein involves poisoning of DNA-topoisomerase II complexes. J Mol Biol 226, 735-745.

Cherny, I., and Gazit, E. (2004). The YefM antitoxin defines a family of natively unfolded proteins: implications as a novel antibacterial target. J Biol Chem 279, 8252-8261.

Chopin, M. C., Chopin, A., and Bidnenko, E. (2005). Phage abortive infection in lactococci: variations on a theme. Curr Opin Microbiol 8, 473-479.

Christensen, S. K., Maenhaut-Michel, G., Mine, N., Gottesman, S., Gerdes, K., and Van Melderen, L. (2004). Overproduction of the Lon protease triggers inhibition of translation in Escherichia coli: involvement of the yefM-yoeB toxin-antitoxin system. Mol Microbiol 51, 1705-1717.

Christensen, S. K., Mikkelsen, M., Pedersen, K., and Gerdes, K. (2001). RelE, a global inhibitor of translation, is activated during nutritional stress. Proc Natl Acad Sci USA 98, 14328-14333.

Christensen, S. K., Pedersen, K., Hansen, F. G., and Gerdes, K. (2003). Toxin-antitoxin loci as stress-response-elements: ChpAK/MazF and ChpBK cleave translated RNAs and are counteracted by tmRNA. J Mol Biol 332, 809-819.

Daines, D. A., Wu, M. H., and Yuan, S. Y. (2007). VapC-1 of nontypeable Haemophilus influenzae is a ribonuclease. J Bacteriol 189, 5041-5048.

Deveau, H., Garneau, J. E., and Moineau, S. (2010). CRISPR/Cas system and its role in phage-bacteria interactions. Annu Rev Microbiol 64, 475-493.

Duman, R. E., and Lowe, J. (2010). Crystal structures of Bacillus subtilis Lon protease. J Mol Biol 401, 653-670.

Engelberg-Kulka, H., Reches, M., Narasimhan, S., Schoulaker-Schwarz, R., Klemes, Y., Aizenman, E., and Glaser, G. (1998). rexB of bacteriophage lambda is an anti-cell death gene. Proc Natl Acad Sci USA 95, 15481-15486.

Fico, S., and Mahillon, J. (2006). TasA-tasB, a new putative toxin-antitoxin (TA) system from Bacillus thuringiensis pGI1 plasmid is a widely distributed composite mazE-doc TA system. BMC Genomics 7, 259.

Fineran, P. C., Blower, T. R., Foulds, I. J., Humphreys, D. P., Lilley, K. S., and Salmond, G. P. (2009). The phage abortive infection system, ToxIN, functions as a protein-RNA toxin-antitoxin pair. Proc Natl Acad Sci USA 106, 894-899.

Fozo, E. M., Makarova, K. S., Shabalina, S. A., Yutin, N., Koonin, E. V., and Storz, G. Abundance of type I toxin-antitoxin systems in bacteria: searches for new candidates and discovery of novel families. Nucleic Acids Res 38, 3743-3759.

Goldberg, A. L., Moerschell, R. P., Chung, C. H., and Maurizi, M. R. (1994). ATP-dependent protease La (lon) from Escherichia coli. Methods Enzymol 244, 350-375.

Gomez, J. E., and McKinney, J. D. (2004). M. tuberculosis persistence, latency, and drug tolerance. Tuberculosis (Edinb) 84, 29-44.

Gottesman, S. (2003). Proteolysis in bacterial regulatory circuits. Annu Rev Cell Dev Biol 19, 565-587.

Goulard, C., Langrand, S., Carniel, E., and Chauvaux, S. The Yersinia pestis chromosome encodes active addiction toxins. J Bacteriol 192, 3669-3677.

Guglielmini, J., Szpirer, C., and Milinkovitch, M. C. (2008). Automated discovery and phylogenetic analysis of new toxin-antitoxin systems. BMC Microbiol 8, 104.

Hayes, F., and Van Melderen, L. (2011). Toxins-antitoxins: diversity, evolution and function. Crit Rev Biochem Mol Biol 46, 386-408.

Hazan, R., and Engelberg-Kulka, H. (2004). Escherichia coli mazEF-mediated cell death as a defense mechanism that inhibits the spread of phage P1. Mol Genet Genomics 272, 227-234.

Hazan, R., Sat, B., and Engelberg-Kulka, H. (2004). Escherichia coli mazEF-mediated cell death is triggered by various stressful conditions. J Bacteriol 186, 3663-3669.

Hood, R. D., Singh, P., Hsu, F., Guvener, T., Carl, M. A., Trinidad, R. R., Silverman, J. M., Ohlson, B. B., Hicks, K. G., Plemel, R. L., et al. (2010). A type VI secretion system of Pseudomonas aeruginosa targets a toxin to bacteria. Cell Host Microbe 7, 25-37.

Horvath, P., and Barrangou, R. (2010). CRISPR/Cas, the immune system of bacteria and archaea. Science 327, 167-170.

Hurley, J. M., and Woychik, N. A. (2009). Bacterial toxin HigB associates with ribosomes and mediates translation-dependent mRNA cleavage at A-rich sites. J Biol Chem 284, 18605-18613.

Jiang, Y., Pogliano, J., Helinski, D. R., and Konieczny, I. (2002). ParE toxin encoded by the broad-host-range plasmid RK2 is an inhibitor of Escherichia coli gyrase. Mol Microbiol 44, 971-979.

Jorgensen, M. G., Pandey, D. P., Jaskolska, M., and Gerdes, K. (2009). HicA of Escherichia coli defines a novel family of translation-independent mRNA interferases in bacteria and archaea. J Bacteriol 191, 1191-1199.

Kim, Y., Wang, X., Ma, Q., Zhang, X. S., and Wood, T. K. (2009). Toxin-antitoxin systems in Escherichia coli influence biofilm formation through YjgK (TabA) and fimbriae. J Bacteriol 191, 1258-1267.

Kimelman, A., Levy, A., Sberro, H., Kidron, S., Amitai, G., Yoder-Himes, D., Zhu, Y., Wurtzel, O., Rubin, E. M., and Sorek, R. (2012). A vast collection of microbial genes that are toxic to bacteria. Genome Research In press.

King, G., and Murray, N. E. (1994). Restriction enzymes in cells, not eppendorfs. Trends Microbiol 2, 465-469.

Koga, M., Otsuka, Y., Lemire, S., and Yonesaki, T. (2011). Escherichia coli rnlA and rnlB compose a novel toxin-antitoxin system. Genetics 187, 123-130.

Kuchta, K., Knizewski, L., Wyrwicz, L. S., Rychlewski, L., and Ginalski, K. (2009). Comprehensive classification of nucleotidyltransferase fold proteins: identification of novel families and their representatives in human. Nucleic Acids Res 37, 7701-7714.

Labrie, S. J., Samson, J. E., and Moineau, S. (2010). Bacteriophage resistance mechanisms. Nat Rev Microbiol 8, 317-327.

Lehnherr, H., and Yarmolinsky, M. B. (1995). Addiction protein Phd of plasmid prophage P1 is a substrate of the ClpXP serine protease of Escherichia coli. Proc Natl Acad Sci USA 92, 3274-3277.

Leplae, R., Geeraerts, D., Hallez, R., Guglielmini, J., Dreze, P., and Van Melderen, L. (2011). Diversity of bacterial type II toxin-antitoxin systems: a comprehensive search and functional analysis of novel families. Nucleic Acids Res 39, 5513-5525.

Liu, M., Zhang, Y., Inouye, M., and Woychik, N. A. (2008). Bacterial addiction module toxin Doc inhibits translation elongation through its association with the 30S ribosomal subunit. Proc Natl Acad Sci USA 105, 5885-5890.

Maisonneuve, E., Shakespeare, L. J., Jorgensen, M. G., and Gerdes, K. (2011). Bacterial persistence by RNA endonucleases. Proc Natl Acad Sci USA 108, 13206-13211.

Makarova, K. S., Wolf, Y. I., and Koonin, E. V. (2009). Comprehensive comparative-genomic analysis of type 2 toxin-antitoxin systems and related mobile stress response systems in prokaryotes. Biol Direct 4, 19.

Makarova, K. S., Wolf, Y. I., Snir, S., and Koonin, E. V. (2011). Defense islands in bacterial and archaeal genomes and prediction of novel defense systems. J Bacteriol 193, 6039-6056.

Marchler-Bauer, A., Lu, S., Anderson, J. B., Chitsaz, F., Derbyshire, M. K., DeWeese-Scott, C., Fong, J. H., Geer, L. Y., Geer, R. C., Gonzales, N. R., et al. (2011). CDD: a Conserved Domain Database for the functional annotation of proteins. Nucleic Acids Res 39, D225-229.

Masuda, H., Tan, Q., Awano, N., Yamaguchi, Y., and Inouye, M. (2012). A novel membrane-bound toxin for cell division, CptA (YgfX), inhibits polymerization of cytoskeleton proteins, FtsZ and MreB, in *Escherichia coli*. FEMS Microbiol Lett 328, 174-181.

Neubauer, C., Gao, Y. G., Andersen, K. R., Dunham, C. M., Kelley, A. C., Hentschel, J., Gerdes, K., Ramakrishnan, V., and Brodersen, D. E. (2009). The structural basis for mRNA recognition and cleavage by the ribosome-dependent endonuclease RelE. Cell 139, 1084-1095.

O'Connor, L., Coffey, A., Daly, C., and Fitzgerald, G. F. (1996). AbiG, a genotypically novel abortive infection mechanism encoded by plasmid pCI750 of *Lactococcus lactis* subsp. *cremoris* UC653. Appl Environ Microbiol 62, 3075-3082.

Otsuka, Y., and Yonesaki, T. (2012). Dmd of bacteriophage T4 functions as an antitoxin against *Escherichia coli* LsoA and RnlA toxins. Mol Microbiol 83, 669-681.

Pandey, D. P., and Gerdes, K. (2005). Toxin-antitoxin loci are highly abundant in free-living but lost from host-associated prokaryotes. Nucleic Acids Res 33, 966-976.

Pecota, D. C., and Wood, T. K. (1996). Exclusion of T4 phage by the hok/sok killer locus from plasmid R1. J Bacteriol 178, 2044-2050.

Poole, S. J., Diner, E. J., Aoki, S. K., Braaten, B. A., t'Kint de Roodenbeke, C., Low, D. A., and Hayes, C. S. (2011). Identification of functional toxin/immunity genes linked to contact-dependent growth inhibition (CDI) and rearrangement hotspot (Rhs) systems. PLoS Genet. 7, e1002217.

Roberts, R. C., Strom, A. R., and Helinski, D. R. (1994). The parDE operon of the broad-host-range plasmid RK2 specifies growth inhibition associated with plasmid loss. J Mol Biol 237, 35-51.

Rotem, E., Loinger, A., Ronin, I., Levin-Reisman, I., Gabay, C., Shoresh, N., Biham, O., and Balaban, N. Q. (2010). Regulation of phenotypic variability by a threshold-based mechanism underlies bacterial persistence. Proc Natl Acad Sci USA 107, 12541-12546.

Schumacher, M. A., Piro, K. M., Xu, W., Hansen, S., Lewis, K., and Brennan, R. G. (2009). Molecular mechanisms of HipA-mediated multidrug tolerance and its neutralization by HipB. Science 323, 396-401.

Shao, Y., Harrison, E. M., Bi, D., Tai, C., He, X., Ou, H. Y., Rajakumar, K., and Deng, Z. (2011). TADB: a web-based resource for Type 2 toxin-antitoxin loci in bacteria and archaea. Nucleic Acids Res 39, D606-611.

Skorupski, K., Tomaschewski, J., Ruger, W., and Simon, L. D. (1988). A bacteriophage T4 gene which functions to inhibit *Escherichia coli* Lon protease. J Bacteriol 170, 3016-3024.

Smith, P. A., and Romesberg, F. E. (2007). Combating bacteria and drug resistance by inhibiting mechanisms of persistence and adaptation. Nat Chem Biol 3, 549-556.

Sorek, R., Kunin, V., and Hugenholtz, P. (2008). CRISPR—a widespread system that provides acquired resistance against phages in bacteria and archaea. Nat Rev Microbiol 6, 181-186.

Sorek, R., Zhu, Y., Creevey, C. J., Francino, M. P., Bork, P., and Rubin, E. M. (2007). Genome-wide experimental determination of barriers to horizontal gene transfer. Science 318, 1449-1452.

Stahlberg, H., Kutejova, E., Suda, K., Wolpensinger, B., Lustig, A., Schatz, G., Engel, A., and Suzuki, C. K. (1999). Mitochondrial Lon of *Saccharomyces cerevisiae* is a ring-shaped protease with seven flexible subunits. Proc Natl Acad Sci USA 96, 6787-6790.

Stern, A., and Sorek, R. (2011). The phage-host arms race: shaping the evolution of microbes. Bioessays 33, 43-51.

Tan, Q., Awano, N., and Inouye, M. (2010). YeeV is an *Escherichia coli* toxin that inhibits cell division by targeting the cytoskeleton proteins, FtsZ and MreB. Mol Microbiol 79, 109-118.

Tuchscherr, L., Medina, E., Hussain, M., Volker, W., Heitmann, V., Niemann, S., Holzinger, D., Roth, J., Proctor, R. A., Becker, K., et al. (2011). *Staphylococcus aureus* phenotype switching: an effective bacterial strategy to escape host immune response and establish a chronic infection. EMBO Mol Med 3, 129-141.

Unger, T., Jacobovitch, Y., Dantes, A., Bernheim, R., and Peleg, Y. (2010). Applications of the Restriction Free (RF) cloning procedure for molecular manipulations and protein expression. J Struct Biol 172, 34-44.

van der Oost, J., Jore, M. M., Westra, E. R., Lundgren, M., and Brouns, S. J. (2009). CRISPR-based adaptive and heritable immunity in prokaryotes. Trends Biochem Sci 34, 401-407.

Van Melderen, L., and Saavedra De Bast, M. (2009). Bacterial toxin-antitoxin systems: more than selfish entities? PLoS Genet. 5, e1000437.

Van Melderen, L., Thi, M. H., Lecchi, P., Gottesman, S., Couturier, M., and Maurizi, M. R. (1996). ATP-dependent degradation of CcdA by Lon protease. Effects of secondary structure and heterologous subunit interactions. J Biol Chem 271, 27730-27738.

Wang, X., Kim, Y., Hong, S. H., Ma, Q., Brown, B. L., Pu, M., Tarone, A. M., Benedik, M. J., Peti, W., Page, R., et al. (2011). Antitoxin MqsA helps mediate the bacterial general stress response. Nat Chem Biol 7, 359-366.

Wozniak, R. A., and Waldor, M. K. (2009). A toxin-antitoxin system promotes the maintenance of an integrative conjugative element. PLoS Genet. 5, e1000439.

Zhang, X. Z., Yan, X., Cui, Z. L., Hong, Q., and Li, S. P. (2006). mazF, a novel counter-selectable marker for unmarked chromosomal manipulation in *Bacillus subtilis*. Nucleic Acids Res 34, e71.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09353359B2). An electronic copy of the "Sequence Listing" will also be available from the USPTO upon request and payment of the fee set forth in 37 CFR 1.19(b)(3).

What is claimed is:

1. A method of killing a microbe, the method comprising contacting the microbe with an isolated peptide comprising an amino acid sequence of a toxin as set forth in SEQ ID NO: 3001, thereby killing the microbe.

2. A method of killing a microbe, the method comprising contacting the microbe with an isolated peptide comprising an amino acid sequence of a toxin as set forth in SEQ ID NON: 2773, thereby killing the microbe.

3. A method of killing a microbe, the method comprising contacting the microbe with an isolated peptide comprising an amino acid sequence of a toxin as set forth in SEQ ID NO: 2774, thereby killing the microbe.

4. A method of killing a microbe, the method comprising contacting the microbe with an isolated peptide comprising an amino acid sequence of a toxin as set forth in SEQ ID NO: 2775, thereby killing the microbe.

5. A method of killing a microbe, the method comprising contacting the microbe with an isolated peptide comprising an amino acid sequence of a toxin as set forth in SEQ ID NO: 2776, thereby killing the microbe.

6. A method of killing a microbe, the method comprising contacting the microbe with an isolated peptide comprising an amino acid sequence of a toxin as set forth in SEQ ID NO: 2777, thereby killing the microbe.

7. A method of killing a microbe, the method comprising contacting the microbe with an isolated peptide comprising an amino acid sequence of a toxin as set forth in SEQ ID NO: 2778, thereby killing the microbe.

8. A method of killing a microbe, the method comprising contacting the microbe with an isolated peptide comprising an amino acid sequence of a toxin as set forth in SEQ ID NO: 2779, thereby killing the microbe.

9. A method of killing a microbe, the method comprising contacting the microbe with an isolated peptide comprising an amino acid sequence of a toxin as set forth in SEQ ID NO: 2780, thereby killing the microbe.

10. A method of killing a microbe, the method comprising contacting the microbe with an isolated peptide comprising an amino acid sequence of a toxin as set forth in SEQ ID NO: 2781, thereby killing the microbe.

* * * * *